(12) United States Patent
Chen et al.

(10) Patent No.: US 8,933,207 B2
(45) Date of Patent: Jan. 13, 2015

(54) DRUG-LIGAND CONJUGATES, SYNTHESIS THEREOF, AND INTERMEDIATES THERETO

(75) Inventors: Zhiyu Chen, Chicago, IL (US); Thomas M. Lancaster, Stoneham, MA (US); Todd C. Zion, Marblehead, MA (US)

(73) Assignee: SmartCells, Inc., Whitehouse Station, NJ (US)

( * ) Notice: Subject to any disclaimer, the term of this patent is extended or adjusted under 35 U.S.C. 154(b) by 0 days.

(21) Appl. No.: 13/811,745

(22) PCT Filed: Jul. 22, 2011

(86) PCT No.: PCT/US2011/044936
§ 371 (c)(1),
(2), (4) Date: Jan. 23, 2013

(87) PCT Pub. No.: WO2012/015681
PCT Pub. Date: Feb. 2, 2012

(65) Prior Publication Data
US 2013/0190475 A1    Jul. 25, 2013

Related U.S. Application Data

(60) Provisional application No. 61/368,597, filed on Jul. 28, 2010.

(51) Int. Cl.
| | | |
|---|---|---|
| *C07H 15/04* | (2006.01) | |
| *A61K 47/48* | (2006.01) | |
| *C07H 15/26* | (2006.01) | |
| *C07D 487/00* | (2006.01) | |
| *C07C 237/12* | (2006.01) | |
| *A61K 38/28* | (2006.01) | |

(52) U.S. Cl.
CPC ......... *A61K 47/48092* (2013.01); *C07C 237/12* (2013.01); *C07H 15/04* (2013.01); *C07H 15/26* (2013.01)
USPC .............................................. 532/1; 530/303

(58) Field of Classification Search
None
See application file for complete search history.

(56) References Cited

U.S. PATENT DOCUMENTS

| | | | |
|---|---|---|---|
| 3,591,574 A | 7/1971 | Fenichel et al. | |
| 3,684,791 A | 8/1972 | Geiger et al. | |
| 3,847,890 A | 11/1974 | Green et al. | |
| 4,348,387 A | 9/1982 | Brownlee et al. | |
| 4,372,948 A | 2/1983 | Yoshikumi et al. | |
| 4,377,567 A | 3/1983 | Geho | |
| 4,444,683 A | 4/1984 | Kim et al. | |
| 4,603,044 A | 7/1986 | Geho et al. | |
| 4,863,896 A | 9/1989 | Geho et al. | |
| 5,239,062 A | 8/1993 | Blattler et al. | |
| 5,395,924 A | 3/1995 | Blattler et al. | |
| 5,478,575 A | 12/1995 | Miyazaki et al. | |
| 5,527,524 A | 6/1996 | Tomalia et al. | |
| 5,563,056 A | 10/1996 | Swan et al. | |
| 5,723,589 A | 3/1998 | Miljkovic et al. | |
| 5,830,506 A | 11/1998 | Taylor | |
| 5,854,208 A | 12/1998 | Jones et al. | |
| 5,866,538 A | 2/1999 | Norup et al. | |
| 5,902,607 A | 5/1999 | Taylor | |
| 5,905,140 A | 5/1999 | Hansen | |
| 5,922,675 A | 7/1999 | Baker et al. | |
| 5,948,751 A | 9/1999 | Kimer et al. | |
| 5,994,517 A | 11/1999 | Ts'o et al. | |
| 6,034,054 A | 3/2000 | DeFelippis et al. | |
| 6,180,757 B1 | 1/2001 | Bogsnes | |
| 6,214,547 B1 | 4/2001 | Kjeldsen et al. | |
| 6,323,311 B1 | 11/2001 | Liu et al. | |
| 6,342,225 B1 | 1/2002 | Jones et al. | |
| 6,410,053 B1 | 6/2002 | Taylor | |
| 6,500,645 B1 | 12/2002 | Kjeldsen et al. | |
| 6,521,738 B2 | 2/2003 | Kjeldsen et al. | |
| 6,551,992 B1 | 4/2003 | DeFelippis et al. | |
| 6,759,509 B1 * | 7/2004 | King et al. | ..................... 530/330 |

(Continued)

FOREIGN PATENT DOCUMENTS

| | | |
|---|---|---|
| CN | 101273961 | 10/2008 |
| EP | 009842 | 4/1980 |

(Continued)

OTHER PUBLICATIONS

Baudys, et al., "Physical Stabilization of Insulin by Glycosylation" *J Pharma Sci* (1995) 64: 28-33.

(Continued)

*Primary Examiner* — Maury Audet
(74) *Attorney, Agent, or Firm* — John David Reilly; Immac J. Thampoe

(57) ABSTRACT

The present invention relates to methods for synthesizing compounds of formula I or pharmaceutically acceptable salts thereof: I wherein each of X, $Alk_1$, $Alk_2$, and W are as defined and described herein.

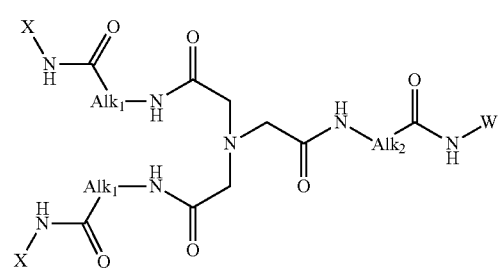

I

1 Claim, 42 Drawing Sheets

(56) References Cited

U.S. PATENT DOCUMENTS

| | | |
|---|---|---|
| 6,777,207 B2 | 8/2004 | Kjeldsen et al. |
| 6,844,166 B1 | 1/2005 | Wolf |
| 6,869,930 B1 | 3/2005 | Havelund et al. |
| RE39,055 E | 4/2006 | Jones et al. |
| 7,063,863 B2 | 6/2006 | Taylor |
| 7,087,408 B2 | 8/2006 | Kjeldsen et al. |
| 7,105,314 B2 | 9/2006 | Kjeldsen |
| 7,316,999 B2 | 1/2008 | Hoeg-Jesen et al. |
| 7,317,000 B2 | 1/2008 | Hoeg-Jensen et al. |
| 7,423,014 B2 | 9/2008 | Ekwuribe et al. |
| 7,531,191 B2 | 5/2009 | Zion et al. |
| 7,687,608 B2 | 3/2010 | Lancaster et al. |
| 8,062,668 B2 | 11/2011 | Ying et al. |
| 2003/0068379 A1* | 4/2003 | Li et al. ............... 424/490 |
| 2006/0019874 A1 | 1/2006 | Radhakrishnan et al. |
| 2006/0216265 A1 | 9/2006 | Goodman et al. |
| 2006/0247154 A1 | 11/2006 | Palmieri et al. |
| 2007/0099820 A1 | 5/2007 | Lancaster et al. |
| 2007/0207498 A1 | 9/2007 | Palmieri et al. |
| 2009/0053167 A1 | 2/2009 | DeFrees |
| 2009/0137454 A1 | 5/2009 | Fynbo et al. |
| 2010/0130726 A1 | 5/2010 | Lancaster et al. |
| 2011/0275560 A1 | 11/2011 | Zion et al. |
| 2011/0281791 A1* | 11/2011 | Zion et al. ............... 514/5.9 |
| 2011/0281792 A1 | 11/2011 | Zion et al. |
| 2011/0281939 A1 | 11/2011 | Zion et al. |
| 2011/0301083 A1 | 12/2011 | Zion et al. |
| 2012/0046223 A1 | 2/2012 | Zion et al. |

FOREIGN PATENT DOCUMENTS

| | | |
|---|---|---|
| EP | 0119650 | 9/1984 |
| EP | 0725648 | 8/1996 |
| RU | 2381238 | 8/2009 |
| WO | WO81/00354 | 2/1981 |
| WO | WO84/01896 | 5/1984 |
| WO | WO90/10645 | 9/1990 |
| WO | WO99/52934 | 10/1999 |
| WO | WO01/92334 | 12/2001 |
| WO | WO03/035011 | 5/2003 |
| WO | WO03/047462 | 6/2003 |
| WO | WO03/048915 | 6/2003 |
| WO | WO03/074087 | 9/2003 |
| WO | WO2004/057002 | 7/2004 |
| WO | WO2006/008238 | 1/2006 |
| WO | WO2006/082184 | 8/2006 |
| WO | WO2006/088473 | 8/2006 |
| WO | WO2006/102762 | 10/2006 |
| WO | WO2007/042470 | 4/2007 |
| WO | WO2007/043050 | 4/2007 |
| WO | WO2008/012440 | 1/2008 |
| WO | WO2008/012528 | 1/2008 |
| WO | WO2008/036147 | 3/2008 |
| WO | WO2009/033588 | 3/2009 |
| WO | WO2009/059450 | 5/2009 |
| WO | WO2009/089396 | 7/2009 |
| WO | WO2009/104199 | 8/2009 |
| WO | WO2011/000823 | 1/2011 |

OTHER PUBLICATIONS

Brownlee & Cerami, "A Glucose-Controlled-Insulin-Delivery-System: Semisynthetic Insulin Bound to Lectin" *Diabetes* (1983) 32L 499-504.

Brownlee & Cerami, "Glycosylated Insulin Complexed to Concanavalin A" *Science* (1979) 206: 1190-1191.

Dea, et al., "Albumin Binding of Acylated Insulin (NN304) Does Not Deter Action to Stimulate Glucose Uptake" *Diabetes* (2002) 51: 762-769.

Eggert, et al., "A New Glucose Selective Fluorescent Bisboronic Acid" *J Org Chem* (1999) 64: 3846-3852.

Heinnemann, et al., "Time-action profile of the soluble, fatty acid acylated, long acting insulin analogue NN304" *Diabetic Med* (1999) 16: 332-338.

Jeong, et al., "Self Regulating Insulin Delivery Systems I. Synthesis and Characterization of Glycosylated Insulin" *J of Controlled Release* (1984) 1: 57-66.

Lee et al., "Biochemistry of crbohydrate-protein interaction" *FASEB J* (1992) 3193-3200.

Monsigny, et al., "Endogenous Lectins and Drug Targeting" *Annals NY Acad Sci* (1988) 551: 399-414.

Ruziak, et al., "Basal activity profiles of NPH and [Ne-palmitoyl Lys (B29) human insulins in subjects with IDDM" *Diabetologia* (1998) 41: 116-120.

Shojaee-Moradie, "Novel Hepatoselective Insulin Analog" *Diabetes Care* (2000) 23: 1124-1129.

Yamazaki, et al., "Endogenous lectins as targets for drug delivery" *Adv Drug Delivery Rev* (2000) 43: 225-244.

PCT Written Opinion—dated: Feb. 7, 2013 RE: WO2012015681, PCTUS2011044936.

\* cited by examiner

Conjugate II-3
TSAT-C6-AEBM-2 (B1)

Conjugate II-4
TSAT-C6-AEBM-1-AETM-1 (B1)

Conjugate II-5
TSAT-C6-GA-2 (B29)

Conjugate II-6
TSAT-C6-AETM-2 (B29)

Conjugate II-7
TSAT-C6-AEM-2 (B29)

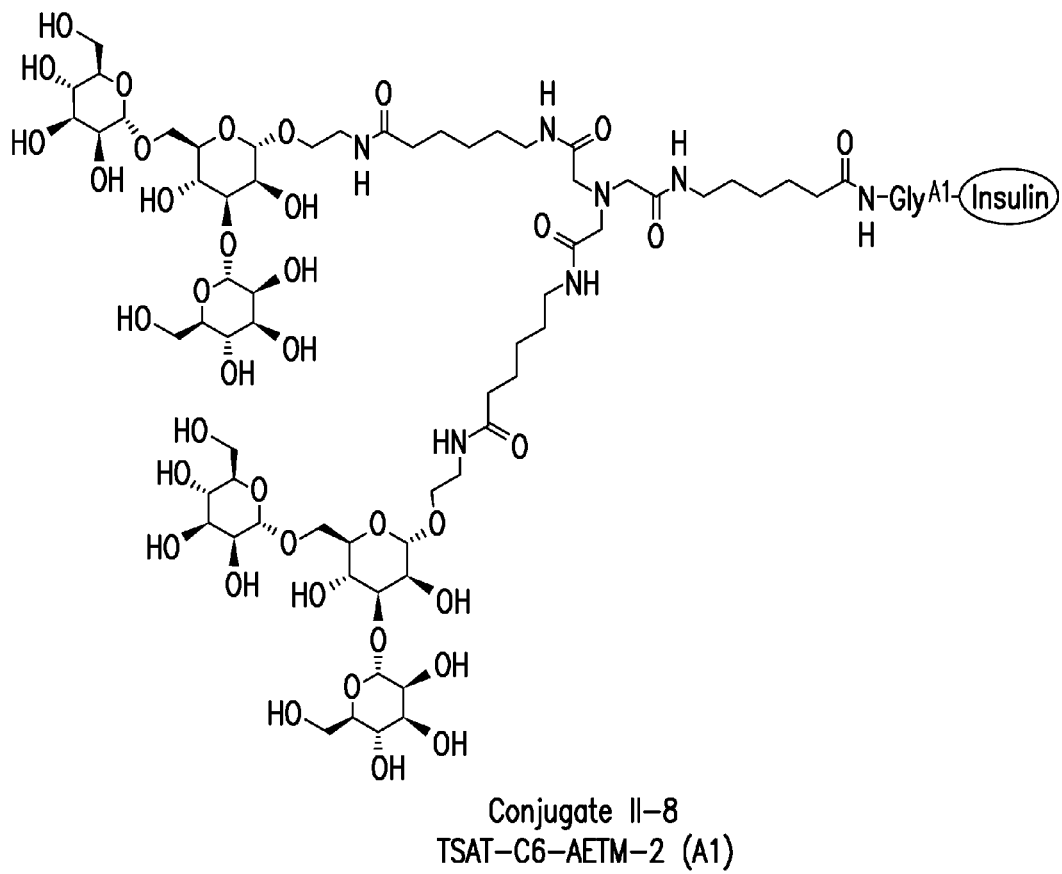
Conjugate II-8
TSAT-C6-AETM-2 (A1)
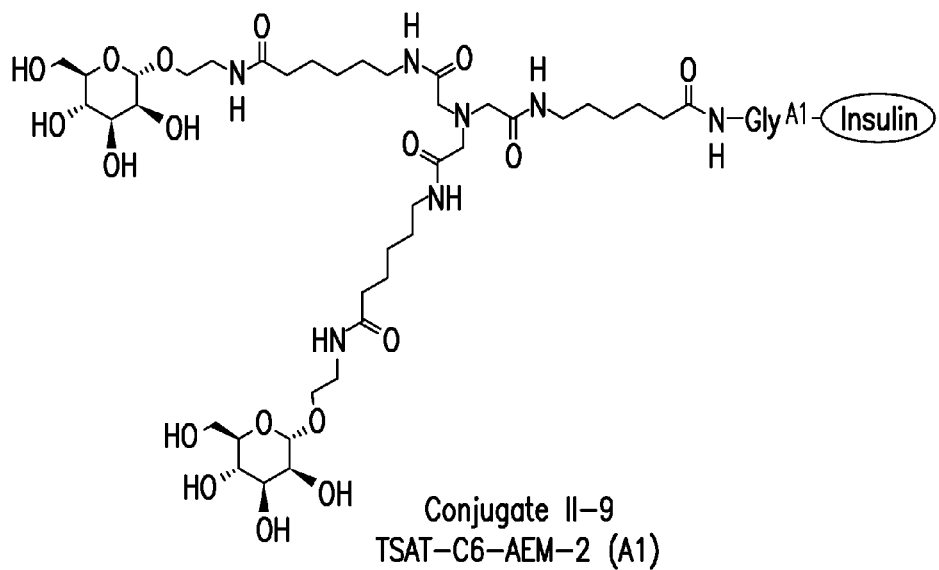
Conjugate II-9
TSAT-C6-AEM-2 (A1)
FIG.1-5

Conjugate II-10
TSAT-C6-Di-sub-AEM-2 (A1,B29)

Conjugate II-11
TSAT-C6-Di-sub-AETM-2 (A1,B29)

Conjugate II-12
TSAT-C6-Di-sub-AETM-2 (A1,B1)

Conjugate II-13
TSAT-C6-Di-sub-AETM-2 (B1,B29)

| Formulation | Scaffold – X | Scaffold – Y | Sugar (n) |
|---|---|---|---|
| RHI | n/a | n/a | n/a |
| II-7: AEM2 | TSAT-$C_6$ | n/a | AEM (2) |
| II-6: AETM2 | TSAT-$C_6$ | n/a | AETM (2) |
| II-11: Di-sub-AETM-2 | TSAT-$C_6$ | TSAT-$C_6$ | AETM (2x2) |

| Formulation | β-phase half-line (min) for each type of infusion | | |
|---|---|---|---|
| | Saline | Glucose | α-methyl mannose |
| RHI | 2.7 | 2.3 | 3.3 |
| II-7: AEM-2 | 5.5 | 5.8 | 5.4 |
| II-6: AETM-2 | 4.8 | 3.3 | 8.1 |
| II-11: Di-sub-AETM-2 | 2.5 | n/a | 20.3 |

FIG.11

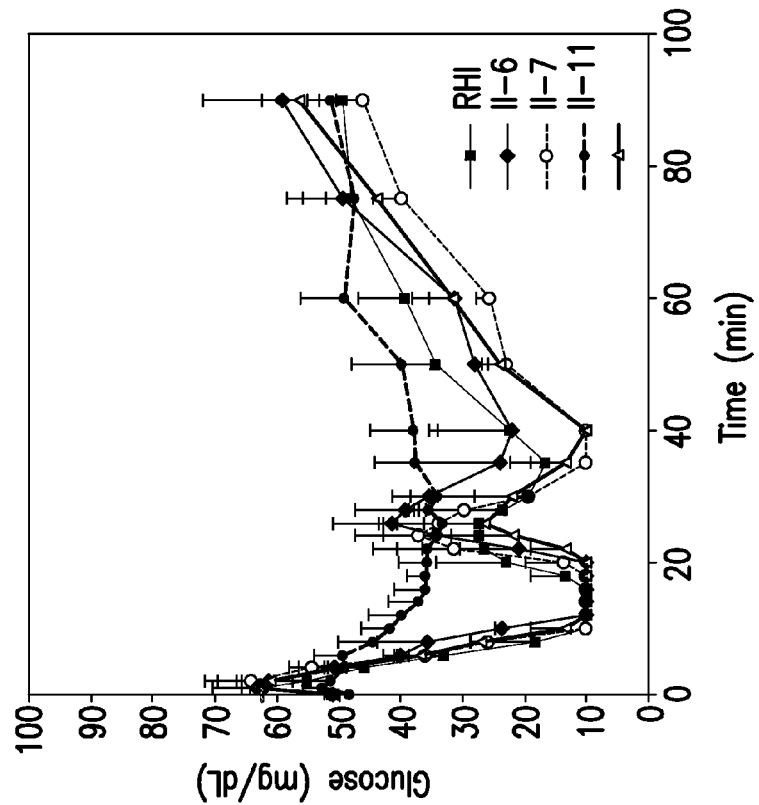
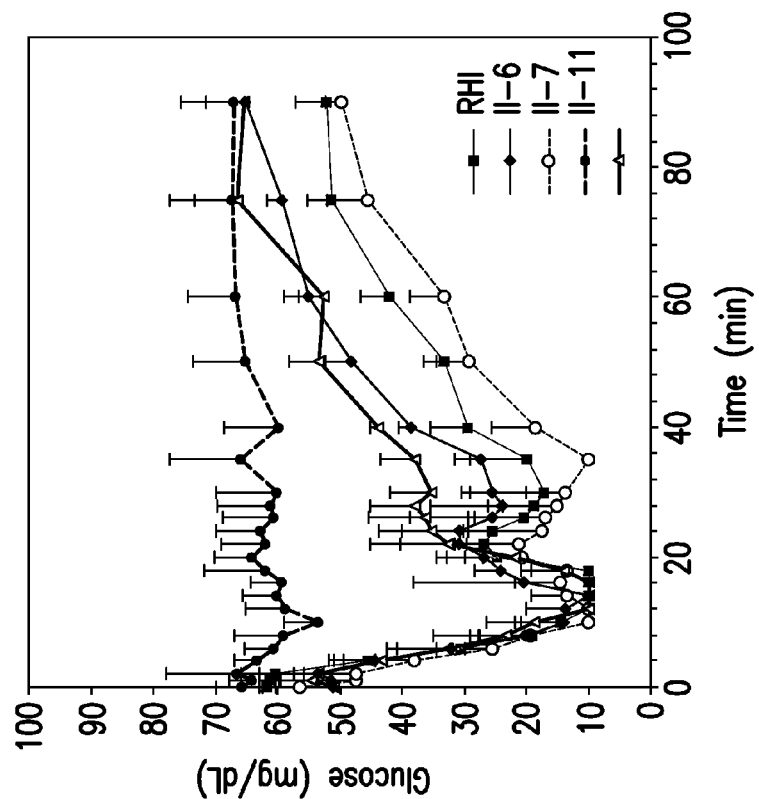
FIG. 13A
FIG. 13B

| Insulin-conjugate | Sugar composition | $t_{1/2,\beta}$ (α-MM) / $t_{1/2,\beta}$ (No Inf) |
|---|---|---|
| II-11 | B29: AETMx2, A1: AETMx2 | 8.1 |
| II-8 | A1: AETMx2 | 2.3 |
| II-6 | B29: AETMx2 | 1.7 |
| II-10 | B29: AEMx2, A1: AEMx2 | 1.5 |
| RHI | n/a | 1.2 |
| II-7 | B29: AEMx2 | 0.9 |

FIG. 18

Second enzymatic step with trypsin cleaves on C-terminal side of Arg in A0 and B0

Conjugated insulin intermediates collapse to desired product

Second enzymatic step with trypsin cleaves on C-terminal side of Arg in B0

Conjugated insulin intermediates collapse to desired product

| | Media | Plasmid | Clone # | mg/L |
|---|---|---|---|---|
| 1 | BMMY | RHI-1 | 1A | 12 |
| 2 | BMMY | | 1.5A | 47 |
| 3 | BMMY | | 2A | 47 |
| 4 | BMMY | | 3A | 48 |
| 5 | BMMY | | 4A | 48 |
| 6 | BMMY | RHI-2 | 1A | 25 |
| 7 | BMMY | | 2A | 13 |
| 8 | BMMY | RHI-3 | 1A | 51 |
| 9 | BMMY | | 1.5A | 48 |
| 10 | BMMY | | 2A-A | 58 |
| 11 | BMMY | | 2B-E | 38 |
| 12 | BMMY | RAT-1 | 0.5A-A | 4 |
| 13 | BMMY | | 0.5B-C | 9 |
| 14 | BMMY | | 1A-A | 8 |
| 15 | BMMY | | 1B-C | 6 |
| 16 | MMY | RHI-1 | 1B | 33 |
| 17 | MMY | | 1.5B | 106 |
| 18 | MMY | | 2B | 38 |
| 19 | MMY | | 3B | 92 |
| 20 | MMY | | 4B | 62 |
| 21 | MMY | RHI-2 | 1B | 33 |
| 22 | MMY | | 2B | 17 |
| 23 | MMY | RHI-3 | 1B | 64 |
| 24 | MMY | | 1.5B | 81 |
| 25 | MMY | | 2A-D | 20 |
| 26 | MMY | | 2B-E | 84 |
| 27 | MMY | RAT-1 | 0.5A-B | 4 |
| 28 | MMY | | 0.5B-D | 5 |
| 29 | MMY | | 1A-B | 12 |
| 30 | MMY | | 1B-D | 7 |

DRUG-LIGAND CONJUGATES, SYNTHESIS THEREOF, AND INTERMEDIATES THERETO

CROSS REFERENCE TO RELATED APPLICATIONS

This application is a U.S. National Phase application under 35 U.S.C. §371 of PCT Application No. PCT/US2011/044936, filed Jul. 22, 2011 which claims priority under 35 U.S.C. §119(e) from U.S. Provisional Application Ser. No. 61/368,597, filed Jul. 28, 2010.

REFERENCE TO SEQUENCE LISTING SUBMITTED ELECTRONICALLY

The sequence listing of the present application is submitted electronically via EFS-Web as an ASCII formatted sequence listing with a file name "23016-SEQTXT18JAN2013.TXT", creation date of 18 Jan. 2013, and a size of 13 KB. This sequence listing submitted via EFS-Web is part of the specification and is herein incorporated by reference in its entirety.

BACKGROUND OF THE INVENTION

International Application No. PCT/US2010/22268 describes conjugate-based systems, methods for their preparation, and use of these conjugates, e.g., as therapeutics. Alternative synthetic methods for drug-ligand conjugates are desired.

SUMMARY OF THE INVENTION

As described herein, the present invention provides methods for preparing drug-ligand conjugates capable of controlling the pharmacokinetic (PK) and/or pharmacodynamic (PD) profiles of a drug such as insulin in a manner that is responsive to the systemic concentrations of a saccharide such as glucose. Such conjugates include those of formula I:

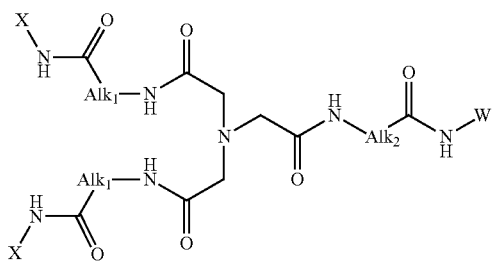

I or a pharmaceutically acceptable salt thereof, wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
W is a drug.

The present invention also provides synthetic intermediates useful for preparing such conjugates. In certain embodiments, an exemplary useful intermediate in the preparation of a drug-ligand conjugate is a conjugate of formula A:

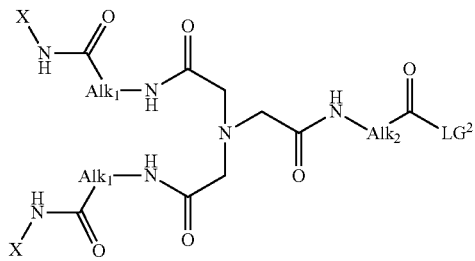

A wherein X, $Alk_1$, $Alk_2$, and $LG^2$ are as defined and described in embodiments herein.

The present invention also provides methods for preparing conjugates that include a detectable label instead of a drug as W.

DEFINITIONS

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

Acyl—As used herein, the term "acyl," refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Alkylene chain—As used herein, the term "alkylene chain" (also referred to as simply "alkylene") is a polymethylene group, i.e., $-(CH_2)_z-$, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group. A methylene unit $-CH_2-$ may also be optionally replaced by other bivalent groups, such as $-O-$, $-S-$, $-NH-$, $-NHC(O)-$, $-C(O)NH-$, $-C(O)-$, $-S(O)-$, $-S(O)_2-$, and the like.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}R^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$_†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable Protecting Group

As used herein, the term "suitable protecting group," refers to amino protecting groups or carboxylic acid protecting groups depending on its location within the compound and includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3- diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), $N^2$-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitable carboxylic acid protecting groups include silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

In any case where a chemical variable (e.g., an R group) is shown attached to a bond that crosses a bond of ring, this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

Biomolecule

As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Drug

As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Exogenous

As used herein, an "exogenous" molecule is one which is not present at significant levels in a patient unless administered to the patient. In certain embodiments the patient is a mammal, e.g., a human, a dog, a cat, a rat, a minipig, etc. As used herein, a molecule is not present at significant levels in a patient if normal serum for that type of patient includes less than 0.1 mM of the molecule. In certain embodiments normal serum for the patient may include less than 0.08 mM, less than 0.06 mM, or less than 0.04 mM of the molecule.

Normal Serum

As used herein, "normal serum" is serum obtained by pooling approximately equal amounts of the liquid portion of coagulated whole blood from five or more non-diabetic patients. A non-diabetic human patient is a randomly selected 18-30 year old who presents with no diabetic symptoms at the time blood is drawn.

Polymer

As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Polynucleotide

As used herein, a "polynucleotide" is a polymer of nucleotides. The terms "polynucleotide", "nucleic acid", and "oligonucleotide" may be used interchangeably. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

Polypeptide

As used herein, a "polypeptide" is a polymer of amino acids. The terms "polypeptide", "protein", "oligopeptide", and "peptide" may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

Polysaccharide

As used herein, a "polysaccharide" is a polymer of saccharides. The terms "polysaccharide", "carbohydrate", and "oligosaccharide", may be used interchangeably. The polymer may include natural saccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Small Molecule

As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 Da. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, are all considered acceptable for use in accordance with the present invention.

Treat

As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition.

BRIEF DESCRIPTION OF THE DRAWINGS

FIG. 11: β-phase elimination half-life results in non-diabetic minipigs during glucose, α-methyl mannose or saline infusion.

FIG. 13: Blood glucose depression curves in non-diabetic male Yucatan minipigs equipped with dual vascular access ports (n=3 per study) following i.v. injection of conjugates at 0.1 U/kg under conditions of (a) no i.v. sugar infusion or (b) i.v. alpha methyl mannose (a-MM) infusion (25% w/v infused at constant rate of 80 ml/h). (■)RHI, (♦) II-6, (○) II-7, and (●) II-11.

FIG. 15: Blood glucose levels in (a, —, closed symbols) alloxan-diabetic Yucatan minipigs (n=3 per dose) and (b, - - -, open symbols) non-diabetic Yucatan minipigs (n=3 per dose) under fasting conditions after a sub-Q injection at time 0 with soluble recombinant human insulin (RHI) at doses of (▲,Δ) 0.063 and (■,□) 0.125 U/kg. Data are plotted as the average values+one standard deviation. NOTE: FIG. 16(b) scale is enlarged for clarity.

FIG. 18: Summary of i.v. half-life results in minipigs for additional insulin-conjugates.

DETAILED DESCRIPTION OF CERTAIN EMBODIMENTS

Figure 1:
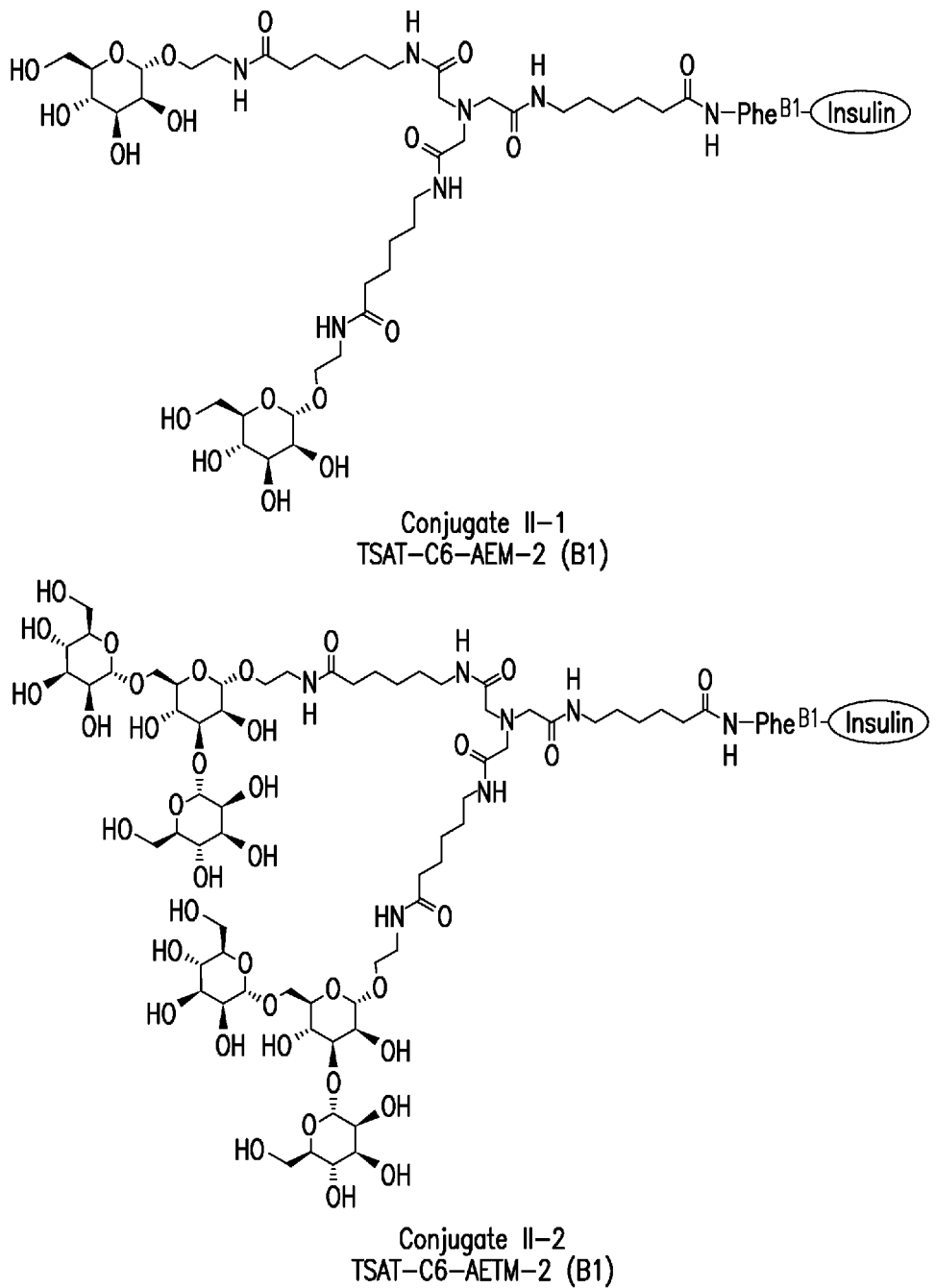
FIG. 1: Structures of exemplary insulin-conjugates. As described in the Examples, these conjugates were each prepared with recombinant wild-type human insulin (see below for the structure of wild-type human insulin). The symbol "insulin" inside an oval as shown in FIG. 1 is therefore primarily intended to represent a wild-type human insulin. As discussed herein, it is to be understood that the present disclosure also encompasses inter alia versions of these and other conjugates that include an insulin molecule other than wild-type human insulin.
Figure 1:
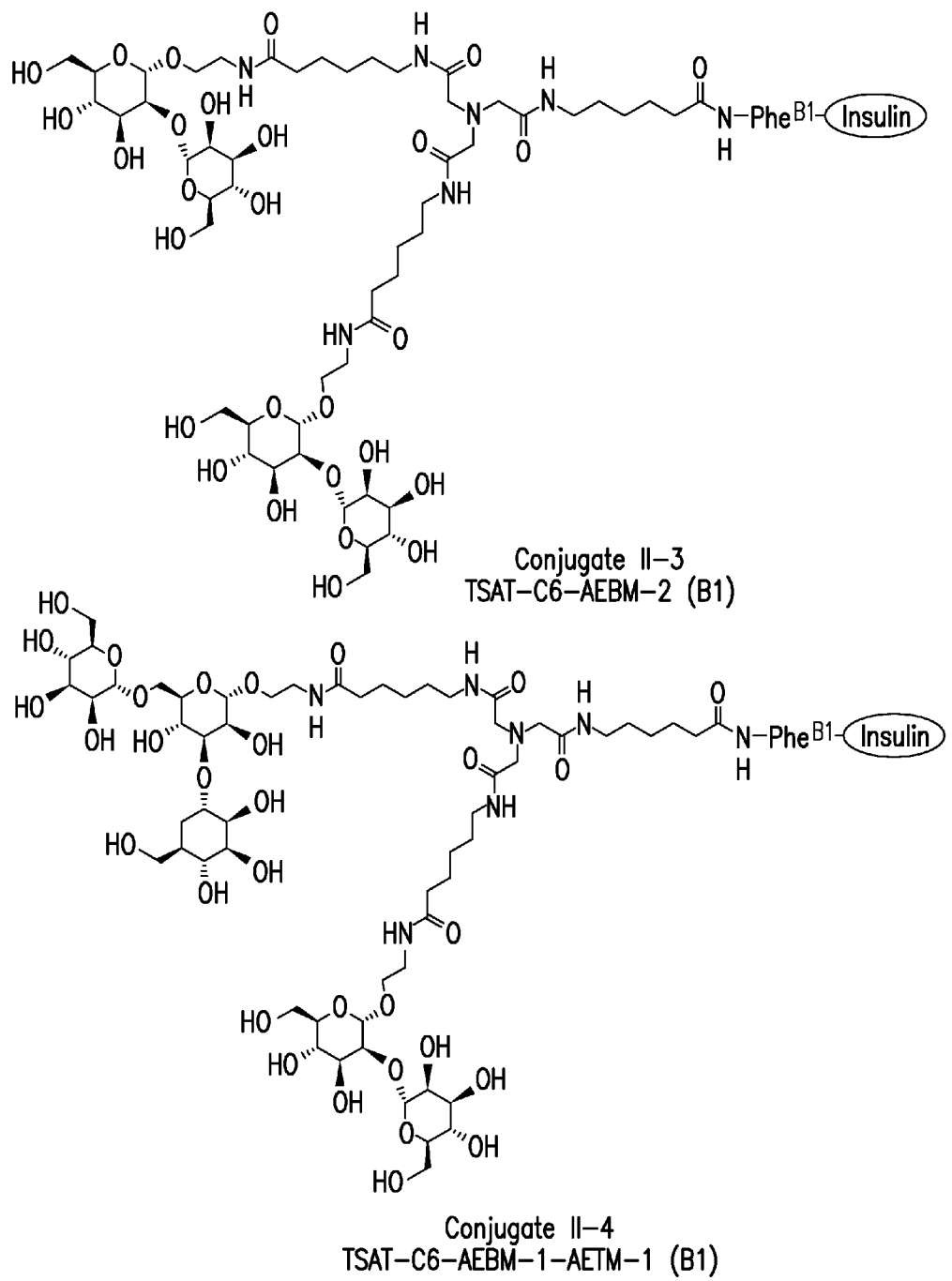
Figures 1, 2:
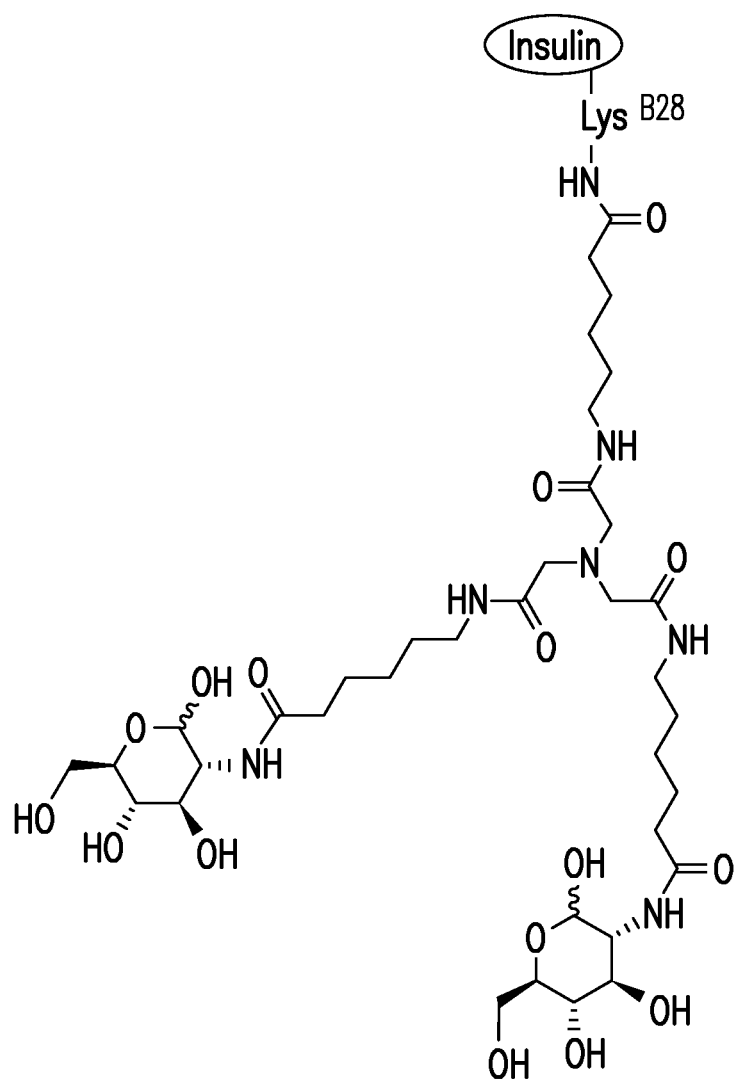
FIG. 2: Plot of serum insulin (left) and blood glucose (right) levels following subcutaneous injection in non-diabetic, male SD rats (n=3) at time 0 with TSAT-C6-AEM-2 conjugate II-1 (3.5 U/kg).
Figures 1, 2, 3:
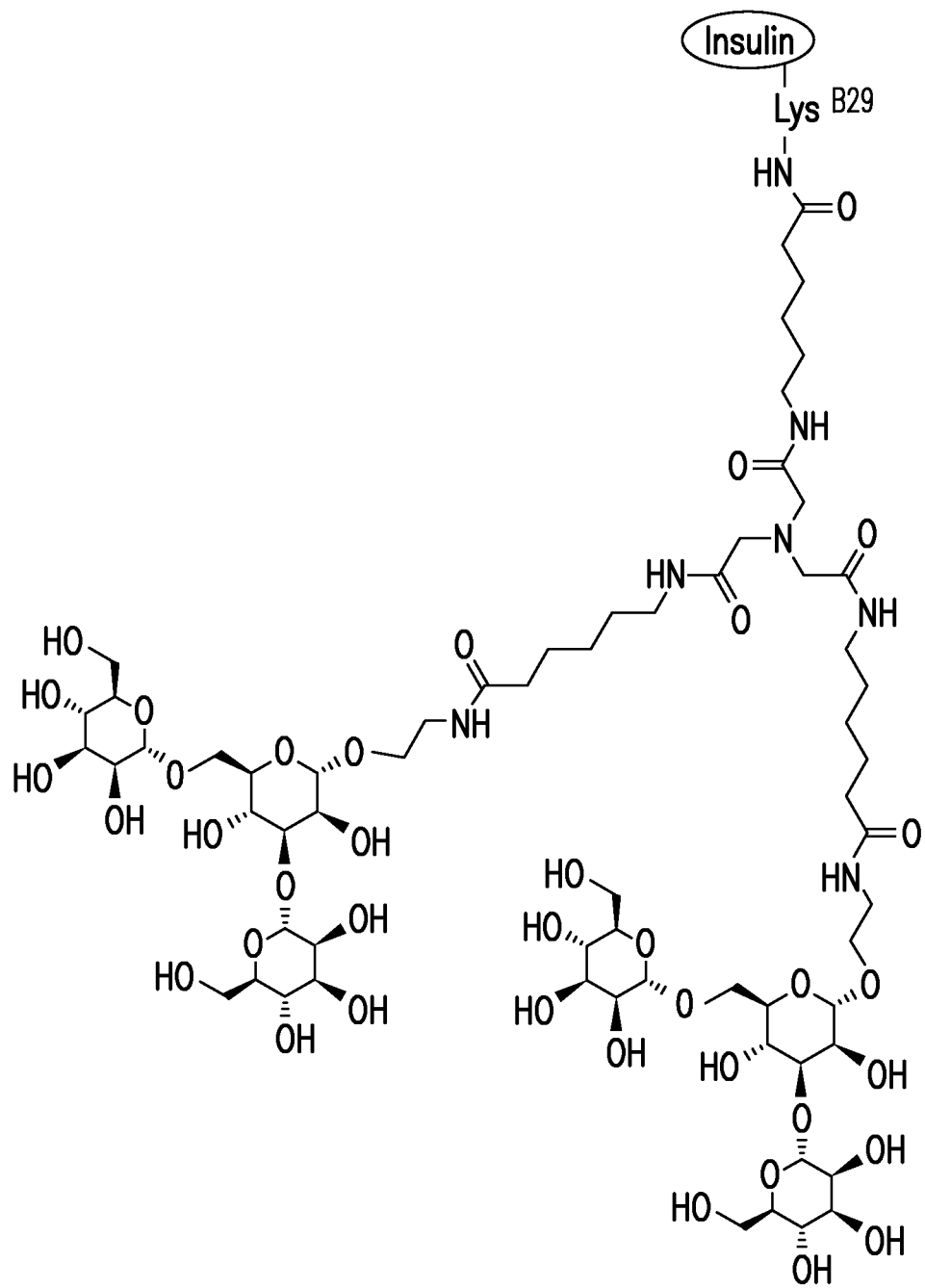
FIG. 3: Plot of serum insulin (left) and blood glucose (right) levels following subcutaneous injection in non-diabetic, male SD rats (n=3) at time 0 with TSAT-C6-AEBM-2 II-3 conjugate (5 U/kg).
Figures 1, 2, 3, 4:
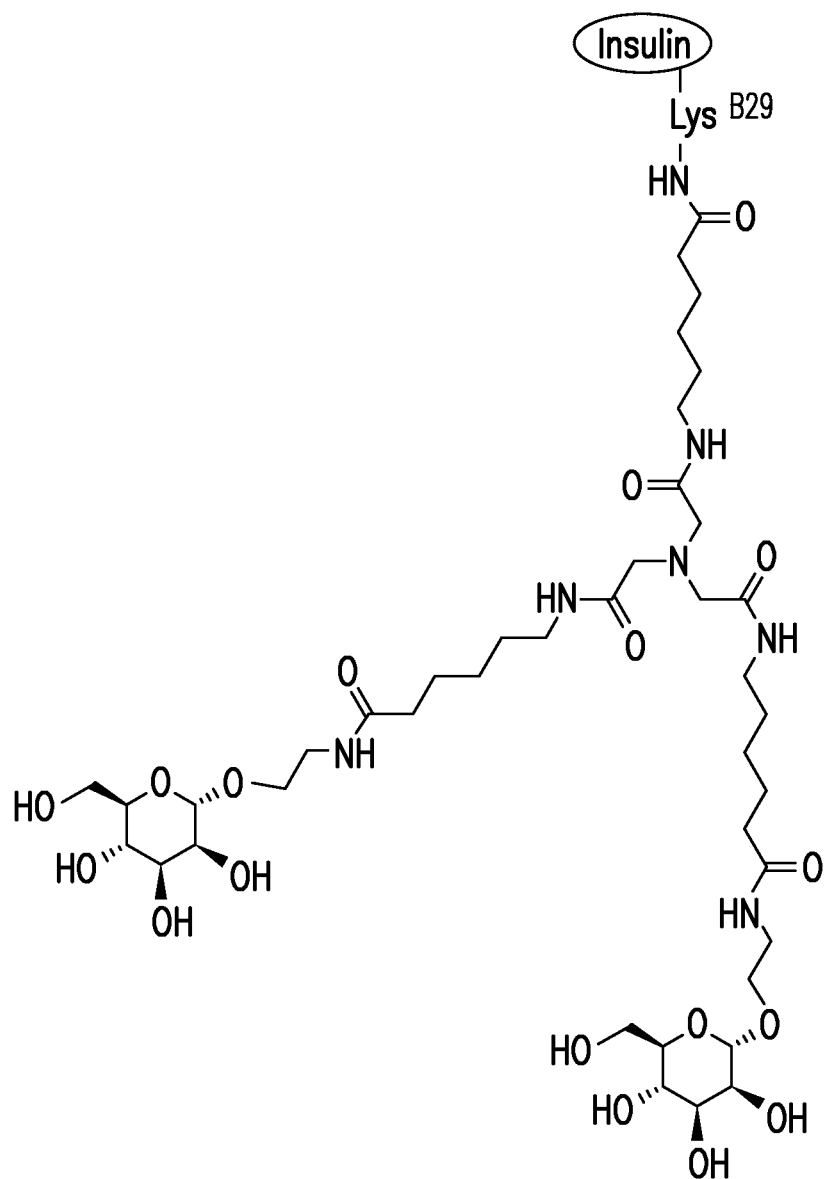
FIG. 4: Plot of serum insulin (left) and blood glucose (right) levels following subcutaneous injection in non-diabetic, male SD rats (n=3) at time 0 with TSAT-C6-AEBM-1 AETM-1 conjugate II-4 (5 U/kg).

The methods and intermediates of the present invention are useful for preparing conjugates described in International patent application number PCT/US10/22268, filed Jan. 27, 2010, the entirety of which is incorporated herein by reference. In certain embodiments, the present conjugates are generally prepared according to Scheme I set forth below:

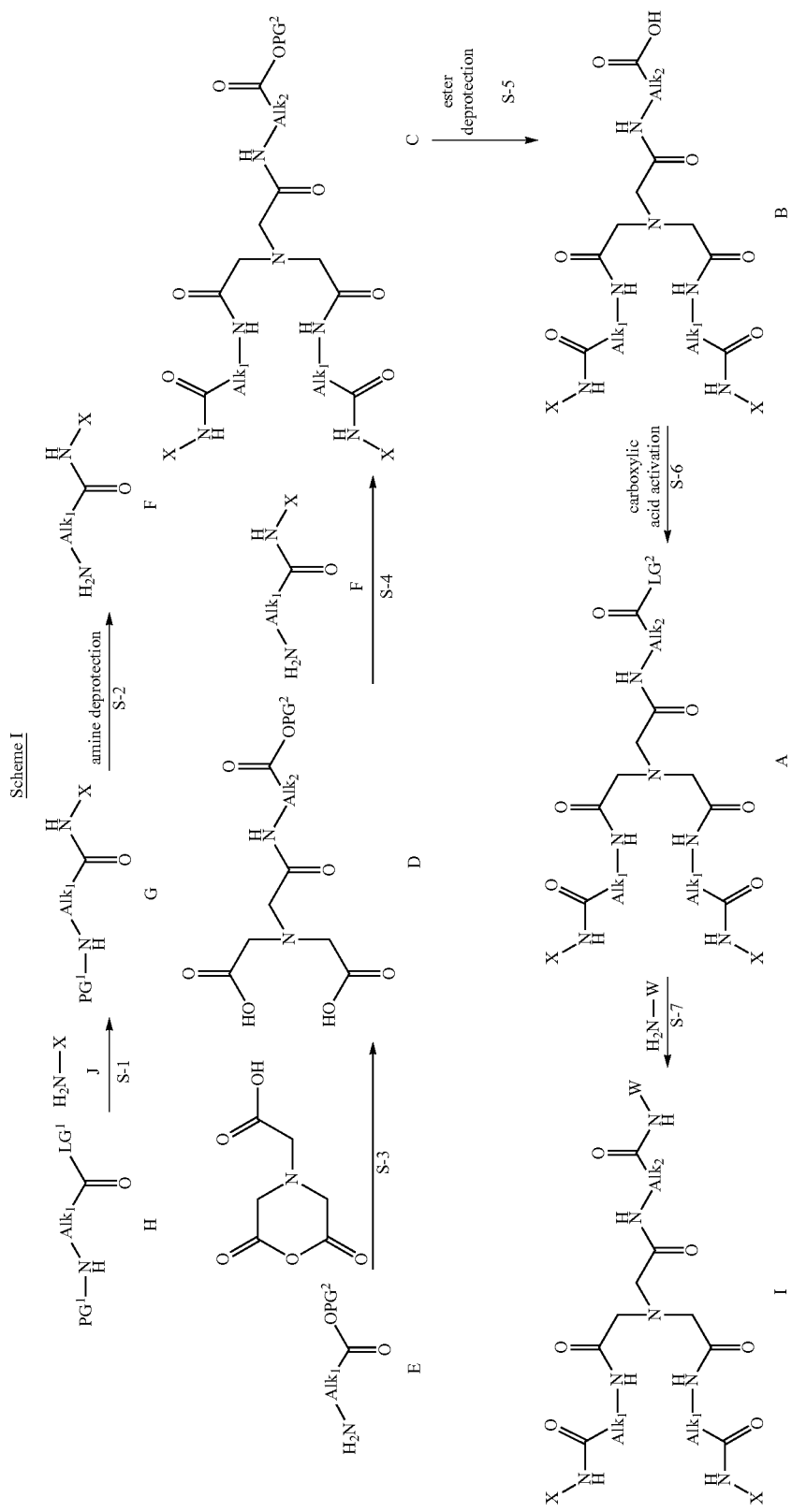

In Scheme I above, each of PG¹, PG², LG¹, LG², Alk₁, Alk₂, X, and W is as defined below and in classes and subclasses as described herein.

Amino Protecting Group (PG¹)

The PG¹ group of formulae H and G is a suitable amino protecting group. Protected amines are well known in the art and include those described in detail in *Protecting Groups in Organic Synthesis*, T. W. Greene and P. G. M. Wuts, 3$^{rd}$ edition, John Wiley & Sons, 1999. Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Notwithstanding the definitions above, the —NHPG¹ moiety of formulae H and G may be azido. In some embodiments, PG¹ is a carbamate protecting group. In certain embodiments, PG¹ is a t-butylcarbamate protecting group.

Leaving Group (LG¹)

The LG¹ group of formula H is a suitable leaving group, making —C(O)LG¹ of formula H an activated ester that is subject to nucleophilic attack. A suitable "leaving group" that is "subject to nucleophilic attack" is a chemical group that is readily displaced by a desired incoming nucleophilic chemical entity. Suitable leaving groups are well known in the art, e.g., see, Smith and March, March's Advanced Organic Chemistry, 5$^{th}$ Edition, John Wiley & Sons, Inc., New York, 2001. Such leaving groups include, but are not limited to, halogen, alkoxy, —O-succinimide (—OSu), —O-pentafluorophenyl, —O-benzotriazole (—OBt), or —O-azabenzotriazole (—OAt). An activated ester may also be an O-acylisourea intermediate generated by treatment of the corresponding carboxylic acid with a carbodiimide reagent (e.g., N,N'-dicyclohexylcarbodiimide (DCC), N,N'-diisopropylcarbodiimide (DIC), 1-ethyl-3-(3-dimethylaminopropyl)carbodiimide (EDC)). In certain embodiments, LG¹ is —OSu.

Carboxylic Acid Protecting Group (PG²)

The PG² group of formulae E, D and C is a suitable carboxylic acid protecting group. Protected acids are well known in the art and include those described in detail in Greene (1999). Examples of suitable carboxylic acid protecting groups include methyl (Me), ethyl (Et), t-butyl (t-Bu), allyl (All), benzyl (Bn), trityl (Trt), 2-chlorotrityl (2-Cl-Trt), 2,4-dimethoxybenzyl (Dmb), 2-phenylisopropyl (2-PhiPr), 9-fluorenylmethyl (Fm), 4-(N-[1-(4,4-dimethyl-2,6-dioxocyclohexylidene)-3-methylbutyl]amino)benzyl (Dmab), carbamoylmethyl (Cam), p-nitrobenzyl (pNB), 2-trimethylsilylethyl (TMSE), 2-phenyl-(2-trimethylsilyl)ethyl (PTMSE), 2-(trimethylsilyl)isopropyl (TMSI), 2,2,2-trichloroethyl (Tce), p-hydroxyphenacyl (pHP), 4,5-dimethoxy-2-nitrobenzyl (Dmnb), and 1,1-dimethylallyl (Dma). In certain embodiments, PG² is benzyl.

Leaving Group (LG²)

The LG² group of formula A is a suitable leaving group, making —C(O)LG² of formula A an activated ester that is subject to nucleophilic attack. A suitable "leaving group" that is "subject to nucleophilic attack" is a chemical group that is readily displaced by a desired incoming nucleophilic chemical entity. Suitable leaving groups are well known in the art, e.g., see, Smith and March (2001). Such leaving groups include, but are not limited to, halogen, alkoxy, —O-succinimide (—OSu), —O-pentafluorophenyl, —O-benzotriazole (—OBt), or —O-azabenzotriazole (—OAt). An activated ester may also be an O-acylisourea intermediate generated by treatment of the corresponding carboxylic acid with a carbodiimide reagent (e.g., N,N'-dicyclohexylcarbodiimide (DCC), N,N'-diisopropylcarbodiimide (DIC), 1-ethyl-3-(3-dimethylaminopropyl)carbodiimide (EDC)). In certain embodiments, LG² is —OSu.

$C_2$-$C_{12}$ Alkylene (Alk₁)

The Alk₁ group of formulae H, G, F, C, B, A, and I is a $C_2$-$C_{12}$ alkylene chain, wherein one or more methylene groups may be substituted by —O— or —S—. In some embodiments, Alk₁ contains one, two, or three oxygens. In certain embodiments, Alk₁ contains one oxygen. In certain embodiments, Alk₁ is a $C_4$-$C_8$ alkylene chain. In some embodiments, Alk₁ is a $C_2$, $C_3$, $C_4$, $C_5$, $C_6$, $C_7$, $C_8$, $C_9$, $C_{10}$, $C_{11}$, or $C_{12}$ alkylene chain. In certain embodiments, Alk₁ is a $C_6$ alkylene chain.

$C_2$-$C_{20}$ Alkylene (Alk₂)

The Alk₂ group of formulae H, G, F, C, B, A, and I is a $C_2$-$C_{20}$ alkylene chain, wherein one or more methylene groups may be substituted by —O— or —S—. In certain embodiments, Alk₂ contains one, two, or three oxygens. In certain embodiments, Alk₂ contains one oxygen. In some embodiments, Alk₂ is a $C_2$-$C_{12}$ alkylene chain. In some embodiments, Alk₂ is a $C_{12}$-$C_{20}$ alkylene chain. In certain embodiments, Alk₂ is a $C_4$-$C_8$ alkylene chain. In some embodiments, Alk₂ is a $C_2$, $C_3$, $C_4$, $C_5$, $C_6$, $C_7$, $C_8$, $C_9$, $C_{10}$, $C_{11}$, $C_{12}$, $C_{13}$, $C_{14}$, C15, $C_{16}$, $C_{17}$, C18, Cl₉, or $C_{20}$ alkylene chain. In certain embodiments, Alk₂ is a $C_6$ alkylene chain.

Ligand (X)

The X group of formulae J, G, F, C, B, A, and I is a ligand. A compound of formula J is an amino-terminal ligand. In certain embodiments, an X group of formulae J, G, F, C, B, A, and I is a ligand that includes a saccharide.

In certain embodiments, a ligand is capable of competing with a saccharide (e.g., glucose or mannose) for binding to an endogenous saccharide-binding molecule (e.g., without limitation surfactant proteins A and D or members of the selectin family). In certain embodiments, a ligand is capable of competing with a saccharide (e.g., glucose or mannose) for binding to cell-surface sugar receptor (e.g., without limitation macrophage mannose receptor, glucose transporter ligands, endothelial cell sugar receptors, or hepatocyte sugar receptors). In certain embodiments, a ligand is capable of competing with glucose for binding to an endogenous glucose-binding molecule (e.g., without limitation surfactant proteins A and D or members of the selectin family). In certain embodiments, a ligand is capable of competing with a saccharide for binding to a non-human lectin (e.g., Con A). In certain embodiments, a ligand is capable of competing with glucose or mannose for binding to a non-human lectin (e.g., Con A). Exemplary glucose-binding lectins include calnexin, calreticulin, N-acetylglucosamine receptor, selectin, asialoglycoprotein receptor, collectin (mannose-binding lectin), mannose receptor, aggrecan, versican, *pisum sativum* agglutinin (PSA), *vicia faba* lectin, *lens culinaris* lectin, soybean lectin, peanut lectin, *lathyrus ochrus* lectin, sainfoin lectin, sophora japonica lectin, bowringia milbraedii lectin, concanavalin A (Con A), and pokeweed mitogen.

In certain embodiments, a ligand is of formula (IIIa) or (IIIb):

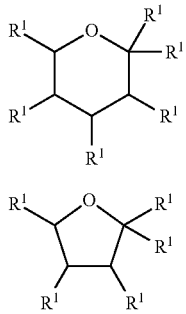

wherein:
each R is independently hydrogen, —OR$^y$, —N(R$^y$)$_2$, —SR$^y$, —O—Y, —CH$_2$R$^x$, or -G-, wherein one of R$^1$ is -G-;
each R$^x$ is independently hydrogen, —OR$^y$, —N(R$^y$)$_2$, —SR$^y$, or —O—Y;
each R$^y$ is independently —R$^2$, —SO$_2$R$^2$, —S(O)R$^2$, —P(O)(OR$^2$)$_2$, —C(O)R$^2$, —CO$_2$R$^2$, or —C(O)N(R$^2$)$_2$;
each Y is independently a monosaccharide, disaccharide, or trisaccharide;
each G is independently a covalent bond or an optionally substituted C$_{1-9}$alkylene, wherein one or more methylene units of G is optionally replaced by —O—, —S—, —N(R$^2$)—, —C(O)—, —OC(O)—, —C(O)O—, —C(O)N(R$^2$)—, —N(R$^2$)C(O), —N(R$^2$)C(O)N(R$^2$)—, —SO$_2$—, —SO$_2$N(R$^2$)—, —N(R$^2$)SO$_2$—, or —N(R$^2$)SO$_2$N(R$^2$)—;
each Z is independently halogen, —N(R$^2$)$_2$, —OR$^2$, —SR$^2$, —N$_3$, —C≡CR$^2$, —CO$_2$R$^2$, —C(O)R$^2$, or —OSO$_2$R$^2$; and
each R$^2$ is independently hydrogen or an optionally substituted group selected from C$_{1-6}$ aliphatic, phenyl, a 4-7 membered heterocyclic ring having 1-2 heteroatoms selected from nitrogen, oxygen, or sulfur, or a 5-6 membered monocyclic heteroaryl ring having 1-4 heteroatoms selected from nitrogen, oxygen, or sulfur.

In certain embodiments, a ligand of formula (IIIa) or (IIIb) is a monosaccharide. In certain embodiments, a ligand is a disaccharide. In certain embodiments, a ligand is a trisaccharide. In certain embodiments, a ligand is a tetrasaccharide. In certain embodiments, a ligand comprises no more than a total of four monosaccharide moieties.

As defined generally above, each R$^1$ is independently hydrogen, —OR$^y$, —N(R$^y$)$_2$, —SR$^y$, —O—Y, —CH$_2$R$^x$, or -G-, wherein one of R$^1$ is -G-. In certain embodiments, R$^1$ is hydrogen. In certain embodiments, R$^1$ is —OH. In other embodiments, R$^1$ is —NHC(O)CH$_3$. In certain embodiments, R$^1$ is —O—Y. In certain other embodiments, R$^1$ is -G-. In some embodiments, R$_1$ is —CH$_2$OH. In other embodiments, R$^1$ is —CH$_2$—O—Y. In yet other embodiments, R$^1$ is —NH$_2$. One of ordinary skill in the art will appreciate that each R$^1$ substituent in formula (IIIa) or (IIIb) may be of (R) or (S) stereochemistry.

As defined generally above, each R$^x$ is independently hydrogen, —OR$^y$, —N(R$^y$)$_2$, —SR$^y$, or —O—Y. In some embodiments, R$^1$ is hydrogen. In certain embodiments, R$^x$ is —OH. In other embodiments, R$^x$ is —O—Y.

As defined generally above, each R$^y$ is independently —R$^2$, —SO$_2$R$^2$, —S(O)R$^2$, —P(O)(OR$^2$)$_2$, —C(O)R$^2$, —CO$_2$R$^2$, or —C(O)N(R$^2$)$_2$. In some embodiments, R$^y$ is hydrogen. In other embodiments, R$^y$ is —R$^2$. In some embodiments, R$^y$ is —C(O)R$^2$. In certain embodiments, R$^y$ is acetyl. In other embodiments, R$^y$ is —SO$_2$R$^2$, —S(O)R$^2$, —P(O)(OR$^2$)$_2$, —CO$_2$R$^2$, or —C(O)N(R$^2$)$_2$.

As defined generally above, Y is a monosaccharide, disaccharide, or trisaccharide. In certain embodiments, Y is a monosaccharide. In some embodiments, Y is a disaccharide. In other embodiments, Y is a trisaccharide. In some embodiments, Y is mannose, glucose, fructose, galactose, rhamnose, or xylopyranose. In some embodiments, Y is sucrose, maltose, turanose, trehalose, cellobiose, or lactose. In certain embodiments, Y is mannose. In certain embodiments, Y is D-mannose. One of ordinary skill in the art will appreciate that the saccharide Y is attached to the oxygen group of —O—Y through anomeric carbon to form a glycosidic bond. The glycosidic bond may be of an alpha or beta configuration.

As defined generally above, each G is independently a covalent bond or an optionally substituted C$_{1-9}$ alkylene, wherein one or more methylene units of G is optionally replaced by —O—, —S—, —N(R$^2$)—, —C(O)—, —OC(O)—, —C(O)O—, —C(O)N(R$^2$)—, —N(R$^2$)C(O)—, —N(R$^2$)C(O)N(R$^2$)—, —SO$_2$—, —SO$_2$N(R$^2$)—, —N(R$^2$)SO$_2$—, or —N(R$^2$)SO$_2$N(R$^2$)—. In some embodiments, G is a covalent bond. In certain embodiments, G is —O—C$_{1-8}$ alkylene. In certain embodiments, G is —OCH$_2$CH$_2$CH—.

In some embodiments, the R$^1$ substituent on the C1 carbon of formula (IIIa) is -G- to give a compound of formula (IIIa-i):

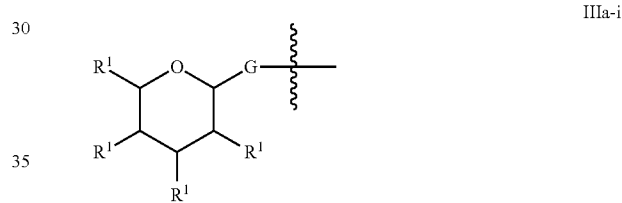

wherein R$^1$ and G are as defined and described herein.

In some embodiments, a ligand is of formula (IIIa-ii):

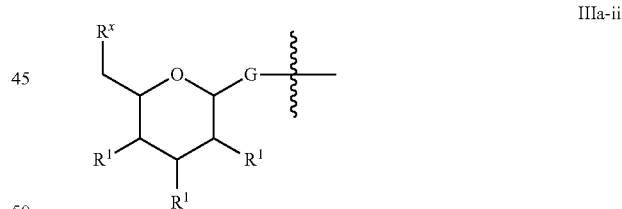

wherein R$^1$, R$^x$, and G are as defined and described herein.

In certain embodiments, a ligand may have the same chemical structure as glucose or may be a chemically related species of glucose. In various embodiments it may be advantageous for a ligand to have a different chemical structure from glucose, e.g., in order to fine tune the glucose response of the conjugate. For example, in certain embodiments, one might use a ligand that includes glucose, mannose, L-fucose or derivatives of these (e.g., alpha-L-fucopyranoside, mannosamine, beta-linked N-acetyl mannosamine, methylglucose, methylmannose, ethylglucose, ethylmannose, propylglucose, propylmannose, etc.) and/or higher order combinations of these (e.g., a bimannose, linear and/or branched trimannose, etc.).

In certain embodiments, a ligand includes a monosaccharide. In certain embodiments, a ligand includes a disaccharide. In certain embodiments, a ligand includes a trisaccharide. In some embodiments, a ligand precursor H$_2$N—X (J) comprises a saccharide and one or more amine groups. In certain embodiments the saccharide and amine group are separated by a C$_1$-C$_6$ alkyl group, e.g., a C$_1$-C$_3$ alkyl group. In some embodiments, J is aminoethylglucose (AEG). In some embodiments, J is aminoethylmannose (AEM). In some embodiments, J is aminoethylbimannose (AEBM). In some embodiments, J is aminoethyltrimannose (AETM). In some embodiments, J is β-aminoethyl-N-acetylglucosamine (AEGA). In some embodiments, J is aminoethylfucose (AEF). In certain embodiments, a saccharide ligand is of the "D" configuration. In other embodiments, a saccharide ligand is of the "L" configuration. Below we show the structures of exemplary J compounds. Other exemplary ligands will be recognized by those skilled in the art.

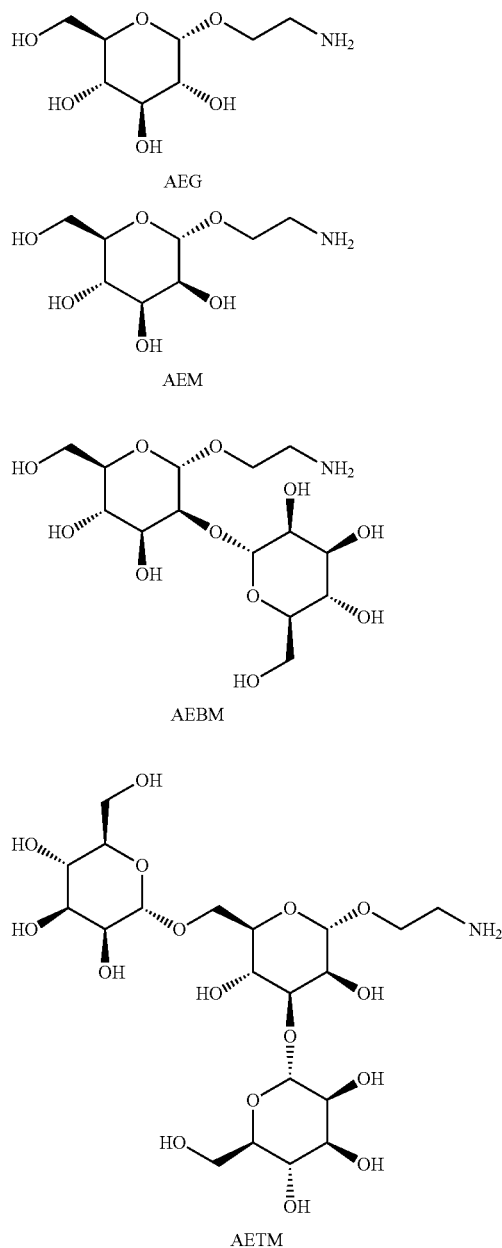

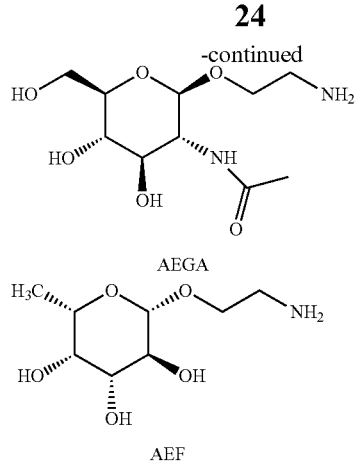

It will be understood by one of ordinary skill in the art that the J compounds shown above react in step S-1 to form an amide bond. Thus, the ligand (X) portions of the compounds shown above are as follows:

Drug (W)

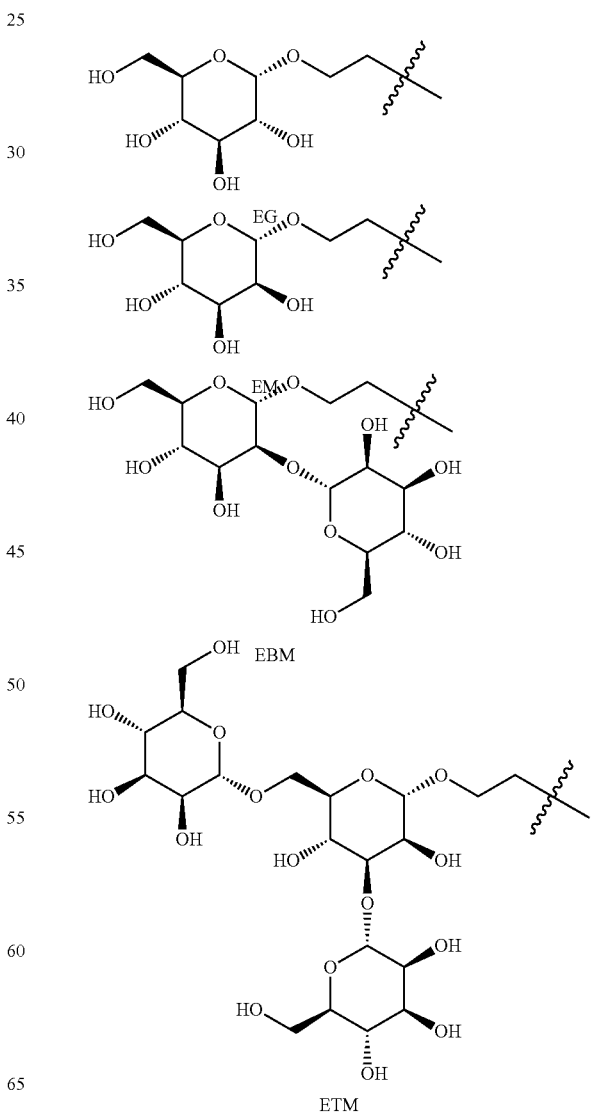

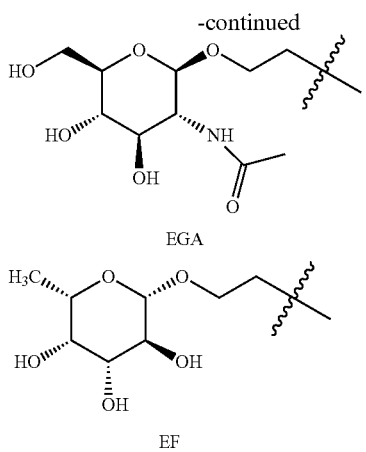

EGA

EF

W—NH$_2$ is an amine-containing drug. It is to be understood that a conjugate can comprise any drug. A conjugate is not limited to any particular drug and may include a small molecule drug or biomolecular drug. In general, a drug used will depend on the disease or disorder to be treated. As used herein, the term "drug" encompasses salt and non-salt forms of the drug. For example, the term "insulin molecule" encompasses all salt and non-salt forms of the insulin molecule. It will be appreciated that the salt form may be anionic or cationic depending on the drug.

For example, without limitation, in various embodiments W is selected from any one of the following drugs: diclofenac, nifedipine, rivastigmine, methylphenidate, fluoroxetine, rosiglitazone, prednison, prednisolone, codeine, ethylmorphine, dextromethorphan, noscapine, pentoxiverine, acetylcysteine, bromhexine, epinephrine, isoprenaline, orciprenaline, ephedrine, fenoterol, rimiterol, ipratropium, cholinetheophyllinate, proxiphylline, bechlomethasone, budesonide, deslanoside, digoxine, digitoxin, disopyramide, proscillaridin, chinidine, procainamide, mexiletin, flecamide, alprenolol, propranolol, nadlol, pindolol, oxprenolol, labetalol, tirnolol, atenolol, pentaeritrityltetranitrate, isosorbiddinitrate, isosorbidmononitrate, niphedipin, phenylamine, verapamil, diltiazem, cyclandelar, nicotinylalcholhol, inositolnicotinate, alprostatdil, etilephrine, prenalterol, dobutamine, dopamine, dihydroergotamine, guanetidine, betanidine, methyldopa, reserpine, guanfacine, trimethaphan, hydralazine, dihydralazine, prazosine, diazoxid, captopril, nifedipine, enalapril, nitroprusside, bendroflumethiazide, hydrochlorthiazide, metychlothiazide, polythiazide, chlorthalidon, cinetazon, clopamide, mefruside, metholazone, bumetanide, ethacrynacide, spironolactone, amiloride, chlofibrate, nicotinic acid, nicheritrol, brompheniramine, cinnarizine, dexchlorpheniramine, clemastine, antazoline, cyproheptadine, proethazine, cimetidine, ranitidine, sucralfat, papaverine, moxaverine, atropin, butylscopolamin, emepron, glucopyrron, hyoscyamine, mepensolar, methylscopolamine, oxiphencyclimine, probanteline, terodilin, sennaglycosides, sagradaextract, dantron, bisachodyl, sodiumpicosulfat, etulos, diphenolxylate, loperamide, salazosulfapyridine, pyrvin, mebendazol, dimeticon, ferrofumarate, ferrosuccinate, ferritetrasemisodium, cyanochobalamine, folid acid heparin, heparin co-factor, diculmarole, warfarin, streptokinase, urokinase, factor VIII, factor IX, vitamin K, thiopeta, busulfan, chlorambucil, cyclophosphamid, melfalan, carmustin, mercatopurin, thioguanin, azathioprin, cytarabin, vinblastin, vinchristin, vindesin, procarbazine, dacarbazine, lomustin, estramustin, teniposide, etoposide, cisplatin, amsachrin, aminogluthetimid, phosphestrol, medroxiprogesterone, hydroxiprogesterone, megesterol, noretisteron, tamoxiphen, ciclosporin, sulfosomidine, bensylpenicillin, phenoxymethylpenicillin, dicloxacillin, cloxacillin, flucoxacillin, ampicillin, amoxicillin, pivampicillin, bacampicillin, piperacillin, meziocillin, mecillinam, pivmecillinam, cephalotin, cephalexin, cephradin, cephydroxil, cephaclor, cefuroxim, cefotaxim, ceftazidim, cefoxitin, aztreonam, imipenem, cilastatin, tetracycline, lymecycline, demeclocycline, metacycline, oxitetracycline, doxycycline, chloramphenicol, spiramycin, fusidic acid, lincomycin, clindamycin, spectinomycin, rifampicin, amphotericin B, griseofulvin, nystatin, vancomycin, metronidazole, timidazole, trimethoprim, norfloxacin, salazosulfapyridin, aminosalyl, isoniazid, etambutol, nitrofurantoin, nalidixic acid, metanamine, chloroquin, hydroxichloroquin, timidazol, ketokonazol, acyclovir, interferon idoxuridin, retinal, tiamin, dexpantenol, pyridoxin, folic acid, ascorbic acid, tokoferol, phytominadion, phenfluramin, corticotropin, tetracosactid, tyrotropin, somatotoprin, somatrem, vasopressin, lypressin, desmopressin, oxytocin, chloriongonadotropin, cortison, hydrocortisone, fluodrocortison, prednison, prednisolon, fluoximesteron, mesterolon, nandrolon, stanozolol, oximetolon, cyproteron, levotyroxin, liotyronin, propylthiouracil, carbimazol, tiamazol, dihydrotachysterol, alfacalcidol, calcitirol, insulin, tolbutamid, chlorpropamid, tolazamid, glipizid, glibenclamid, phenobarbital, methyprylon, pyrityidion, meprobamat, chlordiazepoxid, diazepam, nitrazepam, baclofen, oxazepam, dikaliumclorazepat, lorazepam, flunitrazepam, alprazolam, midazolam, hydroxizin, dantrolene, chlomethiazol, propionmazine, alimemazine, chlorpromazine, levomepromazine, acetophenazine, fluphenazine, perphenazine, prochlorperazine, trifluoperazine, dixyrazine, thiodirazine, periciazin, chloprothixene, tizanidine, zaleplon, zuclopentizol, flupentizol, thithixen, haloperidol, trimipramin, opipramol, chlomipramin, desipramin, lofepramin, amitriptylin, nortriptylin, protriptylin, maptrotilin, caffeine, cinnarizine, cyclizine, dimenhydinate, meclozine, prometazine, thiethylperazine, metoclopramide, scopolamine, phenobarbital, phenyloine, ethosuximide, primidone, carbamazepine, chlonazepam, orphenadrine, atropine, bensatropine, biperiden, metixene, procylidine, levodopa, bromocriptin, amantadine, ambenon, pyridostigmine, synstigmine, disulfuram, morphine, codeine, pentazocine, buprenorphine, pethidine, phenoperidine, phentanyl, methadone, piritramide, dextropropoxyphene, ketobemidone, acetylsalicylic acid, celecoxib, phenazone, phenylbutazone, azapropazone, piroxicam, ergotamine, dihydroergotamine, cyproheptadine, pizitifen, flumedroxon, allopurinol, probenecid, sodiummaurothiomalate auronofin, penicillamine, estradiol, estradiolvalerianate, estriol, ethinylestradiol, dihydrogesteron, lynestrenol, medroxiprogresterone, noretisterone, cyclophenile, clomiphene, levonorgestrel, mestranol, omidazol, timidazol, ekonazol, chlotrimazol, natamycine, miconazole, sulbentin, methylergotamine, dinoprost, dinoproston, gemeprost, bromocriptine, phenylpropanolamine, sodiumchromoglicate, azetasolamide, dichlophenamide, betacarotene, naloxone, calciumfolinate, in particular clonidine, thephylline, dipyradamol, hydrochlothiazade, scopolamine, indomethacine, furosemide, potassium chloride, morphine, ibuprofen, salbutamol, terbutalin, calcitonin, etc. It is to be understood that this list is intended to be exemplary and that any drug, whether known or later discovered, may be used in a conjugate of the present disclosure.

In various embodiments, W is a hormonal drug which may be peptidic or non-peptidic, e.g., adrenaline, noradrenaline, angiotensin, atriopeptin, aldosterone, dehydroepiandrosterone, androstenedione, testosterone, dihydrotestosterone, calcitonin, calcitriol, calcidiol, corticotropin, cortisol, dopamine, estradiol, estrone, estriol, erythropoietin, follicle-stimulating hormone, gastrin, ghrelin, glucagon, gonadotropin-releasing hormone, growth hormone, growth hormone-releasing hormone, human chorionic gonadotropin, histamine, human placental lactogen, insulin, insulin-like growth factor, inhibin, leptin, a leukotriene, lipotropin, melatonin, orexin, oxytocin, parathyroid hormone, progesterone, prolactin, prolactin-releasing hormone, a prostglandin, renin, serotonin, secretin, somatostatin, thrombopoietin, thyroid-stimulating hormone, thyrotropin-releasing hormone (or thyrotropin), thyrotropin-releasing hormone, thyroxine, triiodothyronine, vasopressin, etc.

In certain embodiments, the hormone may be selected from glucagon, insulin, insulin-like growth factor, leptin, thyroid-stimulating hormone, thyrotropin-releasing hormone (or thyrotropin), thyrotropin-releasing hormone, thyroxine, and triiodothyronine.

In certain embodiments, W is insulin-like growth factor 1 (IGF-1). It is to be understood that this list is intended to be exemplary and that any hormonal drug, whether known or later discovered, may be used in a conjugate of the present disclosure.

In various embodiments, W is a thyroid hormone.

In various embodiments, W is an anti-diabetic drug (i.e., a drug which has a beneficial effect on patients suffering from diabetes).

It will be appreciated that in order to carry out step S-7, a drug must contain an amino group. Thus, in certain embodiments, a drug of the present disclosure contains one or more amino groups (e.g., an insulin molecule). In other embodiments, a drug is modified to form a derivative that contains an amino group.

In various embodiments, W is an insulin molecule. As used herein, the term "insulin" or "insulin molecule" encompasses all salt and non-salt forms of the insulin molecule. It will be appreciated that the salt form may be anionic or cationic depending on the insulin molecule. By "insulin" or "an insulin molecule" we intend to encompass both wild-type and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.).

The wild-type sequence of human insulin comprises an amino acid sequence of SEQ ID NO:27 (A-peptide) and an amino acid sequence of SEQ ID NO:28 (B-peptide) and three disulfide bridges as shown below:

As is well known in the art, the β-cells of the pancreatic islets in humans secrete a single chain precursor of insulin, known as proinsulin. In humans, proinsulin has the sequence: [B-peptide]-[C-peptide]-[A-peptide], wherein the C-peptide is a connecting peptide with the sequence of SEQ ID NO:29: Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-Arg.

In humans, prior to secretion of the bioactive insulin molecule by the β-cells of the pancreatic islets, the C-peptide is removed from proinsulin by cleavage at the two dibasic sites, Arg-Arg and Lys-Arg. As shown above, the cleavage releases the bioactive insulin molecule as separate A- and B-peptides that are connected by two disulfide bonds with one disulfide bond within the A-peptide.

Not all organisms recognize and correctly process the human proinsulin sequence. For example, in certain embodiments, yeast may utilize an alternative proinsulin sequence: [Leader peptide]-[B-peptide]-[C-peptide]-[A-peptide].

In the yeast proinsulin sequence, the leader peptide is thought to facilitate appropriate cleavage of the insulin molecule in yeast and may, for example, comprise the sequence: Glu-Glu-Ala-Glu-Ala-Glu-Ala-Glu-Pro-Lys (SEQ ID NO:30) or Asp-Asp-Gly-Asp-Pro-Arg (SEQ ID NO:22). In some embodiments, the leader peptide has a sequence of Xaa'-Pro-[Lys/Arg], where Xaa':

a. is at least 4, at least 5, at least 6, at least 7, at least 8, at least 9, at least 10, at least 11, at least 12, at least 13, at least 14, at least 15, at least 20, or at least 25 amino acids in length, or b. is no more than 5, no more than 10, no more than 15, no more than 20, no more than 25, no more than 50 amino acids in length; and c. comprises at least about 30%, at least about 40%, at least about 50%, at least about 55%, at least about 60%, at least about 65%, at least about 70%, at least about 75%, at least about 80%, at least about 5%, at least about 90%, or at least about 95% of acidic amino acids (e.g., Asp and/or Glu).

In some embodiments, the leader peptide contains the amino acids Pro-Lys at its C-terminus. In some embodiments, the leader peptide contains the amino acids Pro-Arg at its C-terminus.

Additionally, instead of the long C-peptide connecting segment found in human proinsulin, engineered yeast proinsulin sequences may have a much shorter C-peptide sequence, e.g., Ala-Ala-Lys (SEQ ID NO: 16), Asp-Glu-Arg (SEQ ID NO: 17), or Thr-Ala-Ala-Lys (SEQ ID NO:31). In some embodiments, the C-peptide has a sequence of Xaa"-[Lys/Arg], where Xaa":

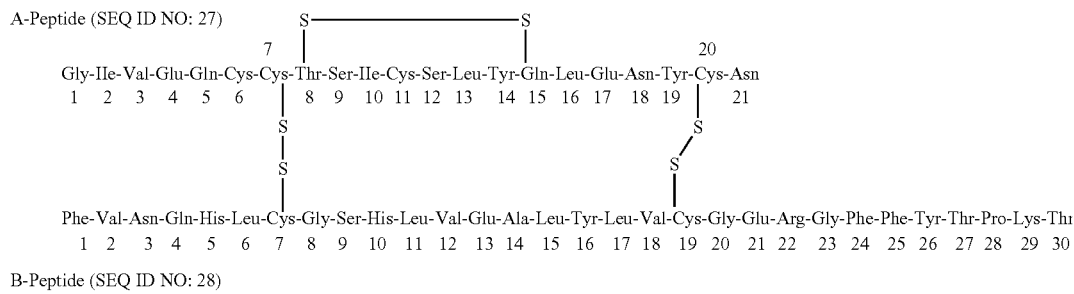

a. is missing, or is at least 1, at least 2, at least 3, at least 4, at least 5, at least 6, at least 7, at least 8, at least 9, at least 10, at least 15, or at least 20 amino acids in length;

b. is no more than 2, no more than 3, no more than 4, no more than 5, no more than 6, no more than 7, no more than 8, no more than 9, no more than 10, no more than 15, no more than 20, or no more than 25 amino acids in length; or c. is exactly 1, 2, 3, 4, 5, 6, 7, 8, 9, 10, 11, 12, 13, 14, 15, 16, 17, 18, 19, 20, 21, 22, 23, 24, or 25 amino acids in length.

In some embodiments, the C-peptide has an amino acid sequence different from that found in human proinsulin. In general, the C-peptide refers to any amino acid sequence in proinsulin that is found between the insulin A-chain and B-chain. In some embodiments, the C-peptide refers to any amino acid sequence in proinsulin that is found between the insulin A-chain and B-chain and that is enzymatically cleaved to produce a bioactive insulin molecule.

Without wishing to be limited to any particular theory, it is thought that the combination of these leader sequences and C-peptide sequences allows for the production of functional insulin from yeast.

The present disclosure is not limited to human insulin molecules (i.e., human proinsulin or bioactive human insulin molecules). In general, the present disclosure encompasses any human or non-human insulin that retains insulin-like bioactivity (i.e., is capable of causing a detectable reduction in glucose when administered to a suitable species at an appropriate dose in vivo). For example, as discussed below, the present disclosure also encompasses modified porcine insulin, bovine insulin, rabbit insulin, sheep insulin, etc.

It is to be understood that an insulin molecule of the present disclosure may include chemical modifications and/or mutations that are not present in a wild-type insulin. A variety of modified insulins are known in the art (e.g., see Crotty and Reynolds, *Pediatr. Emerg. Care.* 23:903-905, 2007 and Gerich, *Am. J. Med.* 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of amino acids).

In certain embodiments, an insulin molecule of the present disclosure will differ from a wild-type insulin by 1-10 (e.g., 1-9, 1-8, 1-7, 1-6, 1-5, 1-4, 1-3, 1-2, 2-9, 2-8, 2-7, 2-6, 2-5, 2-4, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2 or 1) amino acid substitutions, additions and/or deletions. In certain embodiments, an insulin molecule of the present disclosure will differ from a wild-type insulin by amino acid substitutions only. In certain embodiments, an insulin molecule of the present disclosure will differ from a wild-type insulin by amino acid additions only. In certain embodiments, an insulin molecule of the present disclosure will differ from a wild-type insulin by both amino acid substitutions and additions. In certain embodiments, an insulin molecule of the present disclosure will differ from a wild-type insulin by both amino acid substitutions and deletions.

In certain embodiments, amino acid substitutions may be made on the basis of similarity in polarity, charge, solubility, hydrophobicity, hydrophilicity, and/or the amphipathic nature of the residues involved. In certain embodiments, a substitution may be conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine. In certain embodiments, the hydrophobic index of amino acids may be considered in choosing suitable mutations. The importance of the hydrophobic amino acid index in conferring interactive biological function on a polypeptide is generally understood in the art. Alternatively, the substitution of like amino acids can be made effectively on the basis of hydrophilicity. The importance of hydrophilicity in conferring interactive biological function of a polypeptide is generally understood in the art. The use of the hydrophobic index or hydrophilicity in designing polypeptides is further discussed in U.S. Pat. No. 5,691,198.

In certain embodiments, an insulin molecule of the present disclosure comprises an amino acid sequence of SEQ ID NO: 1 (A-peptide) and an amino acid sequence of SEQ ID NO:2 (B-peptide) and three disulfide bridges as shown in formula $X^I$:

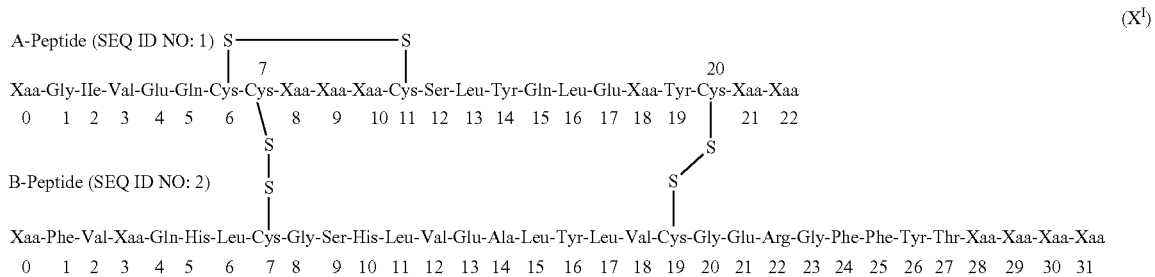

$(X^I)$ where Xaa at each of positions A0, A22, B0 and B31 is independently a codable amino acid, a sequence of codable amino acids, or missing; Xaa at each of positions A8, A9, A10, A18, and A21 is independently a codable amino acid; and Xaa at each of positions B3, B28, B29, and B30 is independently a codable amino acid or missing.

As used herein, a "codable amino acid" is any one of the 20 amino acids that are directly encoded for polypeptide synthesis by the standard genetic code.

In some embodiments, Xaa at each of positions A0, A22, B0 and B31 is independently a codable amino acid, a sequence of 2-50 codable amino acids, or missing.

In some embodiments, Xaa at each of positions A0, A22, B0 and B31 is independently a codable amino acid, a sequence of 2-25 codable amino acids, or missing.

In some embodiments, Xaa at each of positions A0, A22, B130 and B31 is independently a codable amino acid, a sequence of 2-10 codable amino acids, or missing.

In some embodiments, Xaa at each of positions A0, A22, B0 and B31 is independently a codable amino acid, a sequence of 2-9 codable amino acids, or missing.

In some embodiments, Xaa at each of positions A0, A22, B0 and B31 is independently a codable amino acid, a sequence of 2-8 codable amino acids, or missing.

In some embodiments, Xaa at each of positions A0, A22, B0 and B31 is independently a codable amino acid, a sequence of 2-7 codable amino acids, or missing.

In some embodiments, Xaa at each of positions A0, A22, B0 and B31 is independently a codable amino acid, a sequence of 2-6 codable amino acids, or missing.

In some embodiments, Xaa at each of positions A0, A22, B0 and B31 is independently a codable amino acid, a sequence of 2-5 codable amino acids, or missing.

In some embodiments, Xaa at each of positions A0, A22, B0 and B31 is independently a codable amino acid, a sequence of 2-4 codable amino acids, or missing.

In some embodiments, Xaa at each of positions A0, A22, B0 and B31 is independently a codable amino acid, a sequence of 2-3 codable amino acids, or missing.

In some embodiments, Xaa at each of positions A0, A22, B30 and B31 is independently a codable amino acid, a sequence of 2 codable amino acids, or missing.

In some embodiments, Xaa at each of positions A0, A22, B0 and B31 is missing.

In some embodiments, Xaa at each of positions A0, A22 and B31 is missing.

In some embodiments, Xaa at each of positions A22, B0 and B31 is missing.

In some embodiments, Xaa at each of positions A22 and B31 is missing.

In certain embodiments, Xaa at one or more of the positions of the A- and B-peptides in formula $X^I$ is selected from the choices that are set forth in Table 1 and 2 below.

TABLE 1

A-peptide

| Position | Amino Acid Identity |
|---|---|
| A0 | Any codable amino acid, sequence of codable amino acids, or missing |
| A8 | Thr or Ala |
| A9 | Ser or Gly |
| A10 | Ile or Val |
| A18 | Asn, Asp or Glu |
| A21 | Asn, Asp, Glu, Gly or Ala |
| A22 | Any codable amino acid, sequence of codable amino acids, or missing |

TABLE 2

B-peptide

| Position | Amino Acid Identity |
|---|---|
| B0 | Any codable amino acid, sequence of codable amino acids, or missing |
| B3 | Asn, Lys, Asp or Glu, or missing |
| B28 | Pro, Ala, Lys, Leu, Val, or Asp, or missing |
| B29 | Lys, Pro, or Glu, or missing |
| B30 | Thr, Ala, Lys, Glu, Ser or Arg, or missing |
| B31 | Any codable amino acid, sequence of codable amino acids, Arg-Arg, or missing |

In some embodiments, an insulin molecule of formula $X^I$ comprises amino acids at positions A8, A9, A10, and B30 selected from those shown in Table 3 below. In some embodiments, an insulin molecule of formula $X^I$ comprises amino acids at positions A8, A9, A10, and B30 selected from those shown in Table 3 below for a single species (e.g., from the human sequence or Thr at A8, Ser at A9, Ile at A10 and Thr at B30).

TABLE 3

| | Amino Acid Position | | | |
|---|---|---|---|---|
| Species | A8 | A9 | A10 | B30 |
| Human | Thr | Ser | Ile | Thr |
| Rabbit | Thr | Ser | Ile | Ser |
| Porcine | Thr | Ser | Ile | Ala |
| Bovine | Ala | Ser | Val | Ala |
| Sheep | Ala | Gly | Val | Ala |

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin aspart (NOVOLOG®) is another rapid acting insulin mutant in which proline at position B28 has been substituted with aspartic acid ($Asp^{B28}$-human insulin). This mutant also prevents the formation of multimers. In some embodiments, mutation at positions B28 and/or B29 is accompanied by one or more mutations elsewhere in the insulin molecule. For example, insulin glulisine (APIDRA®) is yet another rapid acting insulin mutant in which aspartic acid at position B3 has been replaced by a lysine residue and lysine at position B29 has been replaced with a glutamic acid residue ($Lys^{B3}Glu^{B29}$-human insulin).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin molecules include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS®) is an exemplary long acting insulin mutant in which $Asp^{A21}$ has been replaced by glycine, and two arginine residues have been added to the C-terminus of the B-peptide. The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 is Arg-Arg. It is to be understood that the present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In various embodiments, an insulin molecule of the present disclosure may include one or more deletions. For example, in certain embodiments, a B-peptide sequence of an insulin molecule of the present disclosure is missing B1, B2, B3, B26, B27, B28 and/or B29.

In various embodiments, an insulin molecule of the present disclosure may be truncated. For example, the B-peptide sequence may be missing residues B(1-2), B(1-3), B30, B(29-30) or B(28-30). In some embodiments, these deletions and/ or truncations apply to any of the aforementioned insulin molecules (e.g., without limitation to produce des(B30) insulin lispro, des(B30) insulin aspart, des(B30) insulin glulisine, des(B30) insulin glargine, etc.).

In some embodiments, an insulin molecule contains additional amino acid residues on the N- or C-terminus of the A or B-peptide sequences. In some embodiments, one or more amino acid residues are located at positions A0, A22, B0, and/or B31. In some embodiments, one or more amino acid residues are located at position A0. In some embodiments, one or more amino acid residues are located at position A22. In some embodiments, one or more amino acid residues are located at position B0. In some embodiments, one or more amino acid residues are located at position B31. In certain embodiments, an insulin molecule does not include any additional amino acid residues at positions A0, A22, B0, or B31.

In certain embodiments, an insulin molecule of the present disclosure may have mutations wherein one or more amidated amino acids are replaced with acidic forms. For example, asparagine may be replaced with aspartic acid or glutamic acid. Likewise, glutamine may be replaced with aspartic acid or glutamic acid. In particular, $Asn^{A18}$, $Asn^{A21}$, or $Asn^{B3}$, or any combination of those residues, may be replaced by aspartic acid or glutamic acid. $Gln^{A15}$ or $Gln^{B4}$, or both, may be replaced by aspartic acid or glutamic acid. In certain embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid ($His^{B10} \rightarrow Asp^{B10}$); replacement of the phenylalanine residue at position B1 with aspartic acid ($Phe^{B1} \rightarrow Asp^{B1}$); replacement of the threonine residue at position B30 with alanine ($Thr^{B30} \rightarrow Ala^{B30}$); replacement of the tyrosine residue at position B26 with alanine ($Tyr^{B26} \rightarrow Ala^{B26}$); and replacement of the serine residue at position B9 with aspartic acid ($Ser^{B9} \rightarrow Asp^{B9}$).

In various embodiments, an insulin molecule of the present disclosure has a protracted profile of action. Thus, in certain embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type insulin or may be acylated on lysine residue that has been introduced into the wild-type sequence. In certain embodiments, an insulin molecule may be acylated at position B1. In certain embodiments, an insulin molecule may be acylated at position B29. In certain embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which $Thr^{B30}$ has been deleted, and a C14 fatty acid chain (myristic acid) has been attached to $Lys^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

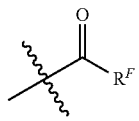

wherein $R^F$ is hydrogen or a $C_{1-30}$ alkyl group. In some embodiments, $R^F$ is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group. In certain embodiments, the insulin molecule is conjugated to the moiety at the A1 position. In certain embodiments, the insulin molecule is conjugated to the moiety at the B1 position. In certain embodiments, the insulin molecule is conjugated to the moiety at the epsilon-amino group of Lys at position B29. In certain embodiments, position B28 of the insulin molecule is Lys and the epsilon-amino group of $Lys^{B28}$ is conjugated to the fatty acid moiety. In certain embodiments, position B3 of the insulin molecule is Lys and the epsilon-amino group of $Lys^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20).

In certain embodiments, an insulin molecule of the present disclosure comprises the mutations and/or chemical modifications of one of the following insulin molecules: $Lys^{B28}Pro^{B29}$-human insulin (insulin lispro), $Asp^{B28}$-human insulin (insulin aspart), $Lys^{B3}Glu^{B29}$-human insulin (insulin glulisine), $Arg^{B31}Arg^{B32}$-human insulin (insulin glargine), $N^{\epsilon B29}$-myristoyl-des(B30)-human insulin (insulin detemir), $Ala^{B26}$-human insulin, $Asp^{B1}$-human insulin, $Arg^{A0}$-human insulin, $Asp^{B1}Glu^{B13}$-human insulin, $Gly^{A21}$-human insulin, $Gly^{A21}Arg^{B31}Arg^{B32}$-human insulin, $Arg^{A0}Arg^{B31}Arg^{B32}$-human insulin, $Arg^{A0}Gly^{A21}Arg^{B31}Arg^{B32}$-human insulin, des(B30)-human insulin, des(B27)-human insulin, des(B28-B30)-human insulin, des(B1)-human insulin, des(B1-B3)-human insulin.

In certain embodiments, an insulin molecule of the present disclosure comprises the mutations and/or chemical modifications of one of the following insulin molecules: $N^{\epsilon B29}$-palmitoyl-human insulin, $N^{\epsilon B29}$-myrisotyl-human insulin, $N^{\epsilon B28}$-palmitoyl-$Ly^{\epsilon B28}Pro^{B29}$-human insulin, $N_{\epsilon B28}$-myristoyl-$Lys^{B28}Pro^{B29}$-human insulin.

In certain embodiments, an insulin molecule of the present disclosure comprises the mutations and/or chemical modifications of one of the following insulin molecules: $N^{\epsilon B29}$-palmitoyl-des(B30)-human insulin, $N^{\epsilon B30}$-myristoyl-$Thr^{B29}Lys^{B30}$-human insulin, $N^{\epsilon B30}$-palmitoyl-$Thr^{B29}Lys^{B30}$-human insulin, $N^{\epsilon B29}$-(N-palmitoyl-γ-glutamyl)-des(B30)-human insulin, $N^{\epsilon B29}$-(N-lithocolyl-γ-glutamyl)-des(B30)-human insulin, $N^{\epsilon B29}$-(ω-carboxyheptadecanoyl)-des(B30)-human insulin, $N^{\epsilon B29}$-(ω-carboxyheptadecanoyl)-human insulin.

In certain embodiments, an insulin molecule of the present disclosure comprises the mutations and/or chemical modifications of one of the following insulin molecules: $N^{\epsilon B29}$-octanoyl-human insulin, $N^{\epsilon B29}$-myristoyl-$Gly^{A21}Arg^{B31}Arg^{B31}$-human insulin, $N^{\epsilon B29}$-myristoyl-$Gly^{A21}Gln^{B3}Arg^{B31}Arg^{B32}$-human insulin, $N^{\epsilon B29}$-myristoyl-$Arg^{A0}Gly^{A21}Arg^{B31}Arg^{B32}$-human insulin, $N^{\epsilon B29}$-$Arg^{A0}Gly^{A21}Gln^{B3}Arg^{B31}Arg^{B32}$-human insulin, $N^{\epsilon B29}$- myristoyl-Arg$^{A0}$Gly$^{A21}$Asp$^{B31}$Arg$^{B31}$Arg$^{B32}$-human insulin, N$^{\epsilon B29}$-myristoyl-Arg$^{B31}$Arg$^{B32}$-human insulin, N$^{\epsilon B29}$-myristoyl-Arg$^{A0}$Arg$^{B31}$Arg$^{B32}$-human insulin, N$^{\epsilon B29}$-octanoyl-Gly$^{A21}$Arg$^{B31}$Arg$^{B32}$-human insulin, N$^{\epsilon B29}$-octanoyl-Gly$^{A21}$Gln$^{B3}$Arg$^{B31}$Arg$^{B32}$-human insulin, N$^{\epsilon B29}$-octanoyl-Arg$^{A0}$Gly$^{A21}$Arg$^{B31}$Arg$^{B32}$-human insulin, N$^{\epsilon B29}$-octanoyl-Arg$^{A0}$Gly$^{A21}$Gln$^{B3}$Arg$^{B31}$Arg$^{B32}$-human insulin, N$^{\epsilon B29}$-octanoyl-Arg$^{B0}$Gly$^{A21}$Asp$^{B31}$Arg$^{B31}$Arg$^{B32}$-human insulin, N$^{\epsilon B29}$-octanoyl-Arg$^{B31}$Arg$^{B32}$-human insulin, N$^{\epsilon B29}$-octanoyl-Arg$^{A0}$Arg$^{B31}$Arg$^{B32}$-human insulin.

In certain embodiments, an insulin molecule of the present disclosure comprises the mutations and/or chemical modifications of one of the following insulin molecules: N$^{\epsilon B28}$-myristoyl-Gly$^{A21}$Lys$^{B28}$Pro$^{B29}$Arg$^{B31}$Arg$^{B32}$-human insulin, N$^{\epsilon B28}$-myristoyl-Gly$^{A21}$Gln$^{B3}$Lys$^{B21}$Pro$^{B30}$Arg$^{B31}$Arg$^{B32}$-human insulin, N$^{\epsilon B28}$-myristoyl-Arg$^{A0}$Gly$^{A21}$Lys$^{B28}$Pro$^{B29}$Arg$^{B31}$Arg$^{B32}$-human insulin, N$^{\epsilon B28}$-myristoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-myristoyl-Arg$^{A0}$Gly$^{A21}$Asp$^{B31}$Lys$^{B28}$Pro$^{B29}$Arg$^{B31}$Arg$^{B32}$-human insulin, N$^{\epsilon B28}$-myristoyl-Lys$^{B28}$Pro$^{B29}$Arg$^{B31}$Arg$^{B32}$-human insulin, N$^{\epsilon B28}$-myristoyl-arg$^{A0}$Lys$^{B28}$Pro$^{B29}$Arg$^{B31}$Arg$^{B32}$-human insulin, N$^{\epsilon B28}$-octanoyl-Gly$^{A21}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B28}$-octanoyl-Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Lys$^{B28}$Pro$^{B29}$Arg$^{B31}$Arg$^{B32}$-human insulin, N$^{\epsilon B28}$-octanoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-octanoyl-Lys$^{B28}$Pro$^{B29}$Arg$^{B31}$Arg$^{B32}$-human insulin, N$^{\epsilon B28}$-octanoyl-Arg$^{A0}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B29}$-tridecanoyl-des(B30)-human insulin, N$^{\epsilon B29}$-tetradecanoyl-des(B30)-human insulin, N$^{\epsilon B29}$-decanoyl-des(B30)-human insulin, N$^{\epsilon B29}$-dodecanoyl-des(B30)-human insulin, N$^{\epsilon B29}$-tridecanoyl-Gly$^{A21}$-des(B30)-human insulin, N$^{\epsilon B29}$-tetradecanoyl-Gly$^{A21}$-des(B30)-human insulin, N$^{\epsilon B29}$-decanoyl-Gly$^{A21}$-des(B30)-human insulin, N$^{\epsilon B29}$-dodecanoyl-Gly$^{A21}$-des(B30)-human insulin, N$^{\epsilon B29}$-tridecanoyl-Gly$^{A21}$Gln$^{B3}$-des(B30)-human insulin, N$^{\epsilon B29}$-tetradecanoyl-Gly$^{A21}$Gln$^{B3}$-des(B30)-human insulin, N$^{\epsilon B29}$-decanoyl-Gly$^{A21}$-Gln$^{B3}$-des(B30)-human insulin, N$^{\epsilon B29}$-dodecanoyl-Gly$_{A21}$-Gln$^{B3}$-des(B30)-human insulin, N$^{\epsilon B29}$-tridecanoyl-Ala$^{A21}$-des(B30)-human insulin, N$^{\epsilon B29}$-tetradecanoyl-Ala$^{A21}$-des(B30)-human insulin, N$^{\epsilon B29}$-decanoyl-Ala$^{A21}$-des(B30)-human insulin, N$^{\epsilon B29}$-dodecanoyl-Ala$^{A21}$-des(B30)-human insulin, N$^{\epsilon B29}$-tridecanoyl-Ala$^{A21}$-Gln$^{B3}$-des(B30)-human insulin, N$^{\epsilon B29}$-tetradecanoyl-Ala$^{A21}$Gln$^{B3}$-des(B30)-human insulin, N$^{\epsilon B29}$-decanoyl-Ala$^{A21}$Gln$^{B3}$-des(B30)-human insulin, N$^{\epsilon B29}$-dodecanoyl-Ala$^{A21}$Gln$^{B3}$-des(B30)-human insulin, N$^{\epsilon B29}$-tridecanoyl-Gln$^{B3}$-des(B30)-human insulin, N$^{\epsilon B29}$-tetradecanoyl-Gln$^{B3}$-des(B30)-human insulin, N$^{\epsilon B29}$-decanoyl-Gln$^{B3}$-des(B30)-human insulin, N$^{\epsilon B29}$-dodecanoyl-Gln$^{B3}$-des(B30)-human insulin.

In certain embodiments, an insulin molecule of the present disclosure comprises the mutations and/or chemical modifications of one of the following insulin molecules: N$^{\epsilon B29}$-tridecanoyl-Gly$^{A21}$-human insulin, N$^{\epsilon B29}$-tetradecanoyl-Gly$^{A21}$-human insulin, N$^{\epsilon B29}$-decanoyl-Gly$^{A21}$-human insulin, N$^{\epsilon B29}$-dodecanoyl-Gly$^{A21}$-human insulin, N$^{\epsilon B29}$-tridecanoyl-Ala$^{A21}$-human insulin, N$^{\epsilon B29}$-tetradecanoyl-Ala$^{A21}$-human insulin, N$^{\epsilon B29}$-decanoyl-Ala$^{A21}$-human insulin, N$^{\epsilon B29}$-dodecanoyl-Ala$^{A21}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Gln$^{B3}$-human insulin, N$^{\epsilon B29}$-tetradecanoyl-Gly$^{A21}$Gln$^{B3}$-human insulin, N$^{\epsilon B29}$-decanoyl-Gly$^{A21}$Gln$^{B3}$-human insulin, N$^{\epsilon B29}$-dodecanoyl-Gly$^{A21}$Gln$^{B3}$-human insulin, N$^{\epsilon B29}$-tridecanoyl-Ala$^{A21}$Gln$^{B3}$-human insulin, N$^{\epsilon B29}$-tetradecanoyl-Ala$^{A21}$Gln$^{B3}$-human insulin, N$^{\epsilon B29}$-decanoyl-Ala$^{A21}$Gln$^{B3}$-human insulin, N$^{\epsilon B29}$-dodecanoyl-Ala$^{A21}$Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Gln$^{B3}$-human insulin, N$^{\epsilon B29}$-tetradecanoyl-Gln$^{B3}$-human insulin, N$^{\epsilon B29}$-decanoyl-Gln$^{B3}$-human insulin, N$^{\epsilon B29}$-dodecanoyl-Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Glu$^{B30}$-human insulin, N$^{\epsilon B29}$-tetradecanoyl-Glu$^{B30}$-human insulin, N$^{\epsilon B29}$-decanoyl-Glu$^{B30}$-human insulin, N$^{\epsilon B29}$-dodecanoyl-Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Glu$^{B30}$-human insulin, N$^{\epsilon B29}$-tetradecanoyl-Gly$^{A21}$Glu$^{B30}$-human insulin, N$^{\epsilon B29}$-decanoyl-Gly$^{A21}$Glu$^{B30}$-human insulin, N$^{\epsilon B29}$-dodecanoyl-Gly$^{A21}$Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$ Gln$^{B3}$Glu$^{B30}$-human insulin, N$^{\epsilon B29}$-tetradecanoyl-Gly$^{A21}$Gln$^{B3}$Glu$^{B30}$-human insulin, N$^{\epsilon B29}$-decanoyl-Gly$^{A21}$Gln$^{B3}$Glu$^{B30}$-human insulin, N$^{\epsilon B29}$-dodecanoyl-Gly$^{A21}$Gln$^{B3}$Glu$^{B30}$-human insulin, N$^{\epsilon B29}$-tridecanoyl-Ala$^{A21}$Glu$^{B30}$-human insulin, N$^{\epsilon B29}$-tetradecanoyl-Ala$^{A21}$Glu$^{B30}$-human insulin, N$^{\epsilon B29}$-decanoyl-Ala$^{A21}$Glu$^{B30}$-human insulin, N$^{\epsilon B29}$-dodecanoyl-Ala$^{A21}$Glu$^{B30}$-human insulin, N$^{\epsilon B29}$-tridecanoyl-Ala$^{A21}$Gln$^{B3}$Glu$^{B30}$-human insulin, N$^{\epsilon B29}$-tetradecanoyl-Ala$^{A21}$Gln$^{B3}$Glu$^{B30}$-human insulin, N$^{\epsilon B29}$-decanoyl-Ala$^{A21}$Gln$^{B3}$Glu$^{B30}$-human insulin, N$^{\epsilon B29}$-dodecanoyl-Ala$^{21}$Gln$^{B30}$Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gln$^{B3}$Glu$^{B30}$-human insulin, N$^{\epsilon B29}$-tetradecanoyl-Gln$^{B3}$Glu$^{B30}$-human insulin, N$^{\epsilon B29}$-decanoyl-Gln$^{B3}$Glu$^{B30}$-human insulin, N$^{\epsilon B29}$-dodecanoyl-Gln$^{B3}$Glu$^{B30}$-human insulin.

In certain embodiments, an insulin molecule of the present disclosure comprises the mutations and/or chemical modifications of one of the following insulin molecules: N$^{\epsilon B29}$-formyl-human insulin, N$^{\alpha B1}$-formyl-human insulin, N$^{\alpha A1}$-formyl-human insulin, N$^{\epsilon B29}$-formyl-N$^{\alpha B1}$-formyl-human insulin, N$^{\epsilon B29}$-formyl-N$^{\alpha A1}$-formyl-human insulin, N$^{\alpha A1}$-formyl-N$^{\alpha B1}$-formyl-human insulin, N$^{\epsilon B29}$-formyl-N$^{\alpha A1}$-formyl-N$^{\alpha B1}$-formyl-human insulin.

In certain embodiments, an insulin molecule of the present disclosure comprises the mutations and/or chemical modifications of one of the following insulin molecules: $N^{\epsilon B29}$-acetyl-human insulin, $N^{\alpha B1}$-acetyl-human insulin, $N^{\alpha A1}$-acetyl-human insulin, $N^{\epsilon B29}$-acetyl-$N^{\alpha B1}$-acetyl-human insulin, $N^{\epsilon B29}$-acetyl-$N^{\alpha A1}$-acetyl-human insulin, $N^{\alpha A1}$-acetyl-$N^{\alpha B1}$-acetyl-human insulin, $N^{\epsilon B29}$-acetyl-$N^{\alpha A1}$-acetyl-$N^{\alpha B1}$-acetyl-human insulin.

In certain embodiments, an insulin molecule of the present disclosure comprises the mutations and/or chemical modifications of one of the following insulin molecules: $N^{\epsilon B29}$-propionyl-human insulin, $N^{\alpha B1}$-propionyl-human insulin, $N^{\alpha A1}$-propionyl-human insulin, $N^{\epsilon B29}$-acetyl-$N^{\alpha B1}$-propionyl-human insulin, $N^{\epsilon B29}$-propionyl-$N^{\alpha A1}$-propionyl-human insulin, $N^{\alpha A1}$-propionyl-$N^{\alpha B1}$-propionyl-human insulin, $N^{\epsilon B29}$-propionyl-$N^{A1}$-propionyl-$N^{\alpha B1}$-propionyl-human insulin.

In certain embodiments, an insulin molecule of the present disclosure comprises the mutations and/or chemical modifications of one of the following insulin molecules: $N^{\epsilon B29}$-butyryl-human insulin, $N^{\alpha B1}$-butyryl-human insulin, $N^{\alpha A1}$-butyryl-human insulin, $N^{\epsilon B29}$-butyryl-$N^{\alpha B1}$-butyryl-human insulin, $N^{\epsilon B29}$-butyryl-$N^{\alpha A1}$-butyryl-human insulin, $N^{\alpha A1}$-butyryl-$N^{\alpha B1}$-butyryl-human insulin, $N^{\epsilon B29}$-butyryl-$N^{\alpha A1}$-butyryl-$N^{\alpha B1}$-butyryl-human insulin.

In certain embodiments, an insulin molecule of the present disclosure comprises the mutations and/or chemical modifications of one of the following insulin molecules: $N^{\epsilon B29}$-pentanoyl-human insulin, $N^{\alpha B1}$-pentanoyl-human insulin, $N^{\alpha A1}$-pentanoyl-human insulin, $N^{\epsilon B29}$-pentanoyl-$N^{\alpha B1}$-pentanoyl-human insulin, $N^{\epsilon B29}$-pentanoyl-$N^{\alpha A1}$-pentanoyl-human insulin, $N^{\alpha A1}$-pentanoyl-$N^{\alpha B1}$-pentanoyl-human insulin, $N^{\epsilon B29}$-pentanoyl-$N^{\alpha A1}$-pentanoyl-$N_{\alpha B1}$-pentanoyl-human insulin.

In certain embodiments, an insulin molecule of the present disclosure comprises the mutations and/or chemical modifications of one of the following insulin molecules: $N^{\epsilon B29}$-hexanoyl-human insulin, $N^{\alpha B1}$-hexanoyl-human insulin, $N^{\alpha A1}$-hexanoyl-human insulin, $N^{\epsilon B29}$-hexanoyl-$N^{\alpha B1}$-hexanoyl-human insulin, $N^{\epsilon B29}$-hexanoyl-$N^{\alpha A1}$-hexanoyl-human insulin, $N^{\alpha A1}$-hexanoyl-$N^{\alpha B1}$-hexanoyl-human insulin, $N^{\epsilon B29}$-hexanoyl-$N^{\alpha A1}$-hexanoyl-$N^{\alpha B1}$-hexanoyl-human insulin.

In certain embodiments, an insulin molecule of the present disclosure comprises the mutations and/or chemical modifications of one of the following insulin molecules: $N^{\epsilon B29}$-heptanoyl-human insulin, $N^{\alpha B1}$-heptanoyl-human insulin, $N^{\alpha A1}$-heptanoyl-human insulin, $N^{\epsilon B29}$-heptanoyl-$N^{\alpha B1}$-heptanoyl-human insulin, $N^{\epsilon B29}$-heptanoyl-$N^{\alpha A1}$-heptanoyl-human insulin, $N^{\alpha A1}$-heptanoyl-$N_{\alpha B1}$-heptanoyl-human insulin, $N^{\epsilon B29}$-heptanoyl-$N^{\alpha A1}$-heptanoyl-$N_{\alpha B1}$-heptanoyl-human insulin.

In certain embodiments, an insulin molecule of the present disclosure comprises the mutations and/or chemical modifications of one of the following insulin molecules: $N^{\alpha B1}$-octanoyl-human insulin, $N^{\alpha A1}$-octanoyl-human insulin, $N^{\epsilon B29}$-octanoyl-$N^{\alpha B1}$-octanoyl-human insulin, $N^{\epsilon B29}$-octanoyl-$N^{\alpha A1}$-octanoyl-human insulin, $N^{\alpha A1}$-octanoyl-$N^{\alpha B1}$-octanoyl-human insulin, $N^{\epsilon B29}$-octanoyl-$N^{\alpha A1}$-octanoyl-$N^{\alpha B1}$-octanoyl-human insulin.

In certain embodiments, an insulin molecule of the present disclosure comprises the mutations and/or chemical modifications of one of the following insulin molecules: $N^{\epsilon B29}$-nonanoyl-human insulin, $N^{\alpha B1}$-nonanoyl-human insulin, $N^{\alpha A1}$-nonanoyl-human insulin, $N^{\epsilon B29}$-nonanoyl-$N^{\alpha B1}$-nonanoyl-human insulin, $N^{\epsilon B29}$-nonanoyl-$N^{\alpha A1}$-nonanoyl-human insulin, $N^{\alpha A1}$-nonanoyl-$N^{\alpha B1}$-nonanoyl-human insulin, $N^{\epsilon B29}$-nonanoyl-$N^{\alpha A1}$-nonanoyl-$N^{\alpha B1}$-nonanoyl-human insulin.

In certain embodiments, an insulin molecule of the present disclosure comprises the mutations and/or chemical modifications of one of the following insulin molecules: $N^{\epsilon B29}$-decanoyl-human insulin, $N^{\alpha B1}$-decanoyl-human insulin, $N^{\alpha A1}$-decanoyl-human insulin, $N^{\epsilon B29}$-decanoyl-$N^{\alpha B1}$-decanoyl-human insulin, $N^{\epsilon B29}$-decanoyl-$N^{\alpha A1}$-decanoyl-human insulin, $N^{\alpha A1}$-decanoyl-$N^{\alpha B1}$-decanoyl-human insulin, $N^{\epsilon B29}$-decanoyl-$N^{\alpha A1}$-decanoyl-$N^{\alpha B1}$-decanoyl-human insulin.

In certain embodiments, an insulin molecule of the present disclosure comprises the mutations and/or chemical modifications of one of the following insulin molecules: $N^{\epsilon B28}$-formyl-$Lys^{B28}Pro^{B29}$-human insulin, $N^{\alpha B1}$-formyl-$Lys^{B28}Pro^{B29}$-human insulin, $N^{\alpha A1}$-formyl-$Lys^{B28}Pro^{B29}$-human insulin, $N^{\epsilon B28}$-formyl-$N^{\alpha B1}$-formyl-$Lys^{B28}Pro^{B29}$-human insulin, $N^{\epsilon B28}$-formyl-$N^{\alpha A1}$-formyl-$Lys^{B28}Pro^{B29}$-human insulin, $N_{\alpha A1}$-formyl-$N^{\alpha B1}$-formyl-$Lys^{B28}Pro^{B29}$-human insulin, $N^{\epsilon B28}$-formyl-$N^{\alpha A1}$-formyl-$N^{\alpha B1}$-formyl-$Lys^{B28}Pro^{B29}$-human insulin, $N^{\epsilon B29}$-acetyl-$Lys^{B28}Pro^{B29}$-human insulin, $N^{\alpha B1}$-acetyl-$Lys^{B28}Pro^{B29}$-human insulin, $N^{\alpha A1}$-acetyl-$Lys^{B28}Pro^{B29}$-human insulin, $N^{\epsilon B28}$-acetyl-$N^{\alpha B1}$-acetyl-$Lys^{B28}Pro^{B29}$-human insulin.

In certain embodiments, an insulin molecule of the present disclosure comprises the mutations and/or chemical modifications of one of the following insulin molecules: $N^{\epsilon B28}$-acetyl-$N^{\alpha A1}$-acetyl-$Lys^{B28}Pro^{B29}$-human insulin, $N^{\alpha A1}$-acetyl-$N^{\alpha B1}$-acetyl-$Lys^{B28}Pro^{B29}$-human insulin, $N^{\epsilon B28}$-acetyl-$N^{\alpha A1}$-acetyl-$N^{60\ B1}$-acetyl-$Lys^{B28}Pro^{B29}$-human insulin.

In certain embodiments, an insulin molecule of the present disclosure comprises the mutations and/or chemical modifications of one of the following insulin molecules: $N^{\epsilon B28}$-propionyl-$Lys^{B28}Pro^{B29}$-human insulin, $N^{\alpha B1}$-propionyl-$Lys^{B28}Pro^{B29}$-human insulin, $N^{\alpha A1}$-propionyl-$Lys^{B28}Pro^{B29}$-human insulin, $N^{\epsilon B28}$-propionyl-$N^{\alpha B1}$-propionyl-$Lys^{B28}Pro^{B29}$-human insulin, $N^{\epsilon B28}$-propionyl-$N^{\alpha A1}$-propionyl-$Lys^{B28}Pro^{B29}$-human insulin, $N^{\alpha A1}$-propionyl-$N^{\alpha B1}$-propionyl-$Lys^{B28}Pro^{B29}$-human insulin, $N^{\epsilon B28}$-propionyl-$N^{\alpha A1}$-propionyl-$N^{\alpha B1}$-propionyl-$Lys^{B28}Pro^{B29}$-human insulin.

In certain embodiments, an insulin molecule of the present disclosure comprises the mutations and/or chemical modifications of one of the following insulin molecules: $N^{\epsilon B28}$-butyryl-$Lys^{B28}Pro^{B29}$-human insulin, $N^{\alpha B1}$-butyryl-$Lys^{B28}Pro^{B29}$-human insulin, $N^{\alpha A1}$-butyryl-$Lys^{B28}Pro^{B29}$-human insulin, $N^{\epsilon B28}$-butyryl-$N^{\alpha B1}$-butyryl-$Lys^{B28}Pro^{B29}$-human insulin, $N^{\epsilon B28}$-butyryl-$N^{\alpha A1}$-butyryl-$Lys^{B28}Pro^{B29}$-human insulin, $N_{\alpha A1}$-butyryl-$N^{\alpha B1}$-butyryl-$Lys^{B28}Pro^{B29}$-human insulin, $N^{\epsilon B28}$-butyryl-$N^{\alpha A1}$-butyryl-$N^{\alpha B1}$-butyryl-$Lys^{B28}Pro^{B29}$-human insulin.

In certain embodiments, an insulin molecule of the present disclosure comprises the mutations and/or chemical modifications of one of the following insulin molecules: $N^{\epsilon B28}$-pentanoyl-$Lys^{B28}Pro^{B29}$-human insulin, $N^{\alpha B1}$-pentanoyl-$Lys^{B28}Pro^{B29}$-human insulin, $N^{\alpha A1}$-pentanoyl-$Lys^{B28}Pro^{B29}$-human insulin, $N^{\epsilon B28}$-pentanoyl-$N^{\alpha B1}$-pentanoyl-$Lys^{B28}Pro^{B29}$-human insulin, $N^{\epsilon B28}$-pentanoyl-$N^{\alpha A1}$-pentanoyl-$Lys^{B28}Pro^{B29}$-human insulin, $N^{\alpha A1}$-pentanoyl-$N^{\alpha B1}$-pentanoyl-$Lys^{B28}Pro^{B29}$-human insulin, $N^{\epsilon B28}$-pentanoyl-$N^{\alpha A1}$-pentanoyl-$N^{\alpha B1}$-pentanoyl-$Lys^{B28}Pro^{B29}$-human insulin.

In certain embodiments, an insulin molecule of the present disclosure comprises the mutations and/or chemical modifications of one of the following insulin molecules: $N^{\epsilon B28}$-hexanoyl-$Lys^{B28}Pro^{B29}$-human insulin, $N^{\alpha B1}$-hexanoyl-$Lys^{B28}Pro^{B29}$-human insulin, $N^{\alpha A1}$-hexanoyl-$Lys^{B28}Pro^{B29}$-human insulin, $N^{\epsilon B28}$-hexanoyl-$N^{\alpha B1}$-hexanoyl- Lys$^{B28}$Pro$^{B29}$-human insulin, N$^{\epsilon B28}$-hexanoyl-N$^{\alpha A1}$-hexanoyl-Lys$^{B28}$Pro$^{B29}$-human insulin, N$^{\alpha A1}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-N$^{\alpha B1}$-hexanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-heptanoyl-Lys$^{B28}$Pro$^{B29}$-human insulin, N$^{\alpha B1}$-heptanoyl-Lys$^{B28}$Pro$^{B29}$-human insulin, N$^{\alpha A1}$-heptanoyl-Lys$^{B28}$Pro$^{B29}$-human insulin, N$^{\epsilon B28}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-Lys$^{B28}$Pro$^{B29}$-human insulin, N$^{\alpha A1}$-heptanoyl-N$^{\alpha B1}$-heptanoyl-Lys$^{B28}$Prob$^{B29}$-human insulin, N$^{\epsilon B28}$-heptanoyl-N$^{\alpha A1}$-heptanoyl-N$^{\alpha B1}$-heptanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-octanoyl-Lys$^{B28}$Pro$^{B29}$-human insulin, N$^{\alpha B1}$-octanoyl-Lys$^{B28}$Pro$^{B29}$-human insulin, N$^{\alpha A1}$-octanoyl-Lys$^{B28}$Pro$^{B29}$-human insulin, N$^{\epsilon B28}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-Lys$^{B28}$Pro$^{B29}$-human insulin, N$^{\alpha A1}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-N$^{\alpha B1}$-octanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-nonanoyl-Lys$^{B28}$Pro$^{B29}$-human insulin, N$^{\alpha B1}$-nonanoyl-Lys$^{B28}$Pro$^{B29}$-human insulin, N$^{\alpha A1}$-nonanoyl-Lys$^{B28}$Pro$^{B29}$-human insulin, N$^{\epsilon B28}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-Lys$^{B28}$Pro$^{B29}$-human insulin, N$^{\alpha A1}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-N-nonanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-decanoyl-Lys$^{B28}$Pro$^{B29}$-human insulin, N$^{\alpha B1}$-decanoyl-Lys$^{B28}$Pro$^{B29}$-human insulin, N$^{\alpha A1}$-decanoyl-Lys$^{B28}$Pro$^{B29}$-human insulin, N$^{\epsilon B28}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-Lys$^{B28}$Pro$^{B29}$-human insulin, N$^{\alpha A1}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-N$^{\alpha B1}$-decanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-pentanoyl-Gly$^{A21}$Arg$^{B31}$Arg$^{B32}$-human insulin, N$^{\alpha B1}$-hexanoyl-Gly$^{A21}$Arg$^{B31}$Arg$^{B32}$-human insulin, N$^{\alpha A1}$-heptanoyl-Gly$^{A21}$Arg$^{B31}$Arg$^{B32}$-human insulin, N$^{\epsilon B29}$-octanoyl-N$^{\alpha B1}$-octanoyl-Gly$^{A21}$Arg$^{B31}$Arg$^{B32}$-human insulin, N$^{\epsilon B29}$-propionyl-N$^{\alpha A1}$-propionyl-Gly$^{A21}$Arg$^{B31}$Arg$^{B32}$-human insulin, N$^{\alpha A1}$-acetyl-N$^{\alpha B1}$-acetyl-Gly$^{A21}$Arg$^{B33}$Arg$^{B32}$-human insulin, N$^{\epsilon B29}$-formyl-N$^{\alpha A1}$-formyl-N$^{\alpha B1}$-formyl-Gly$^{A21}$Arg$^{B31}$Arg$^{B32}$-human insulin, N$^{\epsilon B29}$-formyl-des(B26)-human insulin, N$^{\alpha B1}$-acetyl-Asp$^{B28}$-human insulin, N$^{\epsilon B29}$-propionyl-N$^{\alpha A1}$-propionyl-N$^{\alpha B1}$-propionyl-Asp$^{B1}$Asp$^{B3}$Asp$^{B1}$-human insulin, N$^{\epsilon B29}$-pentanoyl-Gly$^{A21}$-human insulin, N$^{\alpha B1}$-hexanoyl-Gly$^{A21}$-human insulin, N$^{\alpha A1}$-heptanoyl-Gly$^{A21}$-human insulin, N$^{\epsilon B29}$-octanoyl-N$^{\alpha B1}$-octanoyl-Gly$^{A21}$-human insulin, N$^{\epsilon B29}$-propionyl-N$^{\alpha A1}$-propionyl-Gly$^{A21}$-human insulin, N$^{\alpha A1}$-acetyl-N$^{\alpha B1}$-acetyl-Gly$^{A21}$-human insulin, N$^{\epsilon B29}$-formyl-N$^{\alpha A1}$-formyl-N$^{\alpha B1}$-formyl-Gly$^{A21}$-human insulin, N$^{\epsilon B29}$-butyryl-des(B30)-human insulin, N$^{\alpha B1}$-butyryl-des(B30)-human insulin, N$^{\alpha A1}$-butyryl-des(B30)-human insulin, N$^{\epsilon B29}$-butyryl-N$^{\alpha B1}$-butyryl-des(B30)-human insulin, N$^{\epsilon B29}$-butyryl-N$_{\alpha A1}$-butyryl-des(B30)-human insulin, N$^{\alpha A1}$-butyryl-N$^{\alpha B1}$-butyryl-des(B30)-human insulin, N$^{\epsilon B29}$-butyryl-N$^{\alpha A1}$-butyryl-N$^{\alpha B1}$-butyryl-des(B30)-human insulin.

The present disclosure also encompasses modified forms of non-human insulins (e.g., porcine insulin, bovine insulin, rabbit insulin, sheep insulin, etc.) that comprise any one of the aforementioned mutations and/or chemical modifications.

These and other modified insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and in U.S. Pat. Nos. 7,387,996; 6,869,930; 6,174,856; 6,011,007; 5,866,538; and 5,750,497.

In some embodiments, an insulin molecule is modified and/or mutated to reduce its affinity for the insulin receptor. Without wishing to be bound to a particular theory, it is believed that attenuating the receptor affinity of an insulin molecule through modification (e.g., acylation) or mutation may decrease the rate at which the insulin molecule is eliminated from serum. In some embodiments, a decreased insulin receptor affinity in vitro translates into a superior in vivo activity for an insulin conjugate. In certain embodiments, an insulin molecule is mutated such that the site of mutation is used as a conjugation point, and conjugation at the mutated site reduces binding to the insulin receptor (e.g., Lys$^{A3}$). In certain other embodiments, conjugation at an existing wild-type amino acid or terminus reduces binding to the insulin receptor (e.g., Gly$^{A1}$). In some embodiments, an insulin molecule is conjugated at position A4, A5, A8, A9, or B30. In certain embodiments, the conjugation at position A4, A5, A8, A9, or B30 takes place via a wild-type amino acid side chain (e.g., Glu$^{A4}$). In certain other embodiments, an insulin molecule is mutated at position A4, A5, A8, A9, or B30 to provide a site for conjugation (e.g., Lys$^{A4}$, Lys$^{A5}$, LysA8, Lys$^{A9}$, or Lys$^{B30}$).

Methods for conjugating drugs including insulin molecules are described herein. In certain embodiments, an insulin molecule is conjugated via the A1 amino acid residue. In certain embodiments the A1 amino acid residue is glycine. It is to be understood however, that the present disclosure is not limited to N-terminal conjugation and that in certain embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In certain embodiments, an insulin molecule is conjugated via the B1 amino acid residue. In certain embodiments the B1 amino acid residue is phenylalanine. It is to be understood however, that the present disclosure is not limited to N-terminal conjugation and that in certain embodiments an insulin molecule may be conjugated via a non-terminal B-chain amino acid residue. In particular, the present disclosure encompasses conjugation via the epsilon-amine group of a lysine residue present at any position in the B-chain (wild-type or introduced by site-directed mutagenesis). For example, in certain embodiments an insulin molecule may be conjugated via the B29 lysine residue. In the case of insulin glulisine, conjugation to the at least one ligand via the B3 lysine residue may be employed. It will be appreciated that different conjugation positions on the B-chain may lead to different reductions in insulin activity.

In certain embodiments, the ligands are conjugated to more than one conjugation point on a drug such as an insulin molecule. For example, an insulin molecule can be conjugated at both the A1 N-terminus and the B29 lysine. In some embodiments, amide conjugation takes place in carbonate buffer to conjugate at the B29 and A1 positions, but not at the B1 position. In other embodiments, an insulin molecule can be conjugated at the A1 N-terminus, the B1 N-terminus, and the B29 lysine. In yet other embodiments, protecting groups are used such that conjugation takes place at the B1 and B29 or B1 and A1 positions. It will be appreciated that any combination of conjugation points on an insulin molecule may be employed. In some embodiments, at least one of the conjugation points is a mutated lysine residue, e.g., $Lys^{A3}$.

In various embodiments, W is an insulin sensitizer (i.e., a drug which potentiates the action of insulin). Drugs which potentiate the effects of insulin include biguanides (e.g., metformin) and glitazones. The first glitazone drug was troglitazone which turned out to have severe side effects. Second generation glitazones include pioglitazone and rosiglitazone which are better tolerated although rosiglitazone has been associated with adverse cardiovascular events in certain trials.

In various embodiments, W is an insulin secretagogue (i.e., a drug which stimulates insulin secretion by beta cells of the pancreas). For example, in various embodiments, a conjugate may include a sulfonylurea. Sulfonylureas stimulate insulin secretion by beta cells of the pancreas by sensitizing them to the action of glucose. Sulfonylureas can, moreover, inhibit glucagon secretion and sensitize target tissues to the action of insulin. First generation sulfonylureas include tolbutamide, chlorpropamide and carbutamide. Second generation sulfonylureas which are active at lower doses include glipizide, glibenclamide, gliclazide, glibornuride and glimepiride. In various embodiments, a conjugate may include a meglitinide. Suitable meglitinides include nateglinide, mitiglinide and repaglinide. Their hypoglycemic action is faster and shorter than that of sulfonylureas. Other insulin secretagogues include glucagon-like peptide I (GLP-1) and GLP-1 analogs (i.e., a peptide with GLP-1 like bioactivity that differs from GLP-1 by 1-10 amino acid substitutions, additions or deletions and/or by a chemical modification). GLP-1 reduces food intake by inhibiting gastric emptying, increasing satiety through central actions and by suppressing glucagon release. GLP-1 lowers plasma glucose levels by increasing pancreas islet cell proliferation and increases insulin production following food consumption. GLP-1 may be chemically modified, e.g., by lipid conjugation as in liraglutide to extend its in vivo half-life. Yet other insulin secretagogues include exendin-4 and exendin-4 analogs (i.e., a peptide with exendin-4 like bioactivity that differs from exendin-4 by 1-10 amino acid substitutions, additions or deletions and/or by a chemical modification). Exendin-4, found in the venom of the Gila Monster, exhibits GLP-1 like bioactivity. It has a much longer half-life than GLP-1 and, unlike GLP-1, it can be truncated by 8 amino acid residues at its N-terminus without losing bioactivity. The N-terminal region of GLP-1 and exendin-4 are almost identical, a significant difference being the second amino acid residue, alanine in GLP-1 and glycine in exendin-4, which gives exendin-4 its resistance to in vivo digestion. Exendin-4 also has an extra 9 amino acid residues at its C-terminus as compared to GLP-1. Mann et al. *Biochem. Soc. Trans.* 35:713-716, 2007 and Runge et al., *Biochemistry* 46:5830-5840, 2007 describe a variety of GLP-1 and exendin-4 analogs which may be used in a conjugate of the present disclosure. The short half-life of GLP-1 results from enzymatic digestion by dipeptidyl peptidase IV (DPP-IV). In certain embodiments, the effects of endogenous GLP-1 may be enhanced by administration of a DPP-IV inhibitor (e.g., vildagliptin, sitagliptin, saxagliptin, linagliptin or alogliptin).

In various embodiments, W is amylin or an amylin analog (i.e., a peptide with amylin like bioactivity that differs from amylin by 1-10 amino acid substitutions, additions or deletions and/or by a chemical modification). Amylin plays an important role in glucose regulation (e.g., see Edelman and Weyer, *Diabetes Technol. Ther.* 4:175-189, 2002). Amylin is a neuroendocrine hormone that is co-secreted with insulin by the beta cells of the pancreas in response to food intake. While insulin works to regulate glucose disappearance from the bloodstream, amylin works to help regulate glucose appearance in the bloodstream from the stomach and liver. Pramlintide acetate (SYMLIN®) is an exemplary amylin analog. Since native human amylin is amyloidogenic, the strategy for designing pramlintide involved substituting certain residues with those from rat amylin, which is not amyloidogenic. In particular, proline residues are known to be structure-breaking residues, so these were directly grafted from the rat sequence into the human sequence. Glu-10 was also substituted with an asparagine.

Steps of Scheme I

In one aspect, the present invention provides methods for preparing a conjugate of formula I from a prefunctionalized ligand framework (PLF) A according to the steps depicted in Scheme I, above.

At step S-1, a compound of formula J is coupled to a compound of formula H, via an amide bond formation. In some embodiments, the amide bond formation takes place under basic conditions. In some embodiments, the base is an inorganic base. In some embodiments, the base is an organic base. In certain embodiments, the base is a tertiary amine (e.g., triethylamine or diisopropylethylamine). In certain embodiments, the base is triethylamine.

In some embodiments, step S-1 takes place in a polar aprotic solvent. Polar aprotic solvents include dichloromethane (DCM), tetrahydrofuran (THF), acetone, ethyl acetate, dimethylformamide (DMF), acetonitrile, dimethyl sulfoxide (DMSO), and N-methylpyrrolidinone (NMP). In certain embodiments, the solvent is DMF.

In some embodiments, step S-1 is performed at a temperature below room temperature. In some embodiments, step S-1 is performed a temperature above room temperature. In certain embodiments, step S-1 is performed at room temperature. In certain embodiments, step S-1 begins at a temperature below room temperature (e.g., about 0 to 5° C.) and is allowed to warm to room temperature.

At step S-2, removal of the $PG^1$ protecting group in a compound of formula G affords a free amine-containing compound of formula F. Procedures for the removal of suitable amino protecting groups are well known in the art; see Green (1999). In certain embodiments, where the —$NHPG^1$ moiety of formula G is t-butylcarbamate (i.e., $PG^1$ is Boc), $PG^1$ is removed by treatment with an acid or other methods known in the art. In certain embodiments, the Boc group is removed with TFA. In some embodiments, this transformation is conducted in a polar aprotic solvent. In some embodiments, the Boc deprotection is perfomed without additional solvent. In certain embodiments, this transformation is conducted with DCM as solvent. In certain embodiments, the reaction is conducted at a temperature below room temperature. In certain embodiments, the reaction is conducted at a temperature above room temperature. In certain embodiments, the reaction is conducted at a temperature at about room temperature. In certain embodiments, the reaction is conducted at about 0 to 5° C.

At step S-3, a compound of formula E is coupled to 2-(2,6-dioxomorpholino)acetic acid via amide bond formation wherein the nitrogen of a compound of formula E opens the cyclic anhydride to form an amide bond. In some embodiments, amide bond formation takes place under basic conditions. In certain embodiments, the base is an inorganic base. In certain embodiments, the base is a carbonate. In certain embodiments, the base is potassium carbonate.

In some embodiments, step S-3 takes place in a polar aprotic solvent. Polar aprotic solvents include dichloromethane (DCM), tetrahydrofuran (THF), acetone, ethyl acetate, dimethylformamide (DMF), acetonitrile, dimethyl sulfoxide (DMSO), and N-methylpyrrolidinone (NMP). In certain embodiments, the solvent is DMF.

In some embodiments, step S-3 is performed at a temperature below room temperature. In some embodiments, step S-3 is performed a temperature above room temperature. In some embodiments, step S-3 is performed at room temperature. In certain embodiments, step S-3 begins at a temperature below room temperature (e.g., about 0 to 5° C.) and is allowed to warm to room temperature.

At step S-4, two compounds of formula F are coupled to a compound of formula D via amide bond formation. In some embodiments, step S-4 is performed under standard peptide coupling conditions which are known in the art; see, for example, Bailey, *An Introduction to Peptide Chemistry*, Wiley, Chichester (1990); Jones, *The Chemical Synthesis of Peptides*, OUP, Oxford (1991); Bodansky, *Peptide Chemistry: a Practical Textbook*, Springer-Verlag, Berlin (1993); Bodansky, *Principles of Peptide Synthesis*, 2$^{nd}$ ed., Springer-Verlag, Berlin (1993); Bodansky et al., *Practice of Peptide Synthesis*, 2$^{nd}$ ed., Springer-Verlag, Berlin (1994); Albertson, *Org. React.*, 12, 157 (1962); Carpino et al, *Acc. Chem. Res.*, 29, 268 (1996). In some embodiments, a peptide coupling reagent is used in the transformation. Exemplary peptide coupling reagents include, but are not limited to, 1-ethyl-3-(3-dimethylaminopropyl) carbodiimide (EDC), dicyclohexylcarbodiimide (DCC), diisopropylcarbodiimide (DIC), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), O-(6-chlorobenzotriazol-1-yl)-N,N,N',N'-tetramethyluronium hexafluorophosphate (HCTU), O-(benzotriazol-1-yl)-N,N,N',N'-tetramethyluronium tetrafluoroborate (TBTU), (benzotriazol-1-yloxy)tris(dimethylamino)phosphonium hexafluorophosphate (BOP), bis(2-oxo-3-oxazolidinyl)phosphinic chloride (BOP-Cl), (benzotriazol-1-yloxy)tripyrrolidinophosphonium hexafluorophosphate (PyBOP), bromotripyrrolidinophosphonium hexafluorophosphate (PyBrOP), and chlorotripyrrolidinophosphonium hexafluorophosphate (PyClOP). In certain embodiments, a uronium coupling reagent (e.g., HBTU or HATU) is employed in step S-4. In certain embodiments, HBTU is used. In some embodiments, an additive is used in the transformation. Exemplary additives include 1-hydroxybenzotriazole (HOBt), 1-hydroxy-7-azabenzotriazole (HOAt), and 4-(dimethylamino)pyridine (DMAP). In certain embodiments, DMAP is employed in step S-4. In some embodiments, a base is employed in step S-4. In some embodiments, the base is an organic base. In certain embodiments, the base is a tertiary amine (e.g., diisopropylethylamine or triethylamine). In certain embodiments, the base is diisopropylethylamine.

At step S-5, removal of the PG$^2$ protecting group in a compound of formula C affords a free acid-containing compound of formula B. Procedures for the removal of suitable amino protecting groups are well known in the art; see Green (1999). In certain embodiments, where the PG$^2$ moiety of formula B is benzyl, PG$^2$ is removed by hydrogenation or other methods known in the art. In certain embodiments, the benzyl group is removed using catalytic hydrogenation or transfer hydrogenation. In certain embodiments, benzyl group is removed using catalytic hydrogenation. In certain embodiments, the hydrogenation is performed in an alcoholic solvent. In certain embodiments, the hydrogenation is performed in methanol. In certain embodiments, the hydrogenation is performed in the presence of palladium on carbon.

At step S-6, the free acid group of a compound of formula B is activated such that it comprises a suitable leaving group (LG$^2$) subject to nucleophilic displacement. Suitable LG$^2$ groups are described herein. In some embodiments, LG$^2$ is —OSu. In certain embodiments, step S-6 employs a uronium reagent for installing LG$^2$. In certain embodiments, step S-6 employs N,N,N',N'-Tetramethyl-O—(N-succinimidyl)uronium tetrafluoroborate (TSTU). In certain embodiments, step S-6 takes place in a polar aprotic solvent. In certain embodiments, step S-6 takes place in DMF. In some embodiments, activation takes place in the presence of a base. In certain embodiments, the base is an organic base. In certain embodiments, the base is a tertiary amine (e.g., triethylamine or diisopropylethylamine). In certain embodiments, the base is diisopropylethylamine. In some embodiments, step S-6 is performed at a temperature below room temperature. In certain embodiments, the reaction takes place at a temperature between about 0° C. and room temperature. In certain embodiments, the reaction takes place at about 0° C.

Methods of Conjugation

At step S-7, an amine-containing drug W is reacted with a compound of formula A to form an amide bond. In various embodiments, an amine-bearing drug can be coupled to a compound of formula A that contains a terminal activated ester moiety (e.g., see Hermanson in *Bioconjugate Techniques*, 2$^{nd}$ edition, Academic Press, 2008 and references cited therein). Briefly, a compound of formula A having a terminal activated ester (e.g., —OSu, etc.) is dissolved in an anhydrous organic solvent such as DMSO or DMF. The desired number of equivalents of drug are then added and mixed for several hours at room temperature. A drug can also be conjugated to a free acid compound of formula B to produce a stable amide bond as described by Baudys et al., *Bioconj. Chem.* 9:176-183, 1998. This reaction can be achieved by adding tributylamine (TBA) and isobutylchloroformate to a solution of a compound of formula B and drug in dimethylsulfoxide (DMSO) under anhydrous conditions.

Certain drugs may naturally possess more than one amino group. In some examples, it is possible to choose the chemical reaction type and conditions to selectively react the component at only one of those sites. For example, in the case where an insulin molecule is conjugated through reactive amines, in certain embodiments, the A1 and B29 amino groups of the insulin molecule are BOC-protected as described in the Examples so that each insulin molecule can only react at the Phe-B1 α-amino group. In some embodiments, the B1 and B29 amino groups of the insulin molecule are BOC-protected as described in the Examples so that each insulin molecule can only react at the Gly-A1 α-amino group. In certain embodiments, approximately one equivalent of BOC2-insulin as a solution in DMSO is added at room temperature to a solution of a compound of formula A in DMSO containing excess triethylamine and allowed to react for an appropriate amount of time. In certain embodiments, the reaction takes place in approximately one hour. In some embodiments, the resulting conjugate is purified via reverse phase HPLC (C8, acetonitrile/water mobile phase containing 0.1% TFA) to purify the desired product from unreacted BOC2-insulin. In certain embodiments, the desired elution peak is collected pooled and rotovapped to remove acetonitrile followed by lyophilization to obtain a dry powder. Finally, the BOC protecting groups are removed by dissolving the lyophilized powder in 90% TFA/10% anisole for one hour at 4 C followed by 10× superdilution in HEPES pH 8.2 buffer containing 0.150 M NaCl. The pH is adjusted to between 7.0 and 8.0 using NaOH solution after which the material is passed through a Biogel P2 column to remove anisole, BOC, and any other contaminating salts. The deprotected, purified aqueous conjugate solution is then concentrated to the desired level and stored at 4 C until needed.

In another aspect, reaction may take place at the B29 epsilon-amino group using an unprotected insulin molecule in carbonate buffer, since under those conditions the B29 amino group is the most reactive of the three amino groups present in wild-type insulin. In an exemplary synthesis, a compound of formula A is dissolved in anhydrous DMSO followed by the addition of triethylamine (TEA). The solution is stirred rapidly for a desired amount of time at room temperature. The unprotected insulin molecule is then dissolved separately at 17.2 mM in sodium carbonate buffer (0.1 M, pH 11) and the pH subsequently adjusted to 10.8 with 1.0 N sodium hydroxide. Once dissolved, the A/DMSO/TEA solution is added dropwise to the drug/carbonate buffer solution. During the addition, the pH of the resulting mixture is adjusted periodically to 10.8 if necessary using dilute HCl or NaOH. The solution is allowed to stir for a desired amount of time after the dropwise addition to ensure complete reaction.

In certain embodiments, the resulting conjugate is purified using preparative reverse phase HPLC. Once collected, the solution is rotovapped to remove acetonitrile and lyophilized to obtain pure conjugate.

Furthermore, under the carbonate buffer conditions, the A1 amino group is the second most reactive amino group of wild-type insulin. Thus, in certain embodiments, A1,B29-disubstituted insulin-conjugates are synthesized using the conditions described above with approximately ten times the amount of prefunctionalized ligand framework per insulin molecule compared to the B29-monosubstituted insulin-conjugate synthesis.

It will be appreciated that these exemplary procedures may be used to produce other conjugates with different ligands and drugs.

Conjugation Using N-Terminal Protecting Amino Acid Sequences

Figure 21A:
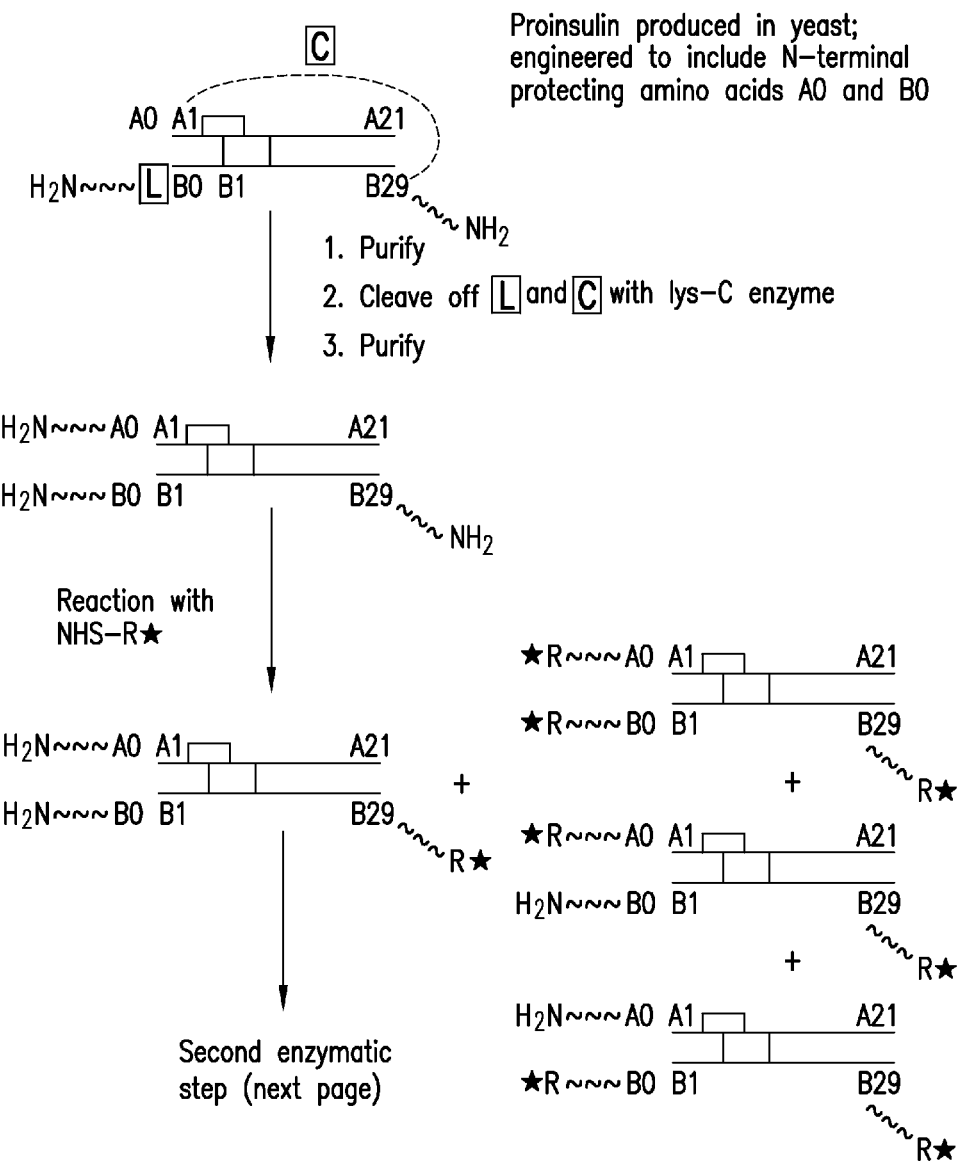
FIG. 21: Exemplary conjugation scheme where N-terminal protecting amino acids were engineered into both the A- and B-peptides of the insulin molecule. The N-terminal protecting amino acids are illustrated as A0 and B0. After treatment with a C-terminal lysine protease to cleave the leader peptide and C-peptide, the insulin molecule is conjugated with NHS—R*. Conjugation is shown to occur preferentially at the $Lys^{129}$ position but occurs also at the A0 and B0 positions. The N-terminal protecting amino acids are then cleaved in a final step with trypsin or trypsin-like protease that is capable of cleaving on the C-terminus of Arg residues (see FIG. 21B) to collapse the various insulin conjugate intermediates to the desired $Lys^{B29}$ conjugate product.
Figure 21B:
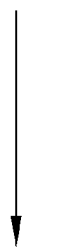
Figure 21B:
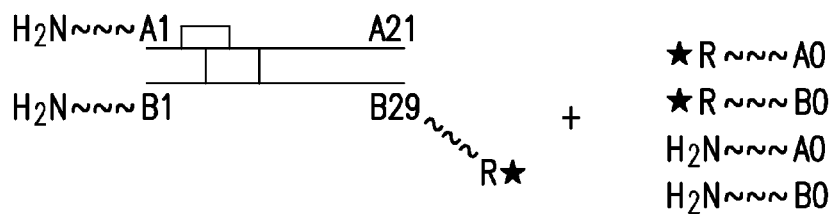

In some embodiments, the conjugation process described above is performed using recombinant insulin molecules that include N-terminal protecting amino acid sequences. FIG. 21 illustrates one embodiment of this process in the context of a recombinant insulin molecule that includes N-terminal protecting amino acid sequences on both the A- and B-peptides (the N-terminal protecting amino acid sequences are shown as A0 and B0, respectively). As described in more detail below, the N-terminal protecting amino acid sequences A0 and B0 may include one or more amino acid residues as long as they include an Arg residue at their C-termini. As shown in FIG. 21A and as described in Example 28, a proinsulin molecule that includes these N-terminal protecting amino acid sequences is initially produced recombinantly in yeast. After purification, the N-terminal leader peptide (L in FIG. 21) and the internal C-peptide (C in FIG. 21) of the proinsulin molecule are cleaved using a C-terminal lysine protease (e.g., *Achromobacter lyticus* protease or ALP). The N-terminal leader peptide is cleaved because it includes a C-terminal Lys residue. The internal C-peptide is cleaved because it is flanked by two Lys residues (the Lys residue at B29 and a Lys residue at the C-terminus of the C-peptide sequence). Conjugation then takes place while the N-terminal protecting amino acid sequences are present on the insulin molecule to produce a mixture of conjugated insulin intermediates (conjugation will generally occur preferentially at the more reactive $Lys^{B29}$ but may also occur at the N-termini of A0 and/or B0). In FIG. 21A, the insulin molecule is conjugated with NHS—R* where R* corresponds to a prefunctionalized ligand framework and NHS corresponds to an NHS ester group. It is to be understood that the NHS ester group in these Figures is exemplary and that here and at any point in this disclosure the NHS ester group could be replaced with another suitable activated ester group. As mentioned above, in certain embodiments, this conjugation step may be performed by dissolving NHS—R* in an anhydrous organic solvent such as DMSO or DMF and then adding the desired number of equivalents of the insulin molecule followed by mixing for several hours at room temperature. The conjugated insulin intermediates are then treated with trypsin or a trypsin-like protease that is capable of cleaving on the C-terminus of Arg residues. As shown in FIG. 21B, this enzymatic processing step collapses all of the conjugated insulin intermediates into the desired insulin-conjugate where only $Lys^{B29}$ is conjugated.

Figure 20:
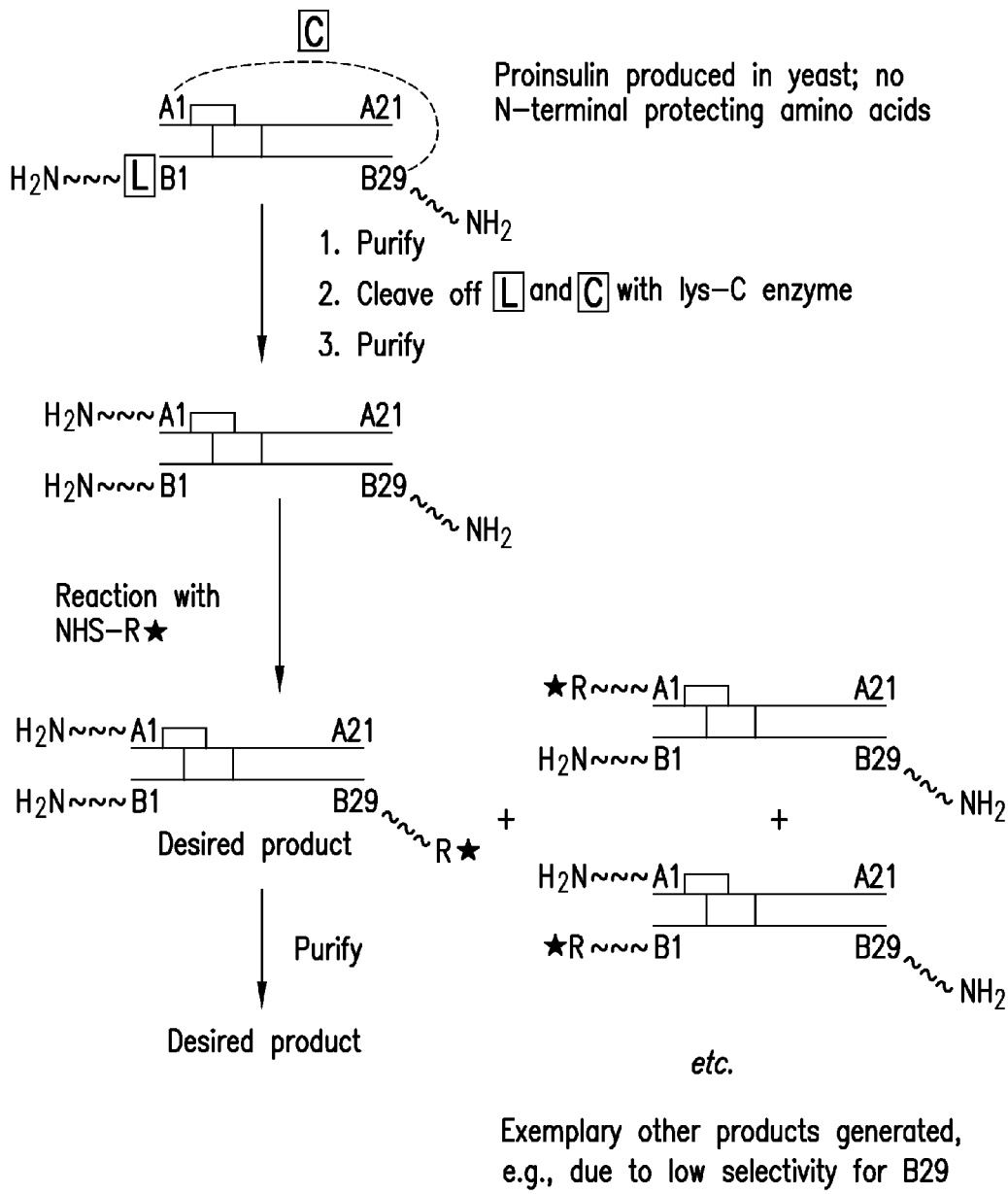
FIG. 20: Exemplary conjugation scheme where N-terminal protecting amino acids were not engineered into the insulin molecule. L is the proinsulin leader peptide. C is the C-peptide that connects the C-terminus of the B-peptide and the N-terminus of the A-peptide. These are cleaved from proinsulin in the first step using a C-terminal lysine protease or lys-C enzyme (e.g., *Achromobacter lyticus* protease or ALP). The resulting bioactive insulin molecule (with A- and B-peptides linked via disulfide bonds) is then conjugated with NHS—R* where R* corresponds to a prefunctionalized ligand framework and NHS corresponds to an NHS ester group. Conjugation is shown to occur non-selectively at the A1, B31 and $Lys^{B29}$ positions. The desired $Lys^{B29}$ conjugate is then purified from the mixture of conjugates.

FIG. 20 illustrates how the same process would proceed in the absence of N-terminal protecting amino acid sequences on the A- and B-peptides. As shown, the process would result in a mixture of conjugated products and the desired product (e.g., the insulin-conjugate where only $Lys^{B29}$ is conjugated) would need to be purified from the mixture (e.g., using preparative reverse phase HPLC).

Figure 22A:
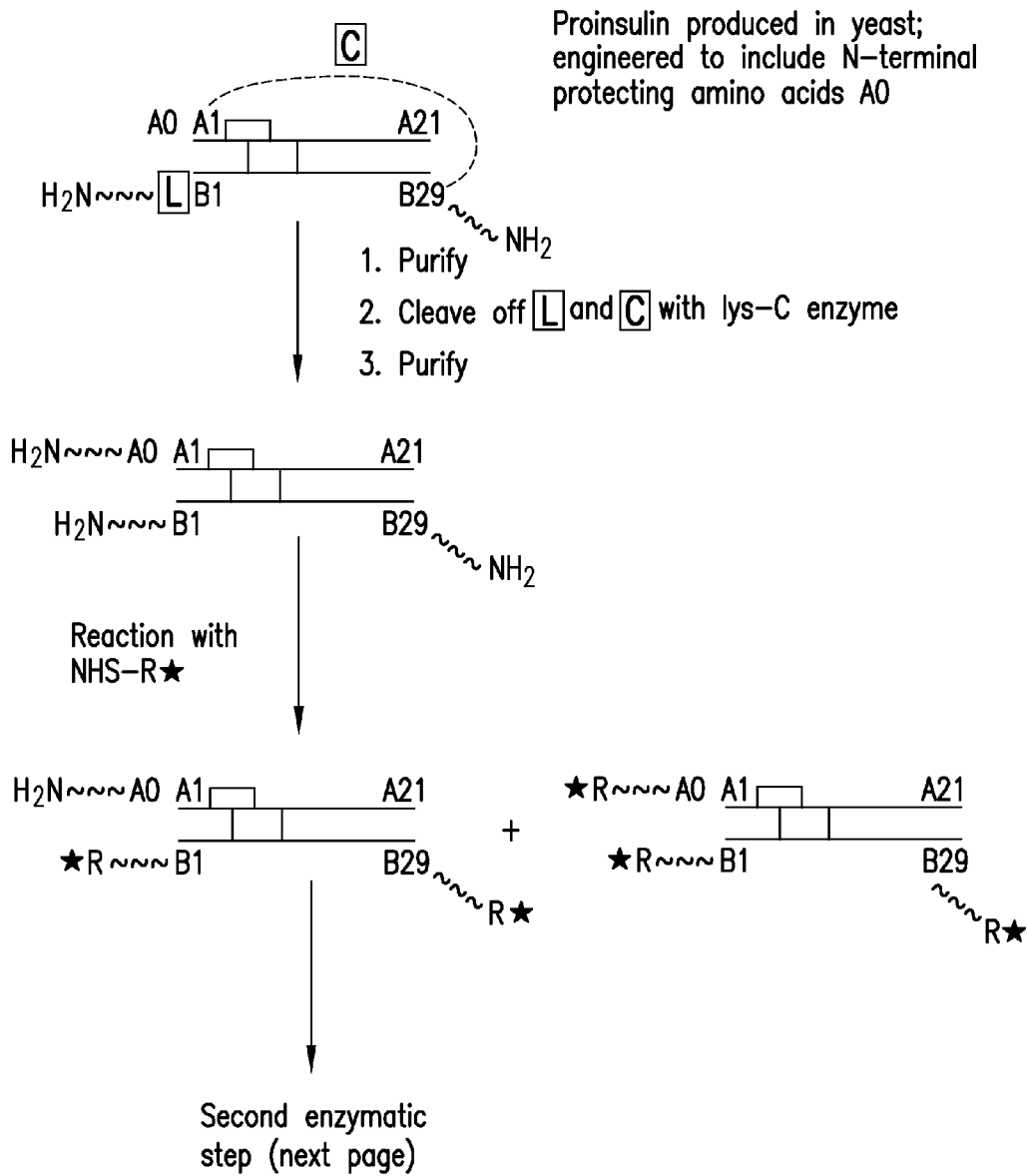
FIG. 22: Exemplary conjugation scheme where N-terminal protecting amino acids were only engineered into the A-peptide of the insulin molecule. The N-terminal protecting amino acids are illustrated as A0.
Figure 22B:
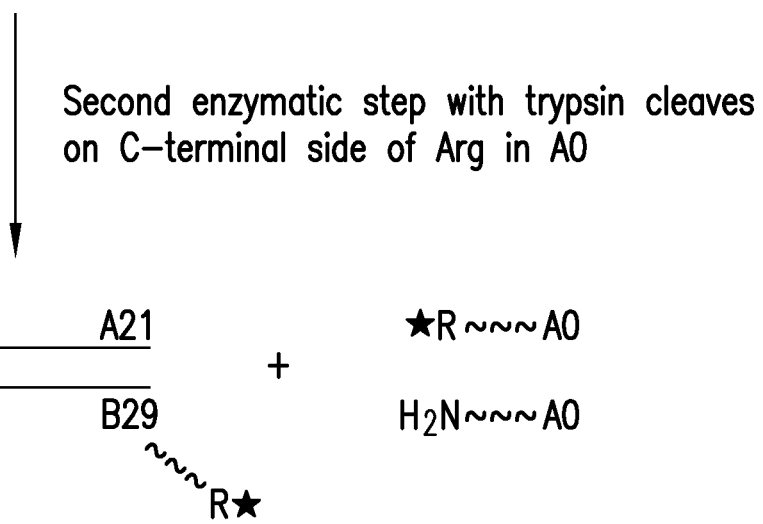

FIG. 22 illustrates another embodiment of this process in the context of a recombinant insulin molecule that includes an N-terminal protecting amino acid sequence on the A-peptide only (the N-terminal protecting amino acid sequences is shown as A0). As shown in FIG. 22, the reaction is performed under conditions that promote conjugation at all available positions (i.e., A0, B1 and B29). For example, this can be achieved by adding an excess of NHS—R* to the reaction. Alternatively, conditions that promote conjugation at the B1 and B29 positions could be used. The conjugated insulin intermediates are then treated with trypsin to produce the desired insulin-conjugate where both B1 and $Lys^{B29}$ are conjugated. In some embodiments, conditions that promote conjugation at the B29 position or at both the A0 and B29 positions could be used (e.g., if the desired product is an insulin-conjugate where only $Lys^{B29}$ is conjugated). The present disclosure also encompasses embodiments where the conjugation reaction produces a more complex mixture of conjugated insulin intermediates (e.g., B29, A0/B29, B1/B29 and A0/B1/B29 conjugated insulin intermediates). In such embodiments, treatment with trypsin will produce a mixture of products (e.g., a B29 conjugated insulin molecule and a B1/B29 conjugated insulin molecule). The desired product is then purified from this mixture by techniques that are disclosed herein (e.g., using preparative reverse phase HPLC).

Figure 23A:
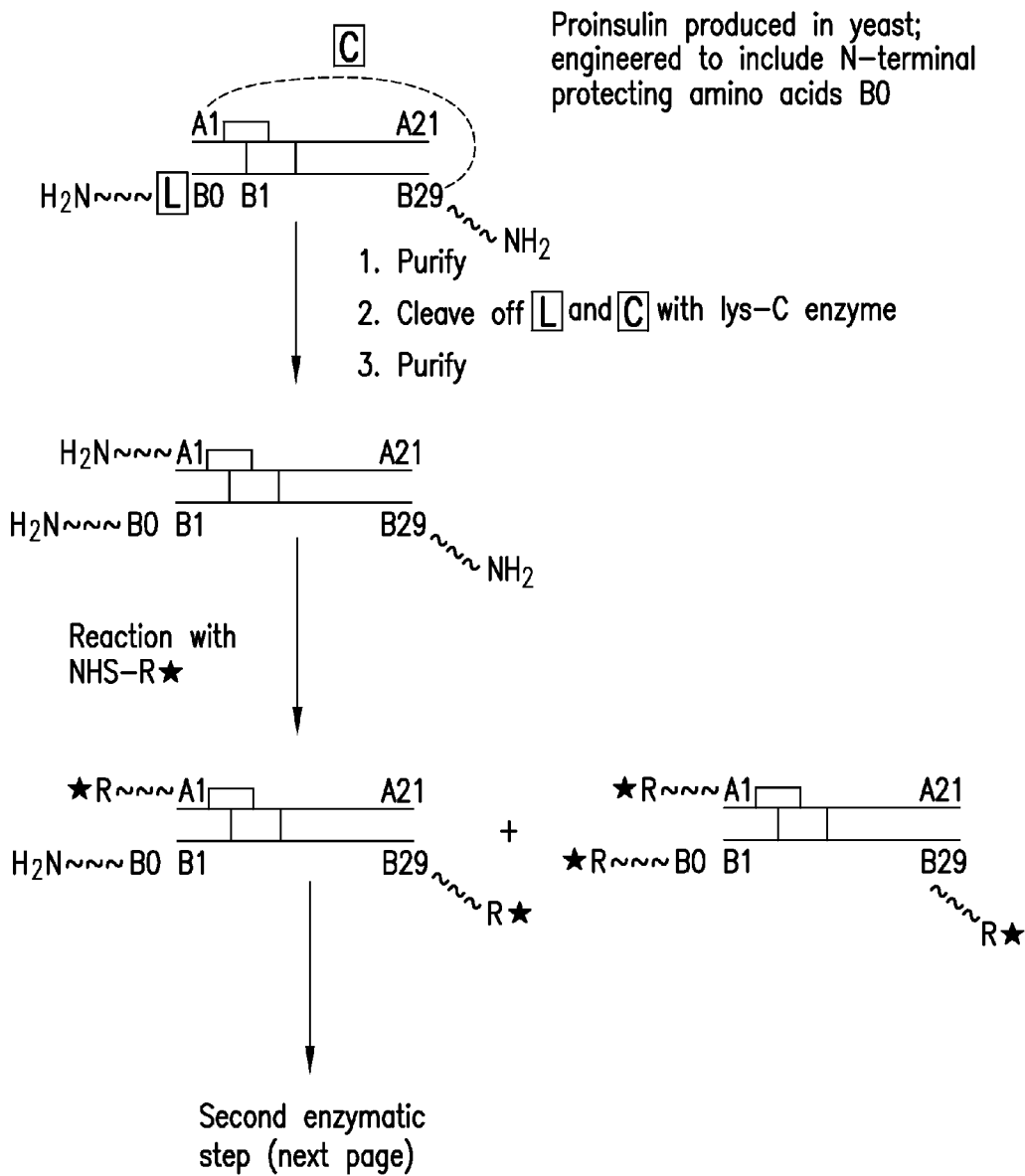
FIG. 23: Exemplary conjugation scheme where N-terminal protecting amino acids were only engineered into the B-peptide of the insulin molecule. The N-terminal protecting amino acids are illustrated as B0.
Figure 23B:
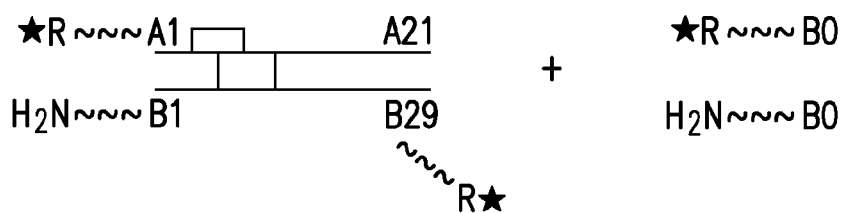

FIG. 23 illustrates yet another embodiment of this process in the context of a recombinant insulin molecule that includes an N-terminal protecting amino acid sequence on the B-peptide only (the N-terminal protecting amino acid sequences is shown as B0). As shown in FIG. 23, the reaction is performed under conditions that promote conjugation at all available positions (i.e., A1, B130 and B29). For example, this can be achieved by adding an excess of NHS—R* to the reaction. Alternatively, conditions that promote conjugation at the A1 and B29 positions could be used (e.g., in sodium carbonate buffer (0.1 M, pH 11) the A1 position is the second most reactive position after B29). The conjugated insulin intermediates are then treated with trypsin to produce the desired insulin-conjugate where both A1 and Lys$^{B29}$ are conjugated. The present disclosure also encompasses embodiments where the conjugation reaction produces a more complex mixture of conjugated insulin intermediates (e.g., B29, A1/B29, B13/B29 and A1/B01/B29 conjugated insulin intermediates). In such embodiments, treatment with trypsin will produce a mixture of products (e.g., a B29 conjugated insulin molecule and an A1/B29 conjugated insulin molecule). The desired product is then purified from this mixture by techniques that are disclosed herein (e.g., using preparative reverse phase HPLC).

In certain embodiments, a recombinant insulin molecule that includes one or more N-terminal protecting amino acid sequences comprises an amino acid sequence of SEQ ID NO:1 (A-peptide) and an amino acid sequence of SEQ ID NO:2 (B-peptide) and three disulfide bridges as shown in formula $X^I$:

Xaa at position B0 is missing. In certain embodiments, Xaa at position A0 is missing and Xaa at position B0 includes an N-terminal protecting amino acid sequence.

In certain embodiments, the N-terminal protecting amino acid sequence comprises the motif [Asp/Glu]-Xaa'''-Arg at the C-terminus where Xaa''' is missing or is a sequence of 1-10 codable amino acids with the proviso that Xaa''' does not include Arg.

In certain embodiments, Xaa''' does not include Cys or Lys.

In certain embodiments, Xaa''' includes 1-10 occurrences of Asp. In certain embodiments, Xaa''' includes 1-10 occurrences of Glu. In certain embodiments, Xaa''' includes 1-5 occurrences of Asp and 1-5 occurrences of Glu.

In certain embodiments, Xaa''' is Pro. In certain embodiments, Xaa''' includes Pro at the C-terminus. In certain embodiments, Xaa''' includes Pro at the C-terminus and 1-occurrences of Asp. In certain embodiments, Xaa''' includes Pro at the C-terminus and 1-occurrences of Glu. In certain embodiments, Xaa''' includes Pro at the C-terminus, 1-5 occurrences of Asp and 1-5 occurrences of Glu.

In certain embodiments, Xaa''' is Gly. In certain embodiments, Xaa''' includes Gly at the C-terminus. In certain

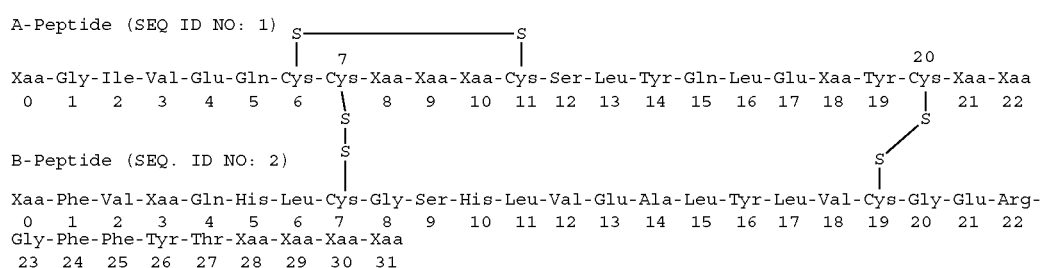

where Xaa at position A0 includes an N-terminal protecting amino acid sequence or is missing; and Xaa at position B30 includes an N-terminal protecting amino acid sequence or is missing, with the proviso that at least one of A0 or B0 includes an N-terminal protecting amino acid sequence.

It is to be understood that Xaa at positions A8, A9, A10, A18, A21, A22, B3, B28, B29, B30 and B31 of formula $X^1$ may be defined in accordance with any of the insulin molecules of formula $X^1$ that are described herein (including those set forth in Tables 1-3). In certain embodiments, A8, A9, A10, and B30 are selected from those shown in Table 3. In certain embodiments, A18 is Asn, Asp or Glu. In certain embodiments, A21 is Asn, Asp, Glu, Gly or Ala. In certain embodiments, A22, B30 and B31 are missing. In certain embodiments, B3 is Asn, Lys, Asp or Glu. In certain embodiments, B28 is Pro, Ala, Lys, Leu, Val, or Asp. In certain embodiments, B29 is Lys, Pro, or Glu. In certain embodiments, B29 is Lys.

In certain embodiments, A8, A9, A10, and B30 are selected from those shown in Table 3; A18 is Asn, Asp or Glu; A21 is Asn, Asp, Glu, Gly or Ala; A22, B30 and B31 are missing; B3 is Asn, Lys, Asp or Glu; B28 is Pro, Ala, Lys, Leu, Val, or Asp; and B29 is Lys.

In certain embodiments A22, B30 and B31 are missing and A8, A9, A10, A18, A21, B3, B28, and B29 are the same as in wild-type human insulin.

In certain embodiments, Xaa at position A0 includes an N-terminal protecting amino acid sequence and Xaa at position B0 includes an N-terminal protecting amino acid sequence. In certain embodiments, Xaa at position A0 includes an N-terminal protecting amino acid sequence and embodiments, Xaa''' includes Gly at the C-terminus and 1-occurrences of Asp. In certain embodiments, Xaa''' includes Gly at the C-terminus and 1-occurrences of Glu. In certain embodiments, Xaa''' includes Gly at the C-terminus, 1-5 occurrences of Asp and 1-5 occurrences of Glu.

In certain embodiments, the N-terminal protecting amino acid sequence comprises the motif [Asp/Glu]-[Asp/Glu]-Arg at the C-terminus.

In certain embodiments, the N-terminal protecting amino acid sequence comprises the motif [Asp/Glu]-Asp-Arg at the C-terminus.

In certain embodiments, the N-terminal protecting amino acid sequence comprises the motif [Asp/Glu]-Glu-Arg at the C-terminus.

In certain embodiments, the N-terminal protecting amino acid sequence comprises the motif Asp-[Asp/Glu]-Arg at the C-terminus.

In certain embodiments, the N-terminal protecting amino acid sequence comprises the motif Glu-[Asp/Glu]-Arg at the C-terminus.

In certain embodiments, the N-terminal protecting amino acid sequence comprises the motif [Asp/Glu]-[Asp/Glu]-[Asp/Glu]-[Asp/Glu]-Pro-Arg at the C-terminus (SEQ ID NO:20).

In certain embodiments, the N-terminal protecting amino acid sequence comprises the motif [Asp/Glu]-[Asp/Glu]-Gly-[Asp/Glu]-Xaa'''-Arg at the C-terminus where Xaa''' is any codable amino acid (SEQ ID NO:21). In certain embodiments, Xaa''' is Gly. In certain embodiments, Xaa''' is Pro.

In certain embodiments, the N-terminal protecting amino acid sequence comprises the motif Asp-Asp-Gly-Asp-Pro-Arg at the C-terminus (SEQ ID NO:22).

In certain embodiments, the N-terminal protecting amino acid sequence comprises the motif Glu-Glu-Gly-Glu-Pro-Arg at the C-terminus (SEQ ID NO:23).

In certain embodiments, the N-terminal protecting amino acid sequence comprises the motif Asp-Asp-Gly-Asp-Gly-Arg at the C-terminus (SEQ ID NO:24).

In certain embodiments, the N-terminal protecting amino acid sequence comprises the motif Glu-Glu-Gly-Glu-Gly-Arg at the C-terminus (SEQ ID NO:25).

In certain embodiments, the N-terminal protecting amino acid sequence comprises the motif Asp-Glu-Arg at the C-terminus (SEQ ID NO:26).

In certain embodiments, the N-terminal protecting amino acid sequence consists of one of the aforementioned motifs. In certain embodiments, Xaa at position A0 and/or B0 consists of one of the aforementioned motifs.

In certain embodiments, the present disclosure provides a method comprising steps of: (a) performing an amide conjugation between a prefunctionalized ligand framework that includes a terminal activated ester and an insulin molecule that includes one or more N-terminal protecting amino acid sequences to produce one or more conjugated insulin intermediates and (b) cleaving the one or more N-terminal protecting amino acid sequences from the one or more conjugated insulin intermediates with a protease that cleaves on the C-terminal side of Arg. In some embodiments, the protease is trypsin. In some embodiments, the protease is a trypsin-like protease. In some embodiments, the desired product is purified (e.g., using preparative reverse phase HPLC) from a mixture of conjugated insulin molecules produced in step (b).

In certain embodiments, the insulin molecule is as shown in formula $X^I$ where Xaa at position A0 includes an N-terminal protecting amino acid sequence and Xaa at position B0 includes an N-terminal protecting amino acid sequence. In some of these embodiments, Xaa at position B29 is Lys and the method produces an insulin molecule of formula $X^I$ where A0 and B0 are missing and a prefunctionalized ligand framework is conjugated at $Lys^{\alpha 29}$.

In certain embodiments, the insulin molecule is as shown in formula $X^I$ where Xaa at position A0 includes an N-terminal protecting amino acid sequence and Xaa at position B0 is missing. In some of these embodiments, Xaa at position B29 is Lys and the method produces an insulin molecule of formula $X^I$ where A0 and B0 are missing and a prefunctionalized ligand framework is conjugated at position B1 and $Lys^{\alpha 29}$. In some of these embodiments, Xaa at position B29 is Lys and the method produces an insulin molecule of formula $X^I$ where A0 and B0 are missing and a prefunctionalized ligand framework is conjugated at $Lys^{B29}$. In certain embodiments, the insulin molecule that is conjugated at position B1 and $Lys^{B29}$ is purified (e.g., using preparative reverse phase HPLC) from a mixture that includes insulin molecules that are conjugated at position B1 and $Lys^{B29}$ and insulin molecules that are conjugated at $Lys^{B29}$. In certain embodiments, the insulin molecule that is conjugated at $Lys^{B29}$ is purified (e.g., using preparative reverse phase HPLC) from a mixture that includes insulin molecules that are conjugated at position B1 and $Lys^{B29}$ and insulin molecules that are conjugated at $Lys^{B29}$.

In certain embodiments, the insulin molecule is as shown in formula $X^I$ where Xaa at position A0 is missing and Xaa at position B0 includes an N-terminal protecting amino acid sequence. In some of these embodiments, Xaa at position B29 is Lys and the method produces an insulin molecule of formula $X^I$ where A0 and B0 are missing and prefunctionalized ligand framework is conjugated at position A1 and $Lys^{\alpha 29}$. In some of these embodiments, Xaa at position B29 is Lys and the method produces an insulin molecule of formula $X^I$ where A0 and B0 are missing and a prefunctionalized ligand framework is conjugated at $Lys^{B29}$. In certain embodiments, the insulin molecule that is conjugated at position A1 and $Lys^{B29}$ is purified (e.g., using preparative reverse phase HPLC) from a mixture that includes insulin molecules that are conjugated at position A1 and $Lys^{B29}$ and insulin molecules that are conjugated at $Lys^{B29}$. In certain embodiments, the insulin molecule that is conjugated at $Lys^{B29}$ is purified (e.g., using preparative reverse phase HPLC) from a mixture that includes insulin molecules that are conjugated at position A1 and $Lys^{B29}$ and insulin molecules that are conjugated at $Lys^{B29}$.

Multiple Sites of Conjugation (Scheme II)

It will be understood that a compound of formula A may react multiple times with a drug having more than one amino group. Thus in certain embodiments, the present invention provides a method for preparing a conjugate of formula I-a from an appropriate number of equivalents of a compound of formula A as depicted in Scheme II, below:

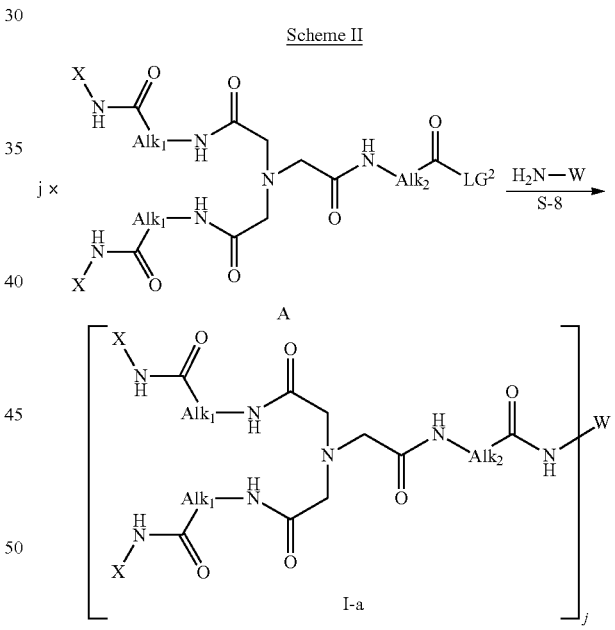

wherein X, $Alk_1$, $Alk_2$ $LG^2$, and W are as defined above, and in classes and subclasses described above and herein, and j is 2 or 3. In general, it is to be understood that any scheme disclosed herein which shows a single point of conjugation encompasses embodiments where two or more compounds of formula A are conjugated to the drug W.

Scheme III

In some embodiments, W is an insulin molecule and the present invention provides a method for preparing a conjugate of formula II from a compound of formula A as depicted in Scheme III, below:

Scheme III

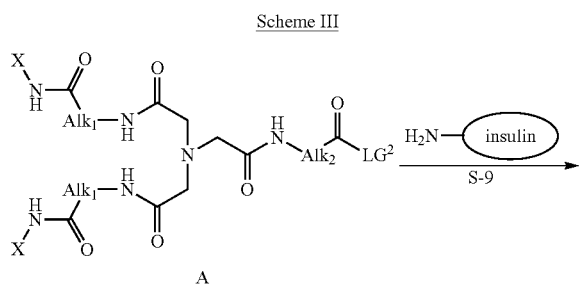

-continued

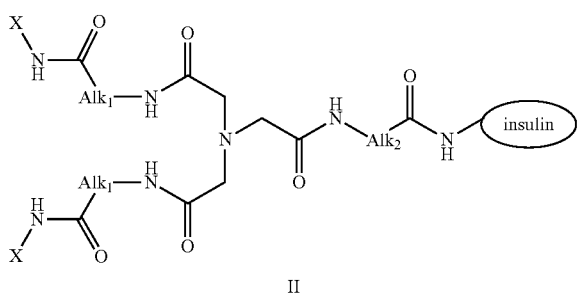

wherein X, $Alk_1$, $Alk_2$ and $LG^2$ are as defined above, and in classes and subclasses described above and herein.

As described herein, an insulin molecule may be conjugated at various amine positions. In certain embodiments, an insulin conjugate is shown in FIG. 1. In certain embodiments, an insulin molecule is conjugated at the B1, A1, or $Lys^{B29}$ position. Formula II in Scheme III shows just one point of conjugation for simplicity but it is to be understood that a compound of formula A may be conjugated at two or more positions on the insulin molecule as shown in Scheme II and formula I-a. In certain embodiments, an insulin molecule is conjugated at the A1 and $Lys^{B29}$ positions. In certain embodiments, an insulin molecule is conjugated at the A1 and B1 positions. In certain embodiments, an insulin molecule is conjugated at the B1 and $Lys^{B29}$ positions. In certain embodiments, an insulin molecule is conjugated at the A1, B1 and $Lys^{B29}$ positions. In certain embodiments, an insulin molecule is conjugated via the side chain of a non-terminal lysine residue which may or may not be present in the wild-type sequence of human insulin (e.g., at positions B3, B28 or B29).

Scheme IV

In some embodiments, W is an insulin molecule, $LG^2$ is —OSu and the present invention provides a method for preparing a conjugate of formula II from a compound of formula A-i as depicted in Scheme IV, below:

Scheme IV

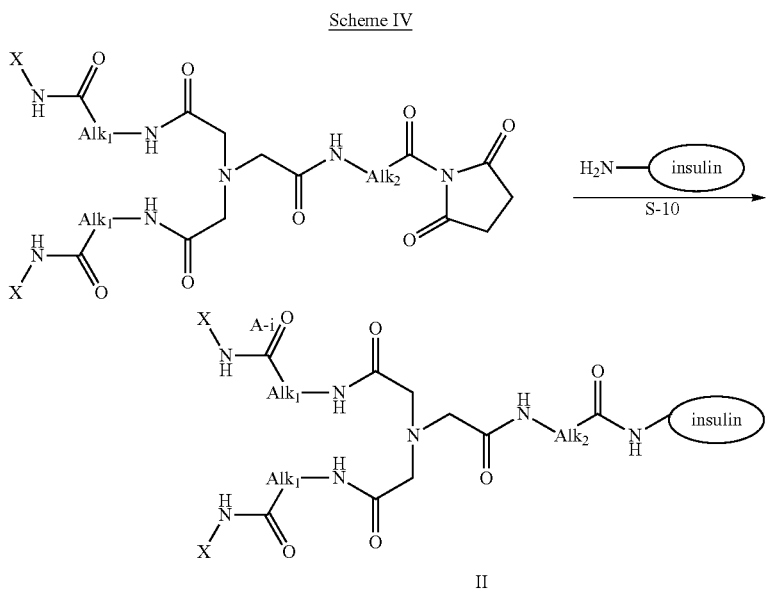

wherein X, $Alk_1$, and $Alk_2$ is as defined above, and in classes and subclasses described above and herein. Formula II in Scheme IV shows just one point of conjugation for simplicity but it is to be understood that a compound of formula A-i may be conjugated at two or more positions on the insulin molecule as shown in Scheme II and formula I-a.

In step S-10, the —OSu group on a compound of formula A-i is displaced by an insulin amino group as described above.

Synthesis of Conjugate I from Compound A

According to another aspect, the present invention provides a method for preparing a conjugate of formula I:

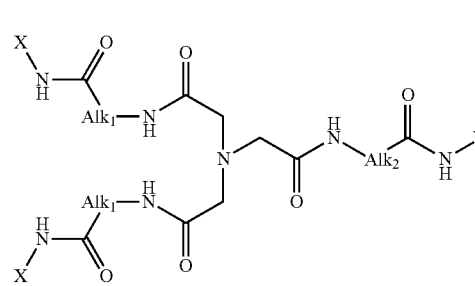

wherein:
    each occurrence of X is independently a ligand;
    each occurrence of Alk$_1$ is independently a C$_2$-C$_{12}$ alkylene chain, wherein one or more methylene units is optionally replaced by —O— or —S—;
    Alk$_2$ is a C$_2$-C$_{20}$ alkylene chain, wherein one or more methylene units is optionally replaced by —O— or —S—; and
    W is a drug;
comprising the steps of:
(a) providing a compound of formula A:

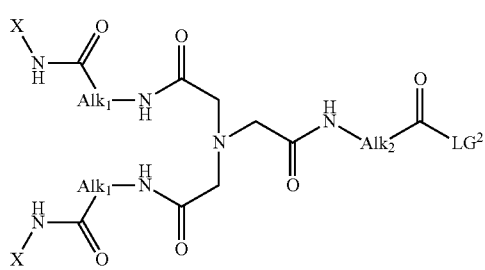

wherein:
    each occurrence of X is independently a ligand;
    each occurrence of Alk$_1$ is independently a C$_2$-C$_{12}$ alkylene chain, wherein one or more methylene units is optionally replaced by —O— or —S—;
    Alk$_2$ is a C$_2$-C$_{20}$ alkylene chain, wherein one or more methylene units is optionally replaced by —O— or —S—; and
    LG$^2$ is a suitable leaving group;
and
(b) reacting said compound of formula A with an amine-containing drug to form a conjugate of formula I.

Formula I above shows just one point of conjugation for simplicity but it is to be understood that a compound of formula A may be conjugated at two or more positions on the drug W as shown in Scheme II and formula I-a.

Synthesis of Conjugate II from Compound A

In certain embodiments, the present invention provides a method for preparing a conjugate of formula II:

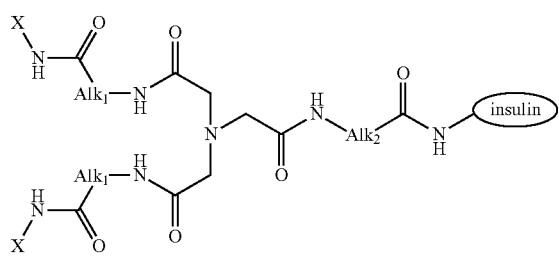

wherein:
    each occurrence of X is independently a ligand;
    each occurrence of Alk$_1$ is independently a C$_2$-C$_{12}$ alkylene chain, wherein one or more methylene units is optionally replaced by —O— or —S—; and
    Alk$_2$ is a C$_2$-C$_{20}$ alkylene chain, wherein one or more methylene units is optionally replaced by —O— or —S—;

comprising the steps of:
(a) providing a compound of formula A:

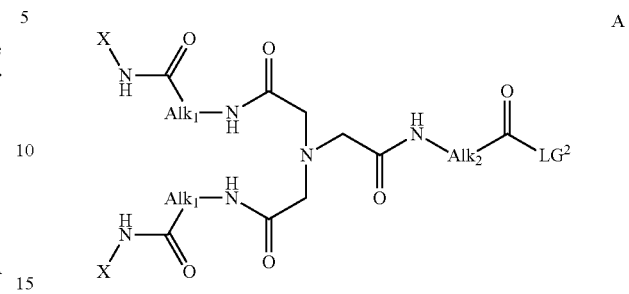

wherein:
    each occurrence of X is independently a ligand;
    each occurrence of Alk$_1$ is independently a C$_2$-C$_{12}$ alkylene chain, wherein one or more methylene units is optionally replaced by —O— or —S—;
    Alk$_2$ is a C$_2$-C$_{20}$ alkylene chain, wherein one or more methylene units is optionally replaced by —O— or —S—; and
    LG$^2$ is a suitable leaving group; and
(b) reacting said compound of formula A with an insulin molecule to form a compound of formula II.

As defined above, in compounds of formulae II and A each occurrence of X is independently a ligand. In certain embodiments, each occurrence of X is the same ligand. As defined above, in compounds of formula A, LG$^2$ is a suitable leaving group. In certain embodiments, LG$^2$ is —OSu.

Formula II above shows just one point of conjugation for simplicity but it is to be understood that a compound of formula A may be conjugated at two or more positions on the insulin molecule as shown in Scheme II and formula I-a.

In certain embodiments, the conjugate of formula II is selected from those depicted in FIG. 1.

Synthesis of Compound A from Compound B

According to another embodiment, the present invention provides a method for preparing a compound of formula A:

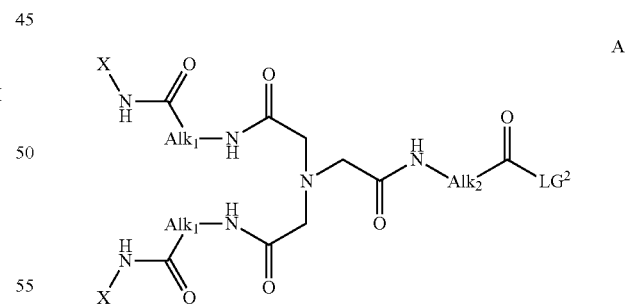

wherein:
    each occurrence of X is independently a ligand;
    each occurrence of Alk$_1$ is independently a C$_2$-C$_{12}$ alkylene chain, wherein one or more methylene units is optionally replaced by —O— or —S—; and
    Alk$_2$ is a C$_2$-C$_{20}$ alkylene chain, wherein one or more methylene units is optionally replaced by —O— or —S—;
    LG$^2$ is a suitable leaving group;

comprising the steps of:
(a) providing a compound of formula B:

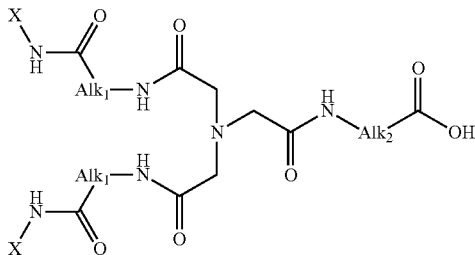

B wherein:
each occurrence of X is independently a ligand;
each occurrence of $Alk_1$ is independently a $C_2$-$C_2$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—;
and
(b) activating the carboxylic acid of said compound of formula B to form a compound of formula A.

Synthesis of Compound B from Compound C

According to another embodiment, the present invention provides a method for preparing a compound of formula B:

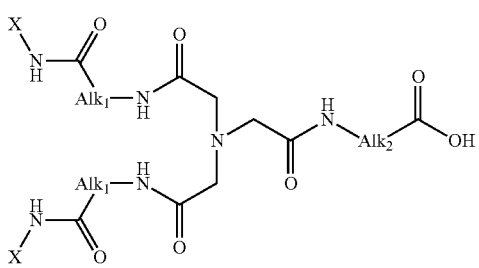

B wherein:
each occurrence of X is independently a ligand;
each occurrence of $Alk_1$ is independently a $C_2$-$C_{12}$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—;

comprising the steps of:
(a) providing a compound of formula C:

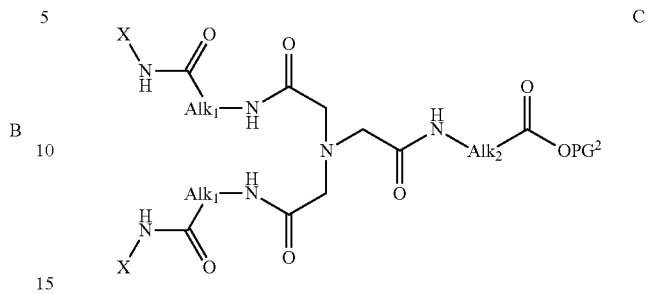

C wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
$PG^2$ is a carboxylic acid protecting group;
and
(b) deprotecting the compound of formula C to form a compound of formula B.

Synthesis of Compound C from Compounds D and F

Yet another aspect of the present invention provides a method for preparing a compound of formula C:

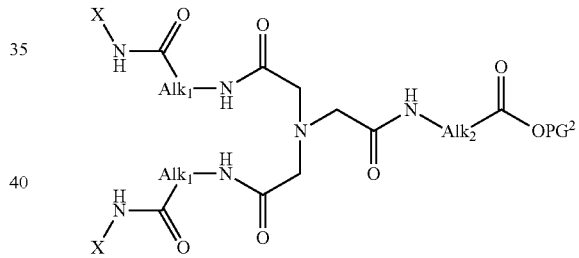

wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
$PG^2$ is a carboxylic acid protecting group;
comprising the steps of:
(a) providing a compound of formula D:

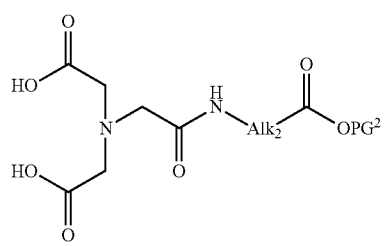

D wherein:
PG$^2$ is a carboxylic acid protecting group; and
Alk$_2$ is a C$_2$-C$_{20}$ alkylene chain, wherein one or more methylene units is optionally replaced by —O— or —S—;
and
(b) reacting the compound of formula D with a compound of formula F:

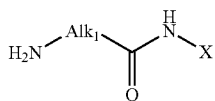

F wherein:
X is a ligand; and
Alk$_1$ is a C$_2$-C$_{12}$ alkylene chain, wherein one or more methylene units is optionally replaced by —O— or —S—;
to form a compound of formula C.

Synthesis of Compound D from Compound E

According to another embodiment, the present invention provides a method for preparing a compound of formula D:

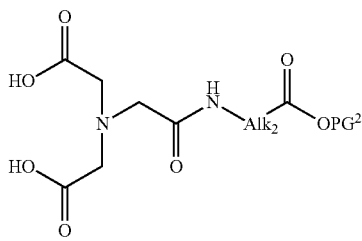

D wherein:
PG$^2$ is a carboxylic acid protecting group; and
Alk$_2$ is a C$_2$-C$_{20}$ alkylene chain, wherein one or more methylene units is optionally replaced by —O— or —S—;
comprising the steps of:
(a) providing a compound of formula E:

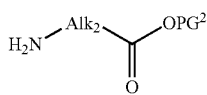

E wherein:
PG$^2$ is a carboxylic acid protecting group; and
Alk$_2$ is a C$_2$-C$_{20}$ alkylene chain, wherein one or more methylene units is optionally replaced by —O— or —S—;
and
(b) reacting the compound of formula E with 2-(2,6-dioxomorpholino)acetic acid to afford a compound of formula D.

Synthesis of Compound F from Compound G

In certain embodiments, the present invention provides a method for preparing a compound of formula F:

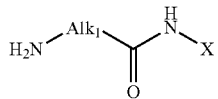

F wherein:
X is a ligand; and
Alk$_1$ is a C$_2$-C$_{12}$ alkylene chain, wherein one or more methylene units is optionally replaced by —O— or —S—;
comprising the steps of:
(a) providing a compound of formula G:

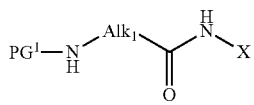

G wherein:
X is a ligand;
Alk$_1$ is a C$_2$-C$_{12}$ alkylene chain, wherein one or more methylene units is optionally replaced by —O— or —S—; and
PG$^1$ is an amino protecting group;
and
(b) deprotecting the compound of formula G to afford a compound of formula F.

Synthesis of Compound G from Compound H

According to another embodiment, the present invention provides a method for preparing a compound of formula G:

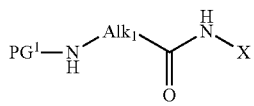

G wherein:
X is a ligand;
Alk$_1$ is a C$_2$-C$_{12}$ alkylene chain, wherein one or more methylene units is optionally replaced by —O— or —S—; and
PG$^1$ is an amino protecting group;
comprising the steps of:
(a) providing a compound of formula H:

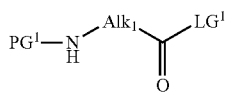

H wherein:
PG$^1$ is an amino protecting group;
Alk$_1$ is a C$_2$-C$_{12}$ alkylene chain, wherein one or more methylene units is optionally replaced by —O— or —S—; and
LG$^1$ is a suitable leaving group;

and (b) reacting the compound of formula H with an amine-containing ligand H$_2$N—X (J) to form a compound of formula G.

Synthesis of Compound A (Steps S-1, S-2, S-4, S-5, and S-6)

According to another embodiment, the present invention provides a method for preparing a compound of formula A:

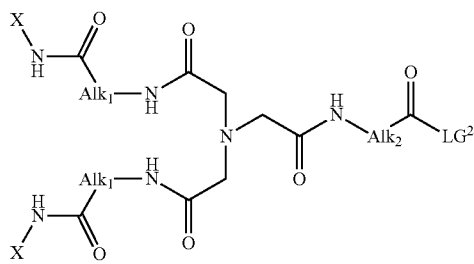

A wherein:
each occurrence of X is independently a ligand;
each occurrence of Alk$_1$ is independently a C$_2$-C$_{12}$ alkylene chain, wherein one or more methylene units is optionally replaced by —O— or —S—;
Alk$_2$ is a C$_2$-C$_{20}$ alkylene chain, wherein one or more methylene units is optionally replaced by —O— or —S—; and
LG$^2$ is a suitable leaving group; comprising the steps of:

(a) providing a compound of formula H:

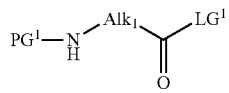

H wherein:
PG$^1$ is an amino protecting group;
Alk$_1$ is a C$_2$-C$_{12}$ alkylene chain, wherein one or more methylene units is optionally replaced by —O— or —S—; and
LG$^1$ is a suitable leaving group;

(b) reacting the compound of formula H with an amine-containing ligand H$_2$N—X (J) to form a compound of formula G:

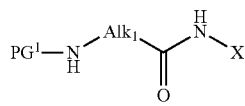

G wherein:
X is a ligand;
Alk$_1$ is a C$_2$-C$_{12}$ alkylene chain, wherein one or more methylene units is optionally replaced by —O— or —S—; and
PG$^1$ is an amino protecting group;

(c) deprotecting the compound of formula G to afford a compound of formula F:

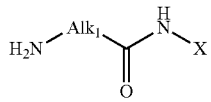

F wherein:
X is a ligand; and
Alk$_1$ is a C$_2$-C$_{12}$ alkylene chain, wherein one or more methylene units is optionally replaced by —O— or —S—;

(d) reacting the compound of formula F with a compound of formula D:

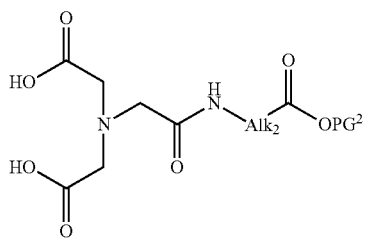

D wherein:
PG$^2$ is a carboxylic acid protecting group; and
Alk$_2$ is a C$_2$-C$_{20}$ alkylene chain, wherein one or more methylene units is optionally replaced by —O— or —S—;

to form a compound of formula C:

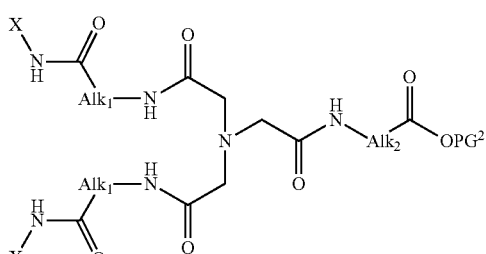

C wherein:
each occurrence of X is independently a ligand;
each occurrence of Alk$_1$ is independently a C$_2$-C$_{12}$ alkylene chain, wherein one or more methylene units is optionally replaced by —O— or —S—;
Alk$_2$ is a C$_2$-C$_{20}$ alkylene chain, wherein one or more methylene units is optionally replaced by —O— or —S—; and
PG$^2$ is a carboxylic acid protecting group;

(e) deprotecting the compound of formula C to form a compound of formula B:

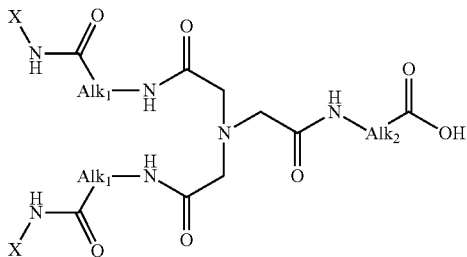

wherein:
each occurrence of X is independently a ligand;
each occurrence of $Alk_1$ is independently a $C_2$-$C_{12}$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—;
and
(f) activating the carboxylic acid of said compound of formula B to form a compound of formula A.

Synthesis of Compound A (Steps S-3 Through S-6)

According to another embodiment, the present invention provides a method for preparing a compound of formula A:

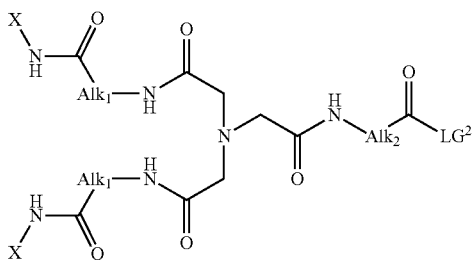

wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
$LG^2$ is a suitable leaving group;
comprising the steps of:
(a) providing a compound of formula E:

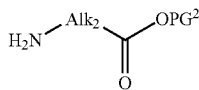

wherein:
$PG^2$ is a carboxylic acid protecting group; and
$Alk_2$ is a $C_2$-$C_{20}$ alkylene chain, wherein one or more methylene units is optionally replaced by —O— or —S—;
(b) reacting the compound of formula E with 2-(2,6-dioxomorpholino)acetic acid to afford a compound of formula D:

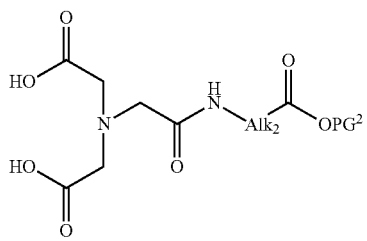

wherein:
$PG^2$ is a carboxylic acid protecting group; and
$Alk_2$ is a $C_2$-$C_{20}$ alkylene chain, wherein one or more methylene units is optionally replaced by —O— or —S—;
(c) reacting the compound of formula D with a compound of formula F:

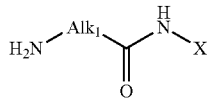

to form a compound of formula C:

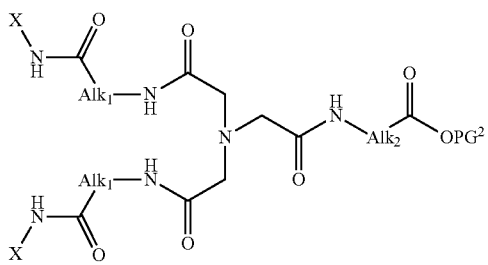

wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
$PG^2$ is a carboxylic acid protecting group;

(d) deprotecting the compound of formula C to form a compound of formula B:

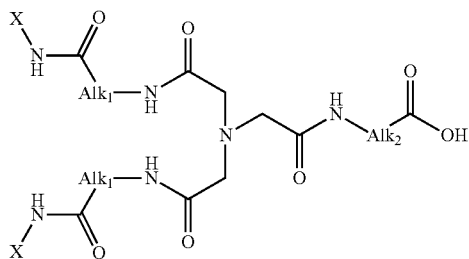

B wherein:
each occurrence of X is independently a ligand,
each occurrence of $Alk_1$ is independently a $C_2$-$C_{12}$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—;
and
(e) activating the carboxylic acid of said compound of formula B to form a compound of formula A.

Synthesis of Conjugate I (Steps S-1, S-2, S-4, S-5, S-6, and S-7)

According to another embodiment, the present invention provides a method for preparing a conjugate of formula I:

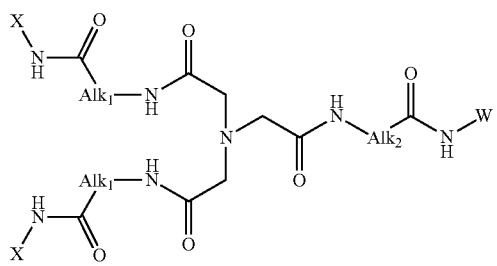

I wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
W is a drug;
comprising the steps of:
(a) providing a compound of formula H:

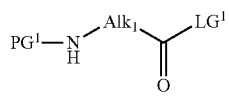

H wherein:
$PG^1$ is an amino protecting group;
$Alk_1$ is a $C_2$-$C_2$ alkylene chain, wherein one or more methylene units is optionally replaced by —O— or —S—; and
$LG^1$ is a suitable leaving group;
(b) reacting the compound of formula H with an amine-containing ligand $H_2N$—X (J) to form a compound of formula G:

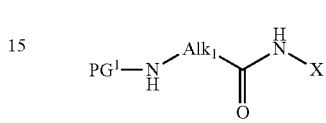

G wherein:
X is a ligand;
$Alk_1$ is a $C_2$-$C_{12}$ alkylene chain, wherein one or more methylene units is optionally replaced by —O— or —S—; and
$PG^1$ is an amino protecting group;
(c) deprotecting the compound of formula G to afford a compound of formula F:

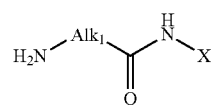

F wherein:
X is a ligand; and
$Alk_1$ is a $C_2$-$C_{12}$ alkylene chain, wherein one or more methylene units is optionally replaced by —O— or —S—;
(d) reacting the compound of formula F with a compound of formula D:

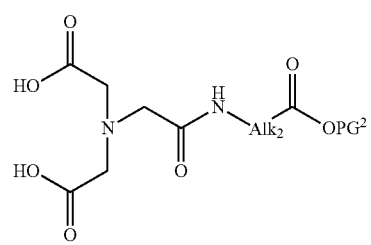

D wherein:
$PG^2$ is a carboxylic acid protecting group; and
$Alk_2$ is a $C_2$-$C_{20}$ alkylene chain, wherein one or more methylene units is optionally replaced by —O— or —S—;

to form a compound of formula C:

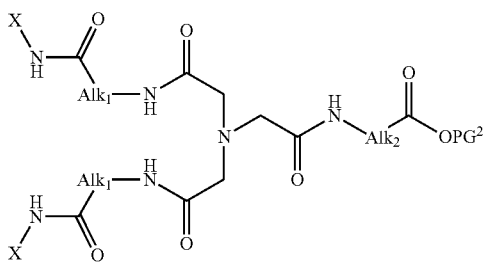

wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
$PG^2$ is a carboxylic acid protecting group;
(e) deprotecting the compound of formula C to form a compound of formula B:

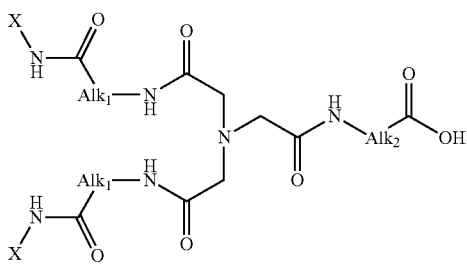

wherein:
each occurrence of X is independently a ligand;
each occurrence of $Alk_1$ is independently a $C_2$-$C_{12}$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—;
and
(f) activating the carboxylic acid of said compound of formula B to form a compound of formula A:

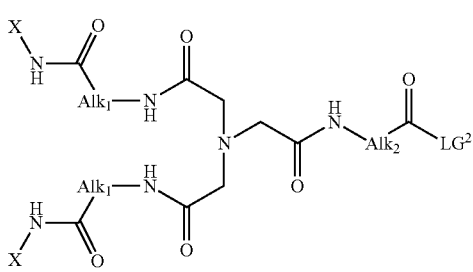

wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
$LG^2$ is a suitable leaving group;
and
(g) reacting the compound of formula A with an amine-containing drug to form a conjugate of formula I.

Formula I above shows just one point of conjugation for simplicity but it is to be understood that a compound of formula A may be conjugated at two or more positions on the drug W as shown in Scheme II and formula I-a.

Synthesis of Conjugate I (Steps S-3 Through S-7)

According to another embodiment, the present invention provides a method for preparing a conjugate of formula I:

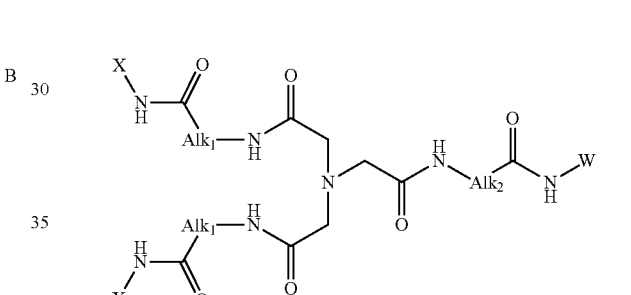

wherein:
each occurrence of X is independently a ligand;
each occurrence of $Akl_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
W is a drug;
comprising the steps of:
(a) providing a compound of formula E:

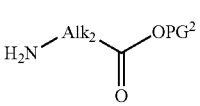

wherein:
$PG^2$ is a carboxylic acid protecting group; and
$Alk_2$ is a $C_2$-$C_{20}$ alkylene chain, wherein one or more methylene units is optionally replaced by —O— or —S—;

(b) reacting the compound of formula E with 2-(2,6-dioxomorpholino)acetic acid to afford a compound of formula D:

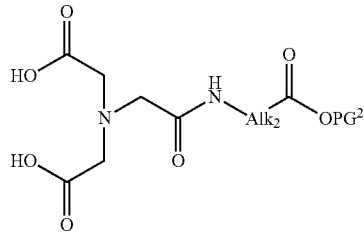

D wherein:

PG$^2$ is a carboxylic acid protecting group; and

Alk$_2$ is a C$_2$-C$_{20}$ alkylene chain, wherein one or more methylene units is optionally replaced by —O— or —S—;

(c) reacting the compound of formula D with a compound of formula F:

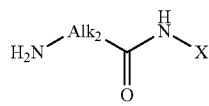

F wherein:

X is a ligand; and

Alk$_1$ is a C$_2$-C$_{12}$ alkylene chain, wherein one or more methylene units is optionally replaced by —O— or —S—;

to form a compound of formula C:

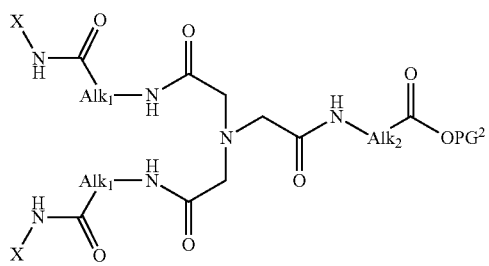

C wherein:

each occurrence of X is independently a ligand;

each occurrence of Alk$_1$ is independently a C$_2$-C$_{12}$ alkylene chain, wherein one or more methylene units is optionally replaced by —O— or —S—;

Alk$_2$ is a C$_2$-C$_{20}$ alkylene chain, wherein one or more methylene units is optionally replaced by —O— or —S—; and PG$^2$ is a carboxylic acid protecting group;

(d) deprotecting the compound of formula C to form a compound of formula B:

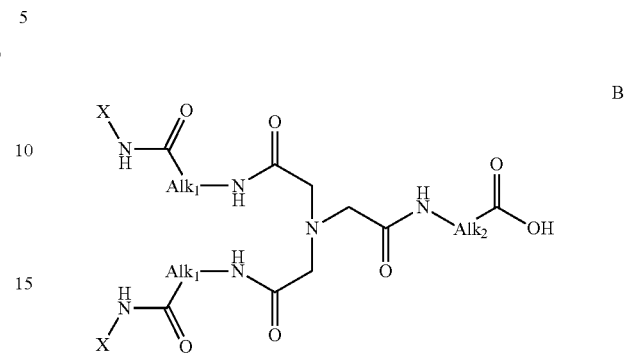

B wherein:

each occurrence of X is independently a ligand;

each occurrence of Alk$_1$ is independently a C$_2$-C$_{12}$ alkylene chain, wherein one or more methylene units is optionally replaced by —O— or —S—; and Alk$_2$ is a C$_2$-C$_{20}$ alkylene chain, wherein one or more methylene units is optionally replaced by —O— or —S—;

(e) activating the carboxylic acid of said compound of formula B to form a compound of formula A:

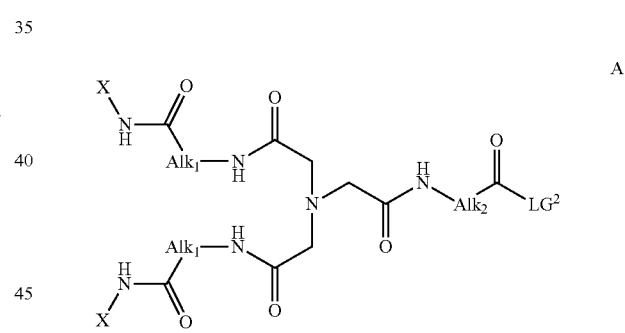

A wherein:

each occurrence of X is independently a ligand;

each occurrence of Alk$_1$ is independently a C$_2$-C$_{12}$ alkylene chain, wherein one or more methylene units is optionally replaced by —O— or —S—;

Alk$_2$ is a C$_2$-C$_{20}$ alkylene chain, wherein one or more methylene units is optionally replaced by —O— or —S—; and LG$^2$ is a suitable leaving group;

and (f) reacting the compound of formula A with an amine-containing drug to form a conjugate of formula I.

Formula I above shows just one point of conjugation for simplicity but it is to be understood that a compound of formula A may be conjugated at two or more positions on the drug W as shown in Scheme II and formula I-a.

Synthesis of Conjugate II (Steps S-1, S-2, S-4, S-5, S-6, and S-9)

According to another embodiment, the present invention provides a method for preparing a conjugate of formula II:

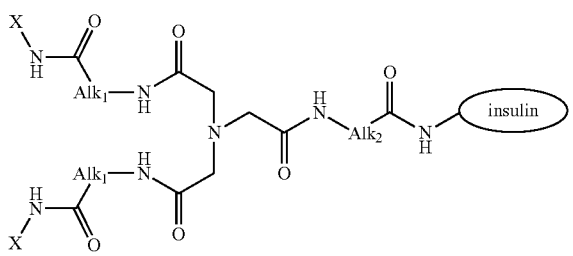

II wherein:
each occurrence of X is independently a ligand;
each occurrence of $Alk_1$ is independently a $C_2$-$C_{12}$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—; comprising the steps of:

(a) providing a compound of formula H:

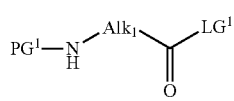

H wherein:
$PG^1$ is an amino protecting group;
$Alk_1$ is a $C_2$-$C_{12}$ alkylene chain, wherein one or more methylene units is optionally replaced by —O— or —S—; and
$LG^1$ is a suitable leaving group;

(b) reacting the compound of formula H with an amine-containing ligand $H_2N$—X (J) to form a compound of formula G:

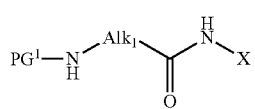

G wherein:
X is a ligand;
$Alk_1$ is a $C_2$-$C_{12}$ alkylene chain, wherein one or more methylene units is optionally replaced by —O— or —S—; and
$PG^1$ is an amino protecting group;

(c) deprotecting the compound of formula G to afford a compound of formula F:

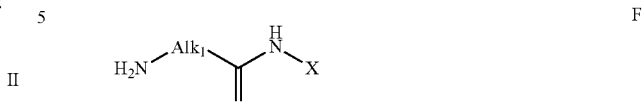

F wherein:
X is a ligand; and
$Alk_1$ is a $C_2$-$C_{12}$ alkylene chain, wherein one or more methylene units is optionally replaced by —O— or —S—;

(d) reacting the compound of formula F with a compound of formula D:

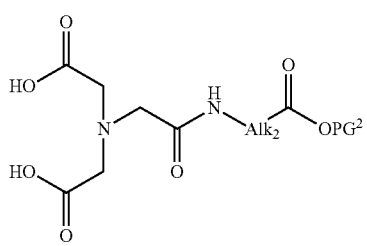

D wherein:
$PG^2$ is a carboxylic acid protecting group; and
$Alk_2$ is a $C_2$-$C_{20}$ alkylene chain, wherein one or more methylene units is optionally replaced by —O— or —S—;

to form a compound of formula C:

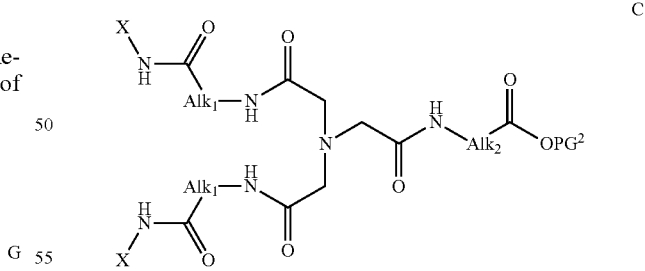

C wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
$PG^2$ is a carboxylic acid protecting group;

(e) deprotecting the compound of formula C to form a compound of formula B:

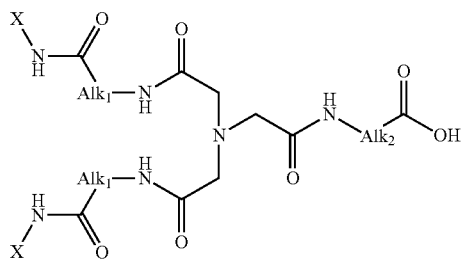

B wherein:
each occurrence of X is independently a ligand;
each occurrence of $Alk_1$ is independently a $C_2$-$C_{12}$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—;

(f) activating the carboxylic acid of said compound of formula B to form a compound of formula A:

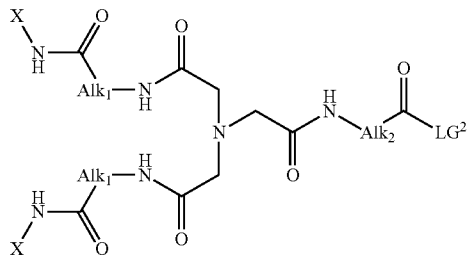

A wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
$LG^2$ is a suitable leaving group;
and (g) reacting the compound of formula A with an insulin molecule to form a conjugate of formula II.

Formula II above shows just one point of conjugation for simplicity but it is to be understood that a compound of formula A may be conjugated at two or more positions on the insulin molecule as shown in Scheme II and formula I-a.

Synthesis of Conjugate II (Steps S-3, S-4, S-5, S-6, and S-8)

According to another embodiment, the present invention provides a method for preparing a conjugate of formula II:

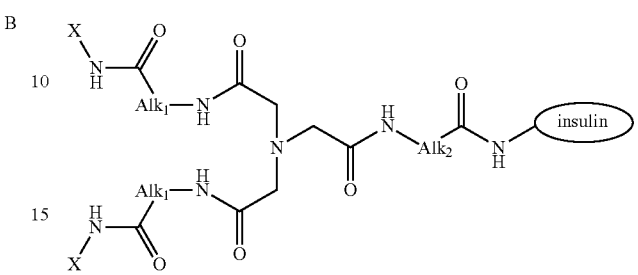

II wherein:
each occurrence of X is independently a ligand;
each occurrence of $Alk_1$ is independently a $C_2$-$C_{12}$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—;

comprising the steps of:
(a) providing a compound of formula E:

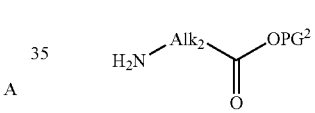

E wherein:
$PG^2$ is a carboxylic acid protecting group; and
$Alk_2$ is a $C_2$-$C_{20}$ alkylene chain, wherein one or more methylene units is optionally replaced by —O— or —S—;

(b) reacting the compound of formula E with 2-(2,6-dioxomorpholino)acetic acid to afford a compound of formula D:

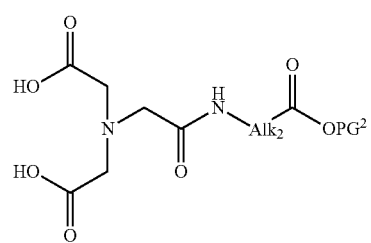

D wherein:
$PG^2$ is a carboxylic acid protecting group; and
$Alk_2$ is a $C_2$-$C_{20}$ alkylene chain, wherein one or more methylene units is optionally replaced by —O— or —S—;

(c) reacting the compound of formula D with a compound of formula F:

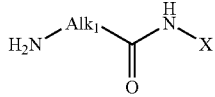

wherein:

X is a ligand; and

Alk$_1$ is a C$_2$-C$_{12}$ alkylene chain, wherein one or more methylene units is optionally replaced by —O— or —S—;

to form a compound of formula C:

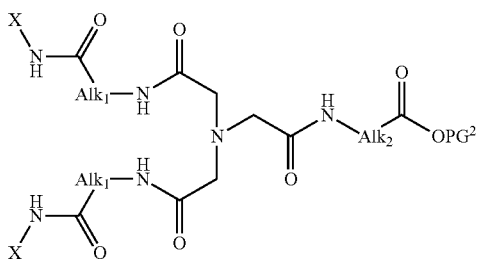

wherein:

each occurrence of X is independently a ligand;

each occurrence of Alk$_1$ is independently a C$_2$-C$_{12}$ alkylene chain, wherein one or more methylene units is optionally replaced by —O— or —S—;

Alk$_2$ is a C$_2$-C$_{20}$ alkylene chain, wherein one or more methylene units is optionally replaced by —O— or —S—; and PG$^2$ is a carboxylic acid protecting group;

(d) deprotecting the compound of formula C to form a compound of formula B:

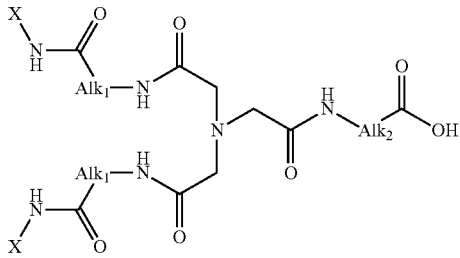

wherein:

each occurrence of X is independently a ligand;

each occurrence of Alk$_1$ is independently a C$_2$-C$_{12}$ alkylene chain, wherein one or more methylene units is optionally replaced by —O— or —S—; and Alk$_2$ is a C$_2$-C$_{20}$ alkylene chain, wherein one or more methylene units is optionally replaced by —O— or —S—;

(e) activating the carboxylic acid of said compound of formula B to form a compound of formula A:

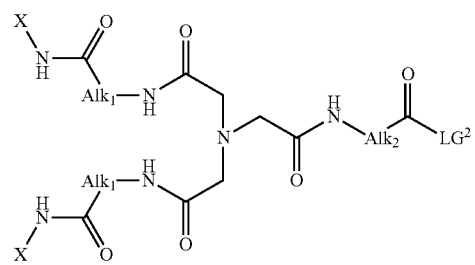

wherein:

each occurrence of X is independently a ligand;

each occurrence of Alk$_1$ is independently a C$_2$-C$_{12}$ alkylene chain, wherein one or more methylene units is optionally replaced by —O— or —S—;

Alk$_2$ is a C$_2$-C$_{20}$ alkylene chain, wherein one or more methylene units is optionally replaced by —O— or —S—; and LG$^2$ is a suitable leaving group;

and (f) reacting the compound of formula A with an insulin molecule to form a conjugate of formula II.

Formula II above shows just one point of conjugation for simplicity but it is to be understood that a compound of formula A may be conjugated at two or more positions on the insulin molecule as shown in Scheme II and formula I-a.

Synthesis of Conjugate I (Steps S-4 Through S-7)

According to another embodiment, the present invention provides a method for preparing a conjugate of formula I:

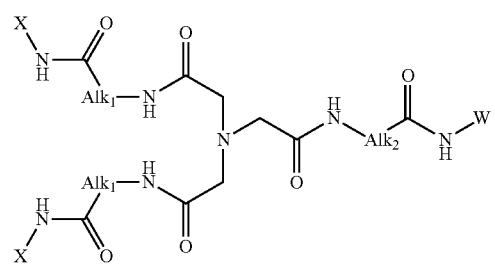

wherein:

each occurrence of X is independently a ligand;

each occurrence of Alk$_1$ is independently a C$_2$-C$_{12}$ alkylene chain, wherein one or more methylene units is optionally replaced by —O— or —S—;

Alk$_2$ is a C$_2$-C$_{20}$ alkylene chain, wherein one or more methylene units is optionally replaced by —O— or —S—; and W is a drug;

comprising the steps of:

(a) providing a compound of formula D:

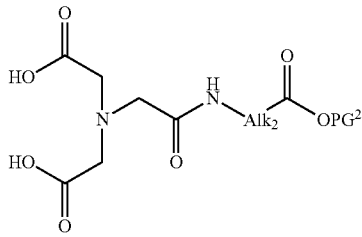

D wherein:
PG² is a carboxylic acid protecting group; and
Alk₂ is a C₂-C₂₀ alkylene chain, wherein one or more methylene units is optionally replaced by —O— or —S—;

(b) reacting the compound of formula D with a compound of formula F:

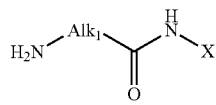

F wherein:
X is a ligand; and
Alk₁ is a C₂-C₁₂ alkylene chain, wherein one or more methylene units is optionally replaced by —O— or —S—;

to form a compound of formula C:

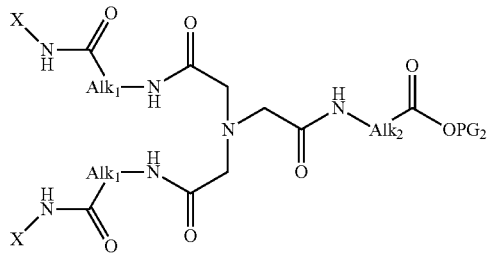

C wherein:
each occurrence of X is independently a ligand;
each occurrence of Alk₁ is independently a C₂-C₁₂ alkylene chain, wherein one or more methylene units is optionally replaced by —O— or —S—;
Alk₂ is a C₂-C₂₀ alkylene chain, wherein one or more methylene units is optionally replaced by —O— or —S—; and
PG² is a carboxylic acid protecting group;

(c) deprotecting the compound of formula C to form a compound of formula B:

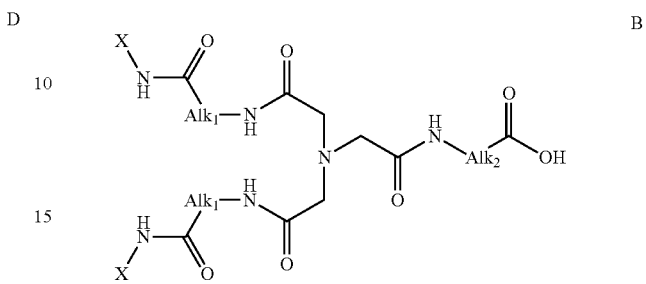

B wherein:
each occurrence of X is independently a ligand;
each occurrence of Alk₁ is independently a C₂-C₁₂ alkylene chain, wherein one or more methylene units is optionally replaced by —O— or —S—; and
Alk₂ is a C₂-C₂₀ alkylene chain, wherein one or more methylene units is optionally replaced by —O— or —S—;

(d) activating the carboxylic acid of said compound of formula B to form a compound of formula A:

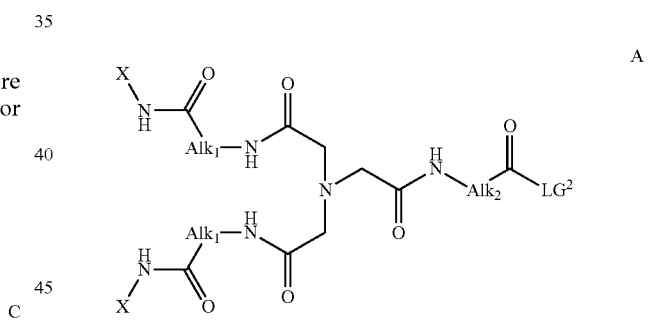

A wherein:
each occurrence of X is independently a ligand;
each occurrence of Alk₁ is independently a C₂-C₁₂ alkylene chain, wherein one or more methylene units is optionally replaced by —O— or —S—;
Alk₂ is a C₂-C₂₀ alkylene chain, wherein one or more methylene units is optionally replaced by —O— or —S—; and
LG² is a suitable leaving group;

and (e) reacting the compound of formula A with an amine containing drug to form a conjugate of formula I.

Formula I above shows just one point of conjugation for simplicity but it is to be understood that a compound of formula A may be conjugated at two or more positions on the drug W as shown in Scheme II and formula I-a.

Synthesis of Conjugate II (Steps S-4, S-5, S-6, and S-8)

According to another embodiment, the present invention provides a method for preparing a conjugate of formula II:

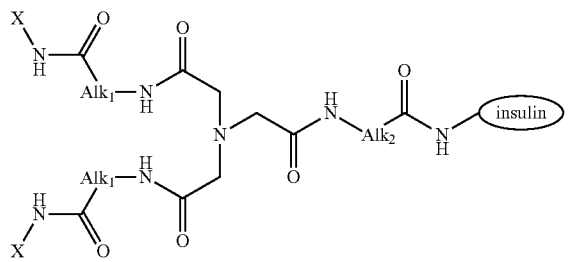

II wherein:
each occurrence of X is independently a ligand;
each occurrence of $Alk_1$ is independently a $C_2$-$C_{12}$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—;

comprising the steps of:
(a) providing a compound of formula D:

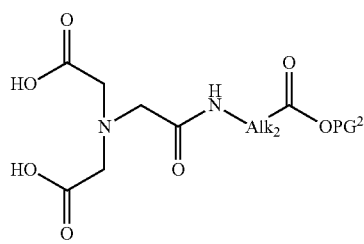

D wherein:
$PG^2$ is a carboxylic acid protecting group; and
$Alk_2$ is a $C_2$-$C_{20}$ alkylene chain, wherein one or more methylene units is optionally replaced by —O— or —S—;

(b) reacting the compound of formula D with a compound of formula F:

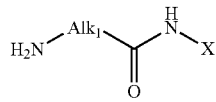

F wherein:
X is a ligand; and
$Alk_1$ is a $C_2$-$C_{12}$ alkylene chain, wherein one or more methylene units is optionally replaced by —O— or —S—;

to form a compound of formula C:

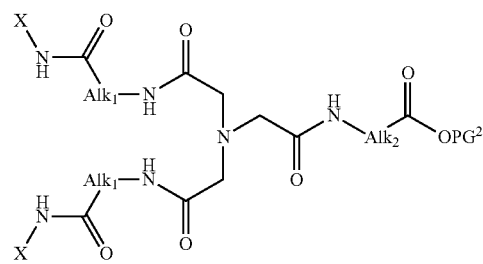

C wherein:
each occurrence of X is independently a ligand;
each occurrence of $Alk_1$ is independently a $C_2$-$C_{12}$ alkylene chain, wherein one or more methylene units is optionally replaced by —O— or —S—;
$Alk_2$ is a $C_2$-$C_{20}$ alkylene chain, wherein one or more methylene units is optionally replaced by —O— or —S—; and
$PG^2$ is a carboxylic acid protecting group;

(c) deprotecting the compound of formula C to form a compound of formula B:

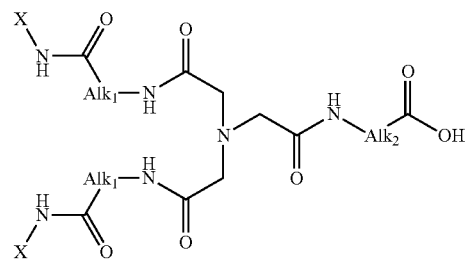

B wherein:
each occurrence of X is independently a ligand;
each occurrence of $Alk_1$ is independently a $C_2$-$C_{12}$ alkylene chain, wherein one or more methylene units is optionally replaced by —O— or —S—; and
$Alk_2$ is a $C_2$-$C_{20}$ alkylene chain, wherein one or more methylene units is optionally replaced by —O— or —S—;

(d) activating the carboxylic acid of said compound of formula B to form a compound of formula A:

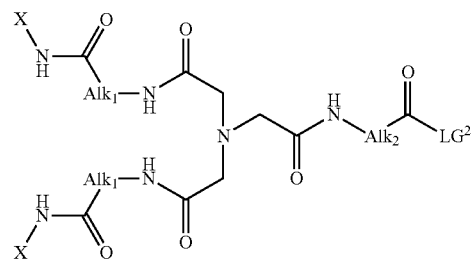

A wherein:
each occurrence of X is independently a ligand;
each occurrence of $Alk_1$ is independently a $C_2$-$C_{12}$ alkylene chain, wherein one or more methylene units is optionally replaced by —O— or —S—;

Alk$_2$ is a C$_2$-C$_{20}$ alkylene chain, wherein one or more methylene units is optionally replaced by —O— or —S—; and LG$^2$ is a suitable leaving group;

and (e) reacting the compound of formula A with an insulin molecule to form a conjugate of formula II.

Formula II above shows just one point of conjugation for simplicity but it is to be understood that a compound of formula A may be conjugated at two or more positions on the insulin molecule as shown in Scheme II and formula I-a.

Intermediate Compound G

Another aspect of the present invention provides a compound of formula G:

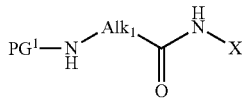

G wherein:

X is a ligand;

Alk$_1$ is a C$_2$-C$_{12}$ alkylene chain, wherein one or more methylene groups may be substituted by —O— or —S—; and PG$^1$ is an amino protecting group.

For compounds of formula G, each of X, Alk$_1$, and PG$^1$ are as described in embodiments herein. In some embodiments, Alk$_1$ is a C$_6$ alkylene chain. In certain embodiments, X is EG, EM, EBM, ETM, EGA, or EF as described herein. According to one aspect of the present invention, the compound of formula G is

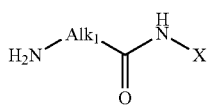

G-1

Intermediate Compound F

Yet another aspect of the present invention provides a compound of formula F:

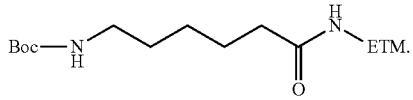

F wherein:

Alk$_1$ is a C$_2$-C$_{12}$ alkylene chain, wherein one or more methylene groups may be substituted by —O— or —S—; and X is a ligand.

For compounds of formula F, each of Alk$_1$ and X are as described in embodiments herein. In some embodiments, Alk$_1$ is a C$_6$ alkylene chain. In certain embodiments, X is EG, EM, EBM, ETM, EGA, or EF as described herein. According to one aspect of the present invention, the compound of formula F is

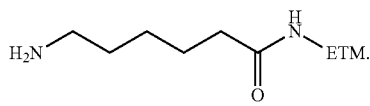

F-1

Intermediate Compound D

Yet another aspect of the present invention provides a compound of formula D:

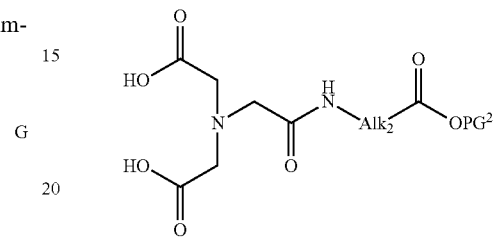

D wherein:

Alk$_2$ is a C$_2$-C$_{20}$ alkylene chain, wherein one or more methylene groups may be substituted by —O— or —S—; and PG$^2$ is a carboxylic acid protecting group.

For compounds of formula D, each of Alk$_2$ and PG$^2$ are as described in embodiments herein. In some embodiments, Alk$_2$ is a C$_6$ alkylene chain. According to one aspect of the present invention, the compound of formula D is

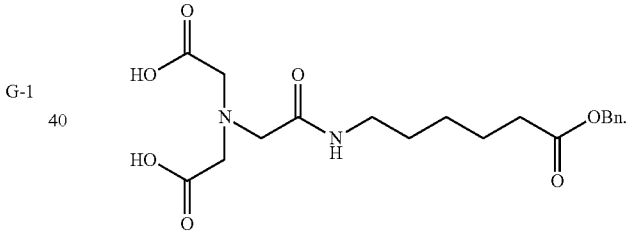

D-1

Intermediate Compound C

Yet another aspect of the present invention provides a compound of formula C:

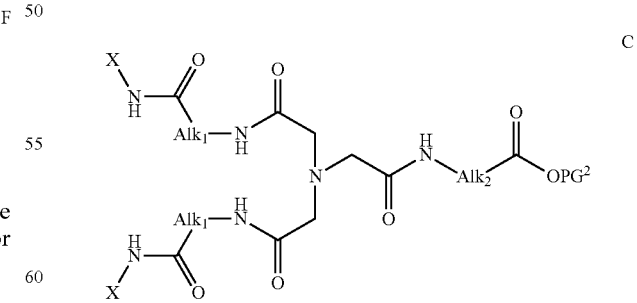

C wherein:

each occurrence of X is independently a ligand;

each occurrence of Alk$_1$ is independently a C$_2$-C$_{12}$ alkylene chain, wherein one or more methylene groups may be substituted by —O— or —S—;

Alk$_2$ is a C$_2$-C$_{20}$ alkylene chain, wherein one or more methylene groups may be substituted by —O— or —S—; and PG$^2$ is a carboxylic acid protecting group.

For compounds of formula C, each of X, Alk$_1$, Alk$_2$, and PG$^2$ are as described in embodiments herein. In some embodiments, Alk$_1$ is a C$_6$ alkylene chain. In certain embodiments, X is EG, EM, EBM, ETM, EGA, or EF as described herein. In some embodiments, Alk$_2$ is a C$_6$ alkylene chain. According to one aspect of the present invention, the compound of formula C is

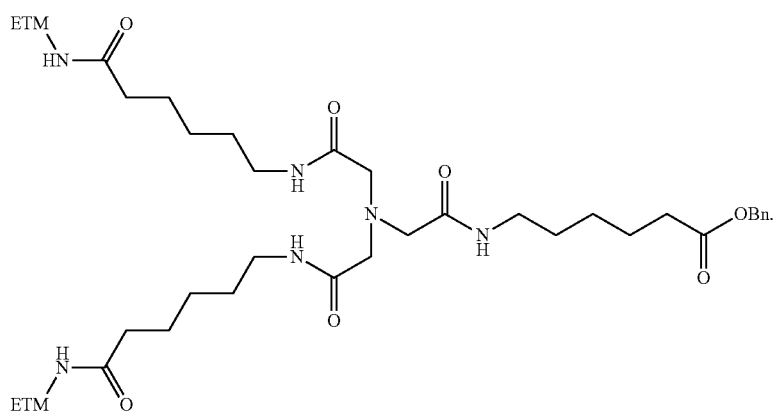

C-1

Intermediate Compound B

Yet another aspect of the present invention provides a compound of formula B:

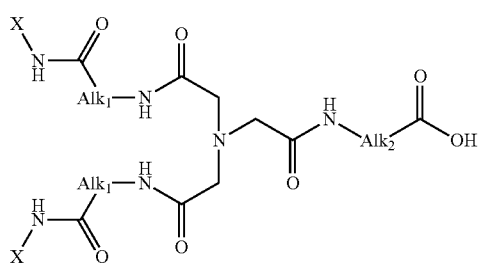

B wherein:

each occurrence of X is independently a ligand;

each occurrence of Alk$_1$ is independently a C$_2$-C$_{12}$ alkylene chain, wherein one or more methylene groups may be substituted by —O— or —S—; and Alk$_2$ is a C$_2$-C$_{20}$ alkylene chain, wherein one or more methylene groups may be substituted by —O— or —S—.

For compounds of formula B, each of X, Alk$_1$, and Alk$_2$ are as described in embodiments herein. In some embodiments, Alk$_1$ is a C$_6$ alkylene chain. In some embodiments, Alk$_2$ is a C$_6$ alkylene chain. In certain embodiments, X is EG, EM, EBM, ETM, EGA, or EF as described herein. According to one aspect of the present invention, the compound of formula B is

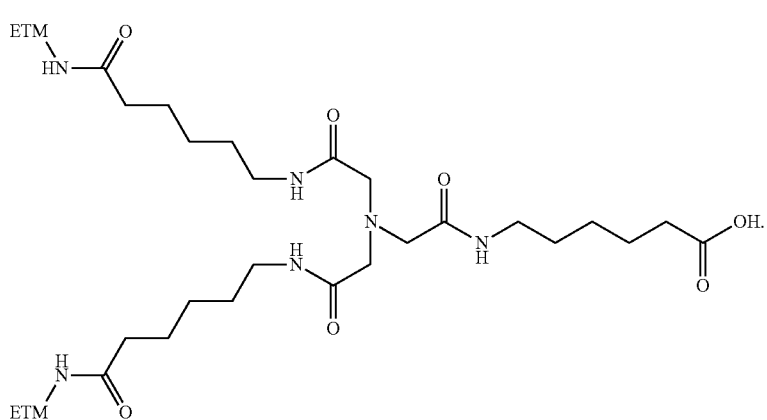

B-1

Intermediate Compound A

Another aspect of the present invention provides a compound of formula A:

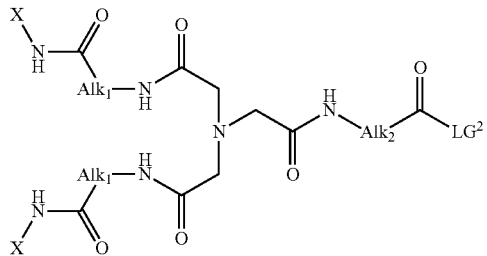

wherein:
  each occurrence of X is independently a ligand;
  each occurrence of Alk1 is independently a $C_2$-$C_{12}$ alkylene chain, wherein one or more methylene groups may be substituted by —O— or —S—;
  $Alk_2$ is a $C_2$-$C_{20}$ alkylene chain, wherein one or more methylene groups may be substituted by —O— or —S—; and
  $LG^2$ is a suitable leaving group.

For compounds of formula A, each of X, $Alk_1$, $Alk_2$, and $LG^2$ are as described in embodiments herein. In some embodiments, $Alk_1$ is a $C_6$ alkylene chain. In certain embodiments, X is EG, EM, EBM, ETM, EGA, or EF as described herein. In some embodiments, $Alk_2$ is a $C_6$ alkylene chain. According to one aspect of the present invention, the compound of formula A is

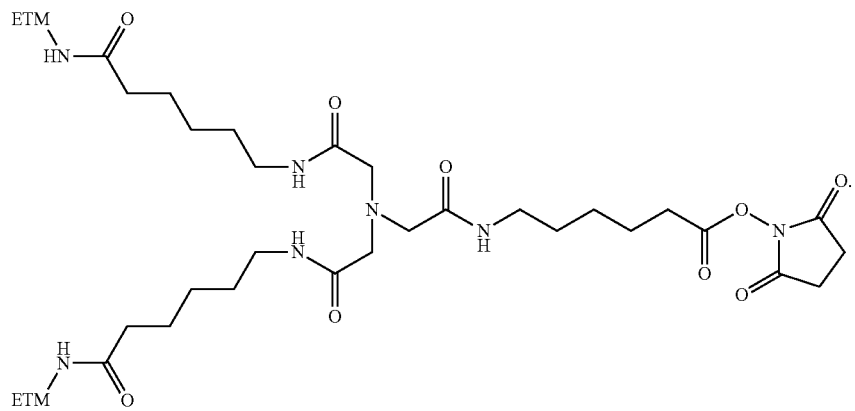

A-1

In any of the aforementioned embodiments, when W is an insulin molecule, the following may apply:

In certain embodiments, X is any one of ETM, EM, EBM, EG, EGA, and EF, and intermediate compound A reacts with the B1 amino group of the insulin molecule.

In certain embodiments, X is any one of ETM, EM, EBM, EG, EGA, and EF, and intermediate compound A reacts with the A1 amino group of the insulin molecule.

In certain embodiments, X is any one of ETM, EM, EBM, EG, EGA, and EF, and intermediate compound A reacts with the $Lys^{B29}$ amino group of the insulin molecule.

In certain embodiments, X is any one of ETM, EM, EBM, EG, EGA, and EF, and intermediate compound A reacts with the A1 and B1 amino groups of the insulin molecule.

In certain embodiments, X is any one of ETM, EM, EBM, EG, EGA, and EF, and intermediate compound A reacts with the B1 and $Lys^{B29}$ amino groups of the insulin molecule.

In certain embodiments, X is any one of ETM, EM, EBM, EG, EGA, and EF, and intermediate compound A reacts with the A1 and $Lys^{B29}$ amino groups of the insulin molecule.

In certain embodiments, X is any one of ETM, EM, EBM, EG, EGA, and EF, and intermediate compound A reacts with the A1, B1, and $Lys^{B29}$ amino groups of the insulin molecule.

In any of the aforementioned embodiments, when W is an insulin molecule, the following may apply:

In certain embodiments, X is ETM, and intermediate compound A reacts with the B1 amino group of the insulin molecule, the A1 amino group of the insulin molecule, the $Lys^{B29}$ amino group of the insulin molecule, the A1 and B1 amino groups of the insulin molecule, the B and $Lys^{B29}$ amino groups of the insulin molecule, the A1 and $Lys^{B29}$ amino groups of the insulin molecule, or the A1, B1, and $Lys^{B29}$ amino groups of the insulin molecule.

In certain embodiments, X is EM, and intermediate compound A reacts with the B1 amino group of the insulin molecule, the A1 amino group of the insulin molecule, the $Lys^{B29}$ amino group of the insulin molecule, the A1 and B1 amino groups of the insulin molecule, the B1 and $Lys^{B29}$ amino groups of the insulin molecule, the A1 and $Lys^{B29}$ amino groups of the insulin molecule, or the A1, B1, and $Lys^{B29}$ amino groups of the insulin molecule.

In certain embodiments, X is EBM, and intermediate compound A reacts with the B1 amino group of the insulin molecule, the A1 amino group of the insulin molecule, the $Lys^{B29}$ amino group of the insulin molecule, the A1 and B1 amino groups of the insulin molecule, the B1 and $Lys^{B29}$ amino groups of the insulin molecule, the A1 and $Lys^{B29}$ amino groups of the insulin molecule, or the A1, B1, and $Lys^{B29}$ amino groups of the insulin molecule.

In certain embodiments, X is EG, and intermediate compound A reacts with the B1 amino group of the insulin molecule, the A1 amino group of the insulin molecule, the $Lys^{B29}$ amino group of the insulin molecule, the A1 and B1 amino groups of the insulin molecule, the B1 and $Lys^{B29}$ amino groups of the insulin molecule, the A1 and $Lys^{B29}$ amino groups of the insulin molecule, or the A1, B1, and $Lys^{B29}$ amino groups of the insulin molecule.

In certain embodiments, X is EGA, and intermediate compound A reacts with the B1 amino group of the insulin molecule, the A1 amino group of the insulin molecule, the $Lys^{B29}$ amino group of the insulin molecule, the A1 and B1 amino groups of the insulin molecule, the B1 and Lys$^{B29}$ amino groups of the insulin molecule, the A1 and Lys$^{B29}$ amino groups of the insulin molecule, or the A1, B1, and Lys$^{B29}$ amino groups of the insulin molecule.

In certain embodiments, X is EF, and intermediate compound A reacts with the B1 amino group of the insulin molecule, the A1 amino group of the insulin molecule, the Lys$^{B29}$ amino group of the insulin molecule, the A1 and B1 amino groups of the insulin molecule, the B1 and Lys$^{B29}$ amino groups of the insulin molecule, the A1 and Lys$^{B29}$ amino groups of the insulin molecule, or the A1, B1, and Lys$^{B29}$ amino groups of the insulin molecule.

Other Embodiments

As noted above, in various embodiments, a conjugate may comprise a detectable label instead of a drug as W. For example, a detectable label may be included in order to detect the location of conjugates within an organism, tissue or cell; when the conjugates are used in a sensor; etc. It is to be understood that a conjugate can comprise any detectable label known in the art. A conjugate can comprise more than one copy of the same label and/or can comprise more than one type of label. In general, the label(s) used will depend on the end application and the method used for detection.

The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Fluorescein isothiocyanate, rhodamine, phycoerythrin phycocyanin, allophycocyanin, y-phthalaldehyde, fluorescamine, etc. are all exemplary fluorescent labels. Chemiluminescent labels, i.e., labels that are capable of converting a secondary substrate to a chromogenic product are examples of indirectly detectable labels. For example, horseradish peroxidase, alkaline phosphatase, glucose-6-phosphate dehydrogenase, malate dehydrogenase, staphylococcal nuclease, delta-V-steroid isomerase, yeast alcohol dehydrogenate, α-glycerophosphate dehydrogenase, triose phosphate isomerase, asparaginase, glucose oxidase, β-galactosidase, ribonuclease, urease, catalase, glucoamylase, acetylcholinesterase, luciferin, luciferase, aequorin and the like are all exemplary protein based chemiluminescent labels. Luminol, isoluminol, theromatic acridinium ester, imidazole, acridinium salt, oxalate ester, etc. are exemplary non-protein based chemiluminescent labels. Another non-limiting and commonly used example of an indirectly detectable label is an affinity ligand, i.e., a label with strong affinity for a secondary binding partner (e.g., an antibody or aptamer) which may itself be directly or indirectly detectable.

In general, a detectable label may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In general, the detectable label will contain an amine group. Specific examples include peptidic labels bearing alpha-terminal amine and/or epsilon-amine lysine groups. It will be appreciated that any of these reactive moieties may be artificially added to a known label if not already present. For example, in the case of peptidic labels a suitable amino acid (e.g., a lysine) may be added or substituted into the amino acid sequence. In addition, as discussed in more detail herein, it will be appreciated that the conjugation process may be controlled by selectively blocking certain reactive moieties prior to conjugation.

EXAMPLES

Example 1

Synthesis of Azidoethylglucose (AzEG)

a. Synthesis of Bromoethyleglucose

DOWEX 50Wx4 resin (Alfa Aesar, Ward Hill, Mass.) was washed with deionized water to remove color. A mixture of 225 gm D-glucose (1.25 mol; 1 equiv., Alfa Aesar) and 140 gm DOWEX 50Wx4 was treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction was monitored by TLC (20% methanol/dichloromethane (DCM)). Reaction was complete after about four hours, and it was allowed to cool to room temperature. The solution was filtered to remove the resin, and the resin washed with ethyl acetate and DCM. The resulting filtrate was stripped to an amber oil in a rotory evaporator. A total of 400 gm after stripping.

The amber oil was purified on silica gel (4 kg silica packed in DCM) in the following manner. The crude was dissolved in DCM and loaded onto the column, and then eluted with 2×4 L 10% methanol/DCM; 2×4 L 15% methanol/DCM; and 3×4 L 20% methanol/DCM. Product containing fractions (on the basis of TLC) were pooled and stripped to dryness to afford 152 gm of 1-α-bromoethyl-glucose (42%).

b. Conversion of Bromoethylglucose to Azidoethylglucose (AzEM)

A 5 L round bottom three-necked flask, equipped with a heating mantle, an overhead stirrer, and a thermometer, was charged with 150 gm bromoethylglucose (525 mmol). The oil was dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution was cooled to room temperature and concentrated to dryness on the rotovap. The solid residue was digested with 3×500 mL of 5:1 vol. CHCl$_3$:MeOH at 40 C. The combined organic portions were filtered and evaporated to dryness to afford azidoethylglucose (86 gm) as an off-white solid. TLC (20% MeOH/DCM; char with H$_2$SO$_4$): single spot, indistinguishable from the starting material.

c. Repurification of Azidoethylglucose 32 gm of azidoethylglucose was taken into 100 mL water. The turbid solution was filtered through a glass microfibre filter (Whatman GF/B). The golden filtrate was evaporated to a solid on a rotovapor. The solid was taken into methanol (100 mL) and the turbid solution was again filtered through a glass microfibre filter. The resulting pale yellow filtrate was stripped to a solid under vacuum.

The solid was taken into a minimum of methanol (50 mL) and ethyl acetate (150 mL) was added slowly with stirring. The heavy slurry was cooled and filtered. The solid was air dried (hygroscopic) and put in a 60 C oven overnight. TLC has very little origin material. Yield 15.4 gm. The Mother Liquor was evaporated under vacuum to a yellow gum. No attempt was made to further purify this material at this time.

Example 2

Synthesis of Azidoethylmannose (AzEM)

a. Synthesis of Bromoethylmannose

DOWEX 50Wx4 resin (Alfa Aesar, Ward Hill, Mass.) is washed with deionized water to remove color. A mixture of 225 gm D-mannose (1.25 mol; 1 equiv., Alfa Aesar) and 140 gm DOWEX 50Wx4 is treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction is monitored by TLC (20% methanol/dichloromethane (DCM)). Reaction is complete after about four hours, and then allowed to cool to room temperature. The solution is filtered to remove the resin, and the resin washed with ethyl acetate and DCM. The resulting filtrate is stripped to an amber oil in a rotory evaporator.

The amber oil is purified on silica gel (4 kg silica packed in DCM) in the following manner. The crude is dissolved in DCM and loaded onto the column, and then eluted with 2×4 L 10% methanol/DCM; 2×4 L 15% methanol/DCM; and 3×4 L 20% methanol/DCM. Product containing fractions (on the basis of TLC) are pooled and stripped to dryness to afford 152 gm of 1-α-bromoethyl-mannose (42%).

b. Conversion of Bromoethylmannose to Azidoethylmannose (AzEM)

A 5 L round bottom three-necked flask, equipped with a heating mantle, an overhead stirrer, and a thermometer, is charged with 150 gm bromoethylmannose (525 mmol). The oil is dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution is cooled to room temperature and concentrated to dryness on the rotovap. The solid residue is digested with 3×500 mL of 5:1 vol. $CHCl_3$:MeOH at 40 C. The combined organic portions are filtered and evaporated to dryness to afford azidoethylmannose as an off-white solid.

c. Repurfication of Azidoethylmannose 32 gm of azidoethylmannose is taken into 100 mL water. The turbid solution is filtered through a glass microfibre filter (Whatman GF/B). The filtrate is evaporated to a solid on a rotovapor. The solid is taken into Methanol (100 mL) and the turbid solution is again filtered through a glass microfibre filter. The resulting pale yellow filtrate is stripped to a solid under vacuum.

The solid is taken into a minimum of methanol (50 mL) and ethyl acetate (150 mL) is added slowly with stirring. The heavy slurry is cooled and filtered. The solid is air dried (hygroscopic) and put in a 60 C oven overnight. The Mother Liquor is evaporated under vacuum to a yellow gum.

Example 3

Synthesis of Azidoethylmannobiose (AzEBM)

The AzEM compound from Example 2 is selectively protected using benzene dimethyl ether, purified by column chromatography and subsequently reacted with benzyl bromide to give 1-α-(2-azidoethyl)-4,6-benzaldehyde diacetal-3-benzyl-mannopyranoside. The product is subsequently glycosylated with 1-α-bromo-2,3,4,6-tetrabenzoylmannopyranoside using silver triflate chemistry under rigorously anhydrous conditions to give the protected-azidoethylmannobiose product. The intermediate product is then deprotected to remove the benzoyl groups to give AzEBM.

Example 4

Synthesis of Azidoethylmannotriose (AzETM)

a. 1-α-bromo-2,3,4,6-tetrabenzoyl-mannose

To a 500 mL 3-neck flask containing a stir bar and nitrogen inlet was added 40 gm (60.9 mmole) of pentabenzoylmannose and 80 mL methylene chloride. The resulting solution was cooled in an ice bath to <5 C, and 80 mL 33% HBr-acetic acid solution was added via an addition funnel at such a rate to maintain the reaction temperature <10 C. Upon complete addition (~30 min.) the ice bath was removed and stirring was continued for 3 hours.

The reaction solution was diluted with an equal volume (160 mL) of DCM and extracted successively with water (2×500 mL), saturated bicarbonate (2×50 mL) and Brine (1×50 mL), dried over magnesium sulfate and the solvent evaporated to give 41 gm of solid foam. (Theoretical yield 40.1 gm) and was stored under $N_2$ in a freezer. This material was used without further purification. The reaction was monitored by TLC: silica gel (Hexane/Ethyl Acetate, 7/3) starting material $R_f$ 0.65, product $R_f$ 0.8 UV visualization. $^1$H NMR ($CDCl_3$) δ 8.11 (d, 2H), 8.01 (m, 4H), 7.84 (d, 2H), 7.58 (m, 4H), 7.41 (m, 6H), 7.28 (t, 2H), 6.58 (s, 1H), 6.28 (m, 2H), 5.8 (m, 1H), 4.75 (dd, 1H) 4.68 (dd, 1H) 4.5 (dd, 1H).

b. 1-Azidoethyl-2,4-dibenzoylmannose

To a 1.0 L, 3-neck flask containing a stir bar, nitrogen inlet and 300 mL of anhydrous acetonitrile was added 25 gm 1-azidoethylmannose (100.4 mmole), and 50 mL triethyl orthobenzoate (220 mmole, 2.2 equiv.). The resulting slurry was stirred at room temperature and 0.8 mL (10 mmole) trifluoroacetic acid (TFA) was added neat. The solution cleared within 10 minutes and stirring was continued for an additional two hours, then 25 mL of 10% aqueous TFA was added and stirring was continued for an additional 2 hours to hydrolyze the intermediate to the ester isomers. The solvent was evaporated under vacuum to a viscous oil, which was triturated with 50 mL DCM and again evaporated to a viscous oil.

Toluene (70 mL) was added to the residue and the viscous solution was seeded with 2,4-dibenzoylazidoethylmannose. A fine precipitate formed within 15 minutes and stirring was continued overnight at room temperature. The resulting heavy suspension was set in the freezer for 2-4 hours, then filtered and the solid washed with ice cold toluene (2×10 mL). The solid was air dried to a constant weight to give 21 gm (TY 22.85 gm @ 50% isomeric purity) of ~95% isomeric purity. The product was taken into 40 mL toluene, stirred for 1 hour and then set in the freezer for an additional 2 hours. The solid was filtered and washed (2×10 mL) with ice cold toluene and air dried to a constant weight to give 18.5 gm of the single isomer product 2,4-dibenzoylazidoethylmannose in 83% yield. The mother liquors contained the undesired isomer and a small amount of the desired isomer. The reaction was monitored by TLC: SG (Hexane/Ethyl Acetate 7/3) Starting Material $R_f$ 0.0, orthoester intermediate $R_f$ 0.9. (Hexane/Ethyl Acetate: 8/2) SM $R_f$ 0.8, desired isomer $R_f$ 0.4, un-desired isomer $R_f$ 0.2

$^1$H NMR 300 MHz (CDCl$_3$) δ 8.12 (t, 4H), 7.66 (t, 2H), 7.5 (m, 4H), 5.56 (t, 1H), 5.48 (m, 1H), 5.14 (m 1H), 4.5 (dd, 1H), 4.0 (m, 2H), 3.8 (m, 3H), 3.56 (m, 1H), 3.44 (m, 1H).

c. Perbenzoylated-man(α-1,3)-man(α-1.6)-α-1-azidoethylmannopyranoside

To a 1.0 L 3-neck flask with a stir bar, nitrogen inlet was added 41 gm crude 1-bromo-tetrabenzoymannose (60.9 mmole, ~2.5 equiv.) in 185 mL DCM. To this was added 11.2 gm 2,4-dibenzoylazidoethylmannose (24.5 mmole) followed by 11.2 gm 4A sieves. The slurry was stirred a room temperature for 10 minutes and cooled to −15° C. in a methanol/ice bath.

In a separate dark vessel was added 190 mL toluene followed by 15.1 gm silver-trifluoromethanesulfonate (AgOTf) (58.8 mmole, 2.4 equiv.) and was stirred into solution in the dark. This solution was transferred to a large addition funnel, and added drop-wise to the stirring suspension while protecting the reaction from light. The reaction temperature was maintained <−10 C by adjusting the AgOTf addition rate. Upon complete addition (~30 minutes) the cold bath was removed and the reaction stirred for an additional 2 hours until a single product remained by TLC (SG, Hexane/Ethyl Acetate: 7/3, Bromo $R_f$ 0.9, azido $R_f$ 0.4, trios product $R_f$ 0.5, uv visualization).

Triethylamine (7 mL, 5.0 equiv.) was added followed by 200 mL DCM. The resulting slurry was filtered through a pad of silica gel and celite and washed with 2×75 mL DCM. The solvent was evaporated under vacuum and the residue taken into ethyl acetate and washed sequentially with water (2×100 mL), bicarb (2×50 mL), brine (1×75 mL) and dried over magnesium sulfate. The solvent was evaporated under vacuum to give 39 gm of solid foam (TY 39.5 gm). $^1$H NMR 300 MHz (CDCl$_3$) δ 8.3 (d, 2H), 8.2 (m, 8H), 7.85 (d, 4H), 7.75 (dd, 4H), 7.3-7.65 (m, 30H), 7.2 (t, 2H), 6.05 (m, 4H), 5.9 (t, 2H), 5.63 (m, 2H), 5.38 (s, 2H), 5.18 (d, 1H), 4.65 (m, 4H), 4.5 (m, 2H), 4.35 (m, 4H), 3.8 (m, 2H), 3.54 (m, 2H).

d. Man(α-1,3)-man(α-1.6)-α-1-azidoethylmannopyranoside

To a stirring suspension of 3.0 gm perbenzoylated-man (α-1,3)-man(α-1.6)-α-1-azidoethylmannopyranoside (1.86 mmole) in 40 mL methanol was added 0.2 mL 4.28M sodium methoxide in methanol. The resulting suspension was stirred 20 hours at room temperature giving a clear solution. The completion of the reaction was monitored by TLC, (SG, hexane/ethyl acetate: 8/2 SM $R_f$ 0.4, product $R_f$ 0.0).

The methanol was evaporated under vacuum giving an oily semi-solid. The residue was taken into ethyl acetate (50 mL) and stirred for 3 hours. The solid was filtered, washed with fresh ethyl acetate (2×20 mL) and air dried to a constant weight to give 1.09 gm (TY 1.07 gm) of product. The mother liquors contained residual methyl benzoate, the deprotection by-product.

Example 5

Synthesis of aminoethyl-saccharides (AEG, AEM, AEBM, AETM) from azidoethyl-saccharides (AzEG, AzEM, AzEBM, AzETM)

The azido-terminated compounds from Examples 1-4 are readily hydrogenated at room temperature by using palladium/carbon catalyst, a small amount of acetic acid, and ethanol as a solvent to give the corresponding amine-terminated compounds. The chemical structures of AEG, AEM, AEBM, and AETM are described herein. The process is identical to the one described for AETM below, except that those skilled in the art will understand that the amounts of reagents, solvents, etc. should be scaled to the number of moles of saccharide-ligand to be hydrogenated.

a. Man (α-1,3)-Man(α-1.6)-α-1-aminoethylmannopyranoside ("aminoethyltrimannose", AETM)

To a solution of 5.3 gm (9.25 mmole) man(α-1,3)-man(α-1.6)-α-1-azidoethylmannopyranoside in 100 mL water and 50 mL ethanol was added 0.8 gm 5% Pd/C. The vigorously stirring suspension was hydrogenated at 30-40 psi for 48 hours or until no starting material was apparent by TLC (SG, Methanol, SM $R_f$ 0.75, Pdt $R_f$ 0.0, PMA vis.). The suspension was filtered over celite, which was rinsed with ethanol (2×50 mL) and the filtrate concentrated under vacuum. HPLC of this material (C18, 3% Acetonitrile/97% 0.1% H$_3$PO$_4$, 220 nm, 2 ml/min) gave uv adsorption of the injection column void material, $R_t$ 2.5 minutes, indicative of benzoate ester.

The filtrate was diluted with 70 mL water and 12 mL of 1N NaOH and the solution stirred overnight at room temperature (HPLC: no uv material at column void $R_t$ 2.5 min., uv material at $R_t$ 10.5 minutes co-eluting with benzoic acid). 2 gm of decolorizing charcoal were added and the stirring suspension heated to 80 C, cooled to room temperature and filtered over celite. The filtrate pH was adjusted to 8.0 with 2N HCl and the colorless solution concentrated under vacuum to about 50% volume.

The solution was loaded onto a resin column (Dowex 50W, 50 gm) and washed with water until eluting fractions were neutral to pH (6×75 mL) removing any residual acid by-products. The amine product was washed off the column with 0.25N ammonium hydroxide (6×75 mL) and the fractions containing the amine product-ninhydrin detection were combined and concentrated to 25-30 mL under vacuum. This concentrated solution was added drop-wise to 300 mL stirring ethanol and stirring continued for an additional 2 hours. The product was filtered, washed with fresh ethanol (2×50 mL) and air dried to a constant weight. The resulting white amorphous solid was dried further in a vacuum oven at 80 C for hours to give 4.1 gm of a white granular solid (TY 5.1 gm). The NMR was clean of any aromatic protons. $^1$H NMR 300 MHz (D$_2$O) δ 5.08 (s, 1H), 4.87 (s, 1H), 4.81 (s, 1H), 4.8-3.6 (m, 18H), 2.9 (m, 2H).

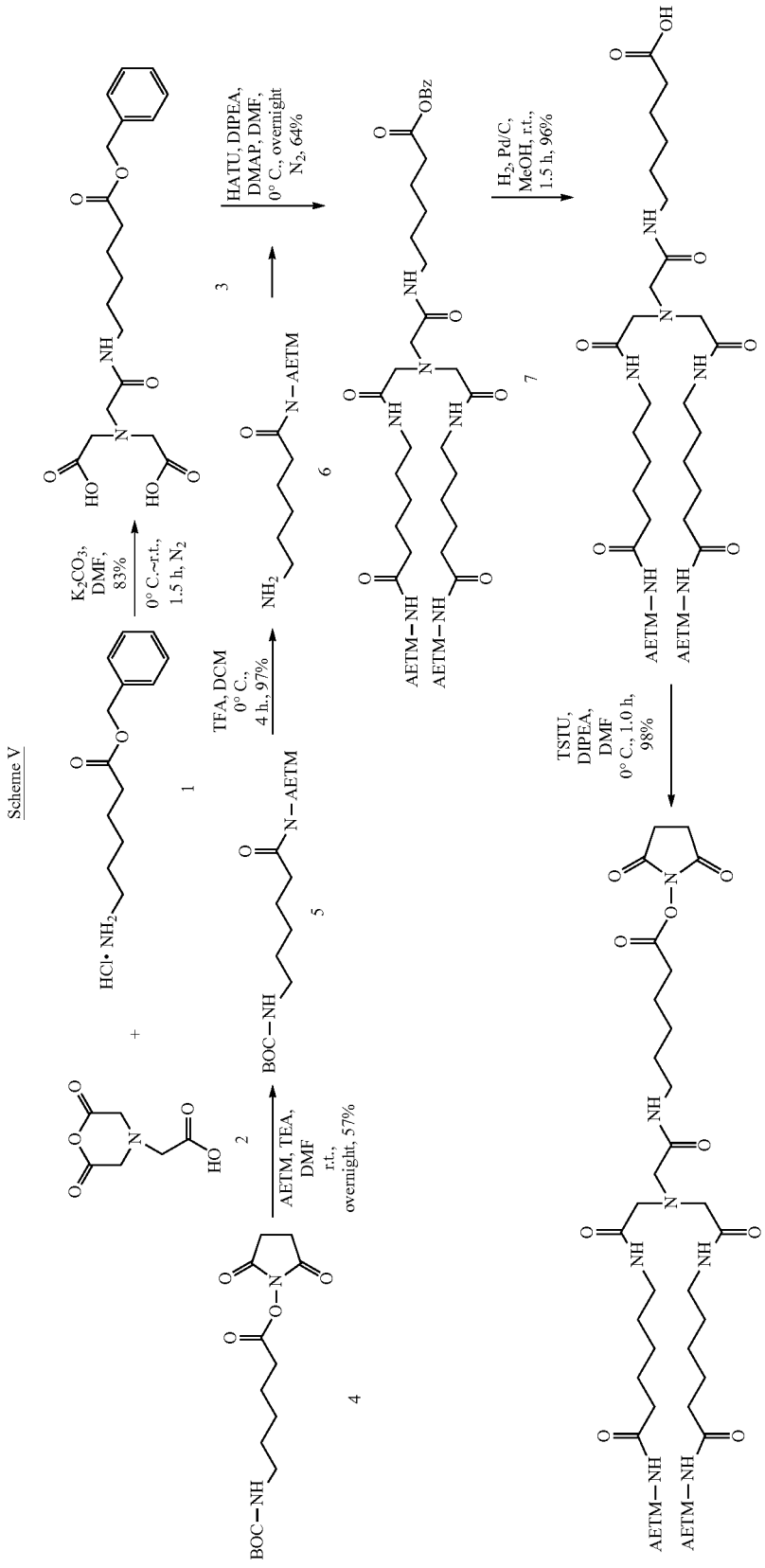

Example 6

Synthesis of (2,2'-[(2-{[6-(benzyloxy)-6-oxohexyl]amino}-2-oxoethyl)imino]acid) (3)

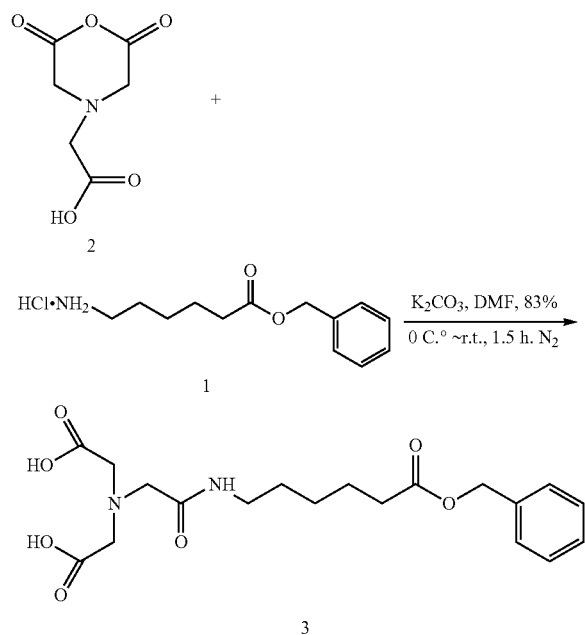

To a solution of compound 1 (17.30 g, 67.14 mmol) in anhydrous DMF (67 ml) in a 500 ml of three-necked round bottom flask (RBF) was added 9.7 g of $K_2CO_3$ (70.5 mmol) in one portion at 0° C. under a nitrogen atmosphere. The resulting mixture was stirred for 2 h at 0° C. under nitrogen until complete conversion of compound 1-HCl salt to the free base form of compound 1. Free amine of compound 1: TLC $R_f$ 0.1 ($CHCl_3$/MeOH/$H_2O$, 5:4:1; dark spot by Ninhydrin). Next, the supernatant was then added dropwise via a cotton-filter-head cannula over a period of 50 min to a stirred solution of 14.5 g of compound 2 (83.9 mmol) in anhydrous DMF (252 ml) inside a 1000 ml, two-neck RBF at 0° C. under nitrogen. To the 500 ml of three-necked RBF was added 20 ml of dry DMF to rinse the flask, and the resulting solution was transferred into the 1000 ml of two-neck RBF. The resulting mixture was stirred at 0° C. for 30 min and then at room temperature (r.t.) for 1 h. (TLC: compound 3, Rf=0.8; free amine of comp.1, Rf=0.1; solution of $CHCl_3$/MeOH/$H_2O$=5:4:1).

The reaction mixture was cooled to 0° C. DI water (200 ml) was added dropwise to the stirring cold mixture over a period of 0.5 h. The resulting mixture was concentrated in a 1000 ml of one-neck RBF at 40° C. via rotary evaporation. To the residue (about 60 g) was added DI water (250 ml or more) at 0 C.° and stirred at 5° C. overnight. The white precipitate was filtered through a 3.5 inch Buchner funnel and washed with DI water (2×60 ml). The wet cake was dried in vacuo overnight. The obtained white solid (about 25 g) was stirred with MeOH (200 ml) at r.t. for 1 h and the then filtered through a 3.5 inch of Buchner funnel. The residual white solid on the funnel was stirred with MeOH (100 ml or more) for 3 h and filtered again. The combined filtrate was concentrated and residue was dried in vacuo to afford about 20 g of the compound 3 (white solid, 83% yield). If necessary, crude compound 3 was purified by a column chromatography on silica gel until compound 3 reached a purity of 99%. Compound 3: TLC $R_f$ 0.8 ($CHCl_3$/MeOH/$H_2O$, 5:4:1; dark spot by PMA); $^1$H NMR (300 MHz, DMSO-$d_6$) δ: 12.61 (br s, 2H, COO$\underline{H}$), 8.06 (s, 1H, Ph$\underline{H}$), 7.39 (s, 4H, Ph$\underline{H}$), 5.12 (s, 2H, C$\underline{H}_2$Ph), 3.47 (s, 4H, [$CO_2C\underline{H}_2$]$_2$N), 3.32 (s, 2H, [$CO_2CH_2$]$_2$NC$\underline{H}_2$CON), 3.10 (m, 2H, CONHC$\underline{H}_2$), 2.38 (m, 2H, $\underline{H}_2$CCOOBn), 1.63-1.30 (m, 6H, C$\underline{H}_2$C$\underline{H}_2$C$\underline{H}_2$). MS calcd for $C_{19}H_{26}N_2O_7$ [M+H]$^+$ 395.4. Found 395.3.

Example 7

Synthesis of (6-Amino-N-(2-{[(α-D-mannopyranosyl)-(1→3)-[(α-D-mannopyranosyl)-(1→6)]-(α-D-mannopyranosyl)]oxy}ethyl)hexanamide) (6)

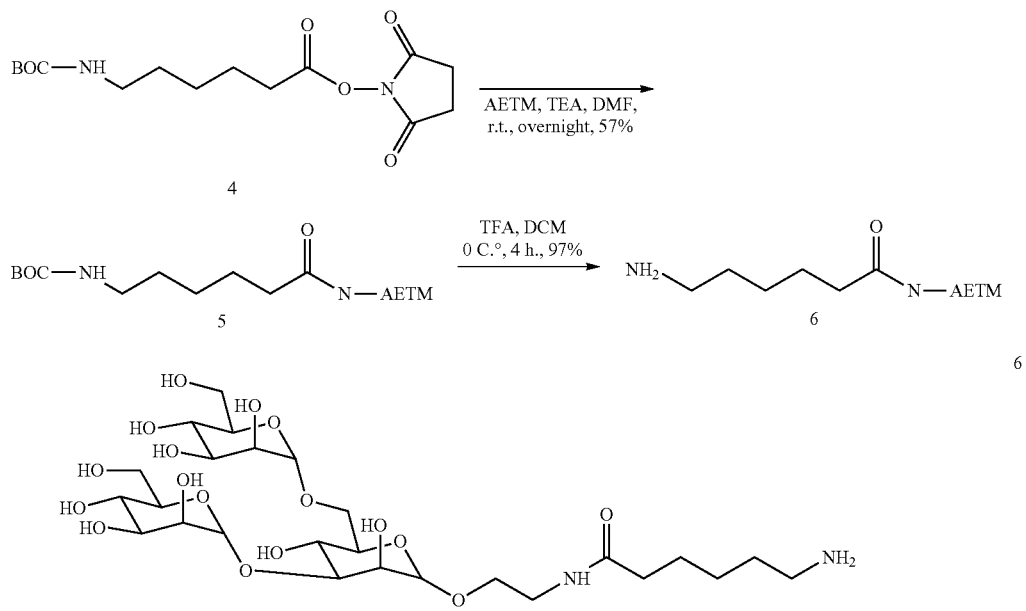

32.6 g of AETM (80%, 60.6 mmol) was dissolved in anhydrous DMF (420 ml) in a 1000 ml, two-neck RBF at r.t. under nitrogen and the solution was cooled to 0° C. To the solution was added 24.4 g of compound 4 (73.2 mmol) portionwise over a period of 15 min and then 12.7 ml of TEA (91.5 mmol) was added dropwise over a period of 30 min. The resulting mixture was stirred at r.t. under nitrogen overnight. (TLC: AETM, Rf=0.5; Compound 5, Rf=0.9; solution of/MeOH/$H_2O$/$NH_4OH$=5:4.5:0.5; dark spot by PMA).

The reaction mixture was concentrated at 40° C. via rotary evaporation. The residue (about 110 g) was purified by column chromatography on silica gel (diameter×height: 9.0×27 cm, silica gel: 1500 ml, DCM/MeOH: 6:1~1:1). The collected fractions were concentrated and residue was dried in vacuo to afford 20.6 g of the compound 5, (white solid, 57% of yield).

21.8 g of compound 5 (28.7 mmol) was stirred in anhydrous DCM (300 ml) in a 1000 ml, one-neck RBF at 0° C. for 0.5 h. 100 ml of trifluoroacetic acid (TFA) was added dropwise via a syringe to the stirring suspension solution of compound 5. The resulting mixture was stirred at 0° C. for 4.0 h. (TLC: compound 5, Rf=0.4; free amine of compound 6, Rf=0.1; solution of $CHCl_3$/MeOH/$H_2O$=3:2:0.2)

The mixture was concentrated at 40° C. The residue (about 15 ml) was diluted with DI water (about 66 g) and loaded on a cation ion exchange column {(diameter×height: 7.2×15 cm, Volume of bed (Vb)=600 ml, Dowex, 50WX2-200(H), 450 G), previously treated with DI water (4000 ml), 1N HCl (700 ml), and DI water (6000 ml)}. The sample-loaded column was eluted with DI water (2000 ml), $NH_4OH$ (0.2N, 1000 ml; 0.4N, 1500 ml; 1.0 N, 1000 ml; 1.25N, 3000 ml and 2.0 N, 500 ml). Collected fractions ($NH_4OH$, 1.0 N, 1000 ml and 1.25N, 3000 ml) were concentrated at 40° C. via rotary evaporation. About 160 ml or more of the residue was lyophilized overnight to yield 18.3 g of compound 6 (off-white solid, 97% yield). The flask was filled with nitrogen and stored in a freezer (−20° C.) until further use. Compound 6: $R_f$ 0.1 ($CHCl_3$/MeOH/$H_2O$, 3:2:0.2; dark spot by PMA); $^1$H NMR (300 MHz, DMSO-$d_6$/$D_2O$) δ: 4.81 (s, 1H, H-$1_{mannose}$), 4.60 (s, 1H, H-$1_{mannose}$), 4.45 (s, 1H, H-b $1_{mannose}$), 3.89-2.44 (m, 24H), 2.04 (m, 2H,), 1.46-1.17 (m, 6H). MS calcd for $C_{26}H_{48}N_2O_{17}$ $[M+H]^+$ 661.7. Found 661.5.

Example 8

Synthesis of (Benzyl 6-{[(bis{2-[(6-[2-[(α-D-mannopyranosyl)-(1→3)-[(α-D-mannopyranosyl)-(1→6)]-(α-D-mannopyranosyl)]ethyl]amino-6-oxohexyl)amino]-2-xoethyl}amino)acetyl]amino}hexanoate) (7)

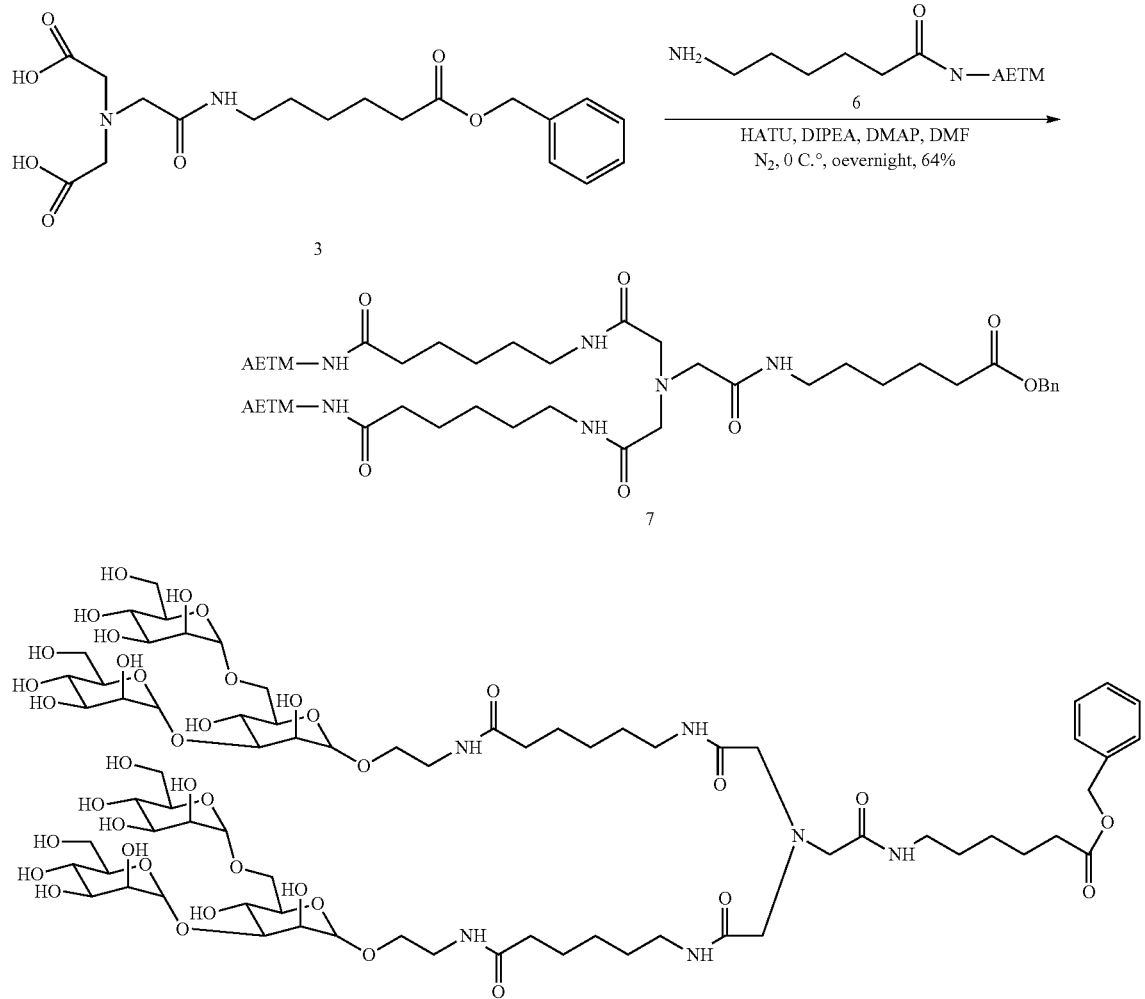

To a solution of 4.75 g of diacid 3 (12.06 mmol) in dry DMF (500 ml) in a 1000 ml, two-neck RBF at 0° C. under nitrogen was added 13.8 g of HATU (36.2 mmol), 17.5 g of amine 6 (26.5 mmol), 9.8 ml of DIPEA (55.5 mmol) and 0.29 g of DMAP (2.4 mmol). The resulting mixture was stirred at 0~5 C.° under nitrogen overnight. (TLC: compound 6, Rf=0.1; compound 7, Rf=0.3; solution of $CH_2Cl_2$/MeOH/$NH_4OH$=5:5:2).

The mixture was quenched by 50 ml of water and concentrated in a one-neck RBF at 35° C. The residue (about 65 g) was purified by column chromatography using silica gel (diameter×height: 7.2×17 cm, silica gel: 700 ml, DCM/MeOH/$H_2O$: 5:4:1). The collected fractions were concentrated and 2[$\underline{H_2}$CCONH-AETM]), 1.57-1.26 (m, 18H, 3[CONHCH$_2$C$\underline{H_2}$C$\underline{H_2}$C$\underline{H_2}$CH$_2$CO]). MS calcd for $C_{71}H_{118}N_6O_{39}$ [M+H]$^+$ 1680.7. Found 1681.0.

Example 9

Synthesis of (6-{[(bis{2-[(6-[2-[(α-D-mannopyranosyl)-(1→3)-[(α-D-mannopyranosyl)-(1→6)]-(α-D-mannopyranosyl)]ethyl]amino-6-oxohexyl)amino]-2-oxoethyl}amino)acetyl]amino}hexanoic acid) (8)

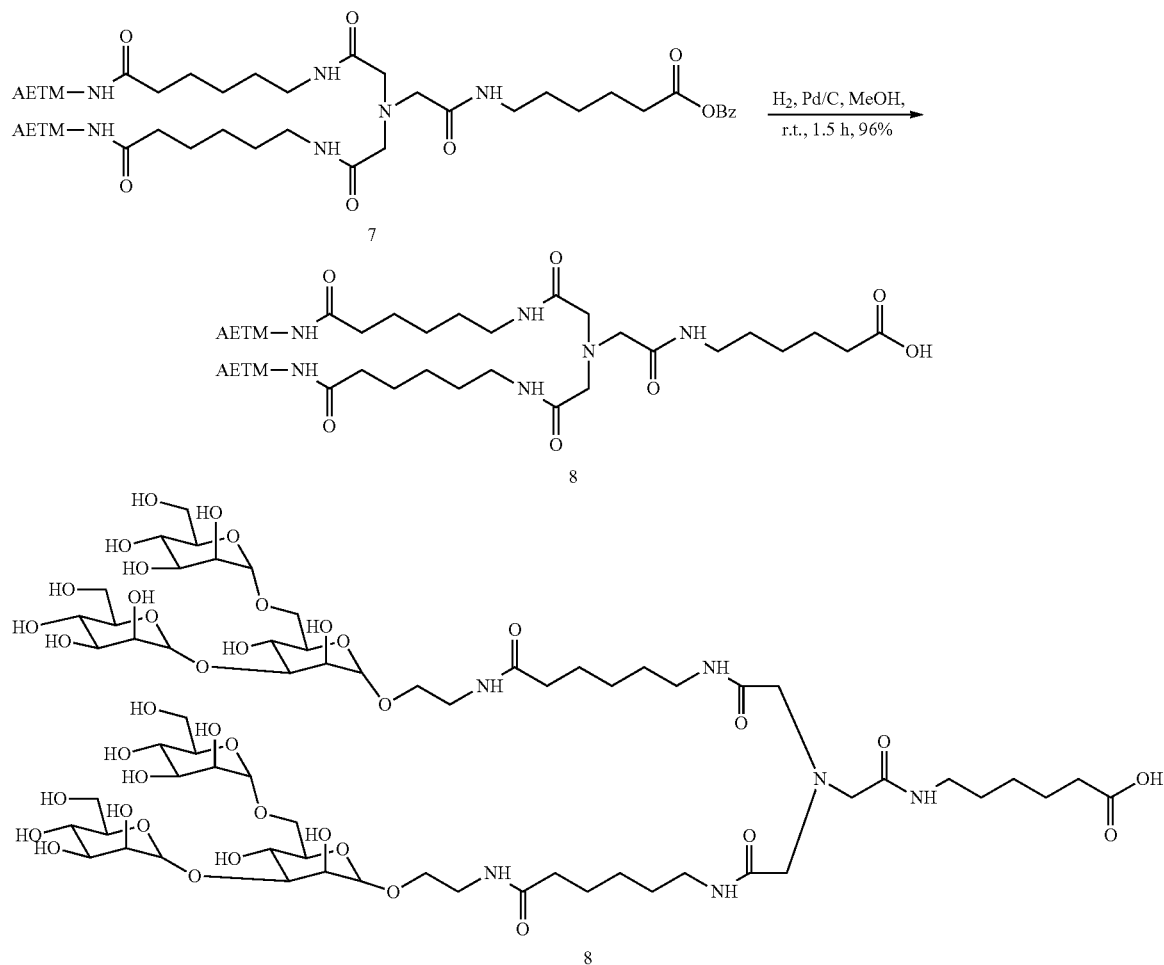

the residue (about 36.5 g) was dissolved with DI water (35 ml) and lyophilized to give 13 g of crude product 7 (white solid). The crude product was dissolved with MeOH (60 ml, HPLC grade) at 0° C. and then purified by C18 reverse phase column chromatography (Biotage, SNAP 120 g), running four programmed separations (4×15 ml of sample, UV=210, $H_2O$/MeOH=10%-60%). The collected fractions were concentrated to 200 g at 35° C. and the residue was lyophilized overnight to afford 12 g of compound 7 (white solid, 64% of yield, purity: >97% of HPLC). TLC $R_f$ 0.4 ($CHCl_3$/MeOH/$H_2O$, 5:4:1; dark spot by PMA); $^1$H NMR (300 MHz, DMSO-$d_6$/$D_2O$) δ: 7.39 (m, 5H, PhH), 5.11 (s, 2H, PhC$\underline{H}$), 4.87 (s, 2H, H-1$_{mannose}$), 4.66 (s, 2H, H-1$_{mannose}$), 4.62 (s, 2H, H-1$_{mannose}$), 3.88-3.09 (m, 56H), 2.40 (m, 2H), 2.09 (m, 4H, To a solution of 13.01 g of benzyl hexanoate 7 (7.75 mmol) in 360 ml of anhydrous MeOH in a 1000 ml, single-neck RBF at 0° C. was added 3.3 g of Pd/C (10% Wt). The resulting mixture was stirred under a hydrogen atmosphere for 1.5 h at r.t. (TLC: compound 7, Rf=0.8; compound 8, Rf=0.7; solution of $CH_2Cl_2$/MeOH/$H_2O$=5:10:2).

The resulting black suspension was filtered through a pad of Celite (1.0 cm deep), and the pad rinsed with MeOH (3×50 ml). The combined filtrate was concentrated to 105 g. The concentrated filtrate was added dropwise to 650 ml of stirring dry diethyl ether in a 1000 ml, one-neck RBF. The cloudy solution was stored in a cold room overnight. The supernatant was removed via a porosity-head cannula under nitrogen. 250 ml of anhydrous diethyl ether was added to the 1000 ml, one-neck RBF and stirred for 0.5 h. The supernatant in the flask was again removed via a porosity-head cannula, and the ether-washing procedure was repeated another time. Solid remaining in the flask after filtration was dried in vacuo to afford 11.9 g of acid compound 8, (white solid, yield: 96%, purity: >98% of HPLC). TLC $R_f$ 0.7 (CHCl$_3$/MeOH/H$_2$O, 5:10:2; dark spot by PMA); $^1$H NMR (300 MHz, DMSO-d$_6$/D$_2$O) δ: 4.80 (s, 2H, H-1$_{mannose}$), 4.59 (s, 2H, H-1$_{mannose}$), 4.54 (s, 2H, H-1$_{mannose}$), 3.85-3.01 (m, 56H), 2.14 (m, 2H), 2.10 (m, 4H, 2[H$_2$CCONH-AETM]), 1.43-1.15 (m, 18H, 3[CONHCH$_2$CH$_2$CH$_2$CH$_2$CH$_2$CO]). MS calcd for C$_{64}$H$_{112}$N$_6$O$_{39}$ [M+H]$^+$ 1590.6. Found 1590.3.

Example 10

Synthesis of (N-{6-{[(bis{2-[(6-[2-[(α-D-mannopyranosyl)-(1→3)-[(α-D-mannopyranosyl)-(1→+6)]-(α-D-mannopyranosyl)]ethyl]amino-6-oxohexyl)amino]-2-oxoethyl}amino)acetyl]amino}hexanoyloxy}succinimide) (9)

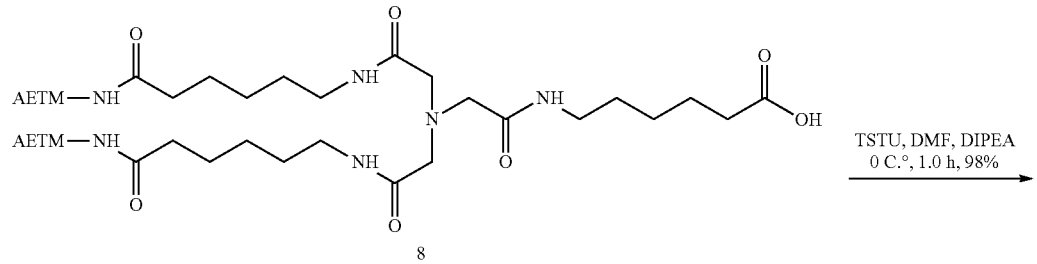

8

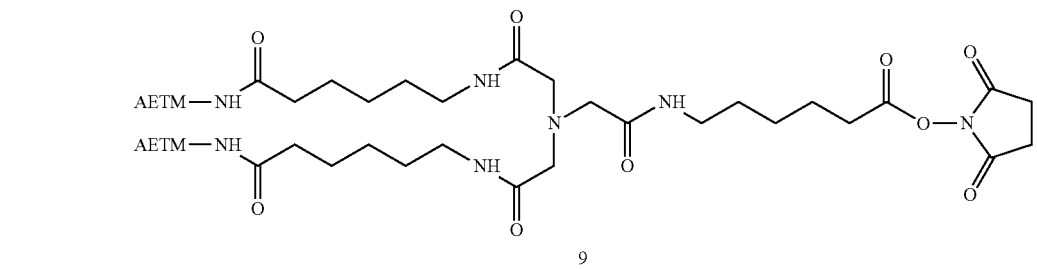

9

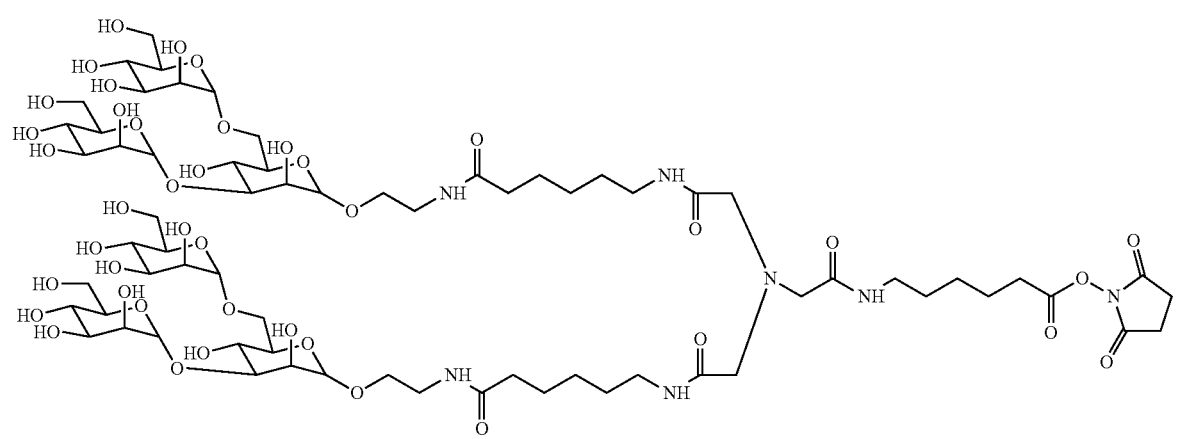

9

To a solution of 11.01 g of acid compound 8 (6.92 mmol) in 380 ml of anhydrous DMF in a 1000 ml, one-neck RBF was added dropwise a solution of TSTU (2.52 g, 8.31 mmol) in anhydrous DMF (5 ml) and DIPEA (1.60 ml, 0.457 mmol) at 0° C. under nitrogen. The resulting mixture was stirred for 1.0 h at 0° C.

The mixture was concentrated at 35° C. via rotary evaporation. The residue (about 77 g) was added dropwise to 700 ml of anhydrous acetonitrile under stirring in a 1000 ml, one-neck RBF under nitrogen at r.t. The suspension solution was stirred for 0.5 h. The supernatant was removed via a porosity-head cannula.

The residue was dissolved with dry DMF (70 ml) in the 1000 ml, one-neck RBF under nitrogen at 0 C.° and added dropwise to 700 ml of anhydrous stirring ACN in a 1000 ml, one-neck RBF under nitrogen environment via cannula at r.t. The suspension was stirred for 0.5 h. The supernatant was removed via a porosity-head cannula. This precipitation was repeated two additional times.

The final residue was washed with anhydrous acetonitrile, and the suspension was filtered through a funnel (CG-1402-23, Filter Funnel, Buchner, Medium Frit, 350 ml), and flushed with acetonitrile (3×500 ml). During the washing operation, white residual material in the funnel was manually stirred with a stainless-steel spatula and washed with anhydrous acetonitrile under nitrogen. The washed white solid was dried in vacuo for 48 h at r.t. and then stored in air-tight vials under nitrogen. The drying in the vials was continued for another 60 h to afford 11.3 g of compound 9 (white solid, yield: 98%, purity: >96% of HPLC). TLC $R_f$ 0.2 (CHCl$_3$/MeOH/H$_2$O, 5:4:1; dark spot by PMA); $^1$H NMR (300 MHz, DMSO-d$_6$/D$_2$O) δ: 4.87 (s, 2H, H-1$_{mannose}$), 4.65 (s, 2H, H-1$_{mannose}$), 4.61 (s, 2H, H-1$_{mannose}$), 3.84-3.23 (m, 50H), 3.10-3.08 (m, 6H, [H$_2$CNHCOCH$_2$]$_3$N), 2.83 (s, 4H, NHS), 2.65 (t, 2H, H$_2$CCH$_2$CO—NHS), 2.08 (m, 4H, 2[H$_2$CCONH-AETM]), 1.64 (m, 2H, H$_2$CCH$_2$CO—NHS), 1.48-1.39 (m, 12H, 3[CONHCH$_2$CH$_2$CH$_2$CH$_2$CO]), 1.22 (m, 4H, 2[H$_2$CCH$_2$CONH-AETM]. MS calcd for C$_{68}$H$_{115}$N$_7$O$_{41}$ [M+H]$^+$ 1687.7. Found 1688.3.

Examples 11 and 12 describe a general method for conjugating a PLF of the present disclosure with an amine-bearing drug in organic solvent or aqueous solvent, respectively, and Example 13 describes a general method of purification after conjugation.

Example 11

Amine-Functionalized Drug Conjugation with Prefunctionalized Ligand Framework in Organic Solvent A prefunctionalized ligand framework (PLF) is dissolved at 60 mM in 11.1 mL of anhydrous DMSO and allowed to stir for 10 minutes at room temperature. An amine-bearing drug is then dissolved separately at a concentration 9.2 mM in 27.6 mL of anhydrous DMSO containing 70 mM anhydrous triethylamine. Once dissolved, the PLF solution is added portionwise to the amine-bearing drug/DMSO/TEA solution followed by room temperature mixing for ~1 hr. At this point, the reaction is analyzed by analytical HPLC to assess the extent of reaction, after which more PLF solution is added if necessary to achieve the desired extent of conjugation. When the desired extent of conjugation of the PLF to the amine-bearing drug is achieved, ethanolamine is added to the PLF/amine-bearing drug/DMSO/TEA solution to make the final concentration of ethanolamine 195 mM. The reaction solution is stirred at RT for an additional 0.5 hr.

The resulting solution is then superdiluted by 20× into water followed by a pH adjustment with 1N HCl (and 0.1 N NaOH if needed) to a final pH of 2.0. The resulting aqueous solution is concentrated by ultrafiltration (Millipore Pellicon Mini TFF system, 1 KDa MWCO membrane) to approximately 200 mL, followed by diafiltration (Millipore Pellicon Mini TFF system, 1 KDa MWCO membrane) using 10-15 diavolumes (DV) of water. If desired, the solution is further concentrated through the use of Amicon-15 (3 kDa MWCO) to approximately 10 mg/mL. The aqueous solution is stored overnight at 4° C.

Example 12

Amine-Functionalized Drug Conjugation with Prefunctionalized Ligand Framework in Aqueous Solvent A prefunctionalized ligand framework (PLF) is dissolved at 60 mM in 11.1 mL of anhydrous DMSO and allowed to stir for 10 minutes at room temperature. An amine-bearing drug is then dissolved separately at 17.2 mM in 14.3 mL of a 0.1M, pH 11.0 sodium carbonate buffer, and the pH subsequently was adjusted to 10.8 with 1.0 N sodium hydroxide.

Once dissolved, the PLF/DMSO solution is added portionwise to the amine-bearing drug/carbonate solution followed by room temperature mixing. During the addition, the pH of the resulting mixture is adjusted every 5 min to keep the pH>10.8 if necessary using dilute HCl or NaOH. The solution is allowed to stir for an additional 15 minutes after the dropwise addition to ensure complete reaction. At this point, the reaction is analyzed by analytical HPLC to assess the extent of reaction, after which additional PLF solution is added if necessary to achieve the desired extent of conjugation.

The resulting solution is then superdiluted by 20× into water followed by a pH adjustment with 1N HCl (and 0.1 N NaOH if needed) to a final pH of 2.0. The resulting aqueous solution is concentrated by ultrafiltration (Millipore Pellicon Mini TFF system, 1 KDa MWCO membrane) to approximately 200 mL, followed by diafiltration (Millipore Pellicon Mini TFF system, 1 KDa MWCO membrane) using 10-15 diavolumes (DV) of water. If desired, the solution was further concentrated through the use of Amicon-15 (3 kDa MWCO) to approximately 10 mg/mL. The aqueous solution is stored overnight at 4° C.

Example 13

Amine-Functionalized Drug-PLF Conjugate Purification Via HPLC

The amine-bearing drug-PLF conjugate solution is further purified to obtain the desired product using preparative reverse phase HPLC on a Waters C4, 7 um, 50×250 mm column. Buffer A is deionized water containing 0.1% TFA and Buffer B was acetonitrile containing 0.1% TFA. Before purification, the column is equilibrated at 15 ml/minutes with a 80% A/20% B mobile phase using a Waters DeltraPrep 600HPLC system. Approximately 16 ml of the crude solution is injected onto the column over the course of 2 minutes at a flow rate of 50 ml/minute after which a linear gradient is employed from 80% A/20% B to 75% A/25% B (or higher, depending on the drug conjugate properties) over the next 5 minutes followed by a slower multi-step gradient from 75% A/25% B to 70% A/30% B (or higher, depending on the drug conjugate properties) over the next 70 minutes. The retention time of the desired peak varies depending on the drug, framework, and ligand used. During the elution of the peak of interest a fraction collector and LC-MS (Acquity HPLC, Waters Corp., Milford, Mass.) is employed to further assess the purity of the peak fractions to decide which fractions of the desired peak should be combined to obtain the desired level of drug conjugate purity.

Solvent Removal

Once collected, the solution is rotovapped (Buchi Model R-215, New Castle, Del.) to remove acetonitrile and lyophilized to obtain pure conjugate whose identity is verified by HPLC-MS (HT Laboratories, San Diego, Calif.).

Alternate Solvent Removal

Once the desired fractions are collected, they are combined into a single solution inside a large glass vessel and concentrated to approximately 200 mL via ultrafiltration (Millipore Pellicon Mini TFF system, 1 KDa MWCO membrane). The resulting solution is diafiltered against approximately 15-20 diavolumes of high-purity water (Millipore Pellicon Mini TFF system, 1 KDa MWCO membrane). If desired, the solution is further concentrated through the use of Amicon-15 (3 kDa MWCO) to approximately 10 mg/mL. The aqueous solution is stored overnight at 4° C.

Example 14

Insulin Conjugation to Give a B1-Substituted Insulin Conjugate

Synthesis of NH$_2$—B1-BOC2(A1,B29)-Insulin

In a typical synthesis, 4 g of powdered insulin (Sigma Aldrich, St. Louis, Mo.) is dissolved in 100 ml of anhydrous DMSO at room temperature followed by the addition of 4 ml of triethylamine (TEA). The solution is stirred for 30 minutes at room temperature. Next, 1.79 ml (2.6 equivalents) of di-tert-butyl-dicarbonate/THF solution (Sigma Aldrich, St. Louis, Mo.) is slowly added to the insulin-TEA solution and mixed for approximately one hour. The reaction is quenched via the addition of 4 ml of a stock solution containing 250 ul of ethanolamine in 5 ml of DMSO followed by mixing for five minutes. After quenching, the entire solution is poured into 1600 ml of acetone and mixed briefly with a spatula. Next, 8×400 μl aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×400 μl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains 60% of the desired BOC2 product and 40% of the BOC3 material.

A preparative reverse phase HPLC method is used to isolate the pure BOC2-insulin from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at ml/minutes with a 70% A/30% B mobile phase using a Waters DeltraPrep 600 system. Approximately 5 ml of the crude powder solution is injected onto the column at a flow rate of ml/minutes over the course of 5 minutes after which a linear gradient is employed from 70% A/30% B to 62% A/38% B over the course of the next 3.5 minutes and held there for an additional 2.5 minutes. Using this method, the desired BOC2 peak elutes at approximately 10.6 minutes followed closely by the BOC3 peak. Once collected, the solution is rotovapped to remove acetonitrile and lyophilized to obtain pure BOC2-insulin powder. Identity is verified by LC-MS (HT Laboratories, San Diego, Calif.) and site of conjugation determined by N-terminal sequencing (Western Analytical, St. Louis, Mo.).

Conjugation

NH$_2$—B1-BOC2(A1,B29)-insulin is conjugated to a PLF following Example 11.

The resulting conjugate may then be purified according to Example 13.

Example 15

Insulin Conjugation to Give an A1-Substituted Insulin Conjugate

Synthesis of NH$_2$-A1,B1-BOC(B29)-Insulin

Insulin is dissolved in a 66:37 vol:vol mixture of 100 mM sodium carbonate buffer (pH 11) and acetonitrile at a concentration of 14.7 mM. Separately, a monofunctional protecting group-activated ester (e.g., BOC-NHS) is dissolved at 467 mM in acetonitrile. Once the insulin is dissolved, small aliquots of the monofunctional protecting group-activated ester (e.g., BOC-NHS) are added to the insulin solution. The pH is monitored throughout the process and is maintained between 10.2-11.0 through the addition of 0.1M sodium hydroxide. The reaction is monitored by reverse-phase HPLC. Aliquots of the monofunctional protecting group-activated ester are added until the HPLC chromatogram shows that all of the unmodified insulin has been reacted and that a substantial portion of the reaction mixture has been converted to B29-protected insulin. Typically the protecting group will be more hydrophobic in nature and, once reacted onto the insulin, will elute at an HPLC retention time that is longer than the unmodified insulin.

Conjugation

NH$_2$-A1,B1-BOC(B29)-insulin is conjugated to a PLF following Example 11. The resulting conjugate may then be purified according to Example 13.

Example 16

Insulin Conjugation to Give an A1,B29-Substituted Insulin Conjugate

An A1,B29 insulin conjugate is obtained by conjugating a PLF to unprotected insulin following Example 11. The resulting conjugate may then be purified according to Example 13. This reaction has been carried out using Compound A-1 and recombinant human insulin (RHI).

Example 17

Insulin Conjugation to Give an A1,B1-Substituted Insulin Conjugate

NH$_2$-A1,B1-BOC(B29)-insulin is synthesized as described in Example 14. An A1, B1-substituted insulin conjugate is synthesized following Example 11 and using the appropriate equivalents of PLF and drug. The resulting conjugate may then be purified according to Example 13.

Example 18

Insulin Conjugation to Give a B1,B29-Substituted Insulin Conjugate

Synthesis of NH$_2$—B1,B29-BOC(A1)-Insulin

NH$_2$—B1,B29-BOC(A1)-insulin can be prepared using the procedure in Example 14 but reacting with fewer equivalents of the BOC reagent in order to yield a distribution of A1,B29-diBOC-insulin, A1-BOC-insulin, and B29-BOC-insulin products. NH$_2$—B1,B29-BOC(A1)-insulin can be isolated by RP-HPLC and confirmed by N-terminal sequencing.

Conjugation

NH$_2$—B1,B29-BOC(A1)-insulin is conjugated to a PLF following Example 11. The resulting conjugate may then be purified according to Example 13.

Example 19

Insulin Conjugation to Give a B29-Substituted Insulin Conjugate

A B29 insulin conjugate is obtained by conjugating a PLF to unprotected insulin following Example 12. The resulting conjugate may then be purified according to Example 13.

Example 20

Formulation of Insulin Conjugate in Preparation of In Vivo Testing

After 1.5 g of recombinant human insulin was conjugated and purified according to Example 16, the resulting insulin-conjugate was at a concentration of approximately 760 micromolar in purified water with a total solution volume of approximately 140 mL. To this solution was added 14 mL of a pH 7.4 formulation buffer concentrate that comprised 1.78 mL glycerin, 0.22 g m-cresol, 0.09 g phenol, and 0.53 g sodium phosphate. The resulting solution final volume was 154 mL.

It will be understood by one of ordinary skill in the art that this procedure may be used to formulate any of the conjugates of Examples 11-20.

Example 21

Effect of Ligand on Bioactivity

This example compares the blood glucose profiles obtained for a series of subcutaneously administered exemplary conjugates. The ligand composition varies across the conjugates to cover a range of affinities: AEM-2, AEBM-2, AETM-1-AEBM-1 and AETM-2 (from lowest to higest affinity). The insulin conjugates are shown as II-1, II-2, II-3, and II-4 in FIG. 1. In each case, the conjugates were injected at 5 U/kg (3.5 U/kg for AEM-2) behind the neck of fasted normal non-diabetic rats (Male Sprague-Dawley, 400-500 gm, n=6). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden).

FIGS. 2-5 show the blood glucose levels alongside the serum insulin levels for each of the four conjugates tested. These results show quite clearly that the reduced glucose response for conjugates with higher affinity ligands results from the reduced PK profile of the conjugate (compare FIG. 2 for AEM-2 with FIG. 5 for AETM-2).

Example 22

Long Acting Insulin Conjugate—Dose Response Effect

In order to generate a long acting conjugate, a PZI (protamine zinc insulin) formulation was prepared from a solution of synthetic insulin-conjugate II-6 (see FIG. 1 for a structure of the conjugate). The excipients used in the formulation included protamine, zinc, m-cresol, and salt all of which were obtained commercially from Sigma-Aldrich (St. Louis, Mo.).

TABLE 4

| Component | Variable | Volume (ml) |
| --- | --- | --- |
| II-6 solution at 2.7 mg/ml 250 mM HEPES buffered saline | unmodified insulin = 16.7% NaCl concentration = 1.5M | 1.000 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

Once the formulation was prepared after addition of the components in the order described in Table 4, they were gently mixed for 30 minutes prior to in vivo testing.

To test the sustained release profile as well as the glucose-responsive PK profile, the following experiment was conducted. The formulation was injected at 5 or 15 U/kg (body weight in grams/1.87=microliters of injection volume) of the formulation behind the neck of fasted normal non-diabetic rats (Male Sprague-Dawley, 400-500 gm, n=3). After a 240 minute delay, a glucose dose (4 g/kg) was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4° C. to collect the serum. Serum insulin concentrations were subsequently measured with a commercially available ELISA kit (Iso-Insulin ELISA, Mercodia, Uppsala, Sweden).

Figures 1, 2, 3, 4, 5, 6:
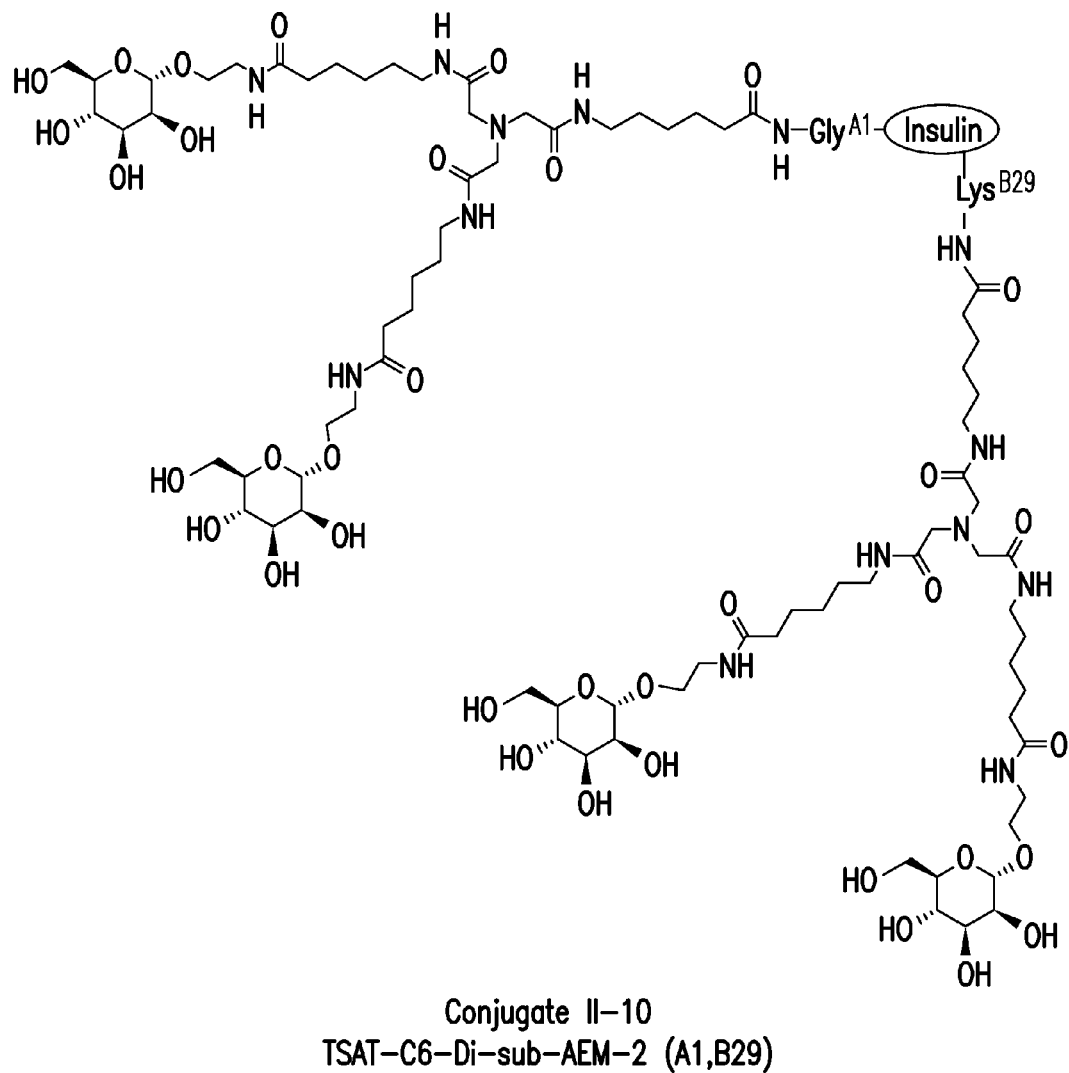
FIG. 5: Plot of serum insulin (left) and blood glucose (right) levels following subcutaneous injection in non-diabetic, male SD rats (n=3) at time 0 with TSAT-C6-AETM-2 conjugate II-2 (5 U/kg).
FIG. 6: Plot of serum insulin (♦) and blood glucose (○) levels following subcutaneous injection in non-diabetic, male SD rats (n=3 per dose) at time 0 with a long-acting protamine zinc (PZI) formulation of synthetic conjugate II-6 followed by IP injection of glucose (4 g/kg) at 240 minutes. As shown, no hypoglycemia is observed as early or late time points. A comparison of the response with 5 U/kg (left) and 15 U/kg (right) doses shows a dramatic dose-dependent glucose response.

As shown in FIG. 6, the synthetic insulin-conjugate exhibited a flat PK profile until the glucose was injected. The glucose response was dramatic and dose-dependent (compare data obtained with a 5 U/kg (left) and 15 U/kg (right) dose of synthetic insulin-conjugate). No hypoglycemia was observed at early or late time points.

Example 23

Long Acting Conjugate in Diabetics and Non-Diabetics

In order to confirm the in viva utility of the long acting synthetic insulin-conjugate formulation, we administered it (5, 10 and 20 U/kg) to normal and STZ-induced diabetic rats (Male Sprague-Dawley, 400-500 gm, n=6). The formulation was prepared using the procedure in Table 5.

TABLE 5

| Component | Variable | Volume (ml) |
| --- | --- | --- |
| II-6 solution at 2.7 mg/ml 250 mM HEPES buffered saline | unmodified insulin = 0% NaCl concentration = 1.5M | 1.000 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

Figures 1, 2, 3, 4, 5, 6, 7:
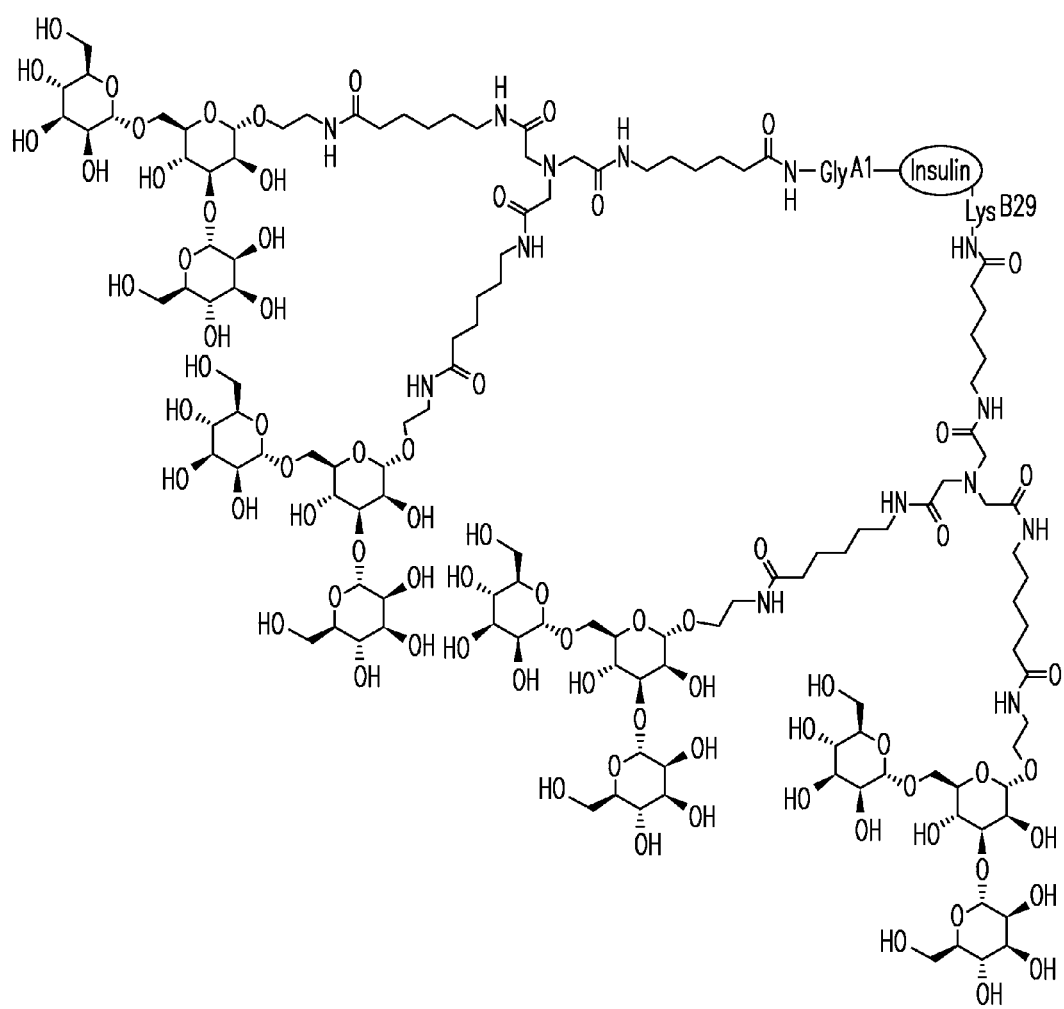
FIG. 7: Plot of blood glucose levels following subcutaneous injection in non-diabetic (normals) and diabetic (DM's) male SD rats at time 0 with a long-acting PZI formulation of synthetic conjugate II-6. The conjugate was administered at 5, 10 and 20 U/kg. As shown, the non-diabetic male SD rats did not show any hypoglycemia while the glucose levels in diabetic male SD rats showed a clear dose proportional response that lasted for over 8 hours at the highest dose.

No external IP injections of glucose were used to trigger the bioactivity of the conjugates. Instead we relied on the endogenous levels of glucose in the rats to control the PK and PD profile of the conjugate formulation. Blood samples were collected via tail vein bleeding at various time points after the initial conjugate injection. Blood glucose values were measured using commercially available test strips (Precision Xtra, Abbott Laboratories, Abbott Park, Ill.). As shown in FIG. 7, no hypoglycemia was observed at early or late time points for the normal or diabetic rats. The glucose profiles observed with the diabetic rats are dramatic and demonstrate that the conjugates were activated by the higher glucose concentrations and exerted their glucose-lowering effect in a dose proportional manner over a long time period (over 8 hours at the highest dose).

Example 24

In Vivo Half Life/Elimination Rate Comparison

In order to determine the rate at which conjugate II-6 was cleared from serum in vivo in the presence or absence of inhibitory sugars such as glucose or alpha-methyl mannose (a-MM), the following experiment was conducted. In each case conjugate II-6 (or RHI as a control) was dosed at 0.4 mg conjugate/kg body weight into dual jugular vein cannulated male Sprague-Dawley rats (Taconic, JV/JV, 350-400 g, n=3).

To determine the elimination rate in the presence of elevated glucose levels, one hour before the start of the experiment one rat cannula was connected to a syringe infusion pump containing a sterile 50% w/v glucose solution. The pump infusion rate was adjusted by the experimenter to ensure that the blood glucose levels in the animal remained above 300 mg/dL at all times during the experiment. Blood glucose was measured using commercially available test strips (Precision Xtra, Abbott Laboratories, Abbott Park, Ill.). In a typical experiment, it was found that the infusion pump rate required to keep the animals above 300 mg/dL was typically greater than 85 µL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

To determine the elimination rate in the presence of a-MM, one hour before the start of the experiment one rat cannula was connected to a syringe infusion pump containing a sterile 25% w/v a-MM solution. The pump infusion rate was adjusted by the experimenter, but was typically set at 85 µL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

Figures 1, 2, 3, 4, 5, 6, 7, 8:
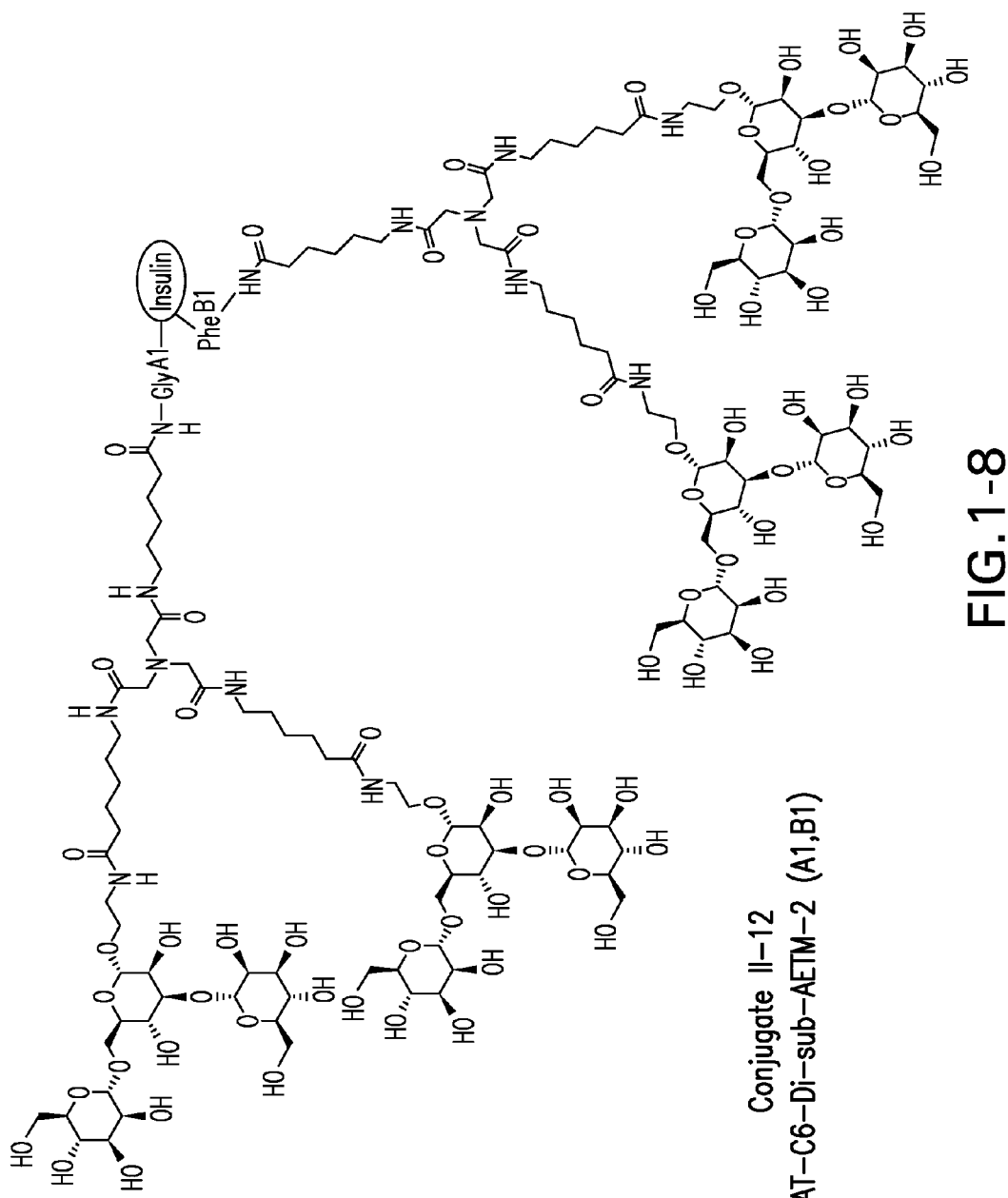
FIG. 8: Plots of serum insulin concentration as a function of time following injection of synthetic conjugate II-6 or recombinant human insulin (RHI) (left) and following injection of synthetic II-6 with and without glucose or α-methyl mannose (right).

Throughout the experiment, blood glucose was measured using commercially available test strips (Precision Xtra, Abbott Laboratories, Abbott Park, Ill.). Blood from each timepoint was centrifuged at 4° C. to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials ($C(t)=a \exp(-k_a t)+b \exp(-k_b t)$) according to the two-compartment model, where $t1/2(a)=(\ln 2)/k_a$ and $t1/2(b)=(\ln 2)/k_b$. Results are shown in FIG. 8. The left panel demonstrates the significantly higher (>5x) elimination rate for conjugate II-6 versus RHI in the absence of a-MM or glucose. The right panel shows that the elimination rate decreases somewhat (~50%) in the presence of glucose (G400 infusion) and quite substantially (~400%) in the presence of a-MM (a-MM infusion).

Example 25

Glucose-Responsive PK for Conjugate I-6
Intravenous (i.v.) Infusion

In this Example, the i.v. elimination rate experiment described in Example 24 was modified from a single i.v. bolus of 0.4 mg conjugate/kg body weight to a continuous i.v. infusion. The goal of the experiment was to maintain a constant input rate of conjugate (or RHI as a control) for six hours with an intraperitoneal (i.p.) injection of glucose administered at the four hour time point to determine the resulting effect on serum conjugate (or RHI) concentration. Dual jugular vein cannulated male Sprague-Dawley rats (Taconic, JV/JV, 350-400 g, n=3) were used in each experiment such that one jugular vein line was used for conjugate or RHI infusion and the other for blood collection.

For RHI, a 50 mU/ml solution was sterile filtered through a 0.2 gm filtration membrane and infused at 0.07 ml/min to provide a constant input rate of 3.5 mU/min for the entire six hour experiment. A blood sample was taken at t=0 min, after which the constant i.v. infusion was initiated. The second cannula was used to collect blood samples at t=30, 60, 120, 180 and 240 min. At t=240 min, a 4 g/kg dose of glucose was administered via i.p. injection followed by blood collection at t=255, 270, 300, 330 and 360 min.

For conjugate II-6, a 150 mU/ml solution was sterile filtered through a 0.2 µm filtration membrane and infused at 0.10 ml/min to provide a constant input rate of 15 mU/min for the entire six hour experiment. A blood sample was taken at t=0 min, after which the constant i.v. infusion was initiated. The second cannula was used to collect blood samples at t=30, 60, 120, 180 and 240 min. At t=240 min, a 1, 2, or 4 g/kg dose of glucose was administered via i.p. injection followed by blood collection at t=255, 270, 300, 330 and 360 min.

Throughout the experiments, blood glucose was measured using commercially available test strips (Precision Xtra, Abbott Laboratories, Abbott Park, Ill.). Blood from each timepoint was centrifuged at 4° C. to collect the serum, and serum insulin or serum conjugate concentrations were subsequently measured with a commercially available ELISA kit (Iso-Insulin ELISA, Mercodia, Uppsala, Sweden).

Figures 1, 2, 3, 4, 5, 6, 7, 8, 9:
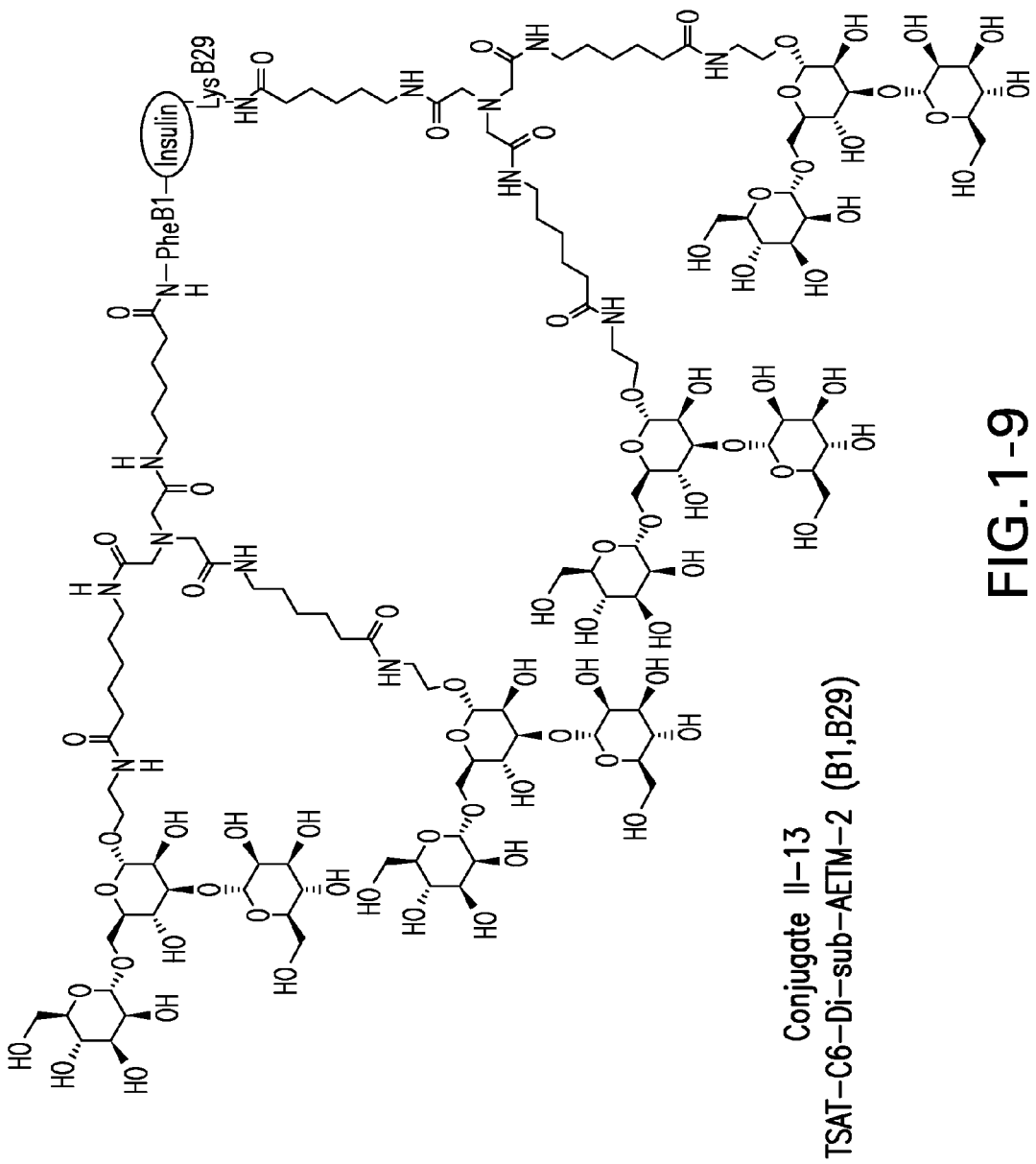
FIG. 9: Plots of serum insulin (♦) and blood glucose (○) levels following constant intravenous (i.v.) infusion of RHI (3.5 mU/min) or synthetic conjugate II-6 (15 mU/min) in non-diabetic, male SD rats (n=3). An IP injection of glucose (1, 2 or 4 g/kg) was given at 240 minutes.
Figure 2:
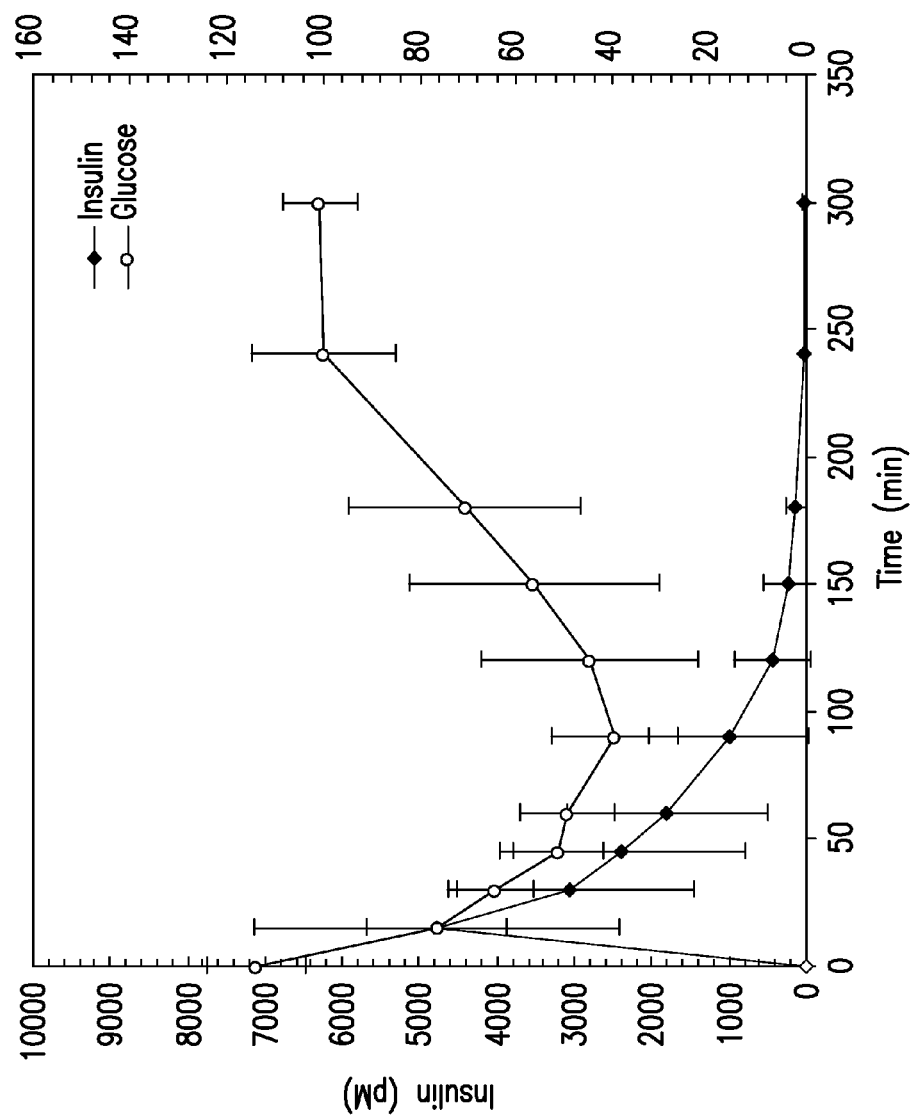
Figure 3:
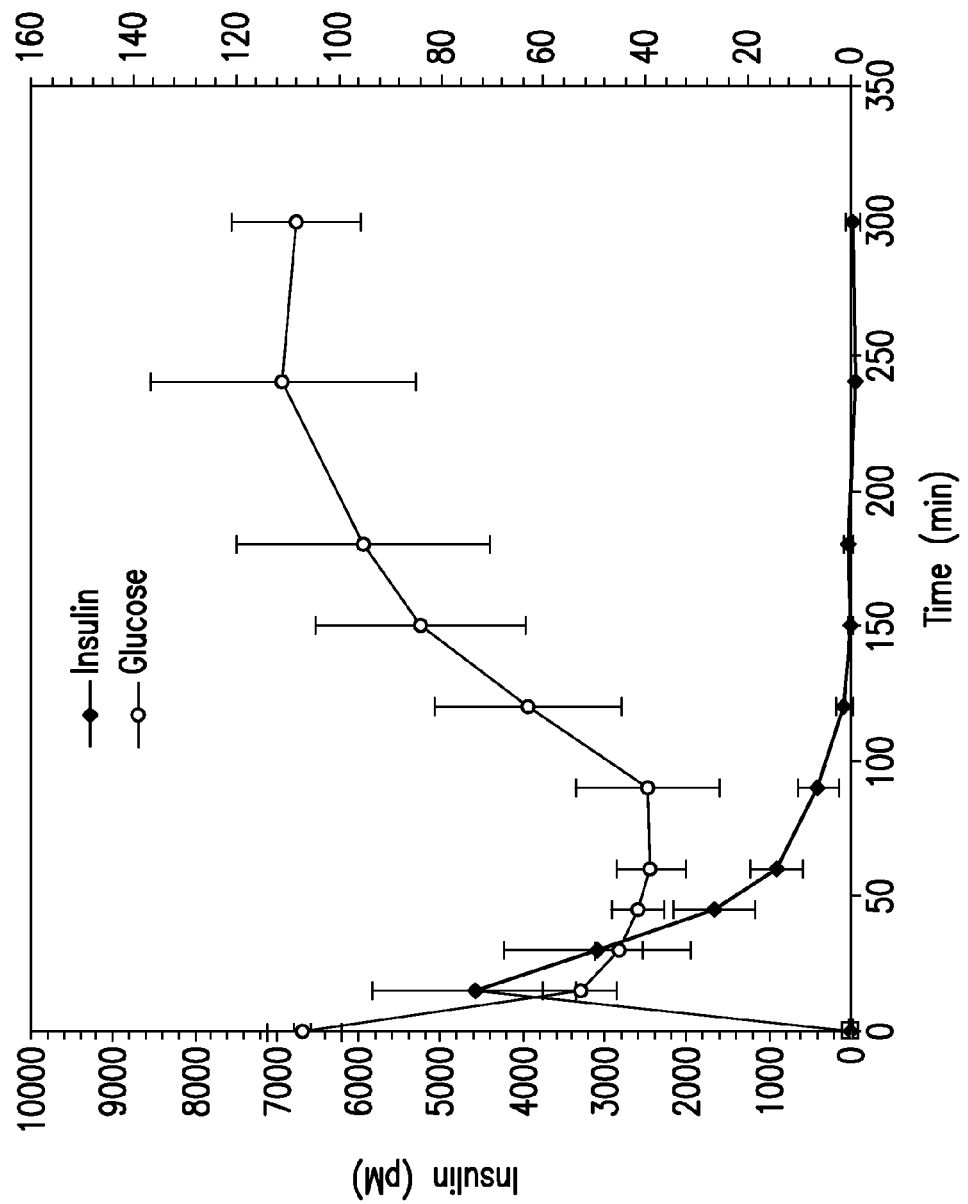
Figure 4:
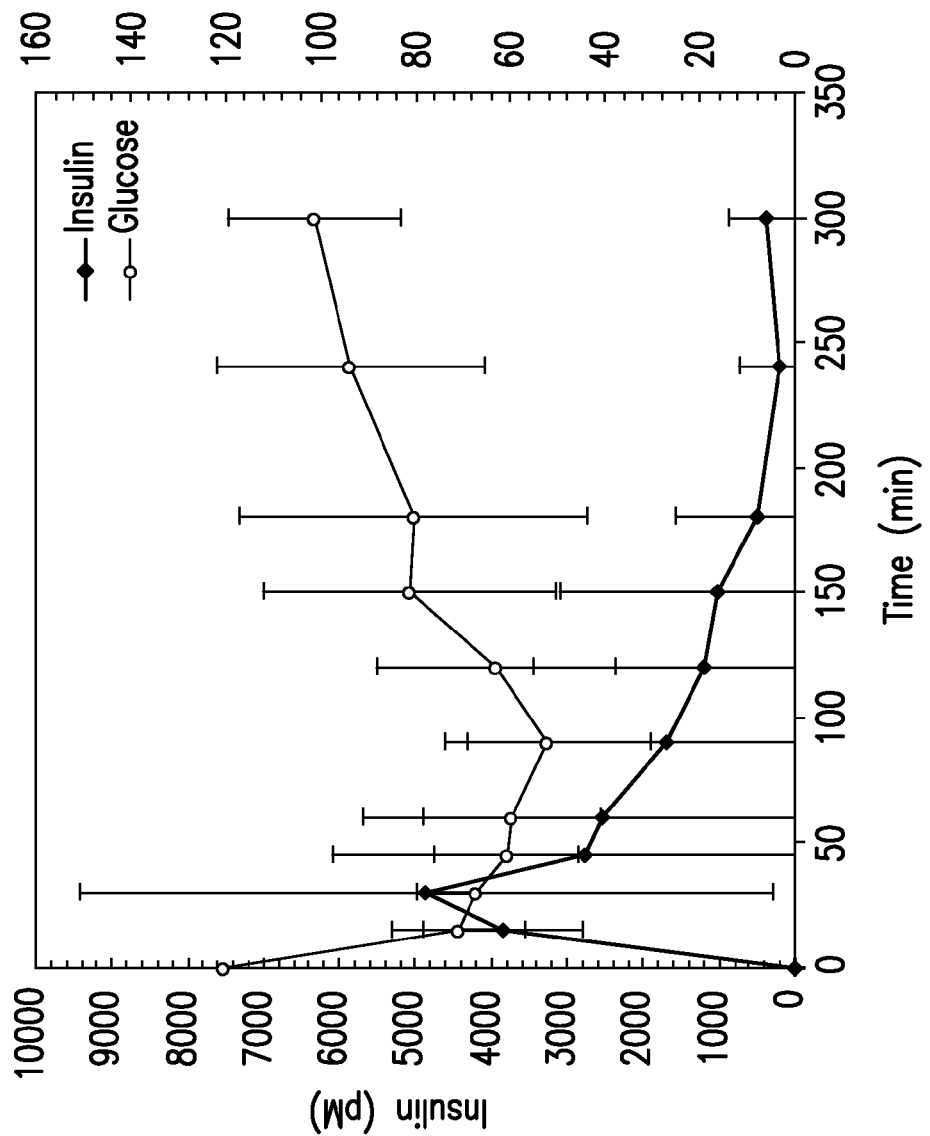
Figure 5:
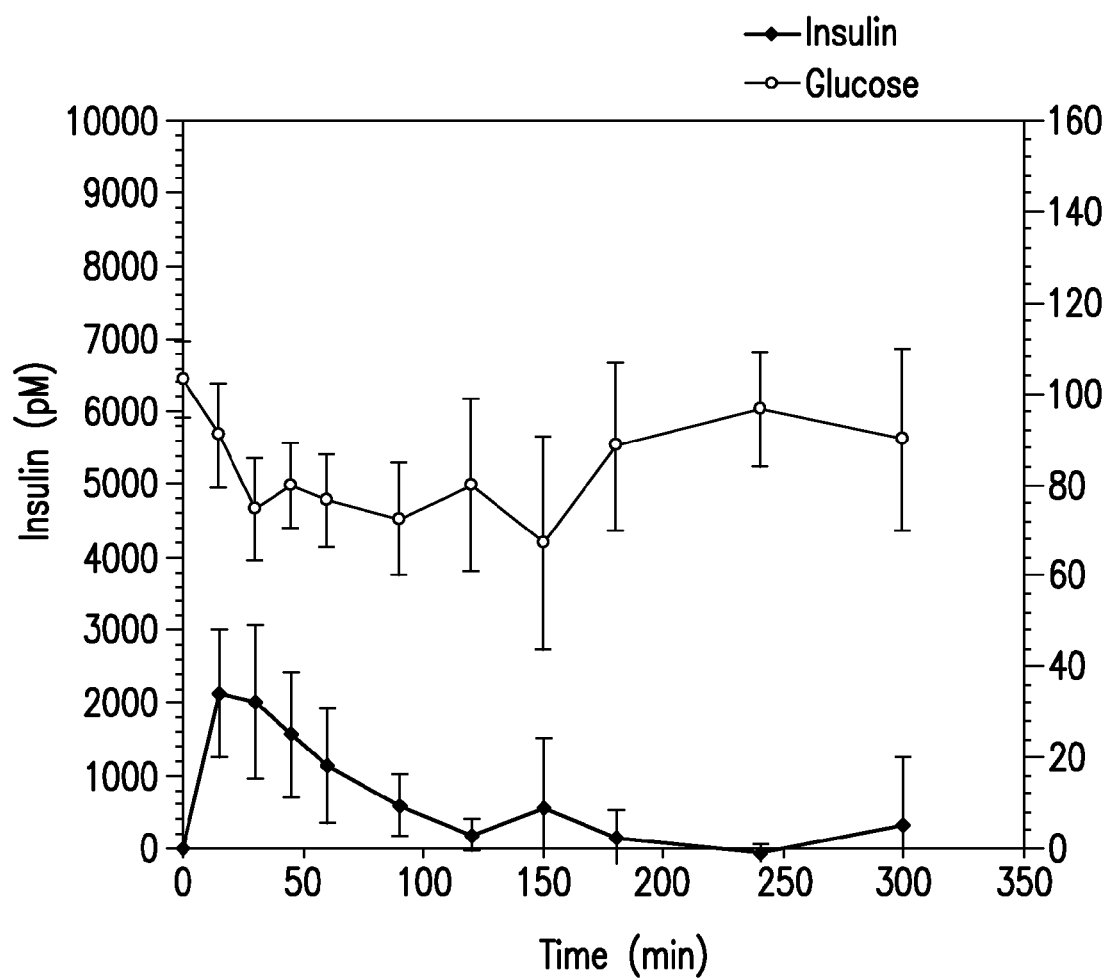
Figure 6:
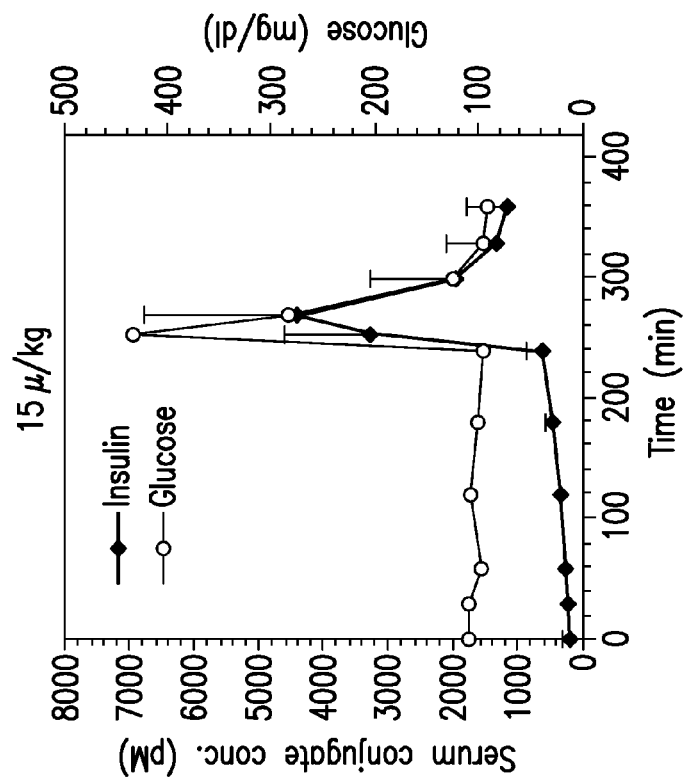
Figure 6:
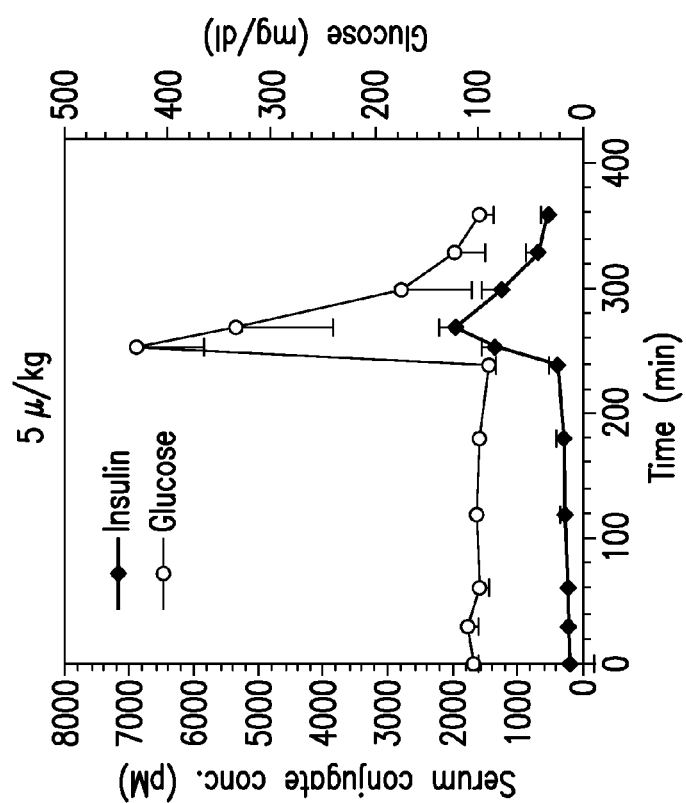
Figure 7:
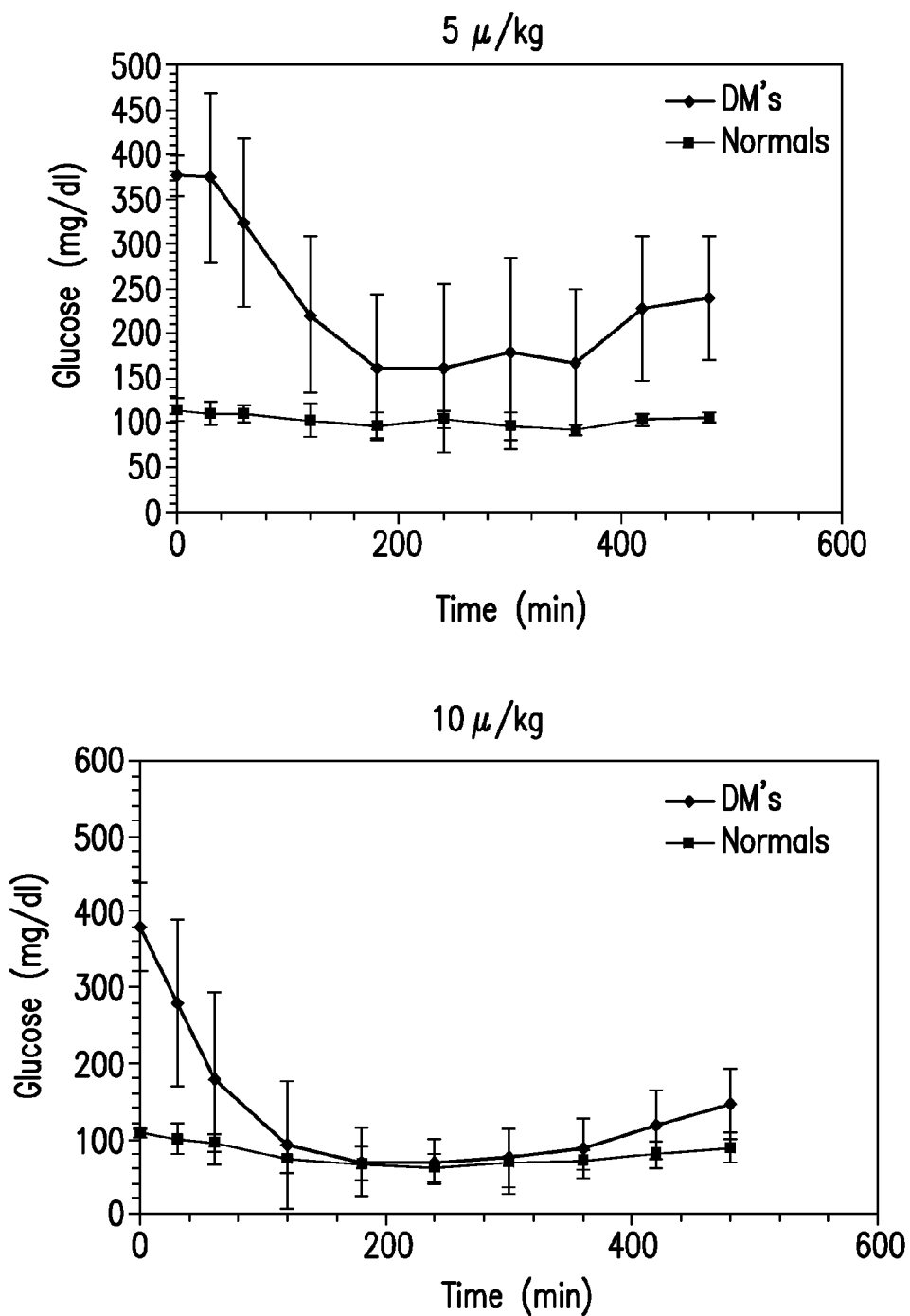
Figures 1, 7:
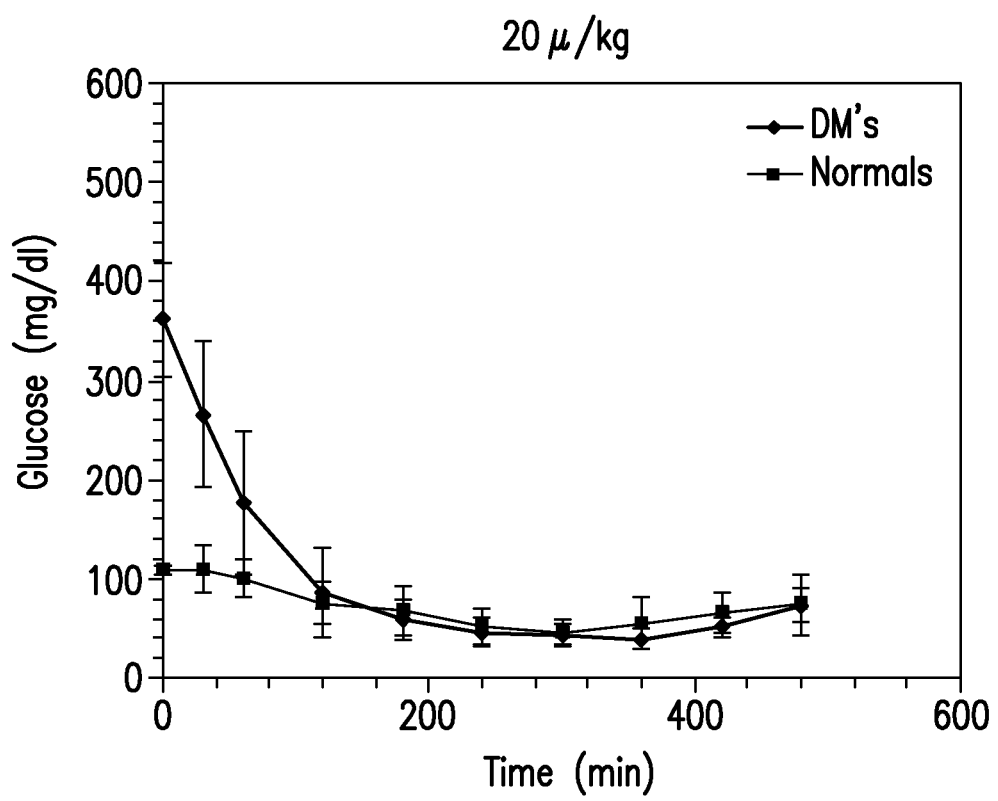
Figure 8:
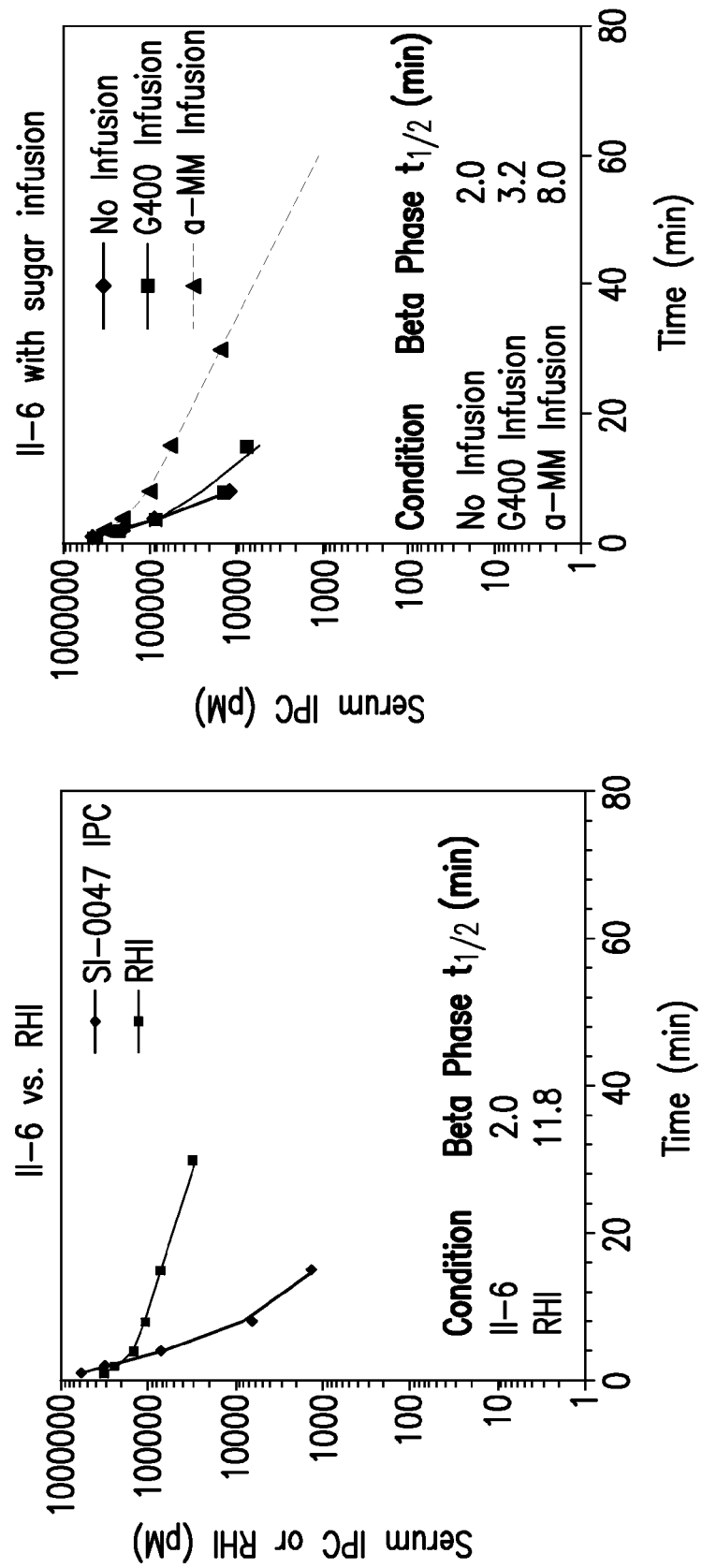
Figure 9:
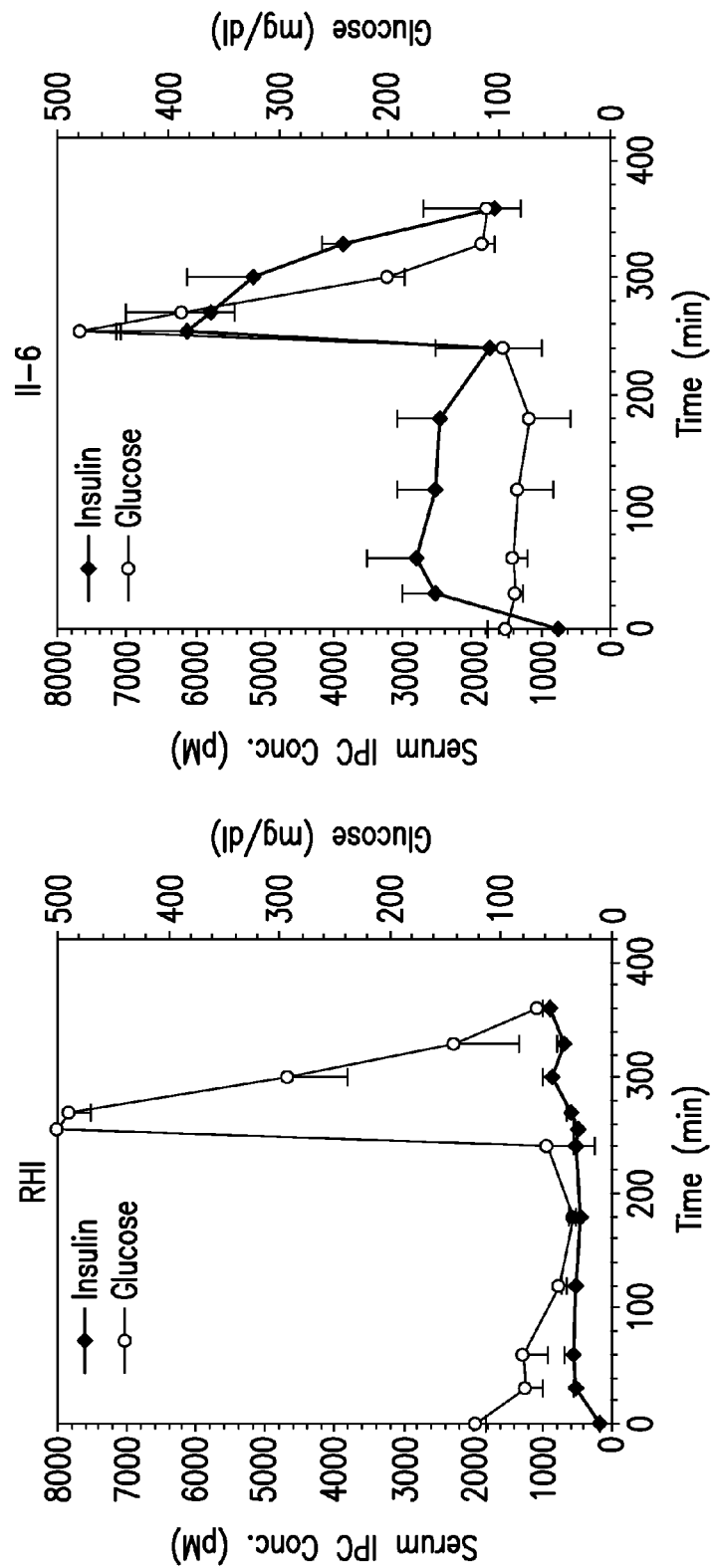
Figure 9:
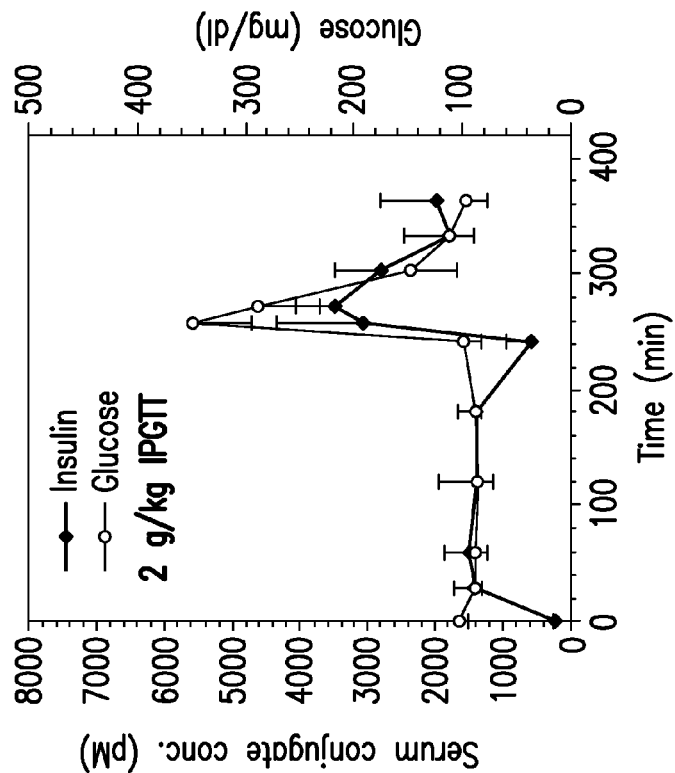
Figure 1:
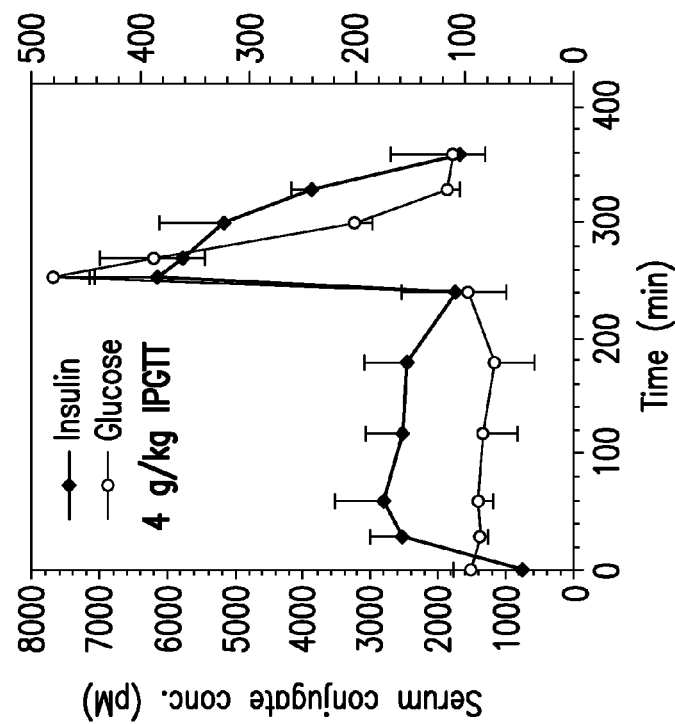
Figures 2, 9:
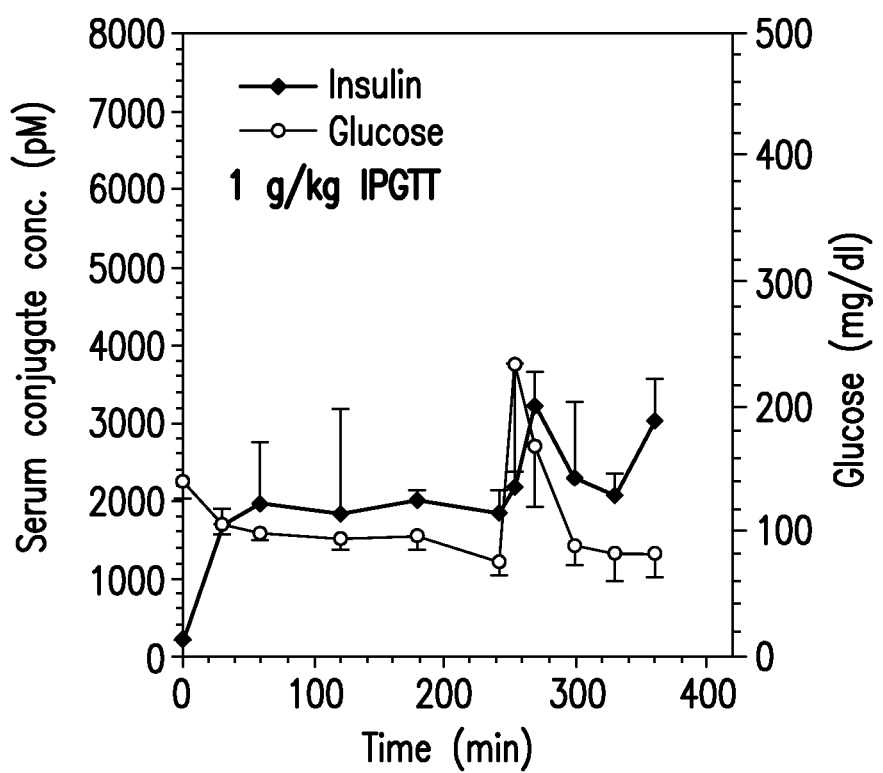
Figure 10:
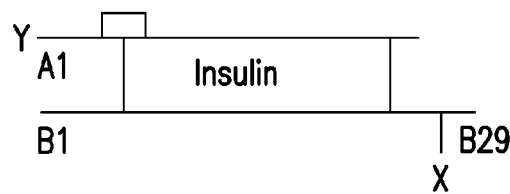
FIG. 10: Composition of insulin conjugates tested in non-diabetic minipig sugar-dependent elimination half-life studies. These conjugates were each prepared with recombinant wild-type human insulin. The schematic in FIG. 10 is therefore primarily intended to represent a wild-type human insulin. As discussed herein, it is to be understood that the present disclosure also encompasses inter alia versions of these and other conjugates that include an insulin molecule other than wild-type human insulin.

The first two panels of FIG. 9 compare the blood glucose and serum insulin/conjugate concentration profiles for a 3.5 mU/min infusion of RHI and 15 mU/min infusion of conjugate II-6 before and after a 4 g/kg i.p. glucose injection. RHI infusion causes significant hypoglycemia prior to glucose injection compared to the II-6 infusion. Following the i.p. glucose injection, the serum concentration of conjugate II-6 immediately increases by over 300% as the blood glucose concentration increases followed by a rapid return to baseline levels as the glucose concentration decreases. On the other hand, there is no significant change in serum RHI concentration after i.p. glucose injection. The next three panels of FIG. 9 show that the extent to which the serum conjugate concentration increases during i.p. glucose injection is directly related to the dose of glucose administered and the resulting blood glucose levels. For example, only a 50% peak to baseline change in serum conjugate concentration is observed for the 1 g/kg glucose injection while a 300% peak to baseline change is observed for the 4 g/kg dose.

Example 26

Mechanism Verification and Glucose-Responsive Performance in Miniature swine This Example investigates the sugar-dependent in vivo elimination rate of certain exemplary conjugates in human-representative, non-diabetic, male miniature swine (Yucatan strain), also called "minipigs" herein. A subset of insulin-conjugates summarized in FIG. 1 were tested to initially determine the effects of sugar affinity and multivalency on sugar-dependent elimination rates. The conjugates are shown in FIG. 1 as II-6, II-7 and II-11.

In each experiment, the insulin-conjugate was dosed i.v. at 0.1 U/kg into non-diabetic, dual-vascular access ported minipigs and blood was collected at frequent time intervals post-injection. To determine the serum elimination rate in the presence of glucose, a sterile 50% w/v glucose solution was infused i.v. into one port using a syringe pump one hour prior to administering the insulin-conjugate, and the rate was adjusted throughout the entire experiment to ensure that the blood glucose levels in the animal remained at or near 400 mg/dl (typically 80-150 ml/h). To determine the serum elimination rate in the presence of a-MM, the glucose solution was replaced with a sterile 25% w/v a-MM solution and the pump infusion rate held constant throughout the experiment at 80 ml/h. In each case, the resulting insulin-conjugate concentration vs. time data was fit with the sum of two independent decaying exponentials ($C(t)=\alpha \exp(-k_\alpha t)+\beta \exp(-k_\beta t)$) according to the two-compartment model.

Figure 12B:
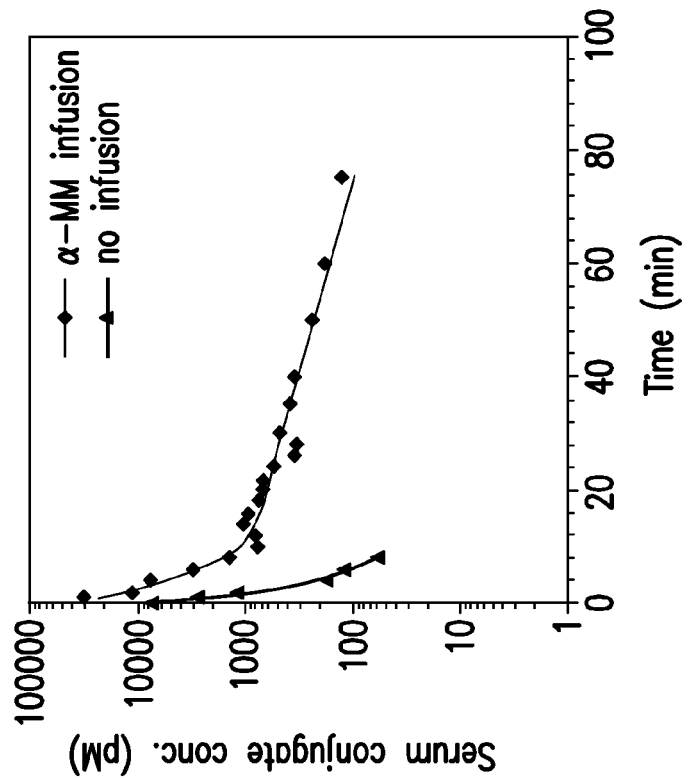
FIG. 12: Plots of serum concentrations of (a) recombinant human insulin (RHI) and (b) Di-Sub-AETM-2 insulin conjugate II-11 following a 0.1 U/kg intravenous (i.v.) injection into non-diabetic male Yucatan minipigs equipped with dual vascular access ports (n=3 per study). In each experiment, the animals were infused with (♦) i.v. alpha methyl mannose (a-MM) solution (25% w/v infused at constant rate of 80 ml/h) or (▲) no solution. Data are plotted as the average values fit with a curve derived from the two-compartment, bi-exponential model.
Figure 12A:
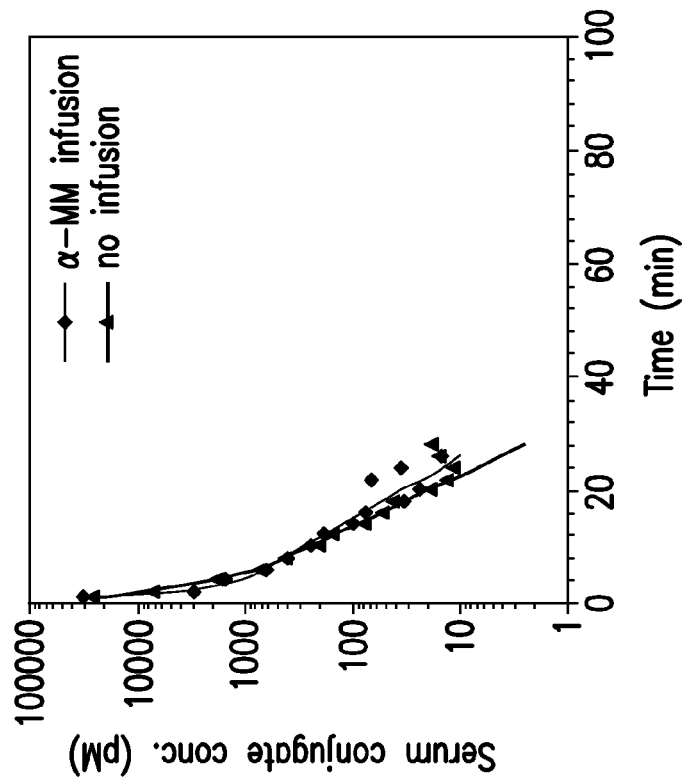
Figure 17:
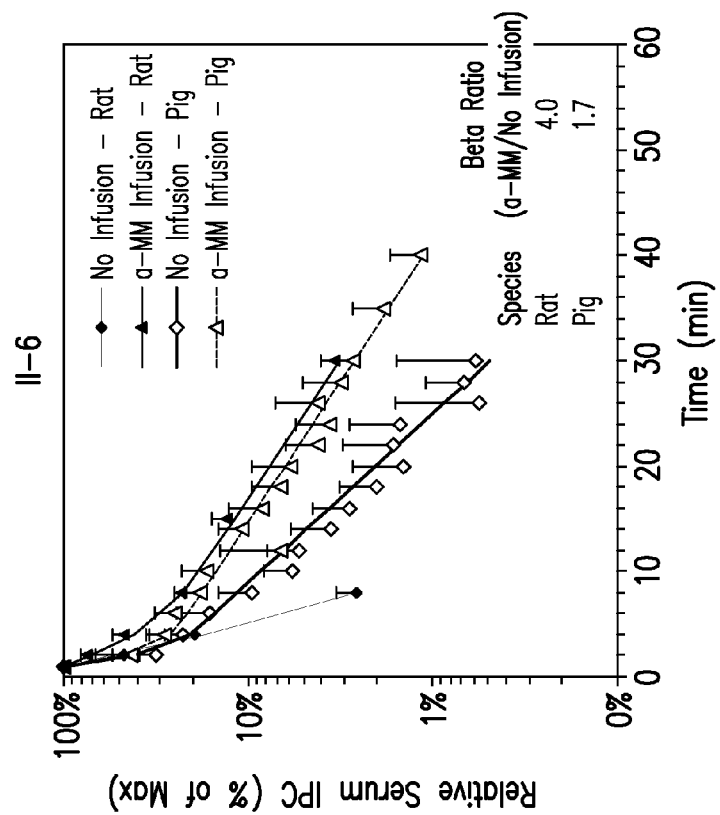
FIG. 17: Plots of serum insulin concentration as a function of time following administration of RHI or conjugate II-6 in rats and minipigs.
Figure 17:
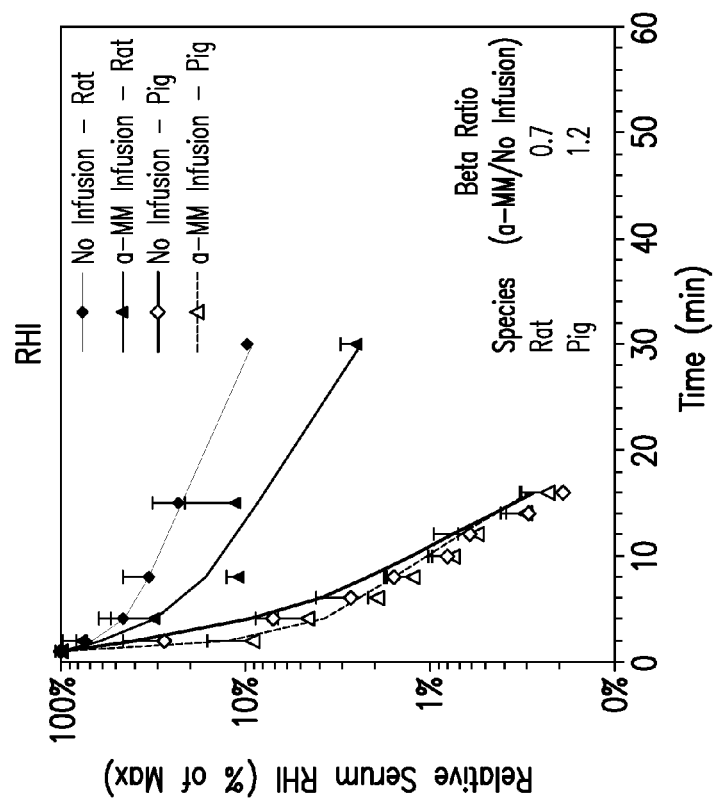

At 400 mg/dl the high levels of endogenous glucose-induced porcine insulin crossreacted with our insulin-conjugate immunoassay. As such, the PK results from the glucose infusion experiments required subtraction of values obtained from a porcine insulin-only assay leading to a particularly "noisy" set of data. Since a-MM does not induce endogenous porcine insulin secretion, data from the a-MM infusion studies were used as our primary indicator of sugar-responsive changes in insulin-conjugate half-life. Interestingly, in the pigs, the AETM-2 insulin-conjugate (II-6) showed only a modest 1.7× increase in $t_{1/2}$ in the presence of a-MM compared to a 4.0× increase in the rats (FIG. 17). However, in the pigs, the A1,B29-di-substituted AETM-2 insulin-conjugate (II-11) demonstrated an almost 10-fold increase in $t_{1/2}$ in the presence of a-MM (FIGS. 11 and 12). Tabular results for other conjugates are shown in FIG. 18.

The area over the glucose lowering curve for the i.v. dose of di-substituted AETM-2 insulin-conjugate (II-11) in the presence of a-MM was approximately 2.6× higher than in the absence of sugar (FIG. 13).

Figure 14B:
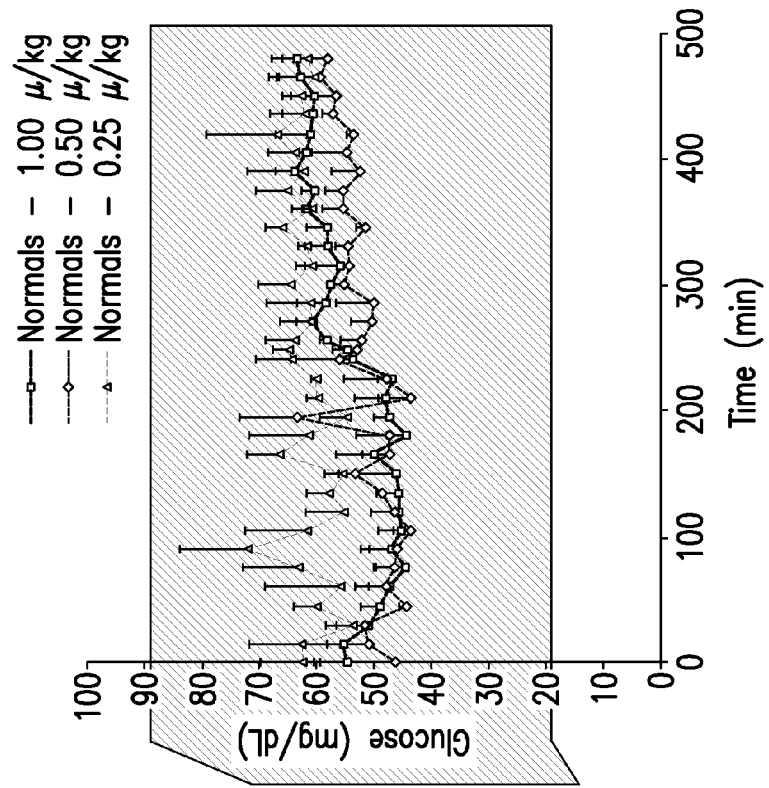
FIG. 14: Blood glucose levels in (a, —, closed symbols) alloxan-diabetic Yucatan minipigs (n=3 per dose) and (b, - - -, open symbols) non-diabetic Yucatan minipigs (n=3 per dose) under fasting conditions after a sub-Q injection at time 0 with soluble Di-Sub-AETM-2 insulin conjugate II-11 at doses of 0.25, 0.50, and 1.00 U/kg. Data are plotted as the average values+one standard deviation. NOTE.
Figure 14A:
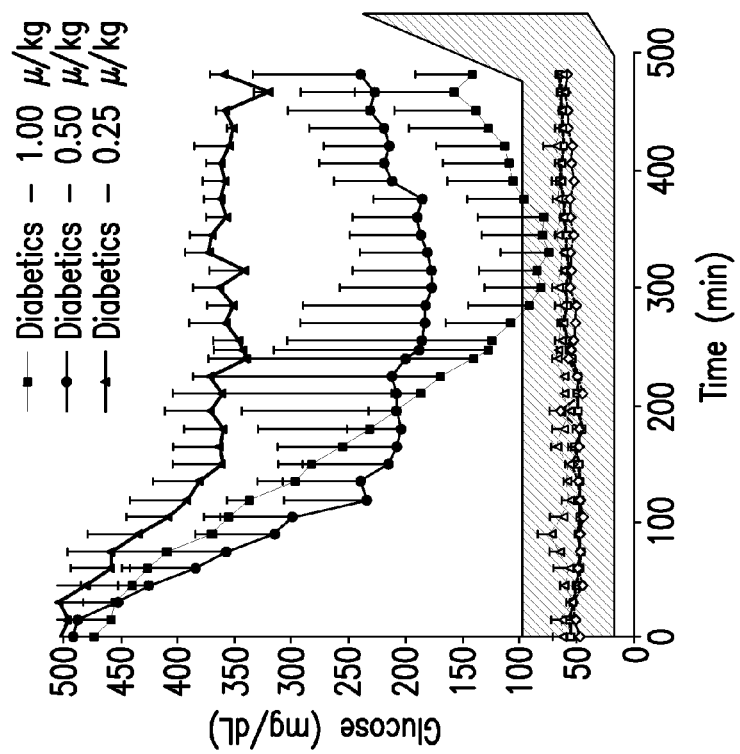
Figures 15A, 15B:
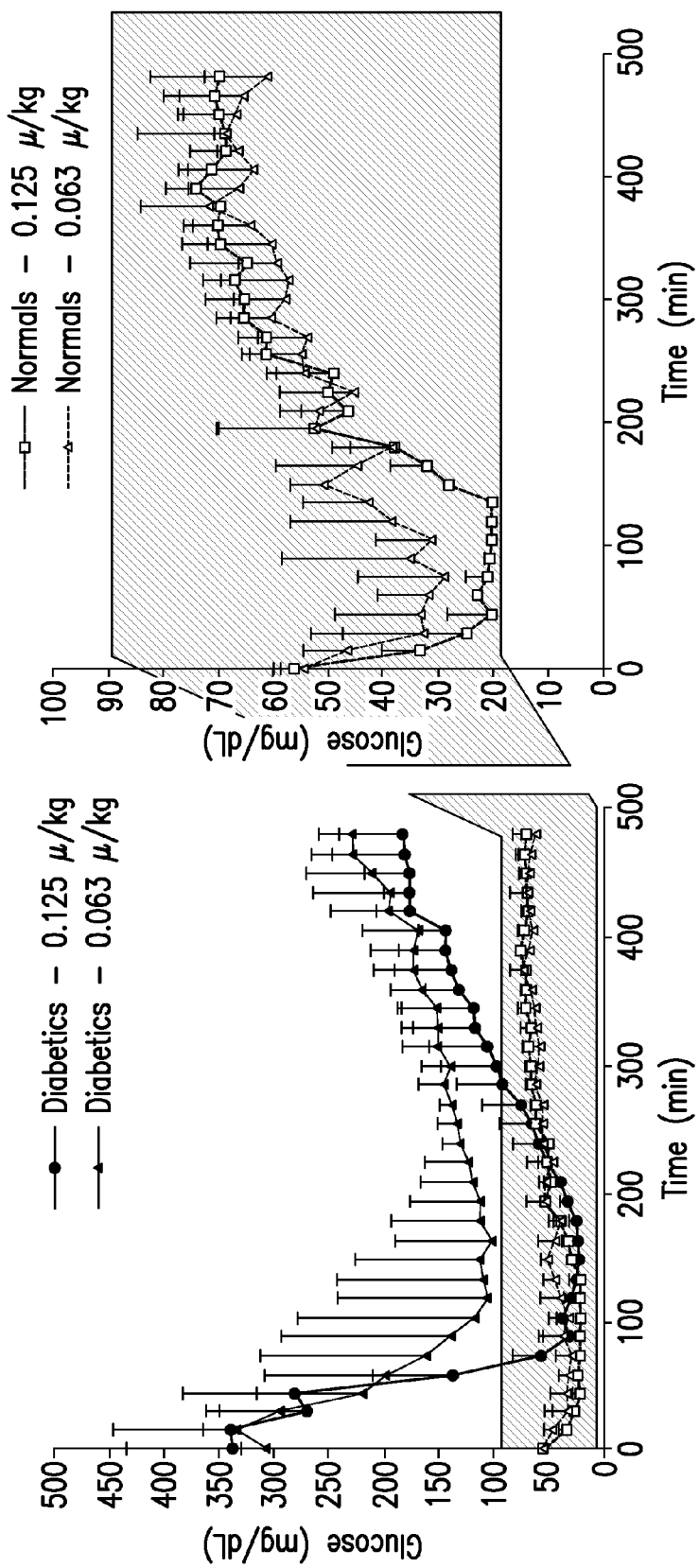
FIG. 15(b) scale is enlarged for clarity.
Figure 19:
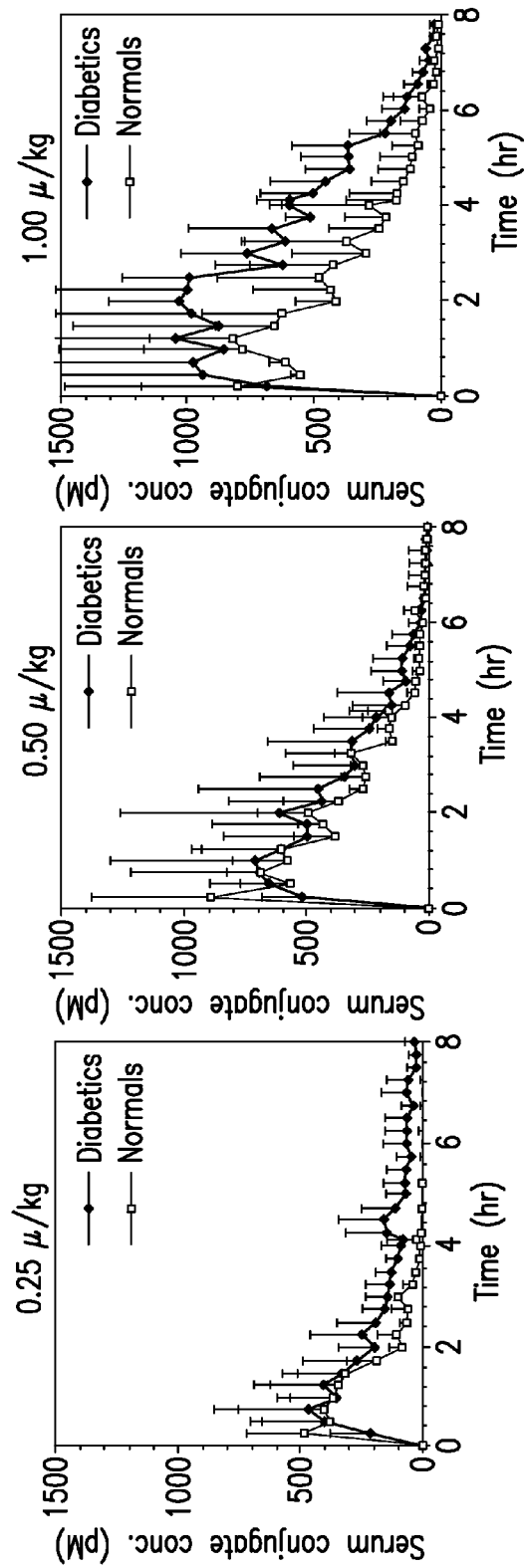
FIG. 19: Plot of serum insulin levels after a single subcutaneous injection of 0.25, 0.5 and 1 U/kg insulin conjugate II-11 in diabetic and normal minipigs.

Conjugate II-11 was injected sub-Q as a soluble solution at doses of 0.25, 0.50, and 1.00 U/kg in both non-diabetic, normoglycemic and alloxan-diabetic, hyperglycemic minipigs to determine its ability to lower glucose in diabetics without causing hypoglycemia in non-diabetic animals. The insulin-conjugate demonstrated a significant dose-dependent reduction in blood glucose levels in the diabetics with absolutely no hypoglycemia or signs of glucose-lowering in the non-diabetics (FIG. 14). In comparison, RHI injected at 0.063 and 0.125 U/kg caused significant glucose-lowering in the diabetic animals with noticeable hypoglycemia and significant glucose-lowering and hypoglycemia in the non-diabetic animals (FIG. 15). Based on these preliminary results, a single injection of approximately 0.5 U/kg of soluble insulin-conjugate II-11 provided hypoglycemia-free glucose control for 6-8 hours in diabetic minipigs. Serum elimination rates of sub-Q injected II-11 were determined in diabetic and normal minipigs (FIG. 19). Similar PK profiles were observed between diabetics and normals for all doses.

Taken together, these results demonstrate that an endogenous lectin-based mechanism exists in the minipigs that can be exploited through selection of sugar affinity and multivalency. It appears that insulin-conjugates with higher affinities and multivalencies provide improved hypoglycemia-free glycemic control in minipigs as compared to rats.

Example 27

Optimization Studies in Miniature Swine

Figure 16:
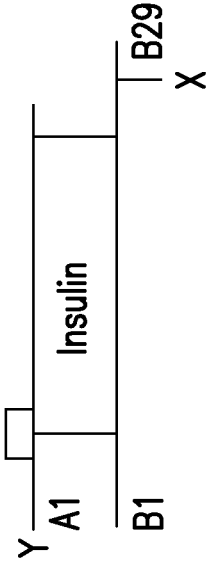
FIG. 16: Additional insulin conjugates for use in non-diabetic minipig sugar-dependent elimination half-life studies. These conjugates were each prepared with recombinant wild-type human insulin. The schematic in FIG. 16 is therefore primarily intended to represent a wild-type human insulin. As discussed herein, it is to be understood that the present disclosure also encompasses inter alia versions of these and other conjugates that include an insulin molecule other than wild-type human insulin.

Based on the stark difference in performance of II-11 versus the other conjugates in FIG. 1, it is desirable to separate and quantify the effect of insulin conjugation site (A1 vs. B29) from the effects of sugar affinity and valency. We therefore tested the insulin-conjugates shown in FIG. 16 (shown in FIG. 1 as II-8, II-9 and II-10).

In general, the sugar-responsive half-lives and glucose-lowering effects of each of these insulin-conjugates were determined as follows. As described above, each insulin-conjugate was dosed i.v. at 0.1 U/kg into non-diabetic, dual-vascular access ported minipigs and blood was collected at frequent time intervals post-injection. To determine the serum elimination rate in the presence of a-MM, a sterile 25% w/v a-MM solution was infused i.v. into one port using a syringe pump (80 ml/h) one hour prior to administering the insulin-conjugate, and the rate was held constant throughout the entire experiment. In each case, the resulting insulin-conjugate concentration vs. time data was fit with the sum of two independent decaying exponentials ($C(t)=\alpha \exp(-k_\alpha t)+\beta \exp(-k_\beta t)$) according to the two-compartment model. Comparison of the j3-phase elimination rates with and without a-MM infusion was used to identify suitable conjugates.

Conjugate II-8 (A1 substitution with AETM-2) was slightly more effective in lowering glucose than conjugate II-6 (B29 substitution with AETM-2). Substitution of conjugate II-6 at the A1 position with polyethylene oxide to give conjugate C3 reduced overall bioactivity but did not increase the a-MM induced bioactivity (data not shown). Substitution of conjugate II-6 at the A1 position with another TSAT-C6-AETM-2 scaffold to give conjugate II-11 reduced overall bioactivity but increased the a-MM induced bioactivity.

Example 28

Recombinant Insulin Molecules: Production in Yeast, Protein Purification, and In Vitro Enzyme Processing This example demonstrates the recombinant production of several exemplary insulin molecules in two different yeast strains (KM71 and GS115) on both small- and large-scales. Some of these insulin molecules were engineered to include N-terminal protecting amino acid sequences. The recombinantly-produced insulin molecules had the expected molecular weight and were recognized by anti-insulin antibodies. The experiments described in this example demonstrate that insulin molecules manufactured in yeast generated commercial scale yields. This example also describes procedures that were used for in vitro enzyme processing of recombinantly produced insulin molecules and conjugation with a prefunctionalized ligand framework.

Materials and Methods
Preparation of Electrocompetent *P. pastoris* Strains

KM71 (Invitrogen, Carlsbad, Calif.) was cultured at 30° C. in YPD broth (per liter: g yeast extract, 20 g peptone, and 20 g glucose, pH 6.5). After successful revival of the strain, electrocompetent KM71 was prepared as described by Wu and Letchworth (Biotechniques 36:152-4). Electrocompetent KM71 were stored in a −80° C. freezer. Electrocompetent *P. pastoris* GS115 (Invitrogen, Carlsbad, Calif.) was prepared by the same procedure.

Preparation of Insulin Molecule Expressing Gene Constructs

Gene synthesis of insulin molecule constructs was performed at GeneArt (Regensburg, Germany). Briefly, genes of interest coding for the expression of insulin molecules are listed in Table 6. The genes were synthesized at GeneArt, then cut with BamI (5' site) and EcoRI (3' site) enzymes and then inserted into the same sites in the pPIC3.5K vector (Invitrogen, Carlsbad, Calif.). The resulting plasmid was then amplified in *E. coli* in culture flasks and then extracted, purified, giving a ~1 mg/mL solution of the plasmid DNA in TE buffer.

TABLE 6

| Construct ID | DNA sequence |
|---|---|
| RHI-1 | ATGAGATTCCCATCTATCTTCACTGCTGTTTTGTTCG<br>CTGCTTCTTCTGCTTTGGCTGCTCCTGTTAACACTAC<br>TACTGAAGACGAAACTGCTCAAATCCCAGCTGAAGCG<br>GTTATCGGTTACTCTGACTTGGAAGGTGACTTCGACG<br>TTGCTGTTTTGCCTTTCTCTAACTCTACTAATAATGG<br>TTTGTTGTTCATCAACACTACTATCGCTTCTATCGCT<br>GCTAAGGAAGAGGGTGTTTCTATGGCTAAGAGAGAAG<br>AAGCTGAAGCTGAAGCTGAACCAAAGTTTGTTAACCA<br>ACACTTGTGTGGTTCTCACTTGGTTGAAGCTTTGTAC<br>TTGGTTTGTGGTGAAAGAGGTTTCTTCTACACTCCAA<br>AGGCTGCTAAGGGTATCGTTGAACAATGTTGTACTTC<br>TATCTGTTCTTTGTACCAATTGGAAAACTACTGTAAC<br>TAA (SEQ ID NO:3) |
| RHI-2 | ATGAGATTCCCATCTATCTTCACTGCTGTTTTGTTCG<br>CTGCTTCTTCTGCTTTGGCTGCTCCTGTTAACACTAC<br>TACTGAAGACGAAACTGCTCAAATCCCAGCTGAAGCG<br>GTTATCGGTTACTCTGACTTGGAAGGTGACTTCGACG<br>TTGCTGTTTTGCCTTTCTCTAACTCTACTAATAATGG<br>TTTGTTGTTCATCAACACTACTATCGCTTCTATCGCT<br>GCTAAGGAAGAGGGTGTTTCTATGGCTAAGAGAGACG<br>ACGGTGACCCAAGATTTGTTAACCAACACTTGTGTGG<br>TTCTCACTTGGTTGAAGCTTTGTACTTGGTTTGTGGT<br>GAAAGAGGTTTCTTCTACACTCCAAAGGACGAAAGAG<br>GTATCGTTGAACAATGTTGTACTTCTATCTGTTCTTT<br>GTACCAATTGGAAAACTACTGTAACTAA<br>(SEQ ID NO:4) |
| RHI-3 | ATGAGATTCCCATCTATCTTCACTGCTGTTTTGTTCG<br>CTGCTTCTTCTGCTTTGGCTGCTCCTGTTAACACTAC<br>TACTGAAGACGAAACTGCTCAAATCCCAGCTGAAGCG<br>GTTATCGGTTACTCTGACTTGGAAGGTGACTTCGACG<br>TTGCTGTTTTGCCTTTCTCTAACTCTACTAATAATGG<br>TTTGTTGTTCATCAACACTACTATCGCTTCTATCGCT<br>GCTAAGGAAGAGGGTGTTTCTATGGCTAAGAGAGAAG |

TABLE 6-continued

| Construct ID | DNA sequence |
|---|---|
|  | AAGCTGAAGCTGAAGCTGAACCAAAGTTTGTTAACCA<br>ACACTTGTGTGGTTCTCACTTGGTTGAAGCTTTGTAC<br>TTGGTTTGTGGTGAAAGAGGTTTCTTCTACACTCCAA<br>AGGACGAAAGAGGTATCGTTGAACAATGTTGTACTTC<br>TATCTGTTCTTTGTACCAATTGGAAAACTACTGTAAC<br>TAA (SEQ ID NO:5) |
| RAT-1 | ATGAGATTCCCATCTATCTTCACTGCTGTTTTGTTCG<br>CTGCTTCTTCTGCTTTGGCTGCTCCTGTTAACACTAC<br>TACTGAAGACGAAACTGCTCAAATCCCAGCTGAAGCG<br>GTTATCGGTTACTCTGACTTGGAAGGTGACTTCGACG<br>TTGCTGTTTTGCCTTTCTCTAACTCTACTAATAATGG<br>TTTGTTGTTCATCAACACTACTATCGCTTCTATCGCT<br>GCTAAGGAAGAGGGTGTTTCTATGGCTAAGAGAGAAG<br>AAGCTGAAGCTGAAGCTGAACCAAAGTTTGTTAAGCA<br>ACACTTGTGTGGTCCTCACTTGGTTGAAGCTTTGTAC<br>TTGGTTTGTGGTGAAAGAGGTTTCTTCTACACTCCAA<br>AGGCTGCTAAGGGTATCGTTGACCAATGTTGTACTTC<br>TATCTGTTCTTTGTACCAATTGGAAAACTACTGTAAC<br>TAA (SEQ ID NO:6) |
| RHI-4 | ATGAGATTCCCATCTATCTTCACTGCTGTTTTGTTCG<br>CTGCTTCTTCTGCTTTGGCTGCTCCTGTTAACACTAC<br>TACTGAAGACGAAACTGCTCAAATCCCAGCTGAAGCG<br>GTTATCGGTTACTCTGACTTGGAAGGTGACTTCGACG<br>TTGCTGTTTTGCCTTTCTCTAACTCTACTAATAATGG<br>TTTGTTGTTCATCAACACTACTATCGCTTCTATCGCT<br>GCTAAGGAAGAGGGTGTTTCTATGGCTAAGAGAGACG<br>ACGGTGACCCAAGATTTGTTAACCAACACTTGTGTGG<br>TTCTCACTTGGTTGAAGCTTTGTACTTGGTTTGTGGT<br>GAAAGAGGTTTCTTCTACACTCCAAAGGCTGCTAAGG<br>GTATCGTTGAACAATGTTGTACTTCTATCTGTTCTTT<br>GTACCAATTGGAAAACTACTGTAACTAA<br>(SEQ ID NO:7) |

DNA Preparation for *P. pastoris* Transformation

Four genetic constructs were initially used for transforming GS115 and KM71. Prior to transformation by electroporation, each construct was linearized by SalI. Complete linearization of each construct was confirmed by agarose gel electrophoresis. QiaQuick PCR purification spin columns (Qiagen) were then used to remove SalI and salts from the linearized plasmids. Linearized plasmids were eluted from the spin columns using autoclaved, deionized water.

Once the DNA has been transformed into the yeast strains, the resulting gene constructs coded for the amino acid sequences shown in Table 7. The Pro-leader peptide sequence is designed to be cleaved by Kex-2 endoprotease within the yeast prior to protein secretion into the media (Kjeldsen et al., 1999, *Biotechnol. Appl. Biochem.* 29:79-86). Thus the resulting insulin molecule secreted into the media includes only the leader peptide sequence attached to the [B-peptide]-[C-peptide]-[A-peptide]sequence.

TABLE 7

| Construct ID | Pro-leader peptide | Leader peptide | B-C-A peptides |
|---|---|---|---|
| RHI-1 | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | FVNQHLCGSHLVEALY LVCGERGFFYTPKAAK GIVEQCCTSICSLYQL ENYCN (SEQ ID NO: 11) |
| RHI-2 | APVNTTTEDETAQIPAEAVI GYSDLEGDFDVAVLPFSNST NNGLLFINTTIASIAAKEEG VSMAKR (SEQ ID NO: 8) | DDGDPR (SEQ ID NO: 10) | FVNQHLCGSHLVEALY LVCGERGFFYTPKDER GIVEQCCTSICSLYQL ENYCN (SEQ ID NO: 12) |
| RHI-3 | APVNTTTEDETAQIPAEAVI GYSDLEGDFDVAVLPFSNST | EEAEAEAEPK (SEQ ID NO: 9) | FVNQHLCGSHLVEALY LVCGERGFFYTPKDER |

TABLE 7-continued

| Construct ID | Pro-leader peptide | Leader peptide | B-C-A peptides |
|---|---|---|---|
| | NNGLLFINTTIASIAAKEEG VSMAKR (SEQ ID NO: 8) | | GIVEQCCTSICSLYQL ENYCN (SEQ ID NO: 12) |
| RAT-1 | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | FVKQHLCGPHLVEALY LVCGERGFFYTPKAAK GIVDQCCTSICSLYQL ENYCN (SEQ ID NO: 12) |
| RHI-4 | APVNTTTEDETAQIPAEAVI GYSDLEGDFDVAVLPFSNST NNGLLFINTTIASIAAKEEG VSMAKR (SEQ ID NO: 8) | DDGDPR (SEQ ID NO: 10) | FVNQHLCGSHLVEALY LVCGERGFFYTPKAAK GIVEQCCTSICSLYQL ENYCN (SEQ ID NO: 11) |

*P. pastoris* Transformation

The linearized plasmids were individually transformed into electrocompetent *P. pastoris* GS115 and KM71 (both are His⁻ strains) according to the procedure reported by Wu and Letchworth (*Biotechniques* 36:152-4). The electroporated cells were re-suspended in 1 mL ice-cold, 1 M sorbitol and plated on minimal dextrose-sorbitol agar (1.34% yeast nitrogen base without ammonium and amino acids, $4 \times 10^{-5}$% biotin, 2% dextrose, 1 M sorbitol, and 2% agar) plates. The agar plates were incubated at 30° C. for 4-7 days. Expression plasmids integrated into GS115 and KM71 genomes render a His⁺ phenotype to the transformants and allow the transformants to grow on minimal dextrose-sorbitol agar without histidine supplementation.

Screening for *P. pastoris* Transformants for Clones with High-Copy Number of Expression Cassettes The clones derived in 2 strains of *P. pastoris* with 4 expression plasmids in the above steps were individually screened for incorporation of high-copy number of the gene constructs. All the transformants were selected on minimal dextrose-sorbitol agar without histidine supplementation. Each transformation generated over 500His⁺ transformants. Some of these transformants were expected to contain multiple copies of the expression plasmid since multiple integration events happen naturally in *P. pastoris*. These high-copy number transformants could produce higher levels of insulin molecule. Therefore, all transformants were screened based on their resistance to geneticin in order to select for those with the highest copy number, since all of the expression plasmids are pPIC3.5K-deriviatives and contain a geneticin-resistant marker (i.e., higher copy clones should lead to higher incorporation of geneticin resistance).

His⁺ transformants were grown on minimal dextrose-sorbitol agar and were pooled together and plated on YPD agar (1% yeast extract, 2% peptone, 2% dextrose, and 2% agar) containing geneticin by the following procedure:

- 1 to 2 ml of sterile water was pipetted over the His⁺ transformants (from each expression plasmid-strain combination) on each minimal dextrose-sorbitol plate.
- His⁺ transformants were resuspended into the water by using a sterile spreader and running it across the top of the agar.
- The cell suspension was transferred and pooled into a sterile, 50 ml conical centrifuge tube and vortexed briefly.
- Cell density of the cell suspension was determined by using a spectrophotometer (1 OD$_{600}$ unit≈$5 \times 10^7$ cells/ml).
- $10^5$ cells were plated on YPD plates containing geneticin at a final concentration of 0.25, 0.5, 1.0, 1.5, 2.0, 3.0, and 4.0 mg/ml.
- Plates were incubated at 30° C. and checked daily. Geneticin-resistant colonies took 3 to 5 days to appear.
- Colonies that grew on YPD-geneticin plates were streaked for purity on YPD agar containing the same concentration of geneticin to ensure the isolated colonies are resistant to high concentration of geneticin. Several clones at various genecitin concentration levels were then selected for insulin molecule expression studies in shake flasks.

Shake-Flask Studies

Shake flask studies were conducted on the 40 geneticin-resistant clones (4 expression plasmids×2 strains×5 transformants) at 2 buffer conditions (buffered vs. unbuffered media) for a total of 80 shake culture flasks.

Half of the transformants were KM71 derivatives, which have Mut$^S$ phenotypes. Isolated KM71 transformant colonies from streaked plates prepared above were used to inoculate 100 mL non-buffered MGY broth (1% yeast extract, 2% peptone, 1.34% yeast nitrogen base, $4 \times 10^{-5}$% biotin, and 1% glycerol) or 100 mL BMGY broth (same as MGY, but with 100 mM potassium phosphate, pH 6). These seed cultures were incubated at 30° C. with orbital shaking at 250 rpm for 16 hours or until OD$_{600}$ values reached 2-6. Then, a small aliquot of each MGY culture was used to prepare glycerol stocks. The remaining MGY cultures were then harvested by centrifugation at 4000×g for 5 min. Culture supernatants were discarded and each cell pellet was re-suspended with 20 mL MMY broth (same as MGY except glycerol was replaced by 0.5% methanol). Similarly, BMGY seed cultures were harvested by centrifugation at 4000×g for 5 min. Culture supernatants were discarded and each cell pellet was re-suspended with 20 mL BMMY broth (same as BMGY except glycerol was replaced by 0.5% methanol).

Methanol in the MMY and BMMY broths induce protein expression. The MMY and BMMY cultures were incubated at 30° C. with orbital shaking at 250 rpm for 96 hours. Every 24 hours, methanol was added to each culture to a final concentration of 0.5%. A 0.5-mL aliquot of culture was also removed from each shake flasks every 24 hours after the start of induction. For these samples, cells were separated from culture supernatants by micro-centrifugation and both fractions were stored at −80° C.

The second half of the transformants were GS115 derivatives, which were expected to be Mut⁺. Isolated GS115 transformant colonies from streaked plates prepared as described previously were used to inoculate 25 mL MGY broth and 25 mL BMGY broth. These seed cultures were incubated at 30° C. with orbital shaking at 250 rpm for 16 hours or until OD$_{600}$ values reached 2-6. Then, a small aliquot of each MGY culture was used to prepare glycerol stocks. Another aliquot of the remaining cells was harvested by centrifugation for inoculating 20 mL MMY broth, such that the starting $OD_{600}$ value was about 1. Similarly, the BMGY seed cultures were used to inoculate 20 mL BMMY broth, such that the starting $OD_{600}$ value was about 1. The MMY and BMMY cultures were incubated at 30° C. with orbital shaking at 250 rpm for 96 hours. Every 24 hours, methanol was added to each culture to a final concentration of 0.5%. A 0.5-mL aliquot of culture was removed from each shake flask every 24 hours after the start of induction. Cells were separated from culture supernatants by micro-centrifugation and both fractions were stored at −80° C.

After 96-hour of induction, all cultures were harvested by centrifugation. Cell pellets were discarded. The final culture supernatants plus culture supernatants collected at various time points during induction were analyzed for insulin molecule expression yields by denaturing polyacrylamide gel electrophoresis (SDS-PAGE, BioRad, Hercules, Calif.; Standard Ladder: SeeBlue@Plus2 Prestain Standard (1X); Stain: SimplylBlue SafeStain; Precast gels: Criterion Precast Gel 16.5% Tris-Tricine/Peptide; Running buffer: 1× Tris/Tricine/SDS Buffer; Loading Buffer: Tricine Sample Buffer) or enzyme-linked immunosorbent assay (ELISA, Mercodia Iso-Insulin ELISA, Uppsala, Sweden).

Media for Large-Scale Insulin Molecule Expression in Yeast

BM_Y=BM_Y Base Medium (Teknova, Cat#B8001)

BMGY=BM_Y+0.1% Glycerol (v/v)

BMMY=BM_Y+Methanol

Preparation of MDS Agar Plates for Large-Scale Insulin Molecule Expression in Yeast 319 g of sorbitol and 35 g of agar were dissolved in 1.4 L of di-$H_2O$. The mixture was autoclaved for 30 minutes. The temperature was allowed to drop to 60° C. before proceeding. Next, 175 mL of sterile 13.4% (w/v) Yeast-Nitrogen Base (YNB) containing ammonium sulfate in deionized water was added. To this mixture was added a portion of 175 mL of sterile 20% glucose in deionized water and 3.5 mL of sterile 0.02% biotin solution in deionized water. The solution was mixed to homogeneity and then poured into plates.

Large-Scale Expression and Culture of Insulin Molecule in Yeast

Using a sterile loop, an aliquot of frozen cells was transferred to an MDS plate, and streaked in order to obtain single colonies. The plate was incubated at 30° C. for 2-4 days to elucidate yeast colonies. One colony was picked at random with a sterile loop and used to inoculate 25 mL of BMGY medium (24.17 mL of BM_Y+0.83 mL of 30% glycerol). This medium was incubated for 24 hrs in an incubator/shaker (~150 rpm) at 30° C.

After this time, 75 mL BMGY (72.5 mL of BM_Y+2.5 mL of 30% glycerol) was added to the culture to give a final volume of φ100 mL. The incubation was continued for another 24 hr under the same conditions. The next day, the Optical Density (OD) was assayed to determine how much preculture was needed to obtain a 10000D aliquot (e.g., if OD=15, then $10000D/150D*mL^{-1}$=>66.7 mL of preculture were needed to get 10000D).

Then the calculated volume of preculture was centrifuged (4000 rpm, 4° C. for 10 min) and the supernatant decanted. The pellet was resuspended in 990 mL of BM_Y medium. The OD was rechecked (it should be around 1.0) and the culture volume was adjusted accordingly if needed. 10 mL of biochemical grade methanol (Sigma-Aldrich, St. Louis, Mo. #494437) was then added to the flask, and the flask was incubated at 30° C., in a incubator/shaker at ~150 rpm for 24 hr. Methanol was added every 24 hr for 2-6 days depending on the desired level of protein expression.

After the desired level of yeast growth was achieved, the culture was centrifuged (10,000 rpm, 4° C. for 30 min). The supernatant was decanted and kept in clean container and frozen at −80° C. until needed.

Large-Scale Purification of Insulin Molecule

Cells from the culture flasks were spun down via centrifuge at 4000×g for 10 min at 4° C. The resulting supernatant was decanted into a clean flask. The pH of supernatant was adjusted to ~3.3 using 1 N HCl or 1 N NaOH, followed by a dilution of the supernatant with an equal volume of deionized water (Milli-Q, Millipore, Billerica, Mass.).

The resulting culture supernatant was clarified via filtration through a 0.2 micron, low binding filter unit (Millipore, Billerica, Mass.). Separately, an ion-exhange column (1.42 cm×1.42 cm×5.0 cm) was prepared SP Sepharose Fast-Flow media (GE Healthcare) that was prepared in 25 mM Citrate buffer, pH 3.3 (Wash Buffer). Once the column had been appropriately packed, the column was connected to a peristaltic pump to allow for loading of the culture supernatant onto the ion exchange column (~10 ml/minute). Once all of the culture supernatant had been loaded onto the column, approximately 10 column volumes (CV) of Wash Buffer was passed through the column using the peristaltic pump. After this was done, the purified insulin molecule was eluted from the column using approximately 2-5 CVs of elution buffer (50 mM, pH 7.6 and 200 mM NaCl).

The resulting purified insulin molecule solution was concentrated and desalted using a diafiltration setup (88 $cm^2$ and 0.11 $m^2$ Cassette holder, 5 kDa MWCO Pellicon3 0.11 $m^2$ Cassette filter, Millipore, Billerica, Mass.) connected to a MasterFlex Model 7523-80 pump (ColePalmer, Vernon Hills, Ill.). The solution was first concentrated or diluted to approximately 250 mL of volume and then diafiltered against Milli-Q deionized water for approximately 8-10 diavolumes.

The desalted, purified insulin molecule solution was then either lyophilized or used directly in a subsequent enzymatic processing step.

In Vitro Enzyme Processing

*Achromobacter lyticus* protease (ALP) was prepared by dissolving 2 U of enzyme in 1 mL of Milli-Q $H_2O$. A working solution was prepared by further diluting the enzyme stock solution 1:9 with Milli-Q $H_2O$ for a concentration of 0.2 U/mL.

Broth from all 10 RHI-1 mutants was used (GS115 RHI-1 A-E and KM71 RHI-1 A-E). Two 200 µL aliquots of each broth sample were prepared and adjusted to pH 10 by addition of 40 µL of 2 M Tris. Two aliquots of ~540 µg/mL human RHI were prepared in the same manner to act as controls. 2.4 µL working enzyme solution was added to one of each pair of aliquots. 2.4 µL Milli-Q $H_2O$ was added to the other to serve as a control. Samples were incubated at room temperature for 4.5 hours on a rocker and then frozen at ~80° C. until analysis.

Samples were prepared for SDS-PAGE and western blotting by adding 20 µL Tricine sample buffer (Bio-rad) to 10 µL of prepared broth and boiling for 5 minutes. Samples, along with peptide and protein ladders, were resolved on 16.5% Tris-Tricine gels run at 125 V for 1.75 hours at room temperature. Proteins were then transferred to nitrocellulose membranes using an iBlot dry transfer system (Invitrogen), program P3 for 5.5 minutes. Membranes were fixed for 15 minutes with 0.25% gluteraldehyde in PBS and then washed 3×5 minutes with TBS. Blocking was carried out in 5% powdered milk in PBS+0.05% Tween-20 (PBST) for 1 hour on a rocker at room temperature. Blots were then incubated in mouse anti-human pro-insulin/insulin antibody (Abcam)

diluted 1:1000 in 1% powdered milk in PBST overnight at 4° C. on a shaker. Blots were washed 2×10 minutes with PBST and incubated for two hours at room temperature in HRP conjugated goat anti-mouse IgG diluted 1:3000 in 1% milk in PBST. Blots were washed 2×10 minutes in PBST followed by a 2 minute wash in dH$_2$O. Bands were developed by incubating for 2 hours at room temperature in TMB substrate (Pierce), followed by extensive washing with dH$_2$O.

Conjugation with a Prefunctionalized Ligand Framework

Once the insulin molecules with N-terminal protected amino acids (on A0/B0, on A0 only or on B0 only) have been treated with ALP they are conjugated with a prefunctionalized ligand framework that includes a terminal activated ester (e.g., —OSu, etc.). The reaction is performed by dissolving the prefunctionalized ligand framework in an anhydrous organic solvent such as DMSO or DMF and then adding the desired number of equivalents of ALP digested insulin molecule followed by mixing for several hours at room temperature.

A conjugation reaction between a prefunctionalized ligand framework and ALP digested insulin molecule may also take place in carbonate buffer to give a B29-conjugated insulin molecule. In an exemplary synthesis, a prefunctionalized ligand framework (PLF) is dissolved in anhydrous DMSO followed by the addition of triethylamine (TEA). The solution is stirred rapidly for a desired amount of time at room temperature. The ALP digested insulin molecule is then dissolved separately at 17.2 mM in sodium carbonate buffer (0.1 M, pH 11) and the pH subsequently adjusted to 10.8 with 1.0 N sodium hydroxide. Once dissolved, the PLF/DMSO/TEA solution is added dropwise to the drug/carbonate buffer solution. During the addition, the pH of the resulting mixture is adjusted periodically to 10.8 if necessary using dilute HCl or NaOH. The solution is allowed to stir for a desired amount of time after the dropwise addition to ensure complete reaction.

Furthermore, under the carbonate buffer conditions, in certain embodiments where the insulin molecule is protected only at B0, A1,B29-disubstituted insulin-conjugates are synthesized using the conditions described above with approximately ten times the amount of prefunctionalized ligand framework per insulin molecule compared to the B29-monosubstituted insulin-conjugate synthesis.

In Vitro Enzyme Cleavage of N-Terminal Amino Acid Protecting Amino Acid Sequences The conjugated insulin intermediates are then treated with trypsin to cleave the N-terminal protecting amino acid sequences that are shown underlined in Table 8. Briefly, 0.5% (w/w) trypsin (e.g., porcine trypsin) is added to the conjugated insulin intermediates. The trypsin may be provided as an aqueous solution in a volume amounting to 10% v/v to 30% v/v (e.g., about 20% v/v) of that of the reaction mixture. After about 1 hour at room temperature, the reaction is terminated. The reaction may be terminated by adjusting the pH, e.g., adjusting the pH to an acidic pH (e.g., to a pH of about 1, about 2, about 3, about 4, about 5, or about 6). Optionally, the desired product is purified (e.g., using preparative reverse phase HPLC).

Results

Production of Insulin Molecules in Yeast

This Example demonstrates insulin molecule production in yeast. In particular, this Example demonstrates insulin molecule (specifically, production of RHI-1, RHI-2, RHI-3, and RAT-1) production in two different yeast strains. The present disclosure encompasses the recognition that these procedures can be useful for expressing and purifying any other recombinant insulin molecule.

Figures 24A, 24B:
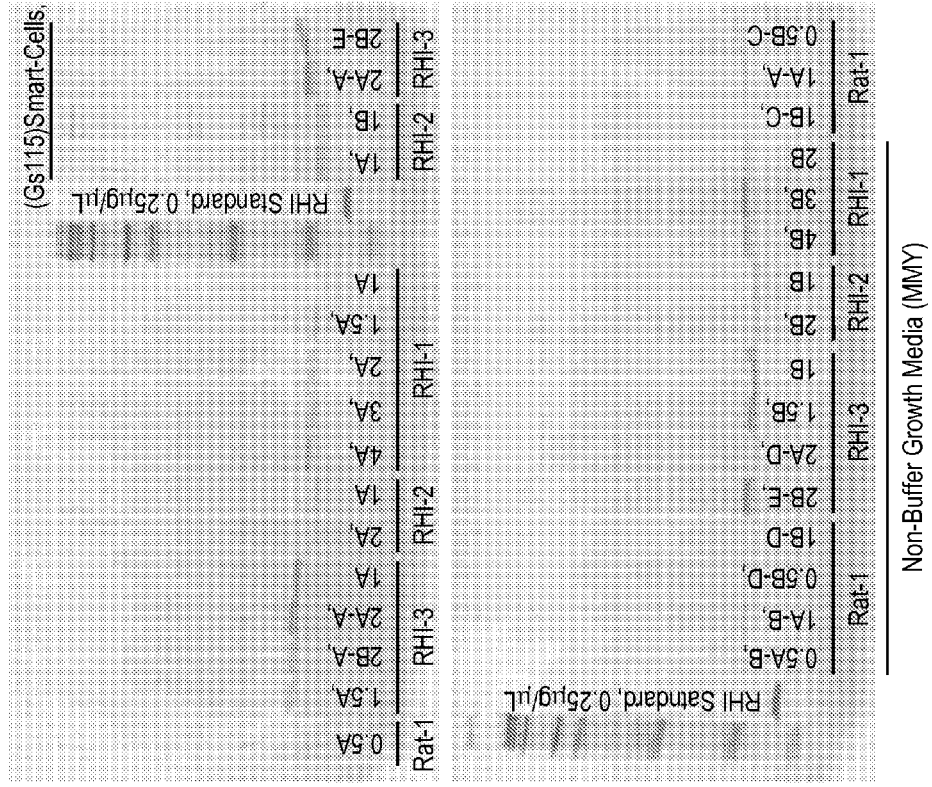
FIG. 24: Unpurified culture supernatant yields from GS115 strain clones grown under buffered (BMMY) and unbuffered (MMY) conditions. (A) Insulin molecule yield in mg/L from various clones ("Clone#" refers to clones obtained from different geneticin plate resistance levels) using ELISA analysis (ISO-Insulin ELISA, Mercodia, Uppsala, Sweden). (B) SDS-PAGE of clones showing the molecular weights of the produced insulin molecules. Recombinant human insulin standard (RHI standard) is shown in lane 14 of the top right gel and in lane 2 of the bottom right gel at 250 mg/L for yield comparison purposes.

FIG. 24 presents unpurified culture supernatant yields from the GS115 strain clones grown under buffered (BMMY) and unbuffered (MMY) conditions. The left panel of FIG. 24 presents the insulin molecule yield in mg/L from various clones ("Clone#" refers to clones obtained from different geneticin plate resistance levels) using ELISA analysis (ISO-Insulin ELISA, Mercodia, Uppsala, Sweden). The right panel of FIG. 24 presents SDS-PAGE of the clones, showing the molecular weights of the produced insulin molecules. Recombinant human insulin standard (RHI standard) is shown in lane 14 of the top right gel and in lane 2 of the bottom right gel at 250 mg/L for yield comparison purposes. As expected, the insulin molecules have a higher MW than that of the RHI standard due to the leader peptide and the connecting peptide ("C-peptide").

Figures 25A, 25B:
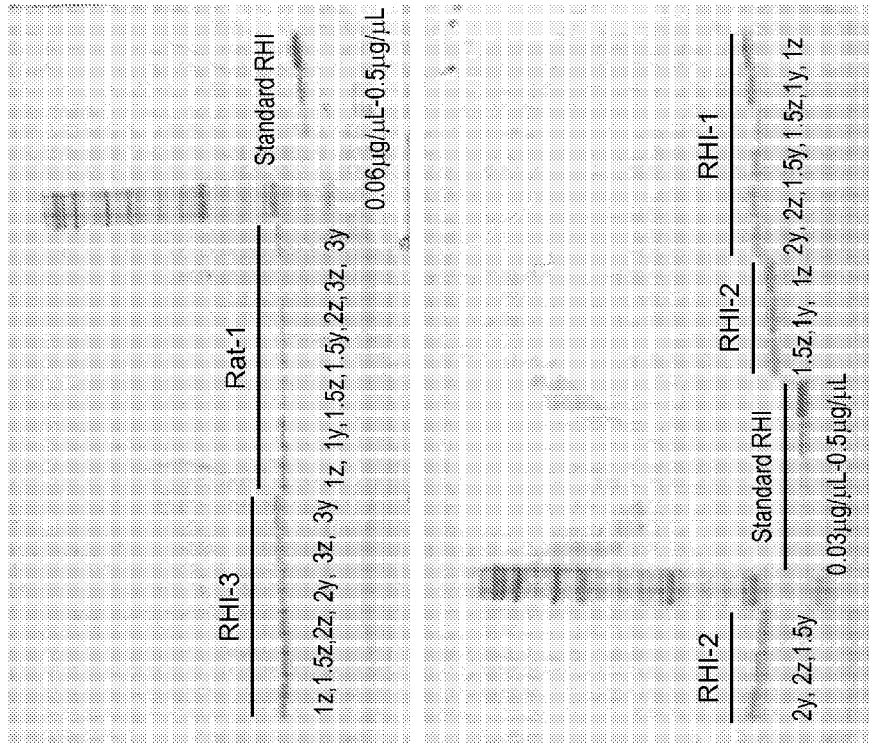
FIG. 25: Unpurified culture supernatant yields from KM71 strain clones grown under buffered conditions. (A) Insulin molecule yield in mg/L from various clones ("Clone#" refers to clones obtained from different geneticin plate resistance levels) using ELISA analysis (ISO-Insulin ELISA, Mercodia, Uppsala, Sweden). (B) SDS-PAGE of clones showing the molecular weights of the produced insulin molecules. Recombinant human insulin standard (RHI standard) is shown in lanes 15-18 of the top right gel (60-500 mg/L) and in lanes 5-9 of the bottom right gel (30-500 mg/L) for yield comparison purposes.

FIG. 25 presents unpurified culture supernatant yields from the KM71 strain clones grown under buffered conditions. The left panel of FIG. 25 presents the insulin molecule yield in mg/L from various clones ("Clone#" refers to clones obtained from different geneticin plate resistance levels) using ELISA analysis (ISO-Insulin ELISA, Mercodia, Uppsala, Sweden). The right panel of FIG. 25 presents SDS-PAGE of the clones, showing the molecular weights of the produced insulin molecules. Recombinant human insulin standard (RHI standard) is shown in lanes 15-18 of the top right gel (60-500 mg/L) and in lanes 5-9 of the bottom right gel (30-500 mg/L) for yield comparison purposes. As expected, the insulin molecules have a higher MW than that of the RHI standard due to the leader peptide and the connecting peptide ("C-peptide").

Figures 26A, 26B:
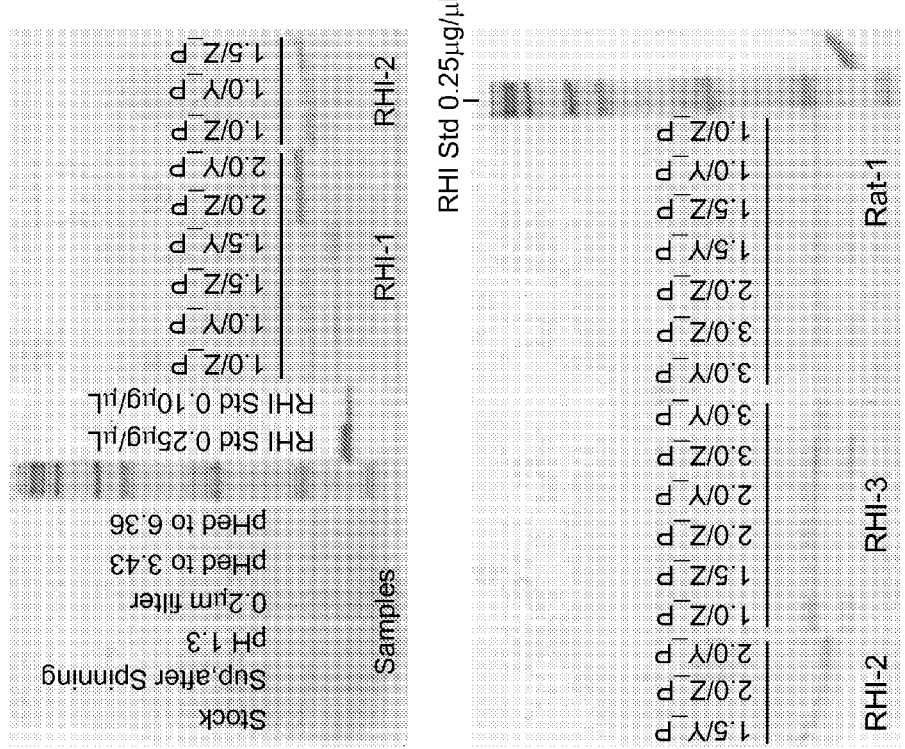
FIG. 26: Unpurified culture supernatant yields from KM71 strain clones grown under unbuffered conditions. (A) Insulin molecule yield in mg/L from various clones ("Clone#" refers to clones obtained from different geneticin plate resistance levels) using ELISA analysis (ISO-Insulin ELISA, Mercodia, Uppsala, Sweden). (B) SDS-PAGE of clones showing the molecular weights of the produced insulin molecules. Recombinant human insulin standard (RHI Standard) is shown in lanes 8 and 9 of the top right gel (250 and 100 mg/L) and in lane 18 of the bottom right gel (250 mg/L) for yield comparison purposes.

FIG. 26 presents unpurified culture supernatant yields from the KM71 strain clones grown under unbuffered conditions. The left panel of FIG. 26 presents the insulin molecule yield in mg/L from various clones ("Clone#" refers to clones obtained from different geneticin plate resistance levels) using ELISA analysis (ISO-Insulin ELISA, Mercodia, Uppsala, Sweden). The right panel of FIG. 26 presents SDS-PAGE of the clones, showing the molecular weights of the produced insulin molecules. Recombinant human insulin standard (RHI Standard) is shown in lanes 8 and 9 of the top right gel (250 and 100 mg/L) and in lane 18 of the bottom right gel (250 mg/L) for yield comparison purposes. As expected, the insulin molecules have a higher MW than that of the RHI standard due to the leader peptide and the connecting peptide ("C-peptide").

The results presented in FIGS. 24-26 demonstrate that the insulin molecules produced by the various plasmid constructs were of the correct MW. In addition, these data show that the insulin molecules are insulin-like, as they were measurable and detectable by a commercial insulin ELISA kit that uses antibodies that are specific for human insulin. These data further demonstrate that insulin molecules could be expressed in yeast at commercially-useful levels (e.g., >25 mg/L). Finally, these data demonstrated a good correlation between ELISA-measured yields and SDS-PAGE-measured yields from crude culture supernatants. In other words, when SDS-PAGE band intensity increased, ELISA measurements also tended to increase. This correlation further demonstrates that the band of interest at the appropriate molecular weight on the SDS-PAGE gel was indeed the insulin molecule.

In Vitro Enzyme Processing of Purified Insulin Molecules

This Example also describes procedures that were used for in vitro enzyme processing of recombinantly produced insulin molecules (to remove the C-peptide and leader peptide).

The present disclosure encompasses the recognition that these procedures can be utilized for purification of insulin molecules at any step of the production process, e.g., from crude cell culture broth, from clarified supernatant, from purified insulin molecule product, etc.

Figure 27A:
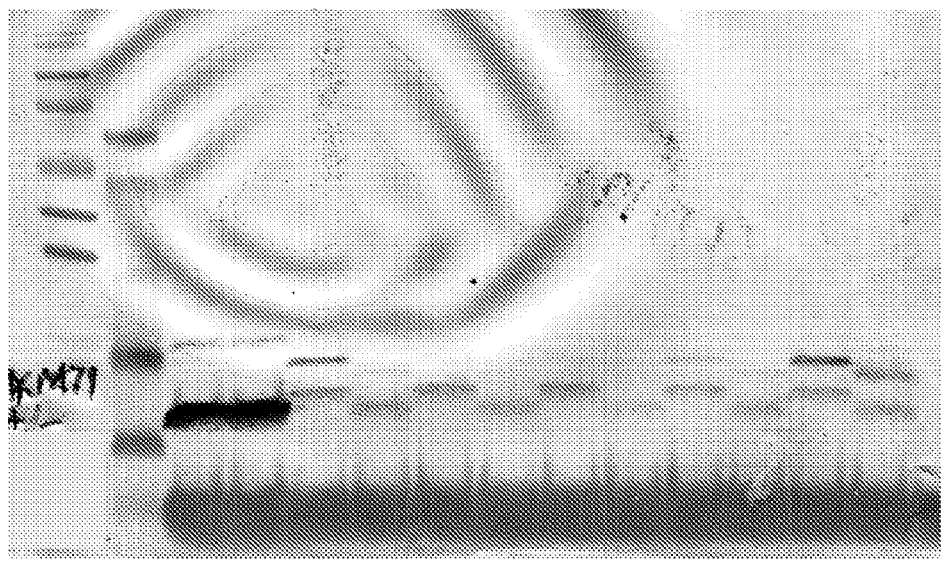
FIG. 27: Western blot of (A) KM71 RHI-1 A-E broth and (B) GS115 RHI-1 A-E broth before and after ALP digestion. "−" indicates no enzyme, "+" indicates with enzyme digestion. Lanes: 1 protein ladder, 2 peptide ladder, 3 RHI−, 4 RHI+, 5 RHI-1 A−, 6 RHI-1 A+, 7 RHI-1 B−, 8 RHI-1 B+, 9 RHI-1 C−, 10 RHI-1 C+, 11 RHI-1 D−, 12 RHI-1 D+, 13 RHI-1 E−, 14 RHI-1 E+.
Figure 27B:
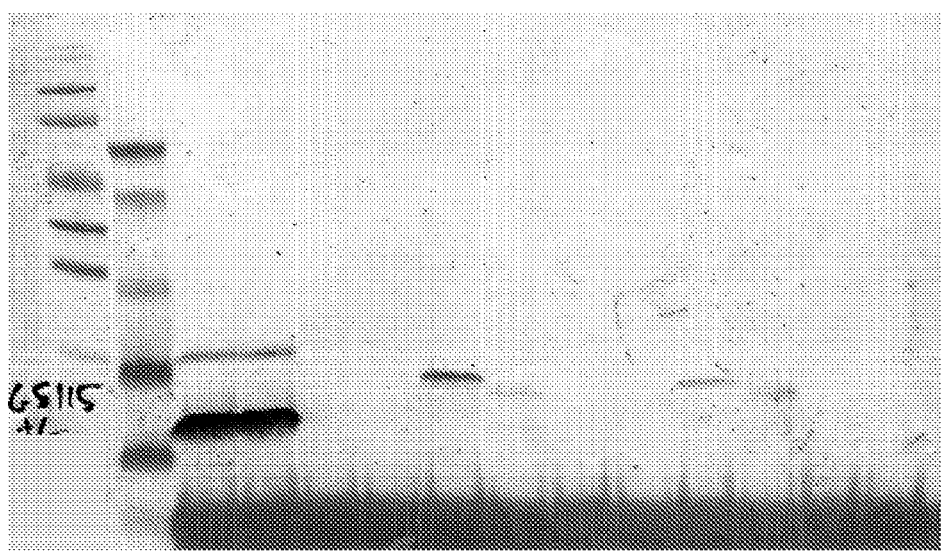

Broth from methanol induced mutants containing gene RHI-1 was digested with *Achromobacter lyticus* protease (ALP). ALP is a C-terminal lysine protease, and as such was expected to cleave the peptide linker between the A- and B-peptides of the insulin molecule (except for RHI-2 and RHI-3 constructs which include a C-peptide that lacks a C-terminal Lys) as well as the leader peptide sequence linked to the N-terminus of the B-peptide. Dried membranes were scanned and are presented in FIG. 27. Two bands were present in most lanes containing broth, and both bands were shifted to a lower molecular weight after enzyme digestion compared to the controls. The lower MW band in each digested pair is at approximately the same location as the RHI control. The RHI control did not change MW following digestion. These results demonstrate that insulin molecules of the appropriate size were generated after enzyme processing. Digestion of the insulin molecules RHI-1, RHI-4 and RAT-1 with ALP would be predicted to produce the products presented in Table 8 (where the A- and B-peptides in the product are connected via three disulfide bridges as shown in formula XI). Since the C-peptides of RHI-2 and RHI-3 do not include a C-terminal Lys they would be expected to remain connected to the N-terminus of the A-peptide until they are further processed with an enzyme that cleaves on the C-terminal side of Arg (e.g., trypsin or a trypsin-like protease as discussed below).

RHI-2, RHI-3 and RHI-4 were each designed to include one or more N-terminal protecting amino acid sequences (underlined in the sequences of Table 8). As shown, RHI-2 includes an N-terminal protecting amino acid sequence at positions A0 and B0 (as mentioned above, the C-peptide of RHI-2 is not cleaved by ALP and is therefore still attached to the N-terminus of the A-peptide). RHI-3 includes an N-terminal protecting amino acid sequence at position A0 only (as mentioned above, the C-peptide of RHI-3 is not cleaved by ALP and is therefore still attached to the N-terminus of the A-peptide). RHI-4 includes an N-terminal protecting amino acid sequence at position B0 only.

Conjugation with a Prefunctionalized Ligand Framework

Once RHI-2, RHI-3 and RHI-4 have been treated with ALP they are conjugated with a prefunctionalized ligand framework that includes a terminal activated ester (e.g., —OSu, etc.). The reaction is performed by dissolving the prefunctionalized ligand framework in an anhydrous organic solvent such as DMSO or DMF and then adding the desired number of equivalents of ALP digested insulin molecule followed by mixing for several hours at room temperature.

Alternatively, the reaction is perfomed in carbonate buffer by dissolving the desired number of equivalents of a prefunctionalized ligand framework (PLF) in anhydrous DMSO followed by the addition of triethylamine (TEA). The solution is stirred rapidly for a desired amount of time at room temperature. The ALP digested insulin molecule is then dissolved separately at 17.2 mM in sodium carbonate buffer (0.1 M, pH 11) and the pH subsequently adjusted to 10.8 with 1.0 N sodium hydroxide. Once dissolved, the PLF/DMSO/TEA solution is added dropwise to the drug/carbonate buffer solution. During the addition, the pH of the resulting mixture is adjusted periodically to 10.8 if necessary using dilute HCl or NaOH. The solution is allowed to stir for a desired amount of time after the dropwise addition to ensure complete reaction.

In Vitro Enzyme Cleavage of N-Terminal Amino Acid Protecting Amino Acid Sequences The conjugated insulin intermediates are then treated with trypsin to cleave the N-terminal protecting amino acid sequences that are shown underlined in Table 8. Briefly, 0.5% (w/w) trypsin (e.g., porcine trypsin) is added to the conjugated insulin intermediates. The trypsin may be provided as an aqueous solution in a volume amounting to 10% v/v to 30% v/v (e.g., about 20% v/v) of that of the reaction mixture. After about 1 hour at room temperature, the reaction is terminated. The reaction may be terminated by adjusting the pH, e.g., adjusting the pH to an acidic pH (e.g., to a pH of about 1, about 2, about 3, about 4, about 5, or about 6). Optionally, the desired product is purified (e.g., using preparative reverse phase HPLC).

TABLE 8

| Construct ID | B-peptide | C-peptide | A-peptide |
|---|---|---|---|
| RHI-1 | FVNQHLCGSHLVEALYLVCGERGFFYTPK (SEQ ID NO: 13) | AAK (SEQ ID NO: 16) | GIVEQCCTSICSLYQLENYCN (SEQ ID NO: 18) |
| RHI-2 | DGGDPRFVNQHLCGSHLVEALYLVCGERGFFYTPK (SEQ ID NO: 14) | DER (SEQ ID NO: 17) | GIVEQCCTSICSLYQLENYCN (SEQ ID NOl 18) |
| RHI-3 | FVNQHLCGSHLVEALYLVCGERGFFYTPK (SEQ ID NO: 13) | DER (SEQ ID NO: 17) | GIVEQCCTSICSLYQLENYCN (SEQ ID NO: 18) |
| RHI-4 | DGGDPRFVNQHLCGSHLVEALYLVCGERGFFYTPK (SEQ ID NO: 14) | AAK (SEQ ID NO: 16) | GIVEQCCTSICSLYQLENYCN (SEQ ID NO: 18) |
| RAT-1 | FVKQHLCGPHLVEALYLVCGERGFFYTPK (SEQ ID NO: 15) | AAK (SEQ ID NO: 16) | GIVDQCCTSICSLYQLENYCN (SEQ ID NO: 19) |

We claim:

1. A compound of the formula

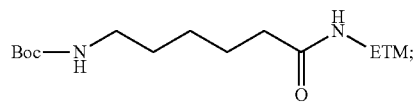

G-1

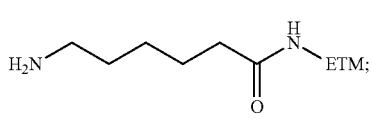

F-1

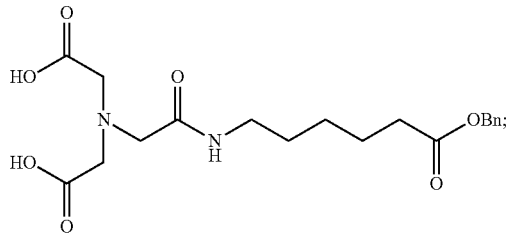

D-1

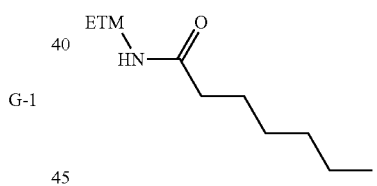

C-1

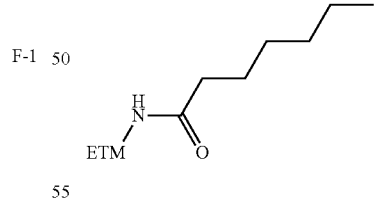

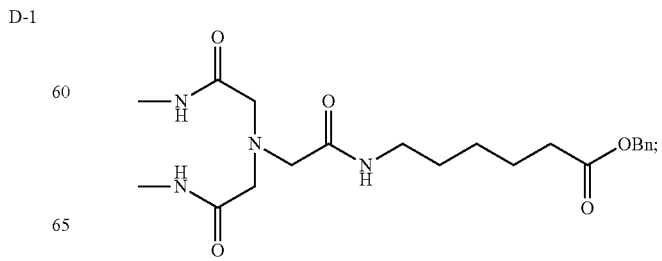

-continued
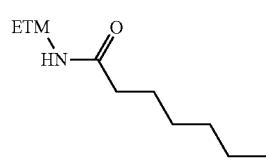
A-1
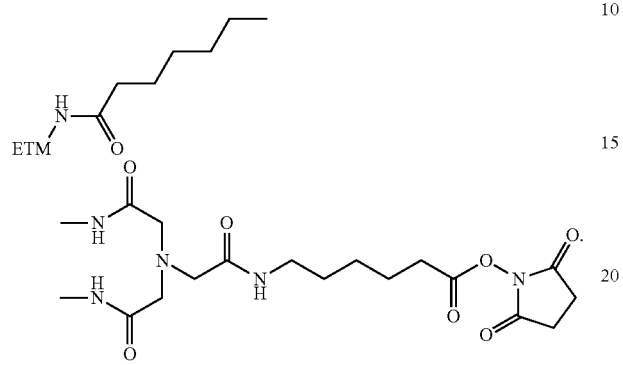
* * * * *

SEQUENCE LISTING

<160> NUMBER OF SEQ ID NOS: 31

<210> SEQ ID NO 1
<211> LENGTH: 122
<212> TYPE: PRT
<213> ORGANISM: Artificial Sequence
<220> FEATURE:
<223> OTHER INFORMATION: Insulin analog A-chain
<220> FEATURE:
<221> NAME/KEY: VARIANT
<222> LOCATION: (1)..(50)
<223> OTHER INFORMATION: Xaa= any codable amino acid sequence of 2-50,
      2-25, 2-10, 2-9, 2-8, 2-7, 2-6, 2-5, 2-4, 2-3, or 2 codable amino
      acids, or missing
<220> FEATURE:
<221> NAME/KEY: MISC_FEATURE
<222> LOCATION: (1)..(50)
<223> OTHER INFORMATION: 2-50, 2-25, 2-10, 2-9, 2-8, 2-7, 2-6, 2-5, 2-4,
      2-3, or 2 codable amino acids may be present or or missing
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: VARIANT
<222> LOCATION: (59)..(59)
<223> OTHER INFORMATION: Xaa= any codable amino acid; or T or A
<220> FEATURE:
<221> NAME/KEY: VARIANT
<222> LOCATION: (60)..(60)
<223> OTHER INFORMATION: Xaa= any codable amino acid; or S or G
<220> FEATURE:
<221> NAME/KEY: VARIANT
<222> LOCATION: (61)..(61)
<223> OTHER INFORMATION: Xaa= any codable amino acid; or I or V
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: VARIANT
<222> LOCATION: (69)..(69)
<223> OTHER INFORMATION: Xaa= any codable amino acid; or N, D, or E
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: VARIANT
<222> LOCATION: (72)..(72)
<223> OTHER INFORMATION: Xaa= any codable amino acid; or N, D, E, G,
      or A
<220> FEATURE:
<221> NAME/KEY: VARIANT
<222> LOCATION: (73)..(122)
<223> OTHER INFORMATION: Xaa= any codable amino acid
<220> FEATURE:
<221> NAME/KEY: MISC_FEATURE
<222> LOCATION: (73)..(122)

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Gly Ile Val Glu Gln Cys Cys Xaa Xaa Xaa Cys Ser Leu Tyr
    50                  55                  60

Gln Leu Glu Xaa Tyr Cys Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa

```
                    85                  90                  95
Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa
        115                 120

<210> SEQ ID NO 2
<211> LENGTH: 33
<212> TYPE: PRT
<213> ORGANISM: Artificial Sequence
<220> FEATURE:
<223> OTHER INFORMATION: Insulin analog B-chain
<220> FEATURE:
<221> NAME/KEY: VARIANT
<222> LOCATION: (1)..(1)
<223> OTHER INFORMATION: Xaa= any codable amino acid, a sequence of
      2-50, 2-25, 2-10, 2-9, 2-8, 2-7, 2-6, 2-5, 2-4, 2-3, or 2 codable
      amino acids, or missing
<220> FEATURE:
<221> NAME/KEY: VARIANT
<222> LOCATION: (3)..(32)
<223> OTHER INFORMATION: Xaa= any codable amino acid, a sequence of
      codable amino acids, Arg-Arg, or missing
<220> FEATURE:
<221> NAME/KEY: VARIANT
<222> LOCATION: (4)..(4)
<223> OTHER INFORMATION: Xaa= any codable amino acid; or N, K, D, or E,
      or missing
<220> FEATURE:
<221> NAME/KEY: VARIANT
<222> LOCATION: (29)..(29)
<223> OTHER INFORMATION: Xaa= any codable amino acid; or P, A, K, L, V,
      or D, or missing
<220> FEATURE:
<221> NAME/KEY: VARIANT
<222> LOCATION: (30)..(30)
<223> OTHER INFORMATION: Xaa= any codable amino acid; or K, P, or E, or
      missing
<220> FEATURE:
<221> NAME/KEY: VARIANT
<222> LOCATION: (31)..(31)
<223> OTHER INFORMATION: Xaa= any codable amino acid or T, A, K, E, S,
      or R, or missing
<220> FEATURE:
<221> NAME/KEY: VARIANT
<222> LOCATION: (32)..(32)
<223> OTHER INFORMATION: Xaa= any codable amino acid, a sequence of
      2-50, 2-25, 2-10, 2-9, 2-8, 2-7, 2-6, 2-5, 2-4, 2-3, or 2 codable
      amino acids, or missing
<220> FEATURE:
<221> NAME/KEY: misc_feature
<222> LOCATION: (33)..(33)
<223> OTHER INFORMATION: Xaa can be any naturally occurring amino acid

<400> SEQUENCE: 2

Xaa Phe Val Xaa Gln His Leu Cys Gly Ser His Leu Val Glu Ala Leu
1               5                   10                  15

Tyr Leu Val Cys Gly Glu Arg Gly Phe Phe Tyr Thr Xaa Xaa Xaa Xaa
            20                  25                  30

Xaa

<210> SEQ ID NO 3
<211> LENGTH: 447
<212> TYPE: DNA
<213> ORGANISM: Artificial Sequence
<220> FEATURE:
<223> OTHER INFORMATION: Encodes RHI-1

<400> SEQUENCE: 3
atgagattcc catctatctt cactgctgtt tgttcgctg  cttcttctgc tttggctgct      60
```

```
cctgttaaca ctactactga agacgaaact gctcaaatcc cagctgaagc ggttatcggt    120
tactctgact tggaaggtga cttcgacgtt gctgttttgc ctttctctaa ctctactaat    180
aatggtttgt tgttcatcaa cactactatc gcttctatcg ctgctaagga gagggtgtt    240 tctatggcta agagagaaga agctgaagct gaagctgaac caaagtttgt taaccaacac    300
ttgtgtggtt ctcacttggt tgaagctttg tacttggttt gtggtgaaag aggtttcttc    360
tacactccaa aggctgctaa gggtatcgtt gaacaatgtt gtacttctat ctgttctttg    420
taccaattgg aaaactactg taactaa                                        447
```

```
<210> SEQ ID NO 4
<211> LENGTH: 435
<212> TYPE: DNA
<213> ORGANISM: Artificial Sequence
<220> FEATURE:
<223> OTHER INFORMATION: Encodes RHI-2

<400> SEQUENCE: 4
atgagattcc catctatctt cactgctgtt ttgttcgctg cttcttctgc tttggctgct     60
cctgttaaca ctactactga agacgaaact gctcaaatcc cagctgaagc ggttatcggt    120
tactctgact tggaaggtga cttcgacgtt gctgttttgc ctttctctaa ctctactaat    180
aatggtttgt tgttcatcaa cactactatc gcttctatcg ctgctaagga gagggtgtt    240 tctatggcta agagagacga cggtgaccca agatttgtta accaacactt gtgtggttct    300
cacttggttg aagctttgta cttggtttgt ggtgaaagag gtttcttcta cactccaaag    360
gacgaaagag gtatcgttga acaatgttgt acttctatct gttctttgta ccaattggaa    420
aactactgta actaa                                                     435
```

```
<210> SEQ ID NO 5
<211> LENGTH: 447
<212> TYPE: DNA
<213> ORGANISM: Artificial Sequence
<220> FEATURE:
<223> OTHER INFORMATION: Encodes RHI-3

<400> SEQUENCE: 5
atgagattcc catctatctt cactgctgtt ttgttcgctg cttcttctgc tttggctgct     60
cctgttaaca ctactactga agacgaaact gctcaaatcc cagctgaagc ggttatcggt    120
tactctgact tggaaggtga cttcgacgtt gctgttttgc ctttctctaa ctctactaat    180
aatggtttgt tgttcatcaa cactactatc gcttctatcg ctgctaagga gagggtgtt    240 tctatggcta agagagaaga agctgaagct gaagctgaac caaagtttgt taaccaacac    300
ttgtgtggtt ctcacttggt tgaagctttg tacttggttt gtggtgaaag aggtttcttc    360
tacactccaa aggacgaaag aggtatcgtt gaacaatgtt gtacttctat ctgttctttg    420
taccaattgg aaaactactg taactaa                                        447
```

```
<210> SEQ ID NO 6
<211> LENGTH: 447
<212> TYPE: DNA
<213> ORGANISM: Artificial Sequence
<220> FEATURE:
<223> OTHER INFORMATION: Encodes RAT-1

<400> SEQUENCE: 6
atgagattcc catctatctt cactgctgtt ttgttcgctg cttcttctgc tttggctgct     60
cctgttaaca ctactactga agacgaaact gctcaaatcc cagctgaagc ggttatcggt    120
```

```
tactctgact tggaaggtga cttcgacgtt gctgttttgc ctttctctaa ctctactaat    180
aatggtttgt tgttcatcaa cactactatc gcttctatcg ctgctaagga agagggtgtt    240
tctatggcta agagaagaa agctgaagct gaagctgaac caaagtttgt taagcaacac    300
ttgtgtggtc ctcacttggt tgaagctttg tacttggttt gtggtgaaag aggtttcttc    360
tacactccaa aggctgctaa gggtatcgtt gaccaatgtt gtacttctat ctgttctttg    420
taccaattgg aaaactactg taactaa                                       447

<210> SEQ ID NO 7
<211> LENGTH: 435
<212> TYPE: DNA
<213> ORGANISM: Artificial Sequence
<220> FEATURE:
<223> OTHER INFORMATION: Encodes RHI-4

<400> SEQUENCE: 7
atgagattcc catctatctt cactgctgtt ttgttcgctg cttcttctgc tttggctgct    60
cctgttaaca ctactactga agacgaaact gctcaaatcc cagctgaagc ggttatcggt   120
tactctgact tggaaggtga cttcgacgtt gctgttttgc ctttctctaa ctctactaat   180
aatggtttgt tgttcatcaa cactactatc gcttctatcg ctgctaagga agagggtgtt   240
tctatggcta agagagacga cggtgaccca agatttgtta accaacactt gtgtggttct   300
cacttggttg aagctttgta cttggtttgt ggtgaaagag gttcttcta cactccaaag   360 gctgctaagg gtatcgttga acaatgttgt acttctatct gttctttgta ccaattggaa   420
aactactgta actaa                                                    435

<210> SEQ ID NO 8
<211> LENGTH: 66
<212> TYPE: PRT
<213> ORGANISM: Artificial Sequence
<220> FEATURE:
<223> OTHER INFORMATION: pro-leader peptide

<400> SEQUENCE: 8

Ala Pro Val Asn Thr Thr Thr Glu Asp Glu Thr Ala Gln Ile Pro Ala
1               5                   10                  15

Glu Ala Val Ile Gly Tyr Ser Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Met Ala
    50                  55                  60

Lys Arg
65

<210> SEQ ID NO 9
<211> LENGTH: 10
<212> TYPE: PRT
<213> ORGANISM: Artificial Sequence
<220> FEATURE:
<223> OTHER INFORMATION: leader peptide

<400> SEQUENCE: 9

Glu Glu Ala Glu Ala Glu Ala Glu Pro Lys
1               5                   10

<210> SEQ ID NO 10
```

```
<211> LENGTH: 6
<212> TYPE: PRT
<213> ORGANISM: Artificial Sequence
<220> FEATURE:
<223> OTHER INFORMATION: leader peptide

<400> SEQUENCE: 10

Asp Asp Gly Asp Pro Arg
1               5

<210> SEQ ID NO 11
<211> LENGTH: 53
<212> TYPE: PRT
<213> ORGANISM: Artificial Sequence
<220> FEATURE:
<223> OTHER INFORMATION: B-C-A peptides

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Asn
    50

<210> SEQ ID NO 12
<211> LENGTH: 53
<212> TYPE: PRT
<213> ORGANISM: Artificial Sequence
<220> FEATURE:
<223> OTHER INFORMATION: B-C-A peptides

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Asp Glu Arg
            20                  25                  30

Gly Ile Val Glu Gln Cys Cys Thr Ser Ile Cys Ser Leu Tyr Gln Leu
        35                  40                  45

Glu Asn Tyr Cys Asn
    50

<210> SEQ ID NO 13
<211> LENGTH: 29
<212> TYPE: PRT
<213> ORGANISM: Homo sapiens

<400> SEQUENCE: 13

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 14
<211> LENGTH: 35
<212> TYPE: PRT
<213> ORGANISM: Artificial Sequence
<220> FEATURE:
<223> OTHER INFORMATION: modified human insulin B chain peptide

<400> SEQUENCE: 14
```

```
Asp Gly Gly Asp Pro Arg Phe Val Asn Gln His Leu Cys Gly Ser His
1               5                   10                  15
Leu Val Glu Ala Leu Tyr Leu Val Cys Gly Glu Arg Gly Phe Phe Tyr
            20                  25                  30
Thr Pro Lys
        35
```

<210> SEQ ID NO 15
<211> LENGTH: 29
<212> TYPE: PRT
<213> ORGANISM: Artificial Sequence
<220> FEATURE:
<223> OTHER INFORMATION: modified human insulin B chain peptide

<400> SEQUENCE: 15

```
Phe Val Lys Gln His Leu Cys Gly Pro His Leu Val Glu Ala Leu Tyr
1               5                   10                  15
Leu Val Cys Gly Glu Arg Gly Phe Phe Tyr Thr Pro Lys
            20                  25
```

<210> SEQ ID NO 16
<211> LENGTH: 3
<212> TYPE: PRT
<213> ORGANISM: Artificial Sequence
<220> FEATURE:
<223> OTHER INFORMATION: synthetic C-peptide

<400> SEQUENCE: 16

```
Ala Ala Lys
1
```

<210> SEQ ID NO 17
<211> LENGTH: 3
<212> TYPE: PRT
<213> ORGANISM: Artificial Sequence
<220> FEATURE:
<223> OTHER INFORMATION: synthetic C-peptide

<400> SEQUENCE: 17

```
Asp Glu Arg
1
```

<210> SEQ ID NO 18
<211> LENGTH: 21
<212> TYPE: PRT
<213> ORGANISM: Homo sapiens

<400> SEQUENCE: 18

```
Gly Ile Val Glu Gln Cys Cys Thr Ser Ile Cys Ser Leu Tyr Gln Leu
1               5                   10                  15
Glu Asn Tyr Cys Asn
            20
```

<210> SEQ ID NO 19
<211> LENGTH: 21
<212> TYPE: PRT
<213> ORGANISM: artificial sequence
<220> FEATURE:
<223> OTHER INFORMATION: modified human insulin A chain peptide

<400> SEQUENCE: 19

```
Gly Ile Val Asp Gln Cys Cys Thr Ser Ile Cys Ser Leu Tyr Gln Leu
1               5                   10                  15
Glu Asn Tyr Cys Asn
```

```
<210> SEQ ID NO 20
<211> LENGTH: 6
<212> TYPE: PRT
<213> ORGANISM: Artificial Sequence
<220> FEATURE:
<223> OTHER INFORMATION: N-terminal protecting peptide
<220> FEATURE:
<221> NAME/KEY: VARIANT
<222> LOCATION: (1)..(1)
<223> OTHER INFORMATION: Xaa= Asp/Glu
<220> FEATURE:
<221> NAME/KEY: VARIANT
<222> LOCATION: (2)..(2)
<223> OTHER INFORMATION: Xaa= Asp/Glu
<220> FEATURE:
<221> NAME/KEY: VARIANT
<222> LOCATION: (3)..(3)
<223> OTHER INFORMATION: Xaa= Asp/Glu
<220> FEATURE:
<221> NAME/KEY: VARIANT
<222> LOCATION: (4)..(4)
<223> OTHER INFORMATION: Xaa= Asp/Glu

<400> SEQUENCE: 20

Xaa Xaa Xaa Xaa Pro Arg
1               5

<210> SEQ ID NO 21
<211> LENGTH: 5
<212> TYPE: PRT
<213> ORGANISM: Artificial Sequence
<220> FEATURE:
<223> OTHER INFORMATION: N-terminal protecting peptide
<220> FEATURE:
<221> NAME/KEY: VARIANT
<222> LOCATION: (1)..(1)
<223> OTHER INFORMATION: Xaa= Asp or Glu
<220> FEATURE:
<221> NAME/KEY: VARIANT
<222> LOCATION: (2)..(2)
<223> OTHER INFORMATION: Xaa= Asp or Glu
<220> FEATURE:
<221> NAME/KEY: VARIANT
<222> LOCATION: (4)..(4)
<223> OTHER INFORMATION: Xaa= Asp or Glu
<220> FEATURE:
<221> NAME/KEY: VARIANT
<222> LOCATION: (5)..(5)
<223> OTHER INFORMATION: Xaa= any codable amino acid or Gly or Pro

<400> SEQUENCE: 21

Xaa Xaa Gly Xaa Xaa
1               5

<210> SEQ ID NO 22
<211> LENGTH: 6
<212> TYPE: PRT
<213> ORGANISM: Artificial Sequence
<220> FEATURE:
<223> OTHER INFORMATION: N-terminal protecting peptide

<400> SEQUENCE: 22

Asp Asp Gly Asp Pro Arg
1               5

<210> SEQ ID NO 23
<211> LENGTH: 6
<212> TYPE: PRT
<213> ORGANISM: Artificial Sequence
<220> FEATURE:
```

```
<223> OTHER INFORMATION: N-terminal protecting peptide

<400> SEQUENCE: 23

Glu Glu Gly Glu Pro Arg
1               5

<210> SEQ ID NO 24
<211> LENGTH: 6
<212> TYPE: PRT
<213> ORGANISM: Artificial Sequence
<220> FEATURE:
<223> OTHER INFORMATION: N-terminal protecting peptide

<400> SEQUENCE: 24

Asp Asp Gly Asp Gly Arg
1               5

<210> SEQ ID NO 25
<211> LENGTH: 6
<212> TYPE: PRT
<213> ORGANISM: Artificial Sequence
<220> FEATURE:
<223> OTHER INFORMATION: N-terminal protecting peptide

<400> SEQUENCE: 25

Glu Glu Gly Glu Gly Arg
1               5

<210> SEQ ID NO 26
<211> LENGTH: 3
<212> TYPE: PRT
<213> ORGANISM: Artificial Sequence
<220> FEATURE:
<223> OTHER INFORMATION: N-terminal protecting peptide

<400> SEQUENCE: 26

Asp Glu Arg
1

<210> SEQ ID NO 27
<211> LENGTH: 21
<212> TYPE: PRT
<213> ORGANISM: HOMO SAPIENS

<400> SEQUENCE: 27

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 28
<211> LENGTH: 30
<212> TYPE: PRT
<213> ORGANISM: HOMO SAPIENS

<400> SEQUENCE: 28

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 29
<211> LENGTH: 35
<212> TYPE: PRT
<213> ORGANISM: Homo spaiens
```

```
<400> SEQUENCE: 29

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 30
<211> LENGTH: 10
<212> TYPE: PRT
<213> ORGANISM: Artificial Sequence
<220> FEATURE:
<223> OTHER INFORMATION: synthetic C-peptide

<400> SEQUENCE: 30

Glu Glu Ala Glu Ala Glu Ala Glu Pro Lys
1               5                   10

<210> SEQ ID NO 31
<211> LENGTH: 4
<212> TYPE: PRT
<213> ORGANISM: Artificial Sequence
<220> FEATURE:
<223> OTHER INFORMATION: synthetic C-peptide

<400> SEQUENCE: 31

Thr Ala Ala Lys
1
```